(12) United States Patent
Johnson et al.

(10) Patent No.: US 10,292,677 B2
(45) Date of Patent: *May 21, 2019

(54) ENDOLUMINAL FILTER HAVING ENHANCED ECHOGENIC PROPERTIES

(71) Applicant: VOLCANO CORPORATION, San Diego, CA (US)

(72) Inventors: Eric Johnson, Woodside, CA (US); Jeremy Stigall, San Diego, CA (US)

(73) Assignee: VOLCANO CORPORATION, San Diego, CA (US)

(*) Notice: Subject to any disclaimer, the term of this patent is extended or adjusted under 35 U.S.C. 154(b) by 507 days.

This patent is subject to a terminal disclaimer.

(21) Appl. No.: 14/864,193

(22) Filed: Sep. 24, 2015

(65) Prior Publication Data

US 2016/0074011 A1  Mar. 17, 2016

Related U.S. Application Data

(63) Continuation-in-part of application No. 14/776,540, filed as application No. PCT/US2014/027083 on Mar. 14, 2014.

(Continued)

(51) Int. Cl.
*A61B 5/00* (2006.01)
*A61B 8/08* (2006.01)
(Continued)

(52) U.S. Cl.
CPC .............. *A61B 8/0833* (2013.01); *A61F 2/01* (2013.01); *A61B 8/0841* (2013.01);
(Continued)

(58) Field of Classification Search
CPC ... A61B 8/0833; A61B 8/0891; A61B 8/0841; A61B 8/12; A61F 2/01; A61F 2240/001;
(Continued)

(56) References Cited

U.S. PATENT DOCUMENTS 152,652 A   6/1874  Knowlton
407,971 A   7/1889  Siersdorfer
(Continued)

FOREIGN PATENT DOCUMENTS

CN   2635045 Y   8/2004
EP   1041373 A2  10/2000
(Continued)

*Primary Examiner* — Joel Lamprecht

(57) ABSTRACT

An endoluminal filter, comprising a first support member having a first end and a second end; and a second support member attached to the first end of the first support member or the second end of the first support member and forming a crossover with the first support member to form two loops one on either side of the crossover, wherein at least a portion of the first or second support member is modified to provide an enhanced echogenic characteristic. A system for positioning a filter within a vasculature including an endoluminal filter, a user interface, a display, and a processor is also provided. A method for positioning a filter within a lumen is also provided wherein the steps are performed using an intravascular ultrasound system and the filter is modified to provide at least one echogenic characteristic.

34 Claims, 83 Drawing Sheets

Related U.S. Application Data

(60) Provisional application No. 61/785,955, filed on Mar. 14, 2013, provisional application No. 62/054,844, filed on Sep. 24, 2014.

(51) Int. Cl.
  *A61B 8/12* (2006.01)
  *A61F 2/01* (2006.01)

(52) U.S. Cl.
  CPC .............. *A61B 8/0891* (2013.01); *A61B 8/12* (2013.01); *A61F 2002/011* (2013.01); *A61F 2220/0016* (2013.01); *A61F 2240/001* (2013.01); *A61F 2250/0096* (2013.01)

(58) Field of Classification Search
  CPC ........ A61F 2220/0016; A61F 2002/011; A61F 2250/0096
  See application file for complete search history.

(56) References Cited

U.S. PATENT DOCUMENTS

| | | |
|---|---|---|
| 621,937 A | 3/1899 | Niemann |
| 796,910 A | 8/1905 | Hernan |
| 1,950,378 A | 3/1934 | Andrews |
| 2,163,324 A | 6/1939 | Reinhold |
| 3,301,258 A | 1/1967 | Werner |
| 3,617,880 A | 11/1971 | Cormack et al. |
| 3,789,841 A | 2/1974 | Antoshkiw |
| 3,841,308 A | 10/1974 | Tate |
| 3,952,747 A | 4/1976 | Kimmell, Jr. |
| 4,140,364 A | 2/1979 | Yamashita et al. |
| 4,265,251 A | 5/1981 | Tickner |
| 4,274,423 A | 6/1981 | Mizuno et al. |
| 4,276,885 A | 7/1981 | Tickner et al. |
| 4,344,438 A | 8/1982 | Schultz |
| 4,398,791 A | 8/1983 | Dorsey |
| 4,401,124 A | 8/1983 | Guess et al. |
| 4,425,908 A | 1/1984 | Simon |
| 4,432,370 A | 2/1984 | Hughes et al. |
| 4,442,843 A | 4/1984 | Rasor et al. |
| 4,466,442 A | 8/1984 | Hilmann et al. |
| 4,494,531 A | 1/1985 | Gianturco |
| 4,552,554 A | 11/1985 | Gould et al. |
| 4,572,203 A | 2/1986 | Feinstein |
| 4,577,543 A | 3/1986 | Wilson |
| 4,619,246 A | 10/1986 | Molgaard-Nielsen et al. |
| 4,643,184 A | 2/1987 | Mobin-Uddin |
| 4,676,980 A | 6/1987 | Segal et al. |
| 4,682,895 A | 7/1987 | Costello |
| 4,718,433 A | 1/1988 | Feinstein |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,817,600 A | 4/1989 | Herms et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,832,055 A | 5/1989 | Palestrant |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,990,156 A | 2/1991 | Lefebvre |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,059,205 A | 10/1991 | El-Nounou et al. |
| 5,065,010 A | 11/1991 | Knute |
| 5,065,769 A | 11/1991 | de Toledo |
| 5,081,997 A | 1/1992 | Bosley, Jr. et al. |
| 5,085,221 A | 2/1992 | Ingebrigtsen et al. |
| 5,095,911 A | 3/1992 | Pomeranz |
| 5,098,440 A | 3/1992 | Hillstead |
| 5,100,424 A | 3/1992 | Jang et al. |
| 5,120,308 A | 6/1992 | Hess |
| 5,125,137 A | 6/1992 | Corl et al. |
| 5,133,733 A | 7/1992 | Rasmussen et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,234,458 A | 8/1993 | Metais |
| 5,240,003 A | 8/1993 | Lancee et al. |
| 5,240,437 A | 8/1993 | Christian |
| 5,242,460 A | 9/1993 | Klein et al. |
| 5,242,462 A | 9/1993 | El-Nounou et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,289,831 A | 3/1994 | Bosley |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,327,891 A | 7/1994 | Rammler |
| 5,336,178 A | 8/1994 | Kaplan et al. |
| 5,344,427 A | 9/1994 | Cottenceau et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,370,657 A | 12/1994 | Irie |
| 5,373,845 A | 12/1994 | Gardineer et al. |
| 5,373,849 A | 12/1994 | Maroney et al. |
| 5,375,602 A | 12/1994 | Lancee et al. |

(56) References Cited

U.S. PATENT DOCUMENTS

| | | |
|---|---|---|
| 5,375,612 A | 12/1994 | Cottenceau et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,601,595 A | 2/1997 | Smith |
| 5,609,606 A | 3/1997 | O'Boyle |
| 5,626,605 A | 5/1997 | Irie et al. |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,725,550 A | 3/1998 | Nadal |
| 5,725,552 A | 3/1998 | Kotula et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,814,064 A | 9/1998 | Daniel et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,921,933 A | 7/1999 | Sarkis et al. |
| 5,925,055 A | 7/1999 | Adrian et al. |
| 5,925,060 A | 7/1999 | Forber |
| 5,944,738 A | 8/1999 | Amplatz et al. |
| 5,949,929 A | 9/1999 | Hamm |
| 5,951,586 A | 9/1999 | Berg et al. |
| 5,957,849 A * | 9/1999 | Munro ............... A61B 18/149 600/459 |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,053,925 A | 4/2000 | Barnhart |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,080,178 A | 6/2000 | Meglin |
| 6,080,182 A | 6/2000 | Shaw et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,160,084 A | 12/2000 | Langer et al. |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,217,600 B1 | 4/2001 | DiMatteo |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,026 B1 | 7/2001 | Ravenscroft et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |

(56) References Cited

U.S. PATENT DOCUMENTS

| | | |
|---|---|---|
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,388,043 B1 | 5/2002 | Langer et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,443,972 B1 | 9/2002 | Bosma et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,514,273 B1 | 2/2003 | Voss et al. |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,544,279 B1 | 4/2003 | Hopkins et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,620,183 B2 | 9/2003 | DiMatteo |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |

(56) References Cited

U.S. PATENT DOCUMENTS

| | | |
|---|---|---|
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Komkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,785,343 B2 * | 8/2010 | Johnson ............... A61F 2/01 606/200 |
| 7,787,127 B2 | 8/2010 | Galle et al. |
| 7,789,892 B2 | 9/2010 | Johnson et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,854,747 B2 * | 12/2010 | Johnson ............... A61F 2/01 606/200 |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |

(56) References Cited

U.S. PATENT DOCUMENTS

| | | |
|---|---|---|
| 8,239,938 B2 | 8/2012 | Simeral et al. |
| 8,273,099 B2 | 9/2012 | DiMatteo |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp, II et al. |
| 2002/0089335 A1 | 7/2002 | Williams |
| 2002/0095171 A1 | 7/2002 | Belef |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0193827 A1 | 12/2002 | McGuckin et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0171774 A1 | 9/2003 | Freudenthal et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186512 A1 | 9/2004 | Bruckheimer et al. |
| 2004/0186558 A1 | 9/2004 | Pavcnik et al. |
| 2004/0195512 A1 | 10/2004 | Crosetto |
| 2004/0199201 A1 | 10/2004 | Kellett et al. |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0177185 A1 | 8/2005 | Becker et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childlers et al. |
| 2006/0015126 A1 | 1/2006 | Sher |
| 2006/0020285 A1 | 1/2006 | Niermann |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0058647 A1 | 3/2006 | Strommer |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0074484 A1 | 4/2006 | Huber |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |

(56) References Cited

U.S. PATENT DOCUMENTS

| | | |
|---|---|---|
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0241675 A1* | 10/2006 | Johnson ............... A61F 2/01 606/200 |
| 2006/0241678 A1* | 10/2006 | Johnson ............... A61F 2/01 606/200 |
| 2006/0241680 A1* | 10/2006 | Johnson ............... A61F 2/01 606/200 |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167801 A1* | 7/2007 | Webler ............... G06T 19/00 600/459 |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0021497 A1* | 1/2008 | Johnson ............... A61F 2/01 606/200 |
| 2008/0027481 A1 | 1/2008 | Gilson et al. |
| 2008/0033534 A1 | 2/2008 | Cook et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1* | 6/2008 | Johnson ............... A61F 2/01 606/200 |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |

(56) References Cited

U.S. PATENT DOCUMENTS

| | | |
|---|---|---|
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0130963 A1 | 5/2010 | Ebert et al. |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0222671 A1 | 9/2010 | Cohen |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0166407 A1* | 7/2011 | Sumanaweera ...... A61B 5/0422 600/1 |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg et al. |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0022638 A1 | 1/2012 | Leewood et al. |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0209116 A1* | 8/2012 | Hossack ............... A61B 8/12 600/439 |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |

(56) References Cited

U.S. PATENT DOCUMENTS

| | | |
|---|---|---|
| 2012/0330141 A1 | 12/2012 | Brown et al. |
| 2013/0012981 A1 | 1/2013 | Johnson et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0023981 A1 | 1/2013 | Dierking et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0131425 A1* | 5/2013 | Sumanaweera ...... A61B 5/0422 600/1 |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0267848 A1* | 10/2013 | Fearnot ................ A61B 8/0841 600/439 |
| 2013/0289519 A1 | 10/2013 | Johnson et al. |
| 2013/0289610 A1 | 10/2013 | Johnson et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0107491 A1 | 4/2014 | Fearnot |
| 2014/0121643 A1 | 5/2014 | McKinnis |
| 2014/0180067 A1 | 6/2014 | Stigall et al. |
| 2014/0180128 A1 | 6/2014 | Corl |
| 2014/0200438 A1 | 7/2014 | Millett et al. |
| 2015/0164630 A1 | 6/2015 | Johnson et al. |
| 2015/0173830 A1 | 6/2015 | Johnson et al. |
| 2015/0173884 A1 | 6/2015 | Johnson et al. |
| 2015/0173924 A1 | 6/2015 | Johnson et al. |
| 2016/0030151 A1 | 2/2016 | Johnson et al. |
| 2016/0030152 A1 | 2/2016 | Johnson et al. |

FOREIGN PATENT DOCUMENTS

| | | |
|---|---|---|
| EP | 01172637 A1 | 1/2002 |
| EP | 2438877 A2 | 4/2012 |
| GB | 1588072 A | 4/1981 |
| GB | 2280261 A | 1/1995 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/044296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 5/2005 |
| WO | 2005/102211 A1 | 11/2005 |
| WO | 2006/029634 A2 | 3/2006 |
| WO | 2006/034233 A1 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006122001 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2010129193 A1 | 11/2010 |
| WO | 2011/06886 A2 | 1/2011 |
| WO | 2011/038048 A1 | 3/2011 |
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |
| WO | 20140139021 | 9/2014 |
| WO | 20140145598 | 9/2014 |

\* cited by examiner

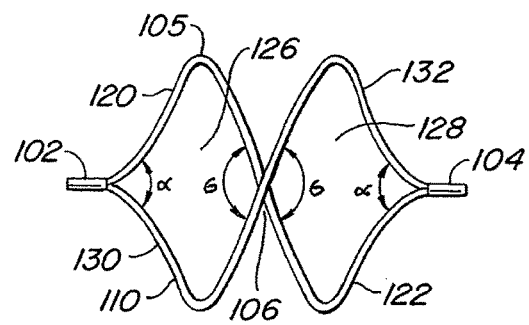
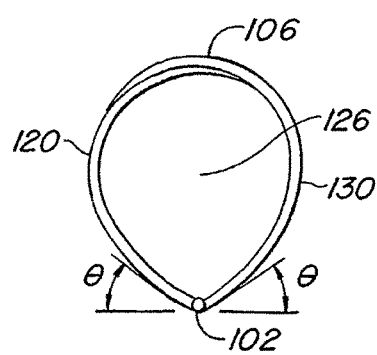
FIG. 7D   FIG. 7E
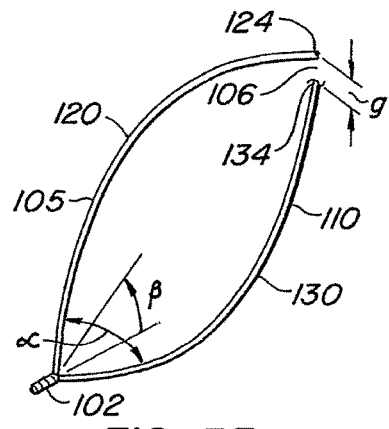
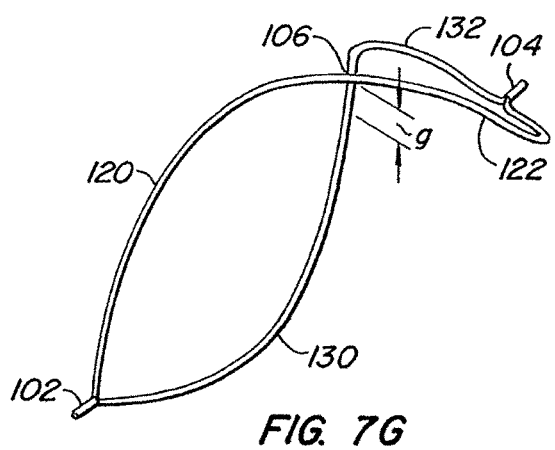
FIG. 7F   FIG. 7G
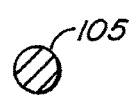 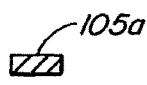 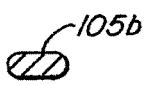 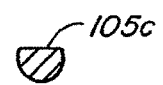
FIG. 8A   FIG. 8B   FIG. 8C   FIG. 8D

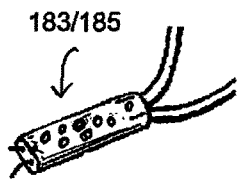 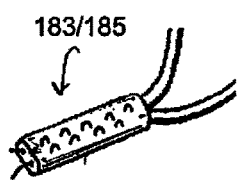 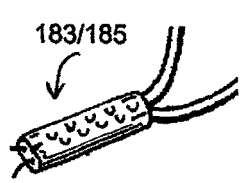 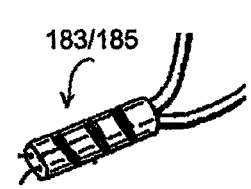
FIG. 23x1    FIG. 23x2    FIG. 23x3    FIG. 23x4
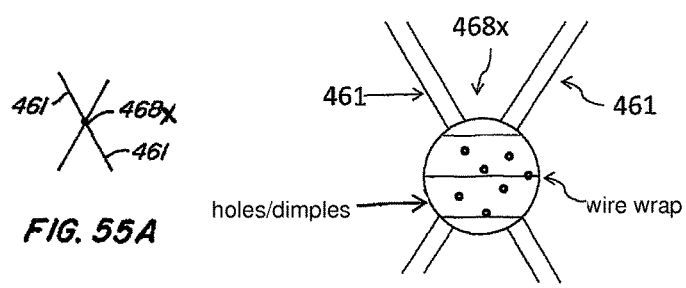
FIG. 55Ax1

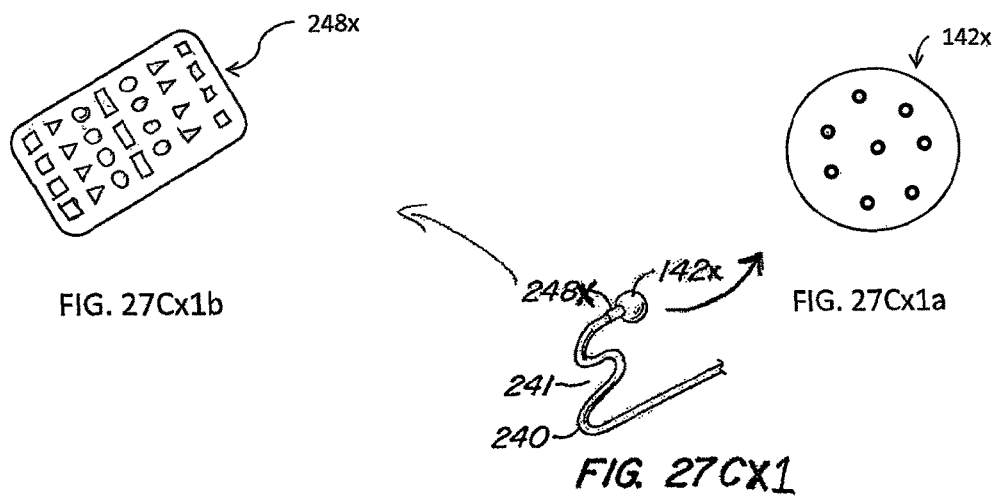
FIG. 27Cx1b  FIG. 27Cx1a
FIG. 27Cx1
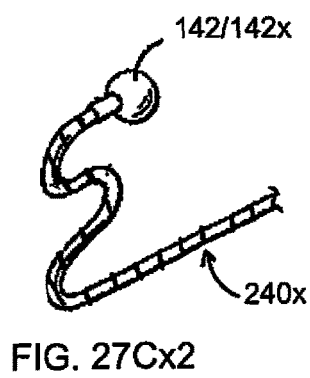
FIG. 27Cx2

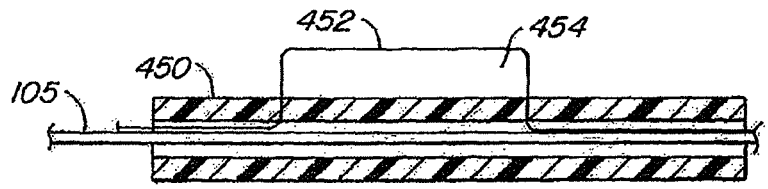
FIG. 50
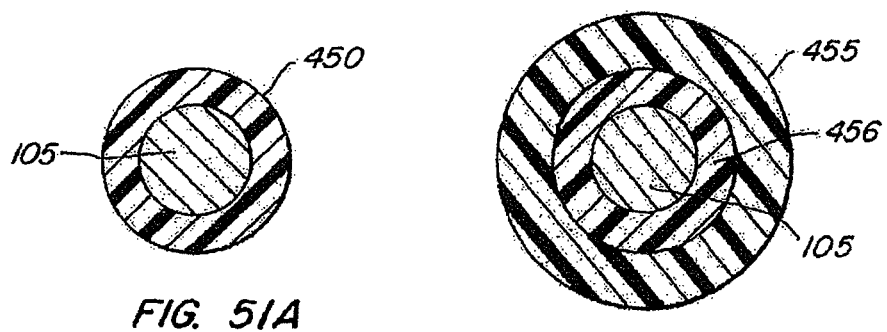
FIG. 51A
FIG. 51B
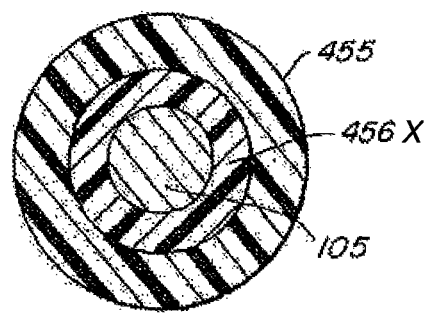
FIG. 51Bx

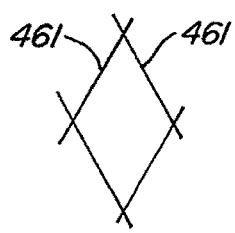
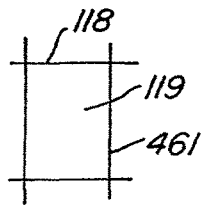
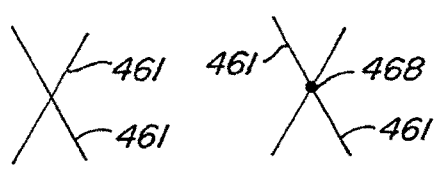
FIG. 54A  FIG. 54B  FIG. 54C  FIG. 55A
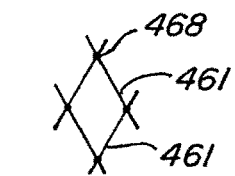
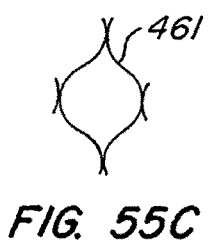
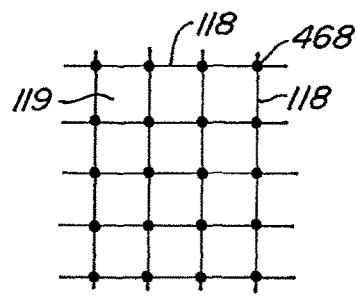
FIG. 55B  FIG. 55C  FIG. 55D
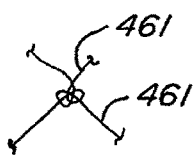
FIG. 55E  FIG. 60A  FIG. 60B
FIG. 60C  FIG. 60D  FIG. 60E

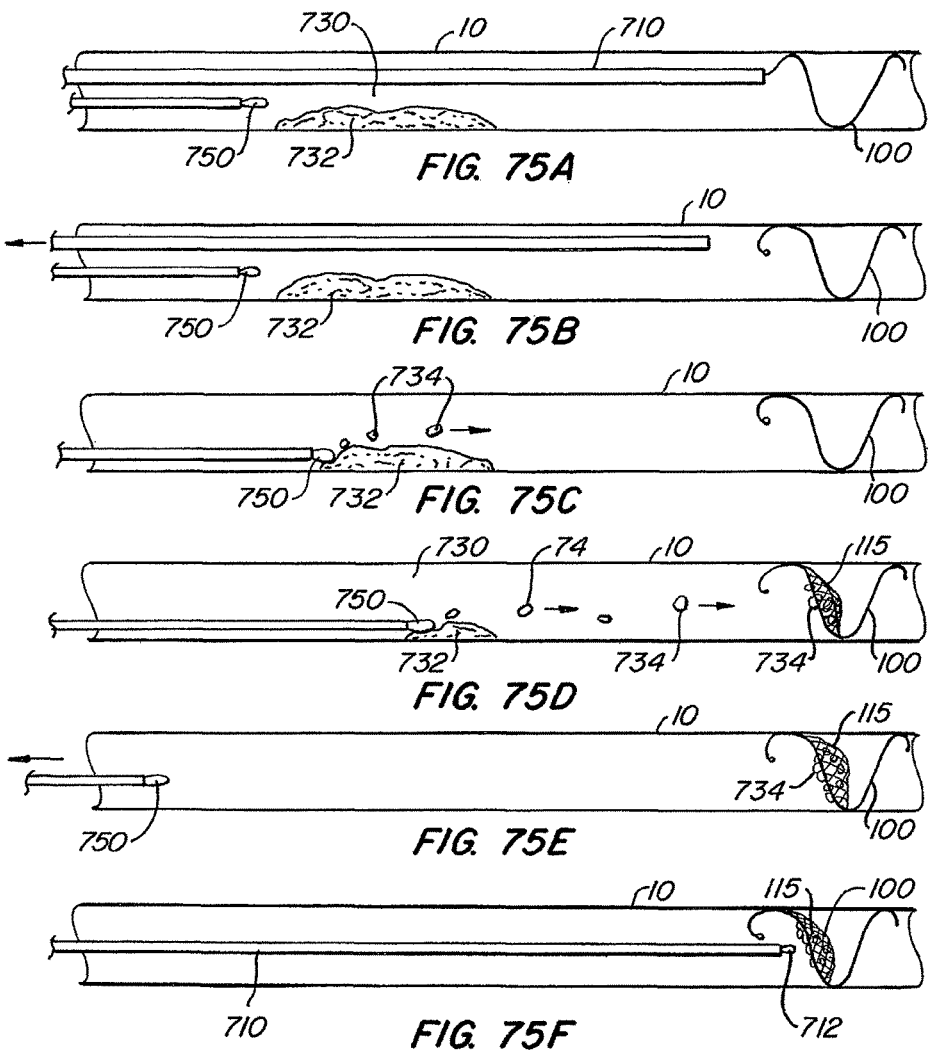

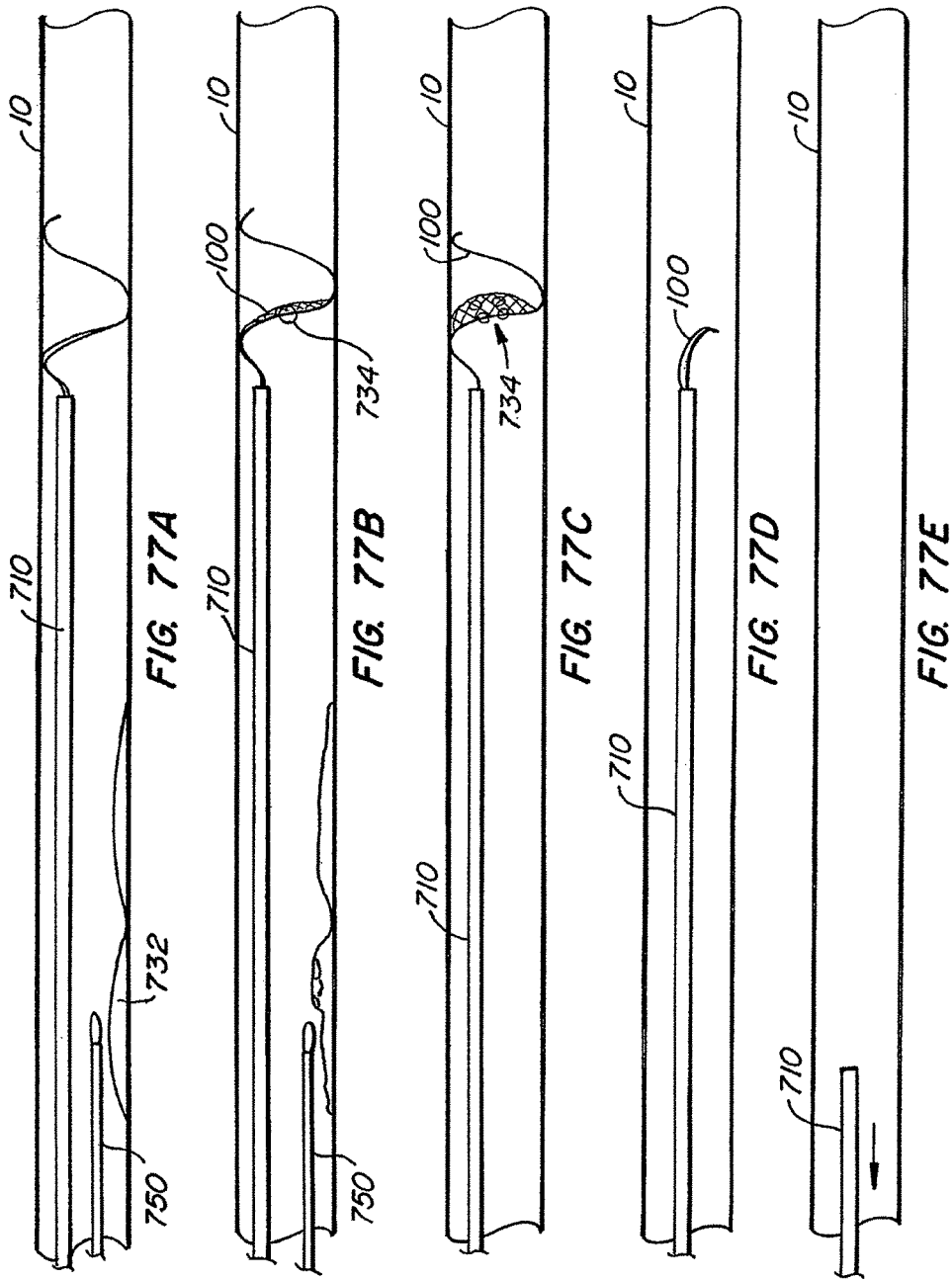

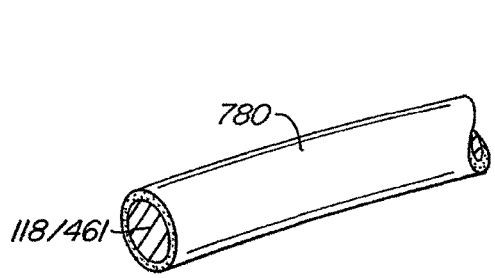
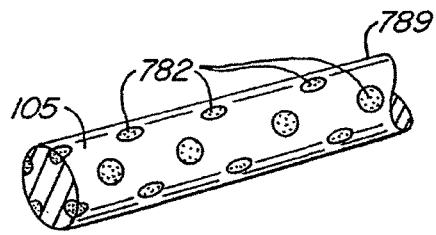
FIG. 79
FIG. 80
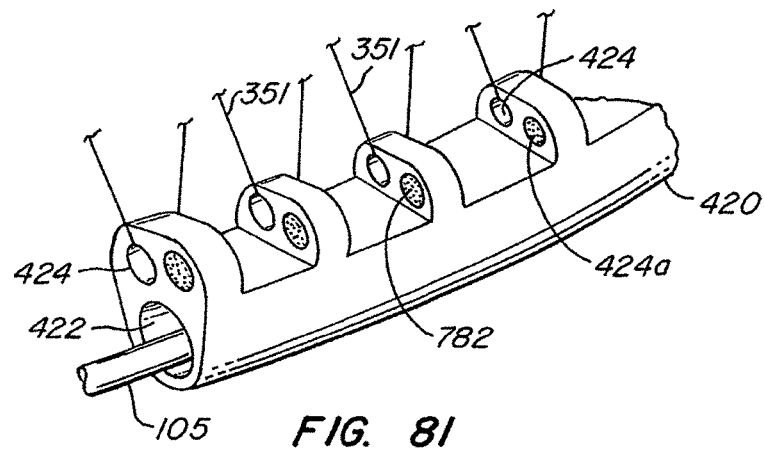
FIG. 81
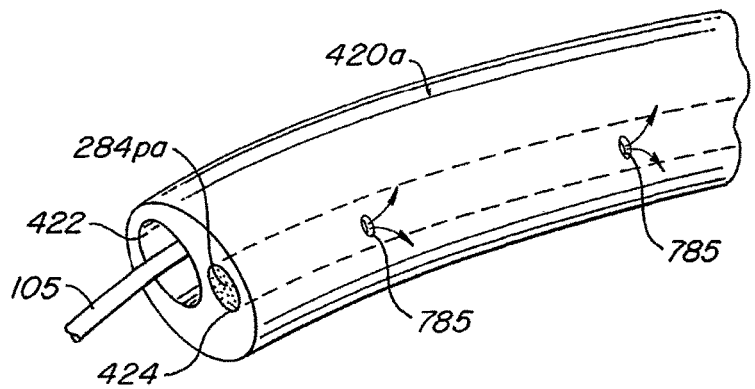
FIG. 82

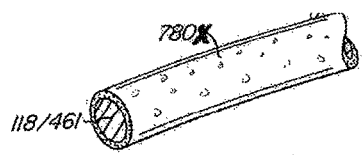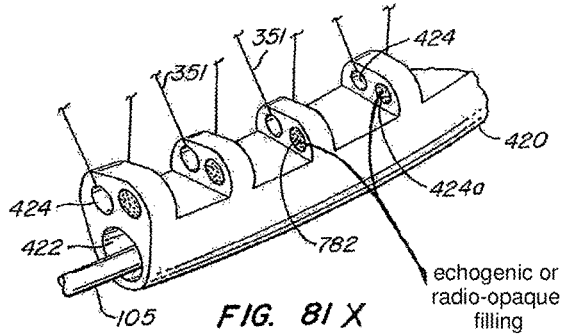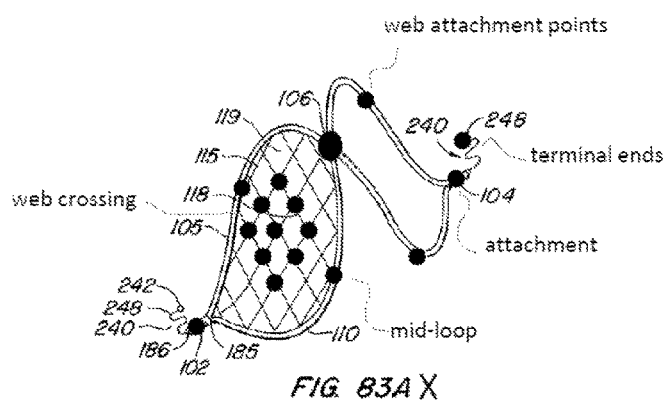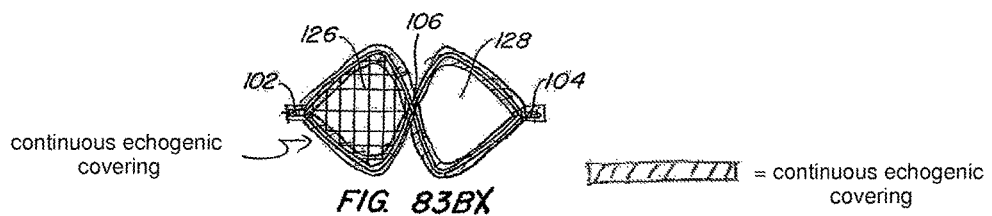

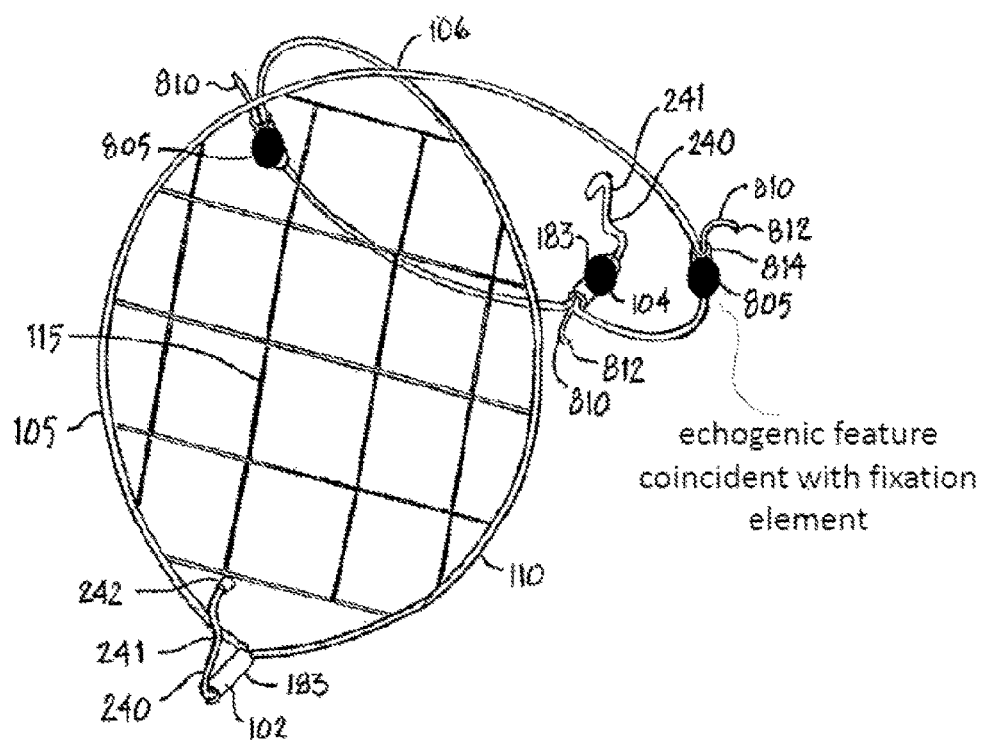
FIG. 88x1
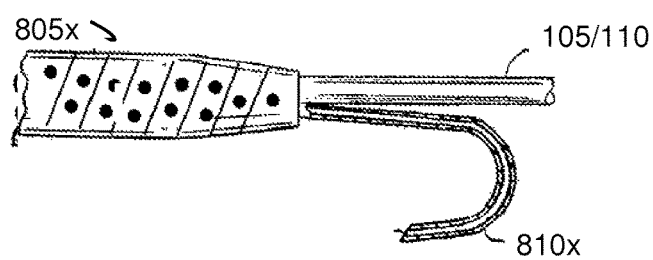
FIG. 88x2

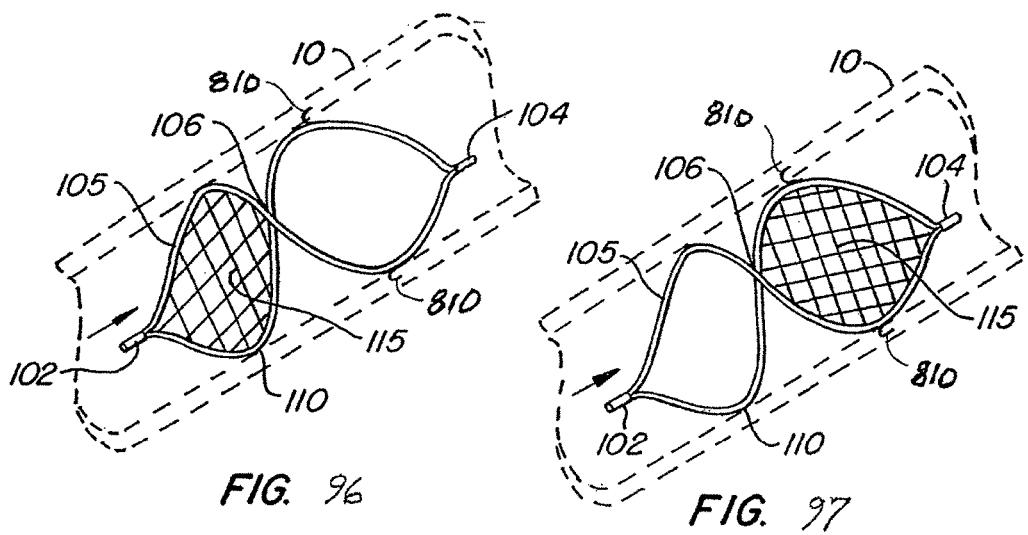
FIG. 96
FIG. 97
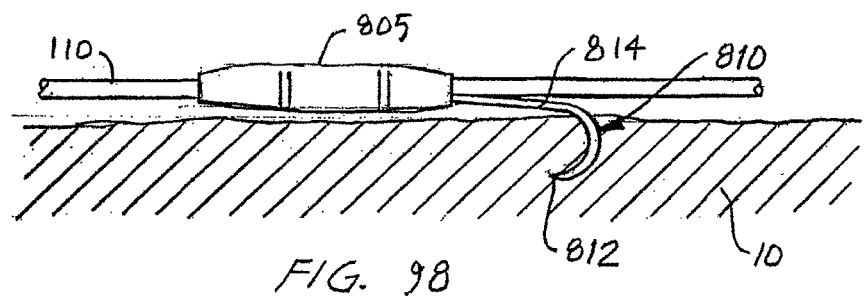
FIG. 98
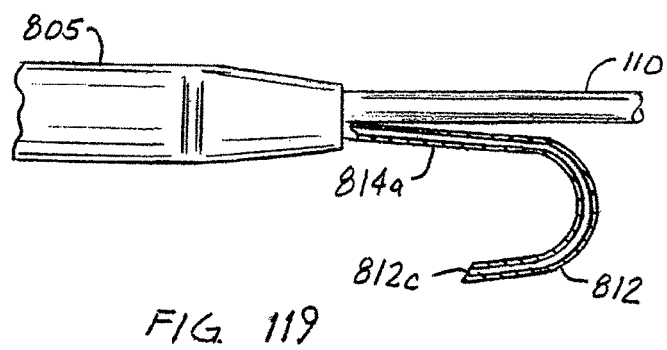
FIG. 119

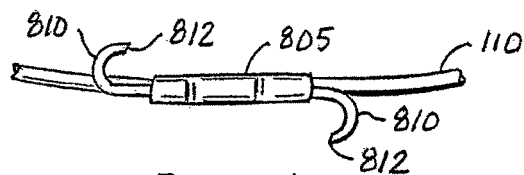
FIG. 104C
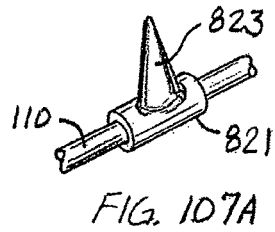
FIG. 107A
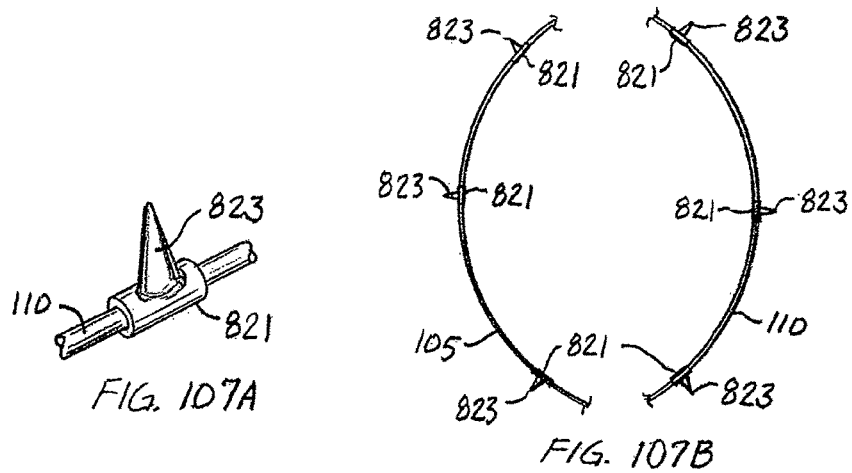
FIG. 107B
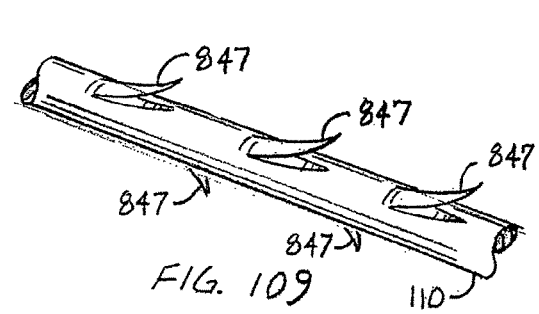
FIG. 108
FIG. 109
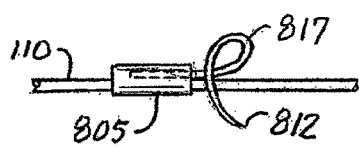
FIG. 105
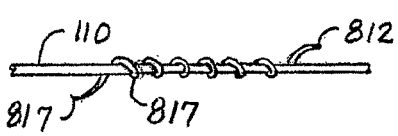
FIG. 106

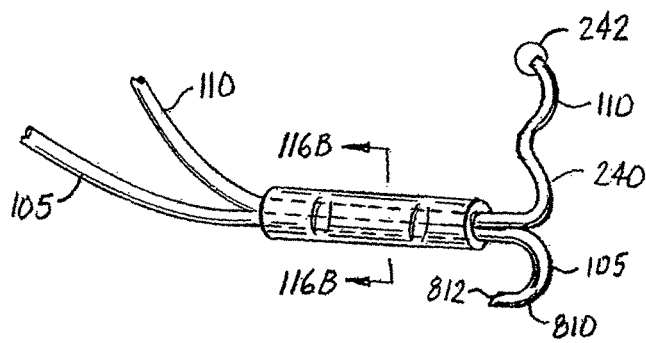
FIG. 116A
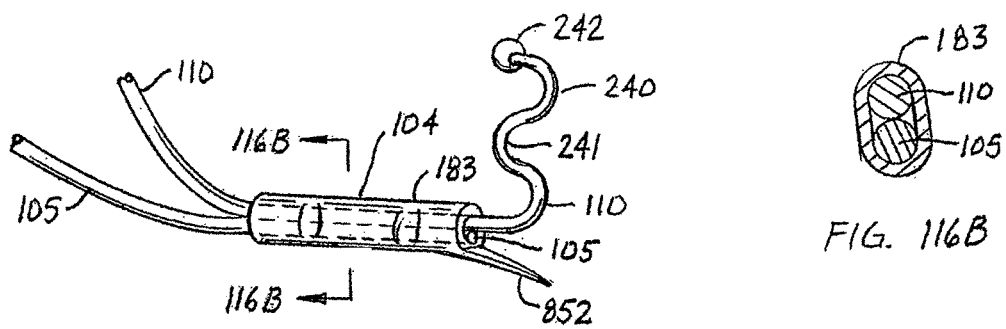
FIG. 117A
FIG. 116B
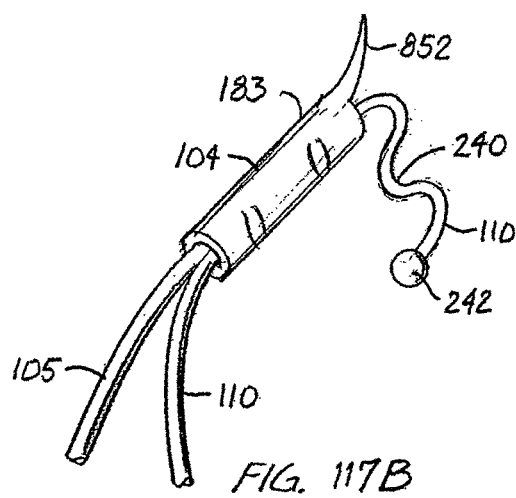
FIG. 117B

TUBE WITH LASER DRILLED HOLES

TUBE WITH ROUGH SURFACE
RAISED FEATURES

TUBE WITH BUBBLES

DIMPLES IN TUBE

TUBE SANDWICH WITH
COIL/BRAID

MEASUREMENT

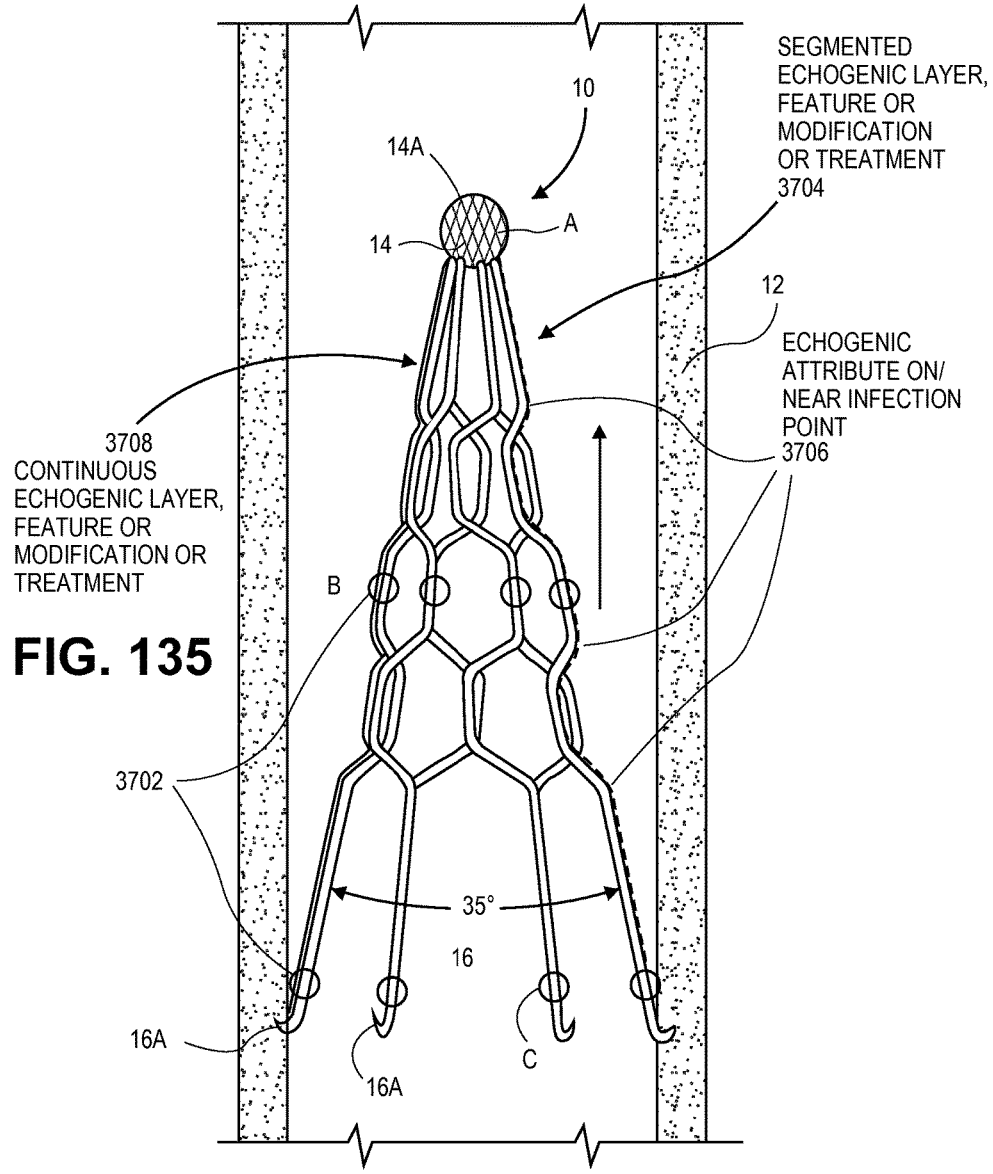

FIG. 135

SECTION A: APEX/TIP/TERMINAL END/: PROVIDES ID OF END OF FILTER FOR RETRIEVAL, POSITIONING, ATTITUDE DETERMINATION, LOCALIZATION ETC.
SECTION B: MID STRUT/MIDDLE/FILTRATION OR CAPTURE REGION/: PROVIDES SIZING, CENTERING, SYMMETRY OF IMPLANT, APPOSITION, CLOT BURDEN, DEPLOYMENT, GAUGE OF FILTER CAPACITY, FILTER CONTENTS
SECTION C: REAR PORTION/TERMINAL END/ANCHOR/FIXATION/PERFORATION: PROVIDES SIZING, CENTERING, SYMMETRY OF IMPLANT, LEGS, ANCHOR INSERTION OR DEPTH.

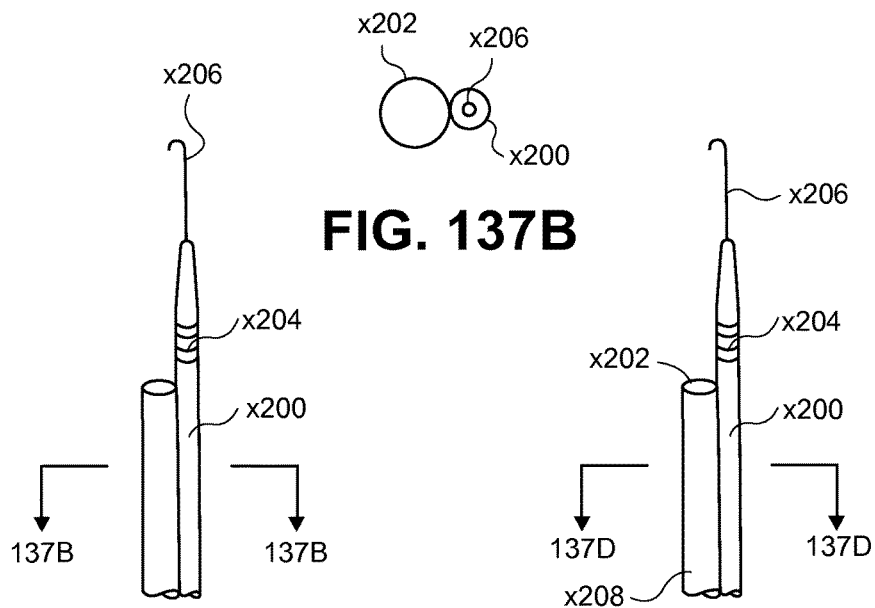
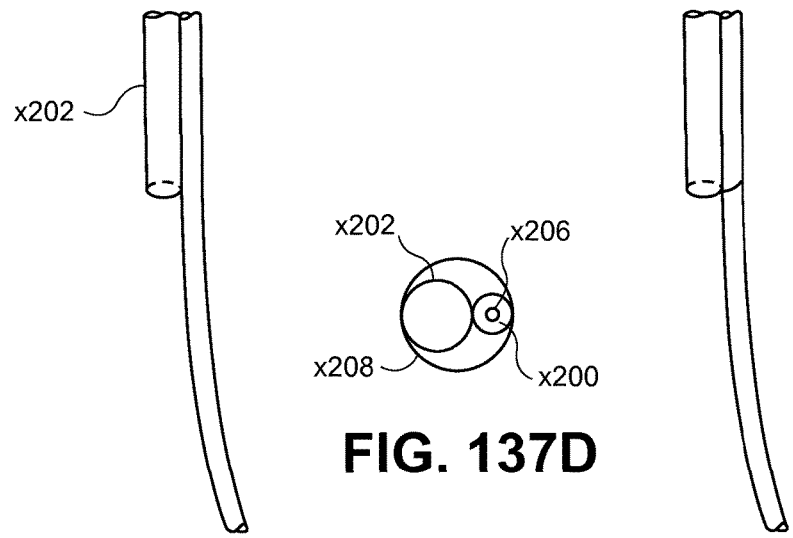
FIG. 137A  FIG. 137B  FIG. 137C  FIG. 137D

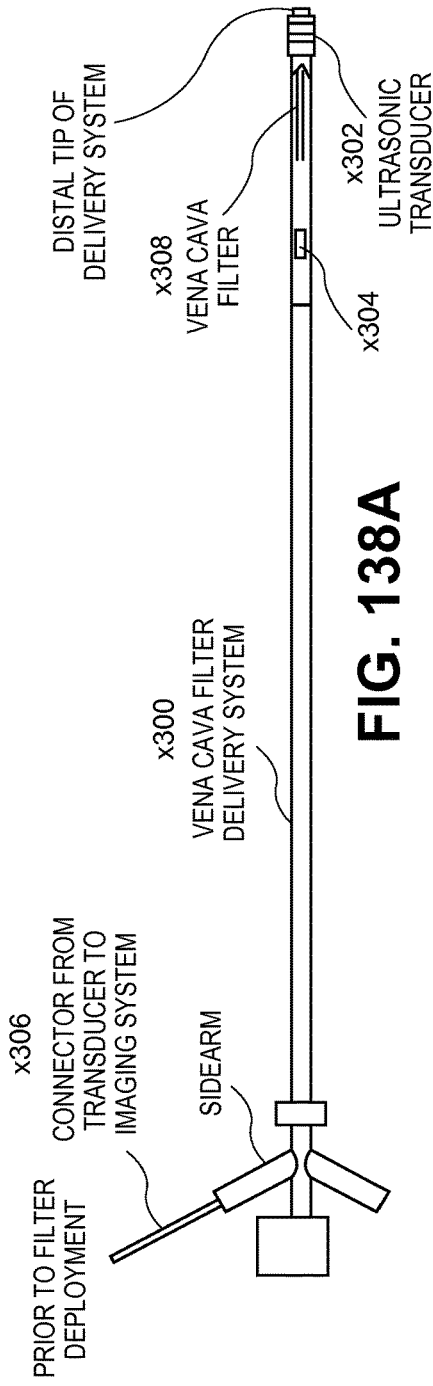
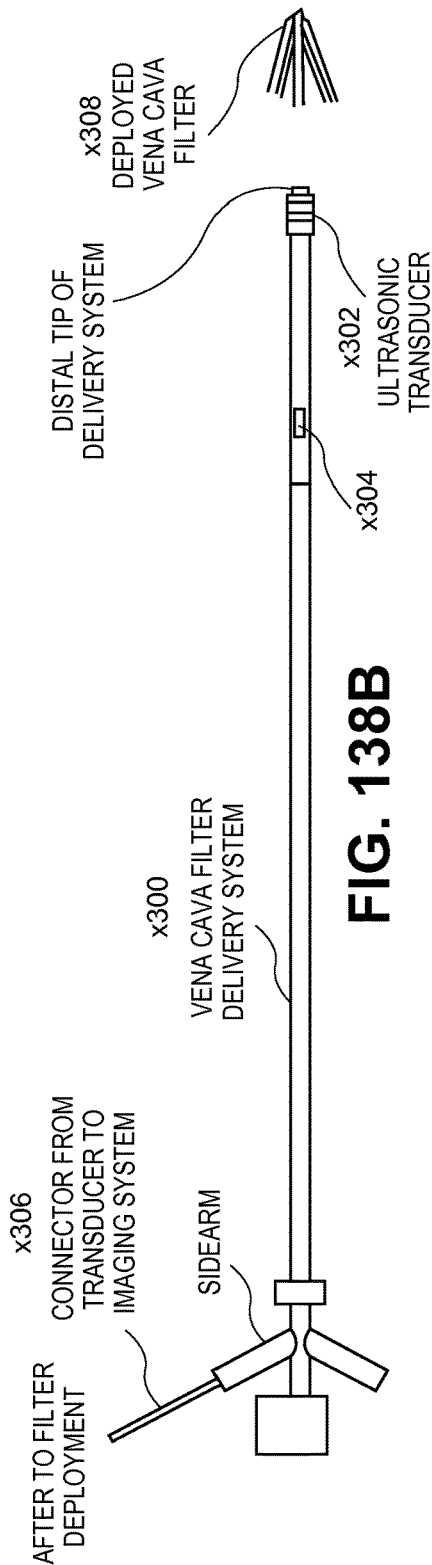
FIG. 138A
FIG. 138B

ENDOLUMINAL FILTER HAVING ENHANCED ECHOGENIC PROPERTIES

CROSS-REFERENCE TO RELATED APPLICATIONS

This application is a continuation in part of U.S. patent application Ser. No. 14/776,540, filed on Sep. 14, 2015, which claims the benefit of International Application No. PCT/US2014/027083, filed Mar. 14, 2014, which claims priority to U.S. Provisional Patent Application No. 61/785,955, filed Mar. 14, 2013, each of which is herein incorporated by reference in its entirety. This application also claims priority to U.S. Provisional Application No. 62/054,844 filed Sep. 24, 2014, of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

The following patents and patent applications are herein incorporated by reference in their entirety: U.S. patent application Ser. No. 11/325,230, filed Jan. 3, 2006, entitled "ENDOLUMINAL FILTER," now U.S. Pat. No. 7,854,747; U.S. patent application Ser. No. 11/969,827, filed Jan. 4, 2008, entitled "ENDOLUMINAL FILTER WITH FIXATION;" and International Patent Application No. PCT/US2013/021285, filed Jan. 11, 2013, entitled ENDOLUMINAL FILTER WITH FIXATION."

BACKGROUND

Field

Aspects of the invention described herein relate generally to filters inserted into a patient's body and more particularly to the provision of echogenic coatings on such devices to enhance their visibility using one or more of in any combination ultrasound imaging, intravascular ultrasound imaging, greyscale intravascular ultrasound imaging, color intravascular ultrasound imaging or ultrasound image signal processing that included spectral analysis of the filter.

Background

Embolic protection is utilized throughout the vasculature to prevent the potentially fatal passage of embolic material in the bloodstream to smaller vessels where it can obstruct blood flow. The dislodgement of embolic material is often associated with procedures which open blood vessels to restore natural blood flow such as stenting, angioplasty, arthrectomy, endarterectomy or thrombectomy. Used as an adjunct to these procedures, embolic protection devices trap debris and provide a means for removal for the body.

One widely used embolic protection application is the placement of filtration means in the vena cava. Vena cava filters (VCF) prevent the passage of thrombus from the deep veins of the legs into the blood stream and ultimately to the lungs. This condition is known as deep vein thrombosis (DVT), which can cause a potentially fatal condition known as pulmonary embolism (PE).

The first surgical treatment for PE, performed by John Hunter in 1874, was femoral vein ligation. The next major advancement, introduced in the 1950's, was the practice of compartmentalizing of the vena cava using clips, suture or staples. While effective at preventing PE, these methods were associated with significant mortality and morbidity (see, e.g., Kinney T B, Update on inferior vena cava filters, JVIR 2003; 14:425-440, incorporated herein by reference).

A major improvement in PE treatment, in which venous blood flow was maintained, was presented by DeWesse in 1955. This method was called the "harp-string" filter, as represented in FIG. 1A and FIG. 1B, in which strands of silk suture 12 were sewn across the vena cava 11 in a tangential plane below the renal veins 13 to trap thrombus. Reported clinical results demonstrated the effectiveness of this method in preventing PE and maintaining caval patency. (see, e.g., DeWeese M S, A vena cava filter for the prevention of pulmonary embolism, Arch of Surg 1963; 86:852-868, incorporated herein by reference). Operative mortality associated with all of these surgical treatments remained high and therefore limited their applicability.

The current generation of inferior vena cava (IVC) filters began in 1967 with the introduction of the Mobin-Uddin umbrella 21 (FIG. 1C) which is described in further detail in U.S. Pat. No. 3,540,431. The Greenfield filter (FIG. 1D) was introduced in 1973 and is described in further detail in U.S. Pat. No. 3,952,747. These conical-shaped devices were placed endoluminaly in the IVC and utilized hooks or barbs 20, 30 to pierce the IVC wall and fix the position of the device. A variety of conical-shaped, percutaneously placed vena cava filters, based upon this concept are now available. For example, the TULIP with a filter structure 41 (FIG. 1E) further described in U.S. Pat. No. 5,133,733; the RECOVERY with a filter structure d51 (FIG. 1F) further described in U.S. Pat. No. 6,258,026; and the TRAPESE with a filter structure 61 (FIG. 1G) further described in U.S. Pat. No. 6,443,972.

The next advancement in filters added the element of recoverability. Retrievable filters were designed to allow removal from the patient subsequent to initial placement. Retrievable filters are generally effective at preventing PE yet they have a number of shortcomings, such as, for example: failure of the device to deploy into the vessel properly, migration, perforation of the vessel wall, support structure fracture, retrievability actually limited to specific circumstances, and formation of thrombosis on or about the device.

Problems associated with retrievable, conical-shaped devices, such as those illustrated in FIG. 1D, FIG. 1E and FIG. 1F, have been reported in the medical literature. These reported problems include tilting which makes it difficult to recapture the device and compromises filtration capacity. Hooks 30, 40, 50, 60 used to secure these devices have been reported to perforate the vessel wall, cause delivery complications, and fracture. A partially retrievable system is described in detail in pending U.S. Pat. No. 2004/0186512 (FIG. 1H). In this system, the filter portion 71 can be removed from the support structure 70, but the support structure remains in-vivo. All of these described devices share the common limitation that they can be retrieved from only one end. Each of the above referenced articles, patents and patent application are incorporated herein in its entirety.

Ultrasonic imaging in the medical field is widely used for a variety of applications. In addition to imaging physiological structures and tissue such as organs, tumors, vessels, and the like, it is often desirable for a physician or technician to have an image of a medical device which has been inserted into the tissue or passageway of a patient. Still further, advancements in the use of intravascular or intraluminal imaging ultrasound (positioned either within or outside of the body) before, during and after procedures has led to increasing requirements for cooperation between device and imaging modality.

A variety of approaches have been used to enhance ultrasonic imaging of devices by increasing the acoustic reflection coefficient of the devices. While echogenic materials have been described for some uses in medical devices, the conventional uses of echogenic materials has not kept pace with the advancements in applications for imaging ultrasound. Moreover, while many approaches have been attempted, there is still need for improvements that are particular to the use of specific device designs. In particular, as medical therapies and procedures continue to advance, there is, in many medical instances, a need for more specific information about a device, its placement, position, orientation or aspect in relation to another object. What is needed are further improvements to the manner and placement of echogenic enhancements to obtain these additional benefits In view of the many shortcomings and challenges that remain in the field of endoluminal filtering, there remains a need for improved retrievable, endoluminal filters and in particular enhancements to the echogenicity of such improved filtering designs, such as those described herein.

SUMMARY OF THE DISCLOSURE

In general, in one embodiment, an endoluminal filter, including a first support member having a first end and a second end; and a second support member attached to the first end of the first support member or the second end of the first support member and forming a crossover with the first support member to form two loops one on either side of the crossover, wherein at least a portion of the first support member, the second support member, the first end, the second end or a region adjacent to the cross over or any portion of one of the above can be modified to provide an enhanced echogenic characteristic of the endoluminal filter.

This and other embodiments can include one or more of the following features. In one aspect, the filter includes a material capture structure extending between the first and second support members, the crossover and the first end or the second end of the first support member, wherein any portion of one of the above can be modified to provide an enhanced echogenic characteristic of the endoluminal filter related to the use, status or of clot burden of the material capture structure. In another aspect, the filter includes at least one tissue anchor on the first support member or the second support member wherein any portion of the tissue anchor or any portion of one of the above can be modified to provide an enhanced echogenic characteristic of the endoluminal filter related to the use, status, position orientation of the at least one tissue anchor or the endoluminal filter. In still another aspect, the modification can provide an enhanced echogenic characteristic of the filter which can be a modification to a portion of the filter to enhance the echogenic characteristics of that portion of the filter. In yet another aspect, the modification can provide an enhanced echogenic characteristic of the filter which can be the formation of dimples into a surface of the filter. In a further aspect, the dimples can be of sufficient number and scaled to a suitable size, shape, orientation and pattern for use with an intravascular ultrasound system. In an additional aspect, the modification can provide an enhanced echogenic characteristic of the filter which can be the formation of protrusions formed in, placed on or joined to a filter surface. In still an additional aspect, the protrusions can be of sufficient number and scaled to a suitable size, shape, orientation and pattern for use with an intravascular ultrasound system. In another aspect, the modification can provide an enhanced echogenic characteristic of the filter including the roughening one or more surfaces of a filter. In a further aspect, the roughening can be performed using a chemical process, a laser or bead blasting technique. In yet another aspect, the roughening can be of sufficient scale to a suitable size, shape, orientation and pattern for use with intravascular ultrasound systems. In an additional aspect, the modification can provide an enhanced echogenic characteristic of the filter including altering one or more steps of a filter manufacturing technique to introduce cavities, voids or pockets to locally modify or adapt one or more acoustic reflection characteristics to improve echogenicity in one or more specific regions of the filter. In yet an additional aspect, the cavities, voids or pockets can be of sufficient number and scaled to a suitable size, shape, orientation and pattern for use with an intravascular ultrasound system. In another aspect, an endoluminal filter can include a retrieval feature on the first end and a retrieval feature on the second end, wherein at least one retrieval feature can be modified to provide an echogenic capability. In a further aspect, the tissue anchor can be formed from or attached to a tube covering at least a portion of the first support member or the second support member; the tissue anchor can be a tube having a tissue engagement surface, the tissue engagement surface includes a raised form or a spiral raised form, or the tissue anchor includes a coil wrapped around the first or the second support member having at least one end adapted to pierce tissue and wherein the modification to provide an enhanced echogenic characteristic of the filter can be a modification to a tissue anchor.

In general, in one embodiment, a filter including a first support member having a first end and a second end; a second support member having a first end and a second end; a filter structure suspended between the first support member and the second support member and a point where the first end of the first support member joins the first end of the second support member and a point where the first support member crosses without being joined to the second support member; and a tissue anchor on at least one of the second end of the first support member or the second end of the second support member, wherein at least a portion of the first support member, the second support member, the first end, the second end or a region adjacent to the cross over, the tissue anchor or any portion of one of the above can be modified to provide an enhanced echogenic characteristic of the filter.

In general, in one embodiment, a method of positioning a filter within a lumen, including advancing a sheath containing a filter through the lumen; deploying a portion of the filter from the sheath into the lumen to engage the lumen wall while maintaining substantially all of a material capture structure of the filter within the sheath; and deploying the material capture structure of the filter from the sheath to a position across the lumen, wherein any of the above steps can be performed using an intravascular ultrasound system and the filter can be modified to provide at least one echogenic characteristic.

This and other embodiments can include one or more of the following features. In one aspect, the method includes deploying a crossover structure of the filter into the lumen before or after the deploying the material capture structure of the filter step, wherein this step can be initiated, performed, confirmed or completed at least in part based on information obtained using intravascular ultrasound from one or more echogenic aspects of the filter. In another aspect, the method includes maneuvering a snare towards the filter in the same direction used during the advancing step; and engaging the snare with a filter retrieval feature positioned against a wall of the lumen, wherein this step can be initiated, performed, confirmed or completed at least in part based on information obtained using intravascular ultrasound from one or more echogenic aspects of the filter. In yet another aspect, the method includes maneuvering a snare towards the filter in the opposite direction used during the advancing step; and engaging the snare with a filter retrieval feature positioned against a wall of the lumen, wherein this step can be initiated, performed, confirmed or completed at least in part based on information obtained using intravascular ultrasound from one or more echogenic aspects of the filter. In still another embodiment, the method includes deploying a filter retrieval feature from the sheath before the deploying the material capture structure step, wherein this step can be initiated, performed, confirmed or completed at least in part based on information obtained using intravascular ultrasound from one or more echogenic aspects of the filter. In a further aspect, the method includes deploying a filter retrieval feature from the sheath after the deploying before the deploying a material capture structure step, wherein this step can be initiated, performed, confirmed or completed at least in part based on information obtained using intravascular ultrasound from one or more echogenic aspects of the filter. In an additional aspect, the deploying a filter retrieval feature step includes placing the filter retrieval feature against the lumen wall, wherein this step can be initiated, performed, confirmed or completed at least in part based on information obtained using intravascular ultrasound from one or more echogenic aspects of the filter. In yet another aspect, the method of positioning a filter within a lumen wherein the deploying a portion of the filter step includes engaging the lumen wall with a fixation device attached to the filter, wherein this step can be initiated, performed, confirmed or completed at least in part based on information obtained using intravascular ultrasound from one or more echogenic aspects of the filter. In a further aspect, the method of positioning a filter within a lumen wherein the deploying a portion of the filter step includes engaging the lumen wall with a radial force generated by a filter support structure, wherein this step can be initiated, performed, confirmed or completed at least in part based on information obtained using intravascular ultrasound from one or more echogenic aspects of the filter.

In general, in one embodiment, an endoluminal filter, includes a first support member having a first end and a second end and a second support member attached to the first end of the first support member or the second end of the first support member and forming a crossover with the first support member to form two loops one on either side of the crossover. At least a portion of the first support member, the second support member, the first end, the second end or a region adjacent to the cross over or any portion of one of the above is modified to provide an enhanced echogenic characteristic of the endoluminal filter.

This and other embodiments can include one or more of the following features. In one aspect, the filter can further include a material capture structure extending between the first and second support members, the crossover and the first end or the second end of the first support member. Any portion of one of the above can be modified to provide an enhanced echogenic characteristic of the endoluminal filter related to the use, status or of clot burden of the material capture structure. In another aspect, the filter can further include at least one tissue anchor on the first support member or the second support member. Any portion of the tissue anchor or any portion of one of the above can be modified to provide an enhanced echogenic characteristic of the endoluminal filter related to the use, status, position orientation of the at least one tissue anchor or the endoluminal filter. In a further aspect, the modification to provide an enhanced echogenic characteristic of the filter can be a modification to a portion of the filter to enhance the echogenic characteristics of that portion of the filter. In an alternative aspect, the modification to provide an enhanced echogenic characteristic of the filter can be the formation of dimples into a surface of the filter. In yet another aspect, the dimples can be of sufficient number and scaled to a suitable size, shape, orientation and pattern for use with an intravascular ultrasound system. In still another aspect, the modification to provide an enhanced echogenic characteristic of the filter can be the formation of protrusions formed in, placed on or joined to a filter surface. In one aspect, the protrusions can be of sufficient number and scaled to a suitable size, shape, orientation and pattern for use with an intravascular ultrasound system. In another aspect, the modification to provide an enhanced echogenic characteristic of the filter can be the roughening one or more surfaces of a filter. In a further aspect, the roughening can be performed using a chemical process, a laser or bead blasting technique. In an alternative aspect, the roughening can be of sufficient scale to a suitable size, shape, orientation and pattern for use with intravascular ultrasound systems. In yet another aspect, the modification to provide an enhanced echogenic characteristic of the filter can alter one or more steps of a filter manufacturing technique to introduce cavities, voids or pockets to locally modify or adapt one or more acoustic reflection characteristics to improve echogenicity in one or more specific regions of the filter. In still another aspect, the cavities, voids or pockets can be of sufficient number and scaled to a suitable size, shape, orientation and pattern for use with an intravascular ultrasound system. In one aspect, an endoluminal filter can further include a retrieval feature on the first end and a retrieval feature on the second end. At least one retrieval feature can be modified to provide an echogenic capability as provided in any of the previously mentioned embodiments. In another aspect, the tissue anchor can be formed from or attached to a tube covering at least a portion of the first support member or the second support member. The tissue anchor can be a tube having a tissue engagement surface, the tissue engagement surface can include a raised form or a spiral raised form, or the tissue anchor can include a coil wrapped around the first or the second support member having at least one end adapted to pierce tissue. The modification to provide an enhanced echogenic characteristic of the filter can be a modification to a tissue anchor.

In general, in one embodiment, a filter includes a first support member having a first end and a second end, a second support member having a first end and a second end, a filter structure suspended between the first support member and the second support member and a point where the first end of the first support member joins the first end of the second support member and a point where the first support member crosses without being joined to the second support member, and a tissue anchor on at least one of the second end of the first support member or the second end of the second support member, wherein at least a portion of the first support member, the second support member, the first end, the second end or a region adjacent to the cross over, the tissue anchor or any portion of one of the above is modified to provide an enhanced echogenic characteristic of the filter.

This and other embodiments may include any of the previously mentioned embodiments.

In general, in one embodiment, a method of positioning a filter within a lumen includes advancing a sheath containing a filter through the lumen, next deploying a portion of the filter from the sheath into the lumen to engage the lumen wall while maintaining substantially all of a material capture structure of the filter within the sheath, and next deploying the material capture structure of the filter from the sheath to a position across the lumen, wherein any of the above steps are performed using an intravascular ultrasound system and the filter is modified to provide at least one echogenic characteristic as in any of the previously mentioned embodiments.

This and other embodiments can include one or more of the following features. In one aspect, the method can further include deploying a crossover structure of the filter into the lumen before or after the deploying the material capture structure of the filter step. This step can be initiated, performed, confirmed or completed at least in part based on information obtained using intravascular ultrasound from one or more echogenic aspects of the filter. In another aspect, the method can further include maneuvering a snare towards the filter in the same direction used during the advancing step and engaging the snare with a filter retrieval feature positioned against a wall of the lumen. This step can be initiated, performed, confirmed or completed at least in part based on information obtained using intravascular ultrasound from one or more echogenic aspects of the filter. In a further aspect, the method can further include maneuvering a snare towards the filter in the opposite direction used during the advancing step; and engaging the snare with a filter retrieval feature positioned against a wall of the lumen. This step can be initiated, performed, confirmed or completed at least in part based on information obtained using intravascular ultrasound from one or more echogenic aspects of the filter. In an alternative aspect, the method can further include deploying a filter retrieval feature from the sheath before the deploying the material capture structure step, wherein this step is initiated, performed, confirmed or completed at least in part based on information obtained using intravascular ultrasound from one or more echogenic aspects of the filter. In yet another aspect, the method can further include deploying a filter retrieval feature from the sheath after the deploying before the deploying a material capture structure step. This step can be initiated, performed, confirmed or completed at least in part based on information obtained using intravascular ultrasound from one or more echogenic aspects of the filter. In still another aspect, the method of the deploying a filter retrieval feature step can further include placing the filter retrieval feature against the lumen wall. This step can be initiated, performed, confirmed or completed at least in part based on information obtained using intravascular ultrasound from one or more echogenic aspects of the filter. In one aspect, deploying a portion of the filter step can further include engaging the lumen wall with a fixation device attached to the filter. This step can be initiated, performed, confirmed or completed at least in part based on information obtained using intravascular ultrasound from one or more echogenic aspects of the filter. In another aspect, deploying a portion of the filter step can further include engaging the lumen wall with a radial force generated by a filter support structure. This step can be initiated, performed, confirmed or completed at least in part based on information obtained using intravascular ultrasound from one or more echogenic aspects of the filter.

In general, in one embodiment, a filter delivery catheter includes a delivery catheter adapted and configured for delivery of an endoluminal filter, an IVUS transducer integrated into the distal portion of the delivery catheter, and one or more connectors on the proximal end of the delivery catheter adapted and configured to connect the IVUS transducer to an appropriate imaging or processing system.

This and other embodiments can include one or more of the following features. In one aspect, the filter delivery catheter can further include a telescoping sleeve moveable relative to the filter delivery catheter. In another aspect, the filter delivery catheter can further include a pusher rod moveable relative to the filter delivery catheter. In a further aspect, the IVUS transducer integrated into the distal portion of the delivery catheter can be adapted and configured whereby advancing and retracting the delivery catheter generates a plurality of images slices from the IVUS transducer. In an alternative aspect, the IVUS transducer integrated into the distal portion of the delivery catheter can be adapted and configured whereby advancing and retracting the delivery catheter can provide an output from the IVUS transducer for positioning guidance of a filter delivered using the delivery catheter. In yet another aspect, the IVUS transducer can be integrated into the distal tip or end of the delivery catheter. In still another aspect, the delivery catheter can further include a pressure transducer. In one aspect, the pressure transducer can be located proximal to the IVUS transducer. In another aspect, the delivery catheter can further include a filter as in any of the previously mentioned embodiments. In a further aspect, a method of positioning a filter within a lumen can include advancing a delivery catheter according to any of the previously mentioned embodiments which can contain a filter as in any of the previously mentioned embodiments through the lumen and can use imaging information provided by the IVUS transducer on the delivery catheter to determine relative position before deploying a portion of the filter from the delivery catheter into the lumen to engage the lumen wall while maintaining substantially all of a material capture structure of the filter within the sheath. In an alternative aspect, the method can further include using imaging information provided by the IVUS transducer on the delivery catheter before deploying the material capture structure of the filter from the delivery catheter to a position across the lumen. In yet another aspect, the method can further include obtaining IVUS imaging of the lumen using the delivery catheter prior to deployment of the filter, after the deployment of the filter or during the deployment of the filter. In still another aspect, the method can further include obtaining IVUS imaging of the lumen using the delivery catheter for imaging a deployment location and estimating the sizing of a filter for the deployment location prior to performing any of the previously mentioned methods. In another aspect, the method can further include estimating treatment during using imaging data collected as in any of the previously mentioned methods. In yet another aspect, a filter can further include an IVUS transducer integrated into the filter.

In general, in one embodiment a system for positioning a filter within the vasculature includes an endoluminal filter; a guidewire having a proximal end, a distal end, and a first pressure sensor located near the distal end of the guidewire; a sheath having a proximal end, a distal end and a lumen, the lumen configured to receive the guidewire, the filter being attached to a distal portion of the sheath; an intravascular ultrasound transducer disposed at the distal end of the sheath; a user interface configured to receive input from an operator regarding a surgical procedure including an insertion site and a destination site for positioning the filter according to the surgical procedure; a display; and a processor.

This and other embodiments can include one or more of the following features. In one aspect, the endoluminal filter comprises a first support member having a first end and a second end and a second support member attached to the first end of the first support member or the second end of the first support member and forming a crossover with the first support member to form two loops one on either side of the crossover, wherein at least a portion of the first support member, the second support member, the first end, the second end or a region adjacent to the cross over or any portion of one of the above is modified to provide an enhanced echogenic characteristic of the endoluminal filter. In another aspect, the processor is programmed to receive input from the user interface regarding the surgical procedure, determine anatomical landmarks between the insertion site and the destination site, process the intravascular ultrasound signal into an image, receive an intravascular ultrasound signal from the intravascular ultrasound transducer, and send the image to the display.

In general, in one embodiment a system for positioning a filter within the vasculature includes a delivery catheter, an IVUS transducer integrated into the distal portion of the delivery catheter, one or more connectors, a user interface configured to receive input from an operator regarding a surgical procedure including an insertion site and a destination site for positioning the filter according to the surgical procedure, a display, and a processor.

BRIEF DESCRIPTION OF THE DRAWINGS

A better understanding of the features and advantages of embodiments of the present invention will be appreciated through reference to the following detailed description that sets forth illustrative embodiments and the accompanying drawings of which:

FIGS. 6A-8D illustrate various aspects of the structural members in a filtering device;

FIGS. 23x1-23x4 illustrate a cylindrical cover or crimp modified to provide enhanced echogenic properties.

FIG. 27Cx1 illustrates an isometric view of a marker band and a ball tip modified for enhanced echogenic characteristics as described herein. FIG. 27CX1a is an enlarged view of the enchogenic enhanced ball tip of FIG. 27CX1. FIG. 27CX1b is an enlarged view of the echogenic enhanced marker band of FIG. 27CX1.

FIG. 27CX2 illustrates an isometric view of a retrieval tail modified for enhanced echogenic characteristics as described herein.

FIG. 38Ax is a variation of FIG. 38A having strands a, b, c, and d of the braided structure with different properties to enhance the echogenic or radio opaque qualities of the braided structure.

FIGS. 30-53D illustrate several alternatives techniques for joining material capture structures to support frames and forming filtering structures;

FIG. 51Bx illustrates a multi-tubular structure similar to those of FIGS. 50, 51A and 51B having echogenic enhanced properties or characteristics.

FIG. 55Ax illustrates an echogenic joint at the intersection of filaments used to enhance the echogenic characteristics of a filter. FIG. 55AX1 is an enlarged view of the echogenic joint in FIG. 55Ax showing a pair of crossing filaments joined using an embodiment of an echogenic joint or joiner described herein.

FIGS. 54A-65F illustrate several alternative filtering structures;

FIGS. 75A-78F illustrate several exemplary methods of using a filtering device;

FIGS. 79-82 illustrate several alternative filtering device configurations adapted for the delivery of pharmacological agents; and FIG. 79x illustrates a biodegradable echogenic coating on a wire support or filament as illustrated and described in FIG. 79.

FIG. 81x illustrates a segmented multi-lumen structure of as in FIG. 81 having an echogenic material or radio-opaque material to fill the holes.

FIG. 83AX illustrates echogenic enhancements of a version of the device of FIG. 83.

FIG. 88X1 is a perspective view of the endoluminal filter of FIG. 88 showing the location of echogenic features coincident with a fixation element. FIG. 88X2 is an enlarged view of an anchor crimp and anchor having an echogenic feature;

FIGS. 96 and 97 illustrate filter devices with fixation elements in use within a lumen with the filtering structure in a upstream (FIG. 96) and downstream (FIG. 97) positions;

FIG. 98 illustrates a fixation element engaged with the side wall of lumen;

FIG. 104C illustrates a double ended fixation element with different tip orientations attached to an elongate body;

FIGS. 105 and 106 illustrate tissue anchor embodiments having an end raised above the support member;

FIG. 107A illustrates a tissue anchor attached to a tube that is attached to a support member;

FIG. 107B illustrates a plurality of the tissue anchors illustrated in FIG. 107A positioned along a pair of support structures;

FIG. 108 illustrates tissue anchors formed in a tube that is placed over an elongate body or other portion of a filtering device;

FIG. 116A illustrates a perspective view of one end of a filtering device where the ends of elongate bodies pass through the securing or attachment feature and are formed into a retrieval feature and a tissue engagement element;

FIG. 116B is a section view through the securing or attachment feature shown in FIG. 116A;

FIGS. 117A and 117B illustrate perspective and bottom up views respectively of one end of a filtering device where the end of one elongate body pass through the securing or attachment feature and is formed into a retrieval feature and a tissue engagement element is formed in a portion of the securing or attachment feature;

FIG. 118 is a perspective view of a separate tissue engagement feature that is joined to a filtering device using the securing or attachment feature;

FIG. 119 illustrates an alternative embodiment of the tissue engagement element of FIG. 98 with the addition of a hollowed tip portion;

FIG. 135 is a view of an exemplary filter illustrating various alternative aspects of providing a filter with improved echogenic characteristics

FIGS. 137A-137D illustrate two embodiments of an intravascular ultrasound catheter joined together in parallel with a catheter.

FIGS. 138A and 138B, the pressure sensor and/or IVUS transducer are integrated into a delivery catheter, a retrieval catheter or a device itself.

DETAILED DESCRIPTION

Figure 1A:
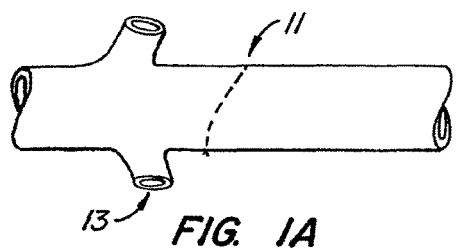
FIGS. 1A-1H illustrate various prior art filters.
Figure 1B:
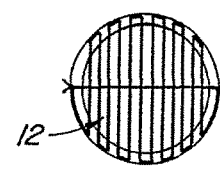
Figure 1C:
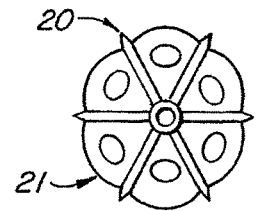
Figure 1D:
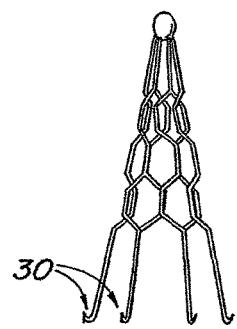
Figure 1E:
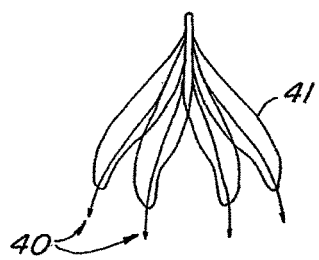
Figure 1F:
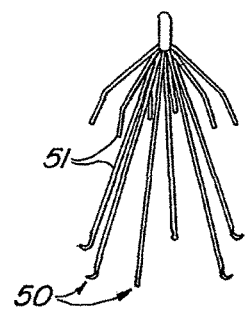
Figure 1G:
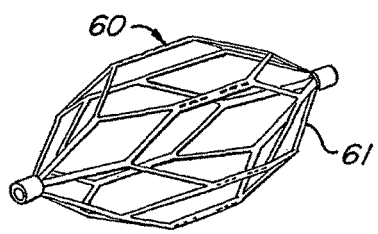
Figure 1H:
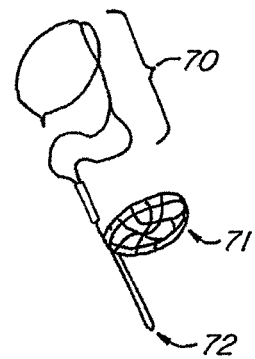

There remains a clinical need for improved endoluminal filter devices and methods. Improved endoluminal filter devices provide effective filtration over a range of lumen sizes and are easy to deploy into and retrieve from a lumen. In addition, improved endoluminal filter devices minimize thrombosis formation or tissue ingrowth on the device and are resistant to migration along the lumen. Embodiments of the filter devices of the present invention provide many and in some cases all of the features of improved endoluminal filters and have a number of uses such but are not limited to: embolic protection, thrombectomy, vessel occlusion, and tethered or untethered distal protection.

Several embodiments of the present invention provide improved filtration devices that are durable, provide effective and nearly constant filter capacity over a range of lumen sizes and are easily delivered and removed from a lumen via either end of the device. Additionally, embodiments of the present invention can be delivered into and retrieved from a lumen using minimally invasive surgical techniques. One aspect of an embodiment of the present invention is the construction of support structure elements using a shape memory material. The shape memory material may have a pre-shaped form that ensures the support elements are uniformly collapsible and, when deployed, provides a predefined range of controllable force against the lumen wall without use of hooks or barbs. Alternatively, hooks barbs, or other fixation elements or devices may be used in conjunction with an embodiment of a filtering device as described below.

The elongate support structure elements are configured to collapse and expand with natural vessel movements while maintaining constant apposition with the vessel wall. One result is that the support structure shape and size track to vessel movements. As a result, the filter density and capacity of embodiments of the present invention remain relatively independent of changes in vessel size. Moreover, the self centering aspect of the support structure ensures the filtration device provides uniform filtration across the vessel diameter. As such, embodiments of the present invention provide generally constant filtration capacity of the device is maintained across the entire vessel lumen and during vessel contractions and expansions.

Uniform filter capacity is a significant improvement over conventional devices. Conventional devices typically have a filter capacity that varies radially across a lumen. The radial variation in filter capacity usually results from the fact that conventional filtration elements have a generally wider spacing at the periphery of the lumen and closer spacing along the central lumen axis. The result is that larger emboli can escape along the lumen periphery. During vessel expansions and contractions, the radial variations in filter capacity are exacerbated in conventional devices.

Another advantage of some embodiments of the present invention is that when released from a constrained state (i.e., within a delivery sheath), the device assumes a pre-determined form with elongate support members that extend along and self center the device in the vessel. These elongate support members exert atraumatic radial force against the vessel wall to prevent or minimize device migration. In some embodiments, radial forces generated by the elongate support members work in cooperation with hooks, barbs or other fixation devices to secure the device within the vessel. Hooks, barbs or other fixation devices or elements may be used as an added precaution against migration of the filtering device while in a lumen. When device retrieval is initiated, the uniformly collapsible form of the elongate support members causes the elongate support members to pull away from the vessel wall as the device is being re-sheathed. The movement of the elongate members away from the vessel wall facilitates the atraumatic removal of the device from the vessel wall. Additionally, in those embodiments having hooks, barbs or other fixation devices or elements, elongate member movement during retrieval also facilitates withdrawal of the fixation elements from the lumen wall.

Additional embodiments of the present invention may include a retrieval feature on one or both ends of the device. The use of retrieval features on both ends of the device allows deployment, repositioning and removal of the device to be accomplished from either end of the device. As a result, the use of retrieval features on both ends of the device enables both antegrade or retrograde approaches to be used with a single device. The retrieval feature may be integral to another structural member or a separate component. In some embodiments, the retrieval feature is collapsible and may have a curved shape or a generally sinusoidal shape. Additional aspects of retrieval features are described below.

General Principals and Construction

Figure 2A:
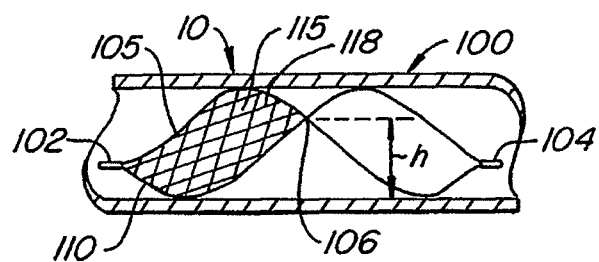
FIGS. 2A-2C illustrate the response of a filtering device to changes in lumen size.

FIG. 2A illustrates an embodiment of a filtering device 100 of the present invention positioned within a lumen 10. The lumen 10 is cut away to show the position of filter 100 deployed into within a lumen and in contact with the lumen wall. The filter 100 includes a first elongate member 105 and a second elongate member 110. The elongate members are joined to form ends 102, 104. The elongate members cross but are not joined to one another at crossover 106. In one embodiment, the elongate members have first and second sections. First sections extend between the end 102 and the crossover 106 and the second sections extend from the crossover 106 to the second end 104. While some embodiments contact the lumen in different ways, the illustrated embodiment has the ends 102, 104 against one side of the lumen interior wall while the crossover 106 contacts the other side of the lumen interior wall with the elongate bodies in constant or nearly constant apposition along the lumen interior wall between the ends 102, 104.

Material (i.e., thrombus, plaque and the like) flowing through the lumen 10 of a size larger than the filtering size of the material capture structure 115 is captured between or cut down by the filaments 118. In the illustrated embodiment of FIG. 2A, the material capture structure 115 is supported by a rounded frame formed by the elongate members 105, 110 formed between the end 102 and the crossover 106. Another rounded frame formed between the crossover 106 and the second end 104 and could also be used to support a material capture structure of the same or different construction and filter capacity of the a material capture structure 115. As such, a material removal structure supported by one rounded frame may be configured to remove material of a first size and the material removal structure supported a the other rounded frame may be configured to remove material of a second size. In one embodiment, the material removal structure in the upstream rounded frame removes larger size debris than material removal structure in the downstream rounded frame. Also illustrated in FIGS. 2A-2C is how the filter cells 119 that make up the material capture structure is 115 maintain their size and shape relatively independent of movement of the first and second structural members 105, 110 over a physiological range of vessel diameters.

Figure 2B:
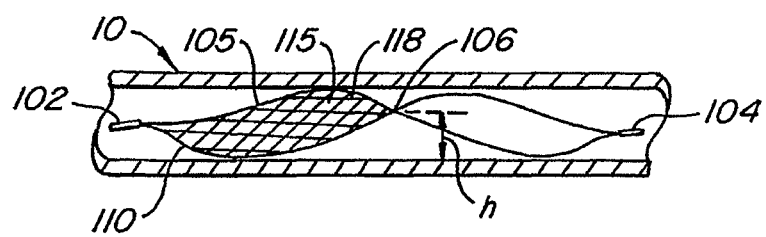
Figure 2C:
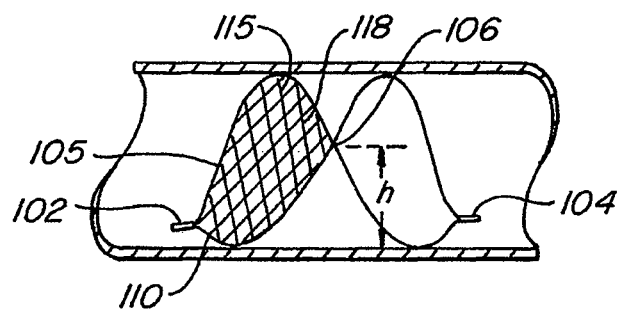

FIGS. 2B and 2C illustrate how the elongate support structure elements of embodiments of the present invention are configured to collapse and expand with natural vessel movements while maintaining constant apposition with the vessel wall. FIGS. 2A, 2B and 2C also illustrate how devices according to embodiments of the present invention are both radially and axially elastic. In response to vessel size changes, ends 102, 104 move out as the vessel size decreases (FIG. 2B) and then move in as the vessel size increases (FIG. 2C). In addition, the device height "h" (measured from the lumen wall in contact with ends 102, 104 to crossover) also changes. Device height "h" changes in direct relation to changes in vessel diameter (i.e., vessel diameter increases will increase device height "h"). As such, device height ("h") in FIG. 2C is greater than device height ("h") in FIG. 2A which is in turn greater than the device height ("h") in FIG. 2B.

FIGS. 2A, 2B and 2C also illustrate how a single sized device can be used to accommodate three different lumen diameters. FIG. 2C illustrates a large lumen, FIG. 2A a medium sized lumen and FIG. 2B a small sized lumen. As these figures make clear, one device can adapt to cover a range of vessel sizes. It is believed that only 3 device sizes are needed to cover the range of human vena cava interior diameters that range from approximately 12-30 mm with an average interior diameter of 20 mm. Also illustrated is the static or nearly static filter capacity of the material capture structure 115. In each different vessel size, the material capture structure 115, the filaments 118 and filter cell 119 maintain the same or nearly the same shape and orientation within the support frame formed by the elongate bodies. These figures also illustrate the dynamic shape changing aspect of the device that may also be used to accommodate and conform to vessel irregularities, tortuosity, flares and tapers and while remaining in apposition to the wall. Because each elongate body may move with a high degree of independence with respect to the other, the loops or support frames formed by the elongate bodies can also independently match the shape/diameter of the lumen section in which it is placed.

Figure 3:
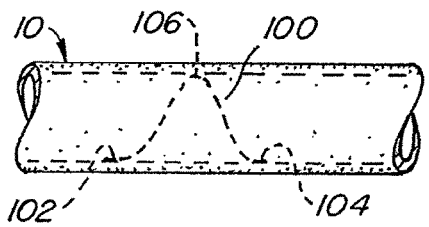
FIGS. 3-5 illustrate the interaction of a structural member with a lumen wall.
Figure 3A:
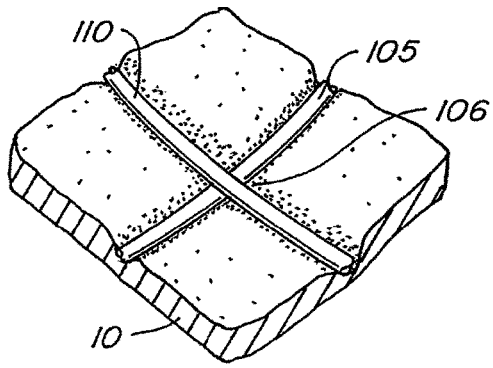
Figure 3B:
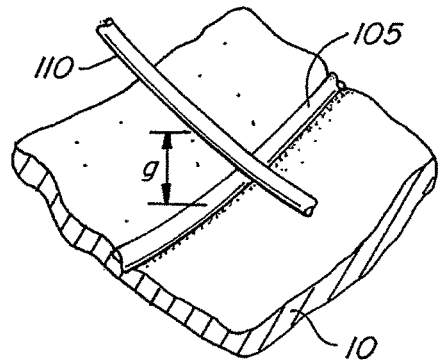

FIGS. 3, 3A and 3B illustrate the device 100 deployed into the lumen 10. As illustrated in FIG. 3, the device 100 is oriented in the lumen with the ends 102, 104 along one side of the interior vessel wall with the crossover 106 on the opposite side. FIG. 3 illustrates an embodiment of a device of the present invention that is shaped to fit within the lumen 10 without distending the lumen. In FIG. 3A the elongate bodies 105, 110 are in contact but are not joined at crossover 106. In FIG. 3B the elongate bodies 105, 110 cross one another at crossover 106 but are separated (i.e., by a gap "g").

Figure 4:
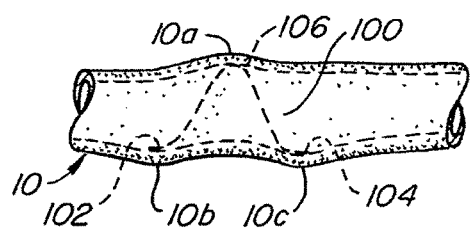
Figure 5:
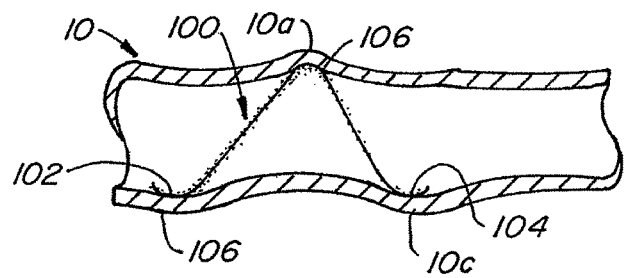

FIGS. 4 and 5 illustrate how aspects of the device design can be modified to increase the radial force applied against the interior wall of lumen 10. Devices having increased fixation force may be useful for some applications, such as vessel occlusion or for distal protection when a large amount of debris is expected. If a device is not intended to be retrieved (i.e., permanently installed into a lumen) then high radial force design devices may be used to ensure the device remains in place and distention may be used to trigger a systemic response (i.e., a tissue growth response) in the lumen to ensure device ingrowth and incorporation with the lumen interior wall.

Filter device embodiments of the present invention having low or atraumatic radial force are particularly useful in retrievable devices. As used herein, atraumatic radial force refer to radial forces produced by a filtering device embodiment that meets one or more of the following: radial forces high enough to hold the device in place with little or no migration and without damaging or overly distending the lumen interior wall; radial forces high enough to hold the device in place but while triggering little or no systemic response for the vessel wall; or forces generated by device operation that trigger reduced systemic response or a systemic response below that of a conventional filter.

In contrast to the device sized in FIG. 3 to minimize vessel distention, FIG. 4 illustrates a device 100 configured to exert greater radial force to a degree to cause lumen wall to distend. FIGS. 4 and 5 illustrate lumen wall distention by the end 102 (distention 10b), by the crossover 106 (distention 10a), and by the end 104 (distention 10c). Although not shown in these figures, the elongate bodies would likely distend the lumen along their length as well.

The radial force of a device may be increased using a number of design factors. Radial force may be increased by increasing the rigidity of the elongate body by, for example, using an elongate body with a larger diameter. Radial force may also be increased when forming the shapes of the elongate bodies (i.e., during the heat treat/set processes for Nitinol devices and the like), as well as in the material composition and configuration.

Figure 6A:
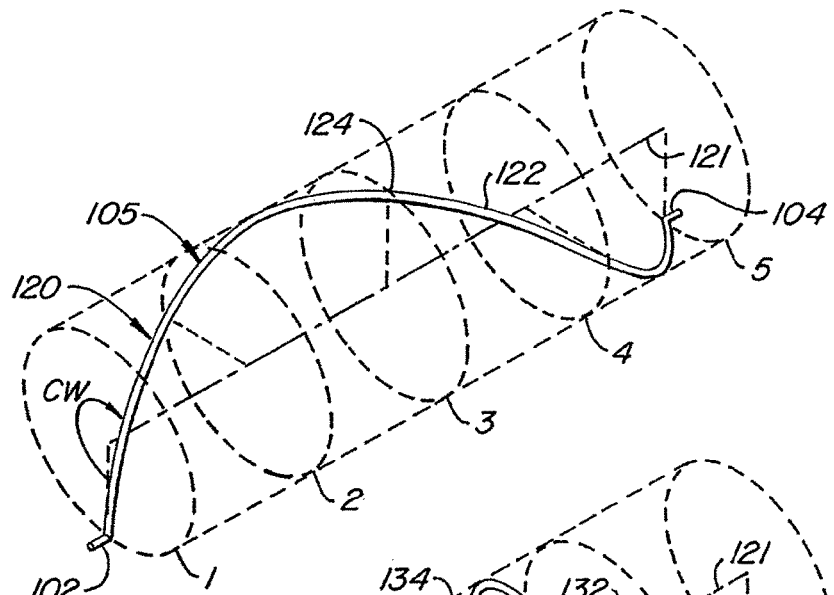
Figure 6B:
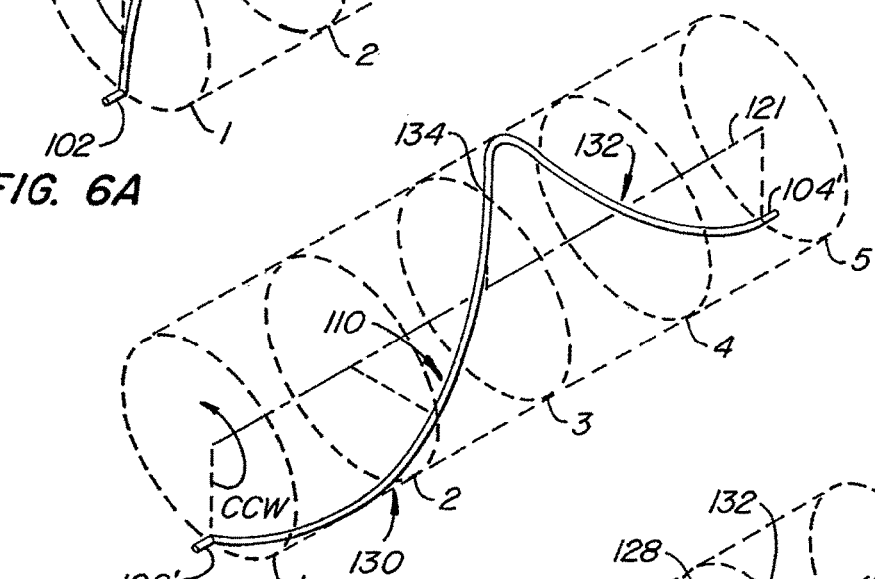
Figure 6C:
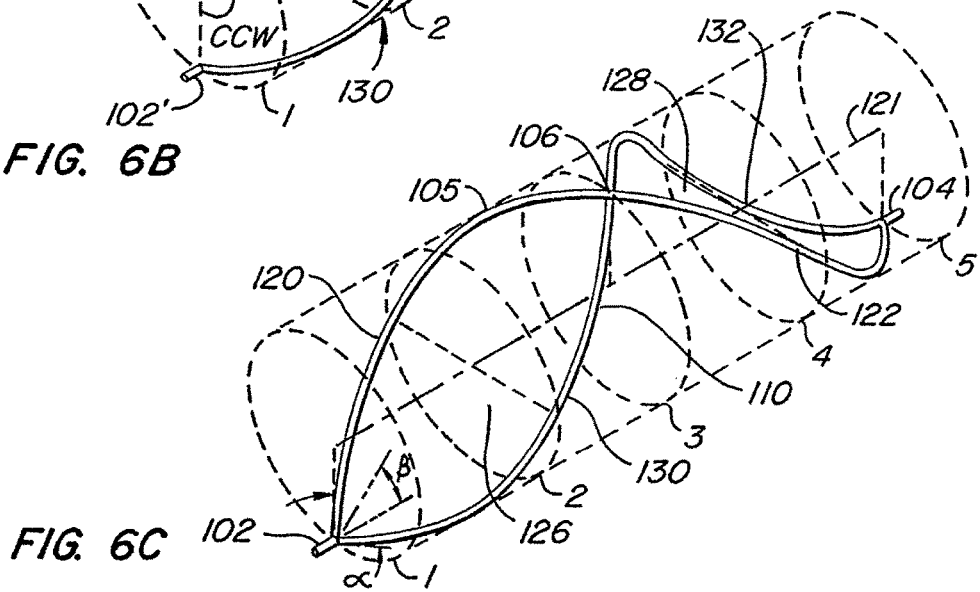

Additional details of an embodiment of the support members 105, 110 may be appreciated with reference to FIGS. 6A, 6B and 6C. FIGS. 6A, 6B illustrate the support members separately and then assembled together (FIG. 6C) about device axis 121. In general, the device axis 121 is the same as the axis along the central of a lumen into which the device is deployed. For purposes of illustration, the support members 105, 110 will be described with reference to a sectioned lumen shown in phantom having a generally cylindrical shape. The support members may also be thought of as deployed within and/or extending along the surface of an imaginary cylinder.

In the illustrative embodiments of FIGS. 6A, 6B and 6C, the support members 105, 110 are shown in an expanded, pre-defined shape. In one embodiment, the support members are formed from MRI compatible materials. The support members contain no sharp bends or angles to produce stress risers that may lead to fatigue issues, vessel erosion, and facilitate device collapse. In some embodiments, each elongate member is conventionally formed by constraining a shape memory material such as a shape memory metal alloy or shape memory polymer on a cylindrical shaping mandrel that contains pins to constrain the material into the desired shape. Thereafter, the material can be subjected to a suitable conventional heat treatment process to set the shape. One or more planes of symmetry (i.e., FIG. 15) may be provided, for example, by forming both elongate members on a single mandrel and at the same time. Other conventional processing techniques may also be used to produce symmetrical filtering device embodiments. Additionally, retrieval features described herein (if present) may be directly formed on the wire ends during support member processing. In addition, multiple devices, in a series on a long mandrel, can be made using these methods.

Examples of suitable shape memory alloy materials include, for example, copper-zinc-aluminium, copper-aluminum-nickel, and nickel-titanium (NiTi or Nitinol) alloys. Nitinol support structures have been used to construct a number of working prototypes of filter devices of the present invention as well as for use in ongoing animal studies and human implants. Shape memory polymers may also be used to form components of the filter device embodiments of the present invention. In general, one component, oligo(e-caprolactone)dimethacrylate, furnishes the crystallizable "switching" segment that determines both the temporary and permanent shape of the polymer. By varying the amount of the comonomer, n-butyl acrylate, in the polymer network, the cross-link density can be adjusted. In this way, the mechanical strength and transition temperature of the polymers can be tailored over a wide range. Additional details of shape memory polymers are described in U.S. Pat. No. 6,388,043 which is incorporated herein by reference in its entirety. In addition, shape memory polymers could be designed to degrade. Biodegradable shape memory polymers are described in U.S. Pat. No. 6,160,084 which is incorporated herein by reference in its entirety.

It is believed that biodegradable polymers may also be suited to form components of the filter device embodiments of the present invention. For example, polylactide (PLA), a biodegradable polymer, has been used in a number of medical device applications including, for example, tissue screws, tacks, and suture anchors, as well as systems for meniscus and cartilage repair. A range of synthetic biodegradable polymers are available, including, for example, polylactide (PLA), polyglycolide (PGA), poly(lactide-co-glycolide) (PLGA), poly(e-caprolactone), polydioxanone, polyanhydride, trimethylene carbonate, poly(ß-hydroxybutyrate), poly(g-ethyl glutamate), poly(DTH iminocarbonate), poly(bisphenol A iminocarbonate), poly(ortho ester), polycyanoacrylate, and polyphosphazene. Additionally, a number of biodegradable polymers derived from natural sources are available such as modified polysaccharides (cellulose, chitin, dextran) or modified proteins (fibrin, casein). The most widely compounds in commercial applications include PGA and PLA, followed by PLGA, poly(e-caprolactone), polydioxanone, trimethylene carbonate, and polyanhydride.

While described as forming the support structures, it is to be appreciated that other portions of the filter device may also be formed from shape memory alloys, shape memory polymers or biodegradable polymers. Other filter device components that may also be formed from shape memory alloys, shape memory polymers or biodegradable polymers include, for example, all or a portion of a retrieval feature, a material capture structure or an attachment between a material capture structure and a support structure. Additionally or alternatively, the devices described herein may have all or a portion of their components formed from medical grade stainless steel.

FIG. 6A illustrates the first support member 105 extending from an end 102 to an end 104 along in a clockwise manner about the lumen interior wall (sectioned phantom lines) and the device axis 121. The support member 105 extends from the end 102 in section 1 at the 6 o'clock position, up to the 9 o'clock position in section 2, the 12 o'clock position in section 3, the 3 o'clock position in section 4 to the end 104 at the 6 o'clock position in section 5. The support member 105 has two sections 120, 122 on either side of an inflection point 124. The inflection point 124 is positioned at about the 12 o'clock position in section 3. The radius of curvature of the sections 120, 122 may be the same or different. The cross section shape of the support member 105 is generally circular but may have one or more different cross section shapes in alternative embodiments.

FIG. 6B illustrates the second support member 105 extending from an end 102' to an end 104' along in a counter-clockwise manner about the lumen interior wall (sectioned phantom lines) and the device axis 121. The support member 110 extends from the end 102' in section 1 at the 6 o'clock position, up to the 3 o'clock position in section 2, the 12 o'clock position in section 3, 9 o'clock position in section 4 to the end 104' at the 6 o'clock position in section 5. The support member 110 has two sections 130, 132 on either side of an inflection point 134. The inflection point 134 is positioned at about the 12 o'clock position in section 3. The radius of curvature of the sections 120, 122 may be the same or different. The cross section shape of the support member 105 is generally circular but may have one or more different cross section shapes in alternative embodiments.

Figure 7A:
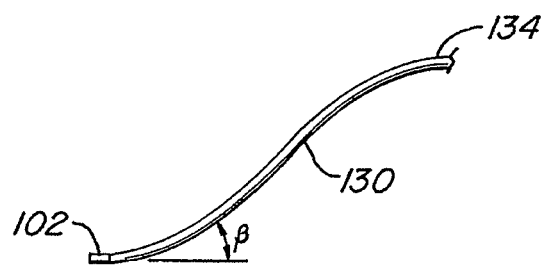
Figure 7B:
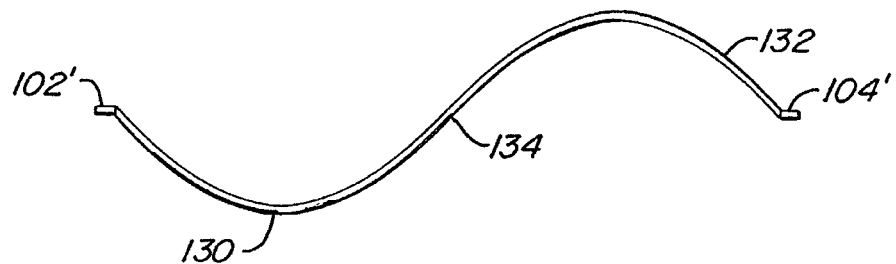
Figure 7C:
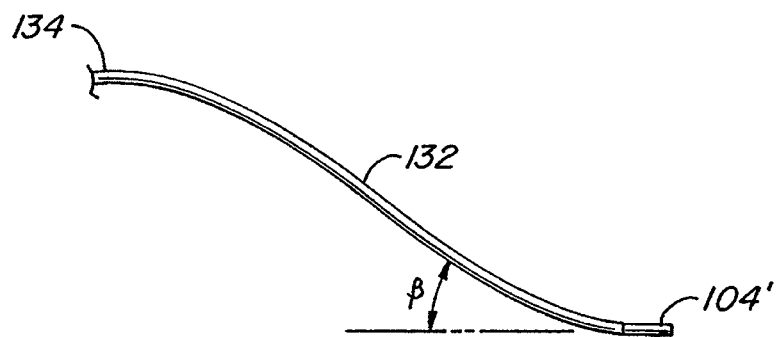

FIG. 6C illustrates the crossover 106 and first and second support members 105, 110 joined together at the ends. The first sections 120, 130 form a rounded frame 126. The angle β is formed by a portion of the lumen wall contacting end 102 and a plane containing the frame 126 and is referred to as the take off angle for the elongate members at end 102. In one alternative, the angle β is formed by a portion of the lumen wall contacting end 102 and a plane containing all or a portion of one or both sections 120, 130. In yet another alternative, the angle β is formed by a portion of the lumen wall contacting end 102 and a plane containing all or a portion of end 102 and all or a portion of the crossover 106. Another angle β is formed on end 104 as discussed above but in the context of end 104, a portion of the lumen wall contacting end 104, sections 122, 132 and the rounded frame 128 as illustrated in FIGS. 7A-7C. An angle formed by the support frames 126, 128 ranges generally between 20 degrees to 160 degrees in some embodiments and generally between 45 degrees to 120 degrees in some other embodiments.

FIG. 7A is a side view of section 130 in FIG. 6B, FIG. 7B is a top down view of FIG. 6B and FIG. 7C is side view of section 132 in FIG. 6B. The angle β ranges generally between 20 degrees to 160 degrees in some embodiments and generally between 45 degrees to 120 degrees in some other embodiments. The angle α is formed by a portion of section 120, a portion of section 130 and the end 102. Alternatively, the angle α is formed by the end 102 and tangents formed with a portion of the sections 120, 130. Another angle α is formed on end 104 as discussed above but in the context of end 104, a portion of the lumen wall contacting end 104 and sections 122, 132. The angle α ranges generally between 40 degrees to 170 degrees in some embodiments and generally between 70 degrees to 140 degrees in some other embodiments.

FIG. 7D illustrates a top down view of FIG. 6C. The angle σ is defined as the angle between a portion of section 120 between the inflection point 124 and the end 102 on one side and a portion of section 130 between the inflection point 134 and the end 102' on the other side. The angle σ is also defined as the angle between a portion of section 122 between the inflection point 124 and the end 104 on one side and a portion of section 132 between the inflection point 134 and the end 104' on the other side. The angle σ defined by sections 120, 130 may be the same, larger, or smaller than the angle σ formed by the sections 122, 132. The angle σ ranges generally between 10 degrees to 180 degrees in some embodiments and generally between 45 degrees to 160 degrees in some other embodiments.

FIG. 7D illustrates an end view of FIG. 6C taken from end 102. The angle θ is defined as the angle between a plane tangent to a portion of section 120 and a plane containing the end 102 that is also generally parallel to the device axis 121. An angle θ may also be defined as the angle between a plane tangent to a portion of section 130 and a plane containing the end 102 that is also generally parallel to the device axis 121. The angle θ defined by section 120 may be the same, larger, or smaller than the angle θ formed by the section 130. Similarly, an angle θ may be defined as discussed above and using as the angle between a plane tangent to a portion of section 122 or 132 and a plane containing the end 102 that is also generally parallel to the device axis 121. The angle θ ranges generally between 5 degrees to 70 degrees in some embodiments and generally between 20 degrees to 55 degrees in some other embodiments.

FIGS. 7F and 7G are perspective views of an alternative embodiment of the device illustrated in FIG. 6C. In the embodiment illustrated in FIGS. 7F and 7G, the support member 110 crosses underneath and does not contact the support member 105 at the crossover 106. The gap "g" between the support members is also illustrated in the FIG. 7G.

FIG. 8A illustrates the elongate body 105 with a generally circular cross section. However, many other cross section shapes are possible and may be used such as, for example, rectangular elongate body 105a (FIG. 8B), rectangular elongate body with rounded edges (not shown), oval elongate body 105b (FIG. 8C) and circular elongate body with a flattened edge 105c (FIG. 8D). In some embodiments, an elongate body will have the same cross section along its length. In other embodiments, an elongate body will have different cross sections along its length. In another embodiment, an elongate body has a number of segments and each segment has a cross section shape. The segment cross section shapes may be the same or different. The cross section shape of the elongate member is a factor used to obtain the desired radial force along the elongate member. The material used to form the elongate body (i.e., a biocompatible metal alloy such as Nitinol) may be drawn to have a desired cross section shape, or drawn in one cross section shape and then treated using conventional techniques such as grinding, laser cutting and the like to obtain the cross section shape were desired.

Figure 9A:
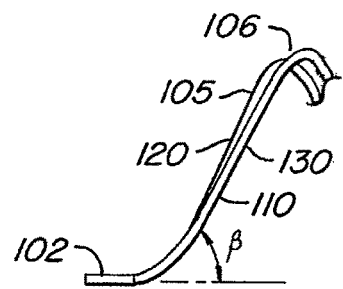
FIGS. 9A and 9B illustrate various aspects of a generally planer support frame.
Figure 9B:
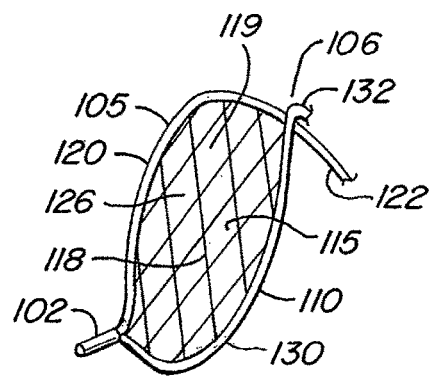

FIGS. 9A, 9B illustrate an embodiment of a material capture structure 115 extended across a generally planar, rounded frame 126 formed by the support members. FIG. 9A is a slight perspective view of a side view of the device. In this embodiment, sections 120, 130 of the support members lie mostly within in a single plane (i.e., in a side view of FIG. 9A section 110 is visible and blocks view of section 120) that also holds the rounded frame 126. FIG. 9B is a perspective view showing the material capture structure 115 extended between and attached to rounded frame 126. In this embodiment, the capture structure 115 extends across and is attached to the first sections 120, 130. In this embodiment, the material capture structure is a plurality of generally rectangular filter cells 119 formed by intersecting filaments 118. Other types of filter structures are described in greater detail below and may also be supported by the support frames formed by the structural members. In some embodiments such as FIGS. 9A and 9B, the angle β may also define the angle between the device axis and a plane containing a material capture structure.

Figure 10A:
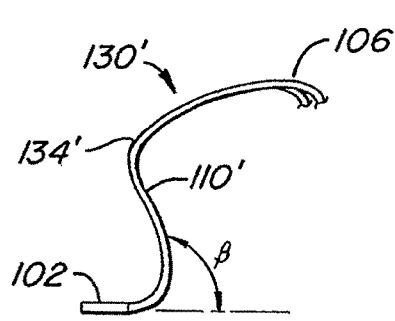
FIGS. 10A and 10B illustrate various aspects of a non-planer support frame.
Figure 10B:
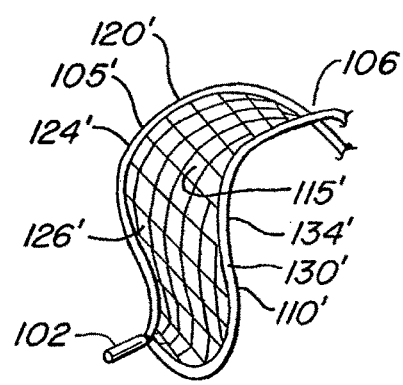

The support frame 126 and the material capture structure 115 is not limited to planar configurations. Non-planar and compound configurations, for example, are also possible as illustrated in FIGS. 10A and 10B. FIG. 10A is a side view of a non-planar structural support 110' having another inflection point 134' between the inflection point 134 and the end 102. The structural support 110' has more than one different radius of curvature between the end 102 and the crossover 106. In some embodiments, there could be more than one radius of curvature between the end 102 and the inflection point 134' as well as be more than one radius of curvature between the inflection point 134' and the inflection point 134. As a result, section 130' is a section possibly having different shapes, a number of different curvatures and at least one inflection point. As seen in FIG. 10B, the support structure 105' is also non-planar with more than one different radius of curvature between the end 102 and the inflection point 124. In some embodiments, there could be more than one radius of curvature between the end 102 and the inflection point 124' as well as be more than one radius of curvature between the inflection point 124' and the inflection point 124. As a result, section 120' is a section having different shapes, a number of different curvatures and one or more inflection points. Similar non-planar configurations may be used on end 104. The material capture structure 115' is adapted to conform to the shape of non-planar frame 126' to produce a non-planar filter support structure.

Figure 11:
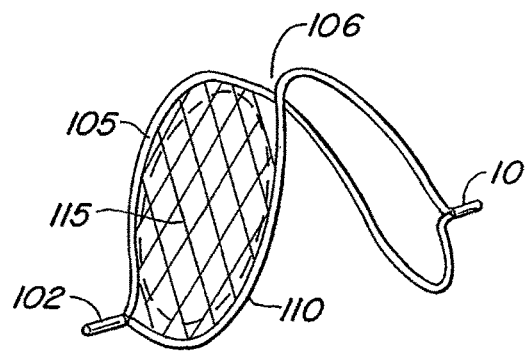
FIGS. 11-13C illustrate various aspects of and configurations for material capture structures.
Figure 12A:
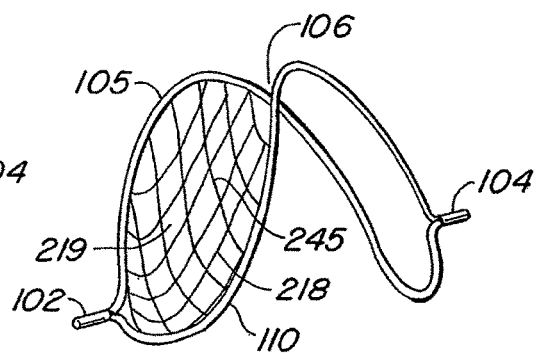
Figure 12B:
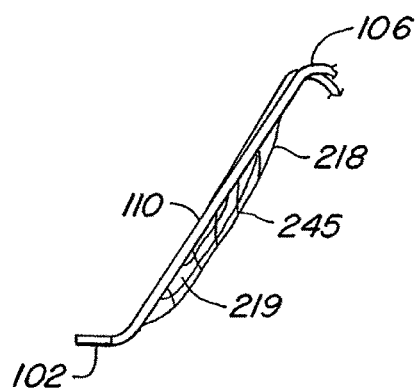

FIG. 11 illustrates a material capture structure 115 that remains in a generally planar arrangement between opposing portions of the support members 105, 110. In addition to FIG. 10B above, other alternative non-planar capture structures are possible even if the support frame is generally planar. FIG. 12A is a perspective view of a non-planar capture structure 245 within a generally planar support frame formed by support members 105, 110. Capture structure 245 is formed by intersecting strands, fibers, filaments or other suitable elongate material 218 to form filter cells 219. The capture structure 245 is slightly larger than the support frame dimensions resulting in a filter structure that is deformed out of the plane formed by the support structure as illustrated in FIG. 12B.

Figure 13A:
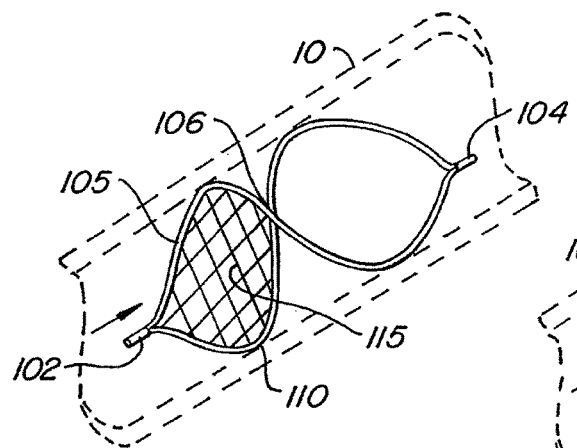
Figure 13B:
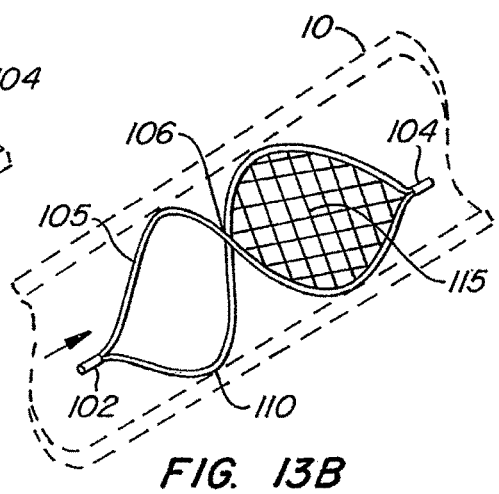
Figure 13C:
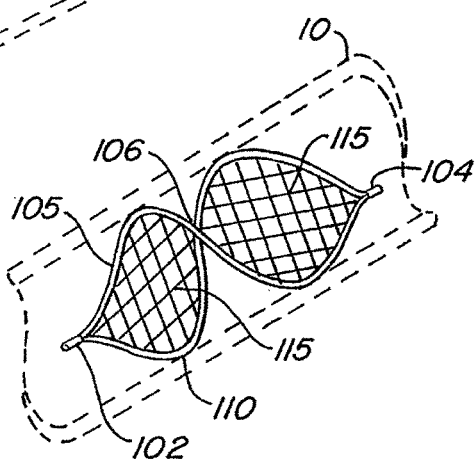

The material capture structure 115 may be in any of a number of different positions and orientations. FIG. 13A illustrates an embodiment of a filter of the present invention having two open loop support frames formed by support members 105, 110. Flow within the lumen 10 is indicated by the arrow. In this embodiment, the material capture structure 115 is placed in the upstream open loop support structure. In contrast, the material capture structure may be positioned in the downstream open loop support structure (FIG. 13B). In another alternative configuration, both the upstream and the downstream support frames contain material capture structures 115. FIG. 13C also illustrates an embodiment where a material capture structure is placed in every support loop in the device.

Figure 14:
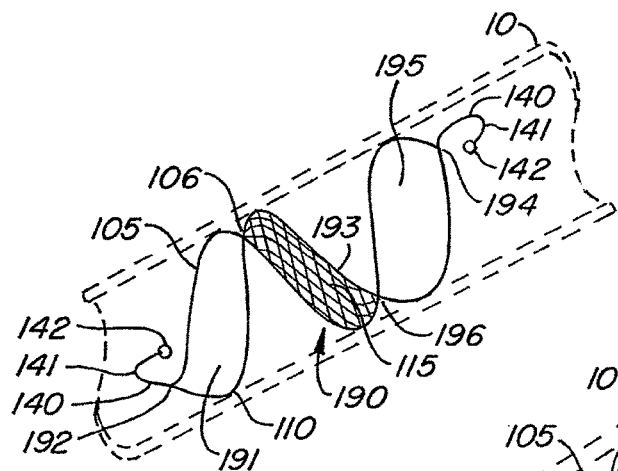
FIGS. 14-14C illustrate various aspects of a filtering device having three support frames.

There are filter device embodiments having equal numbers of support frames with capture structures as support frames without capture structures (e.g., FIGS. 13A and 13B). There are other embodiments having more support frames without capture structures than there are support frames with capture structures. FIG. 14 illustrates a filter embodiment 190 having more support frames without capture structures than support frames with captures structures. The filter device 190 has two support members 105, 110 that are positioned adjacent to one another to form a plurality of support frames that are presented to the flow within the lumen 10. Alternatively, the plurality of support frames positioned to support a material capture structure across the flow axis of the device 190 or the lumen 10. The support members are joined together at end 192 and have two inflection points before being joined at end 194. The support members 105, 110 cross over one another at crossovers 106 and 196. The support frame 191 is between end 192 and crossover 106. The support frame 193 is between the crossovers 106, 196. The support frame 195 is between the cross over 196 and the end 194.

In addition, the filter device 190 has a retrieval feature 140 on each end. The retrieval feature 140 has a curved section 141 ending with an atraumatic tip or ball 142. The retrieval feature 140 rises up above the lumen wall placing the ball 142 and all or a portion of the curved section 141 into the lumen flow path to simplify the process of snaring the device 190 for retrieval or repositioning. Having a retrieval feature on each end of the device allows the device 190 to be recovered from the upstream or downstream approach to the device in the lumen 10. Various aspects of retrieval feature embodiments of the present invention are described in greater detail below.

Figure 14A:
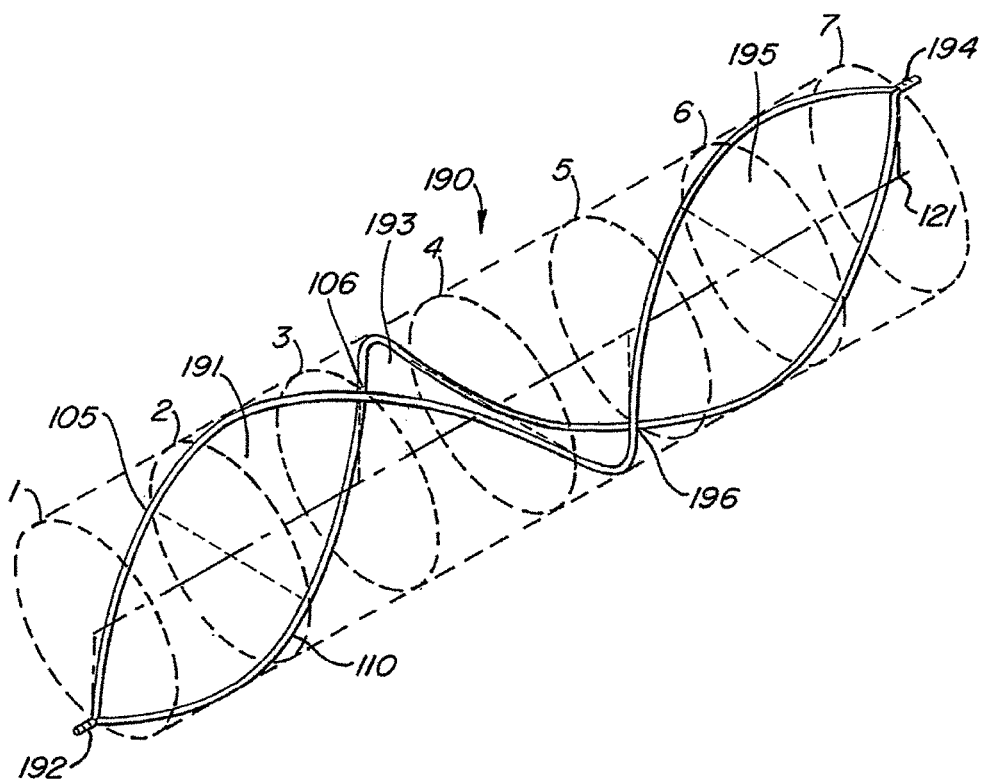
Figure 14B:
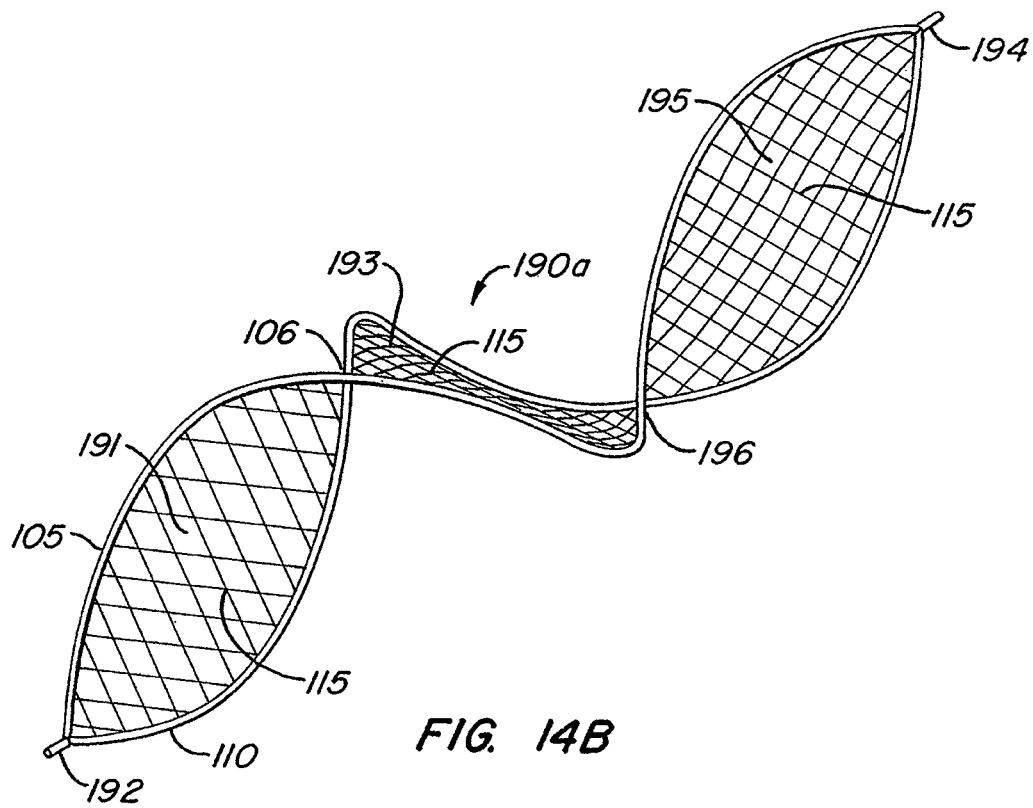

FIG. 14A illustrates the filter 190 imposed on a phantom cylinder having 7 sections. The retrieval features 140 have been omitted for clarity. The first support member 105 extends clock wise from end 192 about and along the axis of the device 121. The first support member 105 crosses section 2 at the 9 o'clock position, section 3 and the crossover 106 at the 12 o'clock position, section 4 at the 3 o'clock position, section 5 and the crossover 196 at the 6 o'clock position, section 6 at the 9 o'clock position and section 7 and the end 194 at the 12 o'clock position. The second support member 110 crosses section 2 at the 3 o'clock position, section 3 and the crossover 106 at the 12 o'clock position, section 4 at the 9 o'clock position, section 5 and the crossover 196 at the 6 o'clock position, section 6 at the 3 o'clock position and section 7 and the end 194 at the 12 o'clock position. FIG. 14B illustrates an alternative device embodiment 190a that is similar to the device 190 except that all support frames formed by the elongate members is used to support a material capture structure. In the illustrated embodiment, frames 191, 193 and 195 each support at material capture structure 115.

Figure 14C:
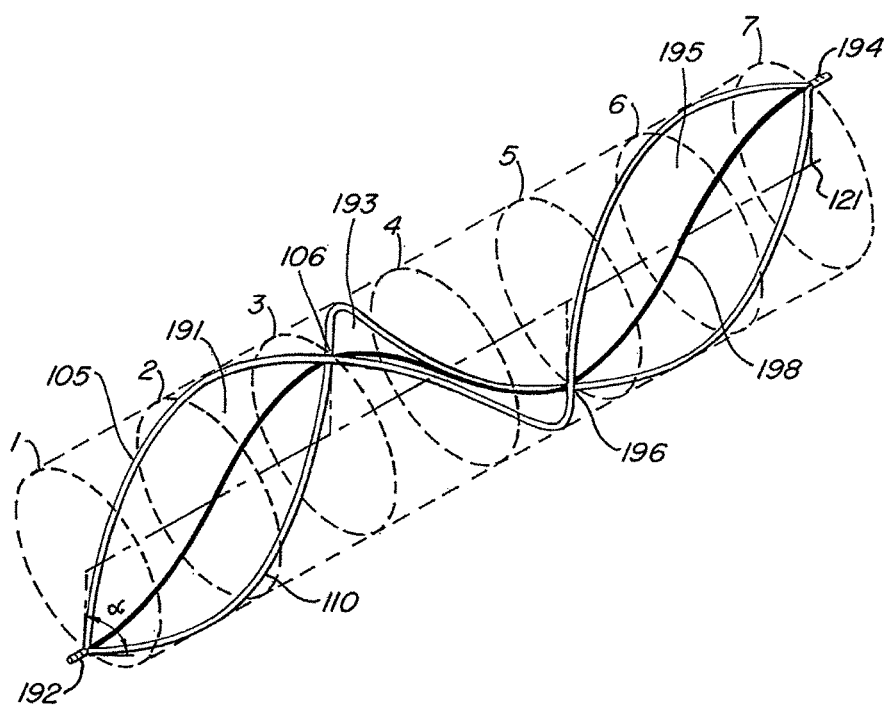

FIG. 14C illustrates an alternative configuration of filter 190. The filter device 190b is similar to device 190 and 190a and includes an additional support member 198 extending along the support member 105. In one embodiment, the additional support member 198 extends along the device axis 121, is positioned between the first and the second support members 105, 110 and is attached to the first end 192 and the second end 194. In the illustrative embodiment, the third support member 198 begins at end 192 and the 6 o'clock position in section 1, crosses section 3 and the crossover 106 at the 12 o'clock position, crosses section 5 and the crossover 196 at the 6 o'clock position, and ends at the 12 o'clock position in section 7 at the end 194.

Figure 15:
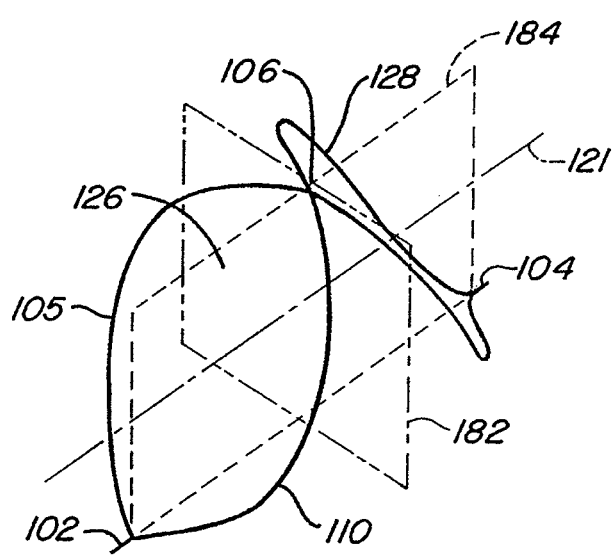
FIG. 15 illustrates planes of symmetry for filtering devices.

FIG. 15 illustrates the planes of symmetry found in some filter device embodiments of the present invention. The filtering structure that would be supported by one or both of the support frames is omitted for clarity. In one aspect, FIG. 15 illustrates an embodiment of an endoluminal filter of the present invention having a support structure that is generally symmetrical about a plane 182 that is orthogonal to the flow direction of the filter or filter axis 121 and contains a crossover point 106 between two structural elements of the support structure 105, 110. In another aspect, FIG. 15 illustrates an embodiment of an endoluminal filter of the present invention having a support structure that is generally symmetrical about a plane 184 that is parallel to the flow direction of the filter (i.e., axis 121) and contains both ends of the support structure 102, 104. It is to be appreciated that some filter device embodiments of the present invention may have either or both of the above described symmetrical attributes. It is to be appreciated that the above described symmetrical attributes are also applicable to the construction of embodiments of the material capture structures alone or as installed in a filter.

Figure 16A:
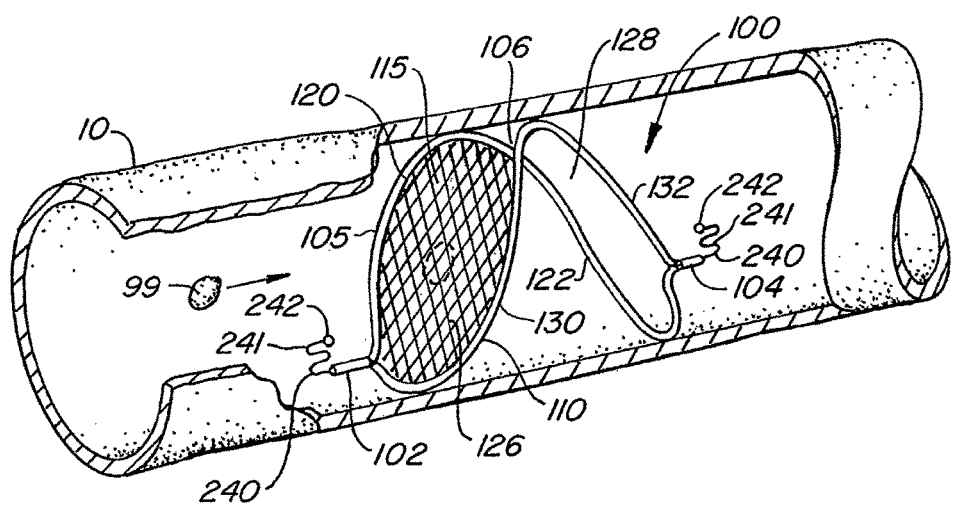
FIGS. 16A and 16B illustrate the response of a filtering device when contacted by debris flowing in a lumen.
Figure 16B:
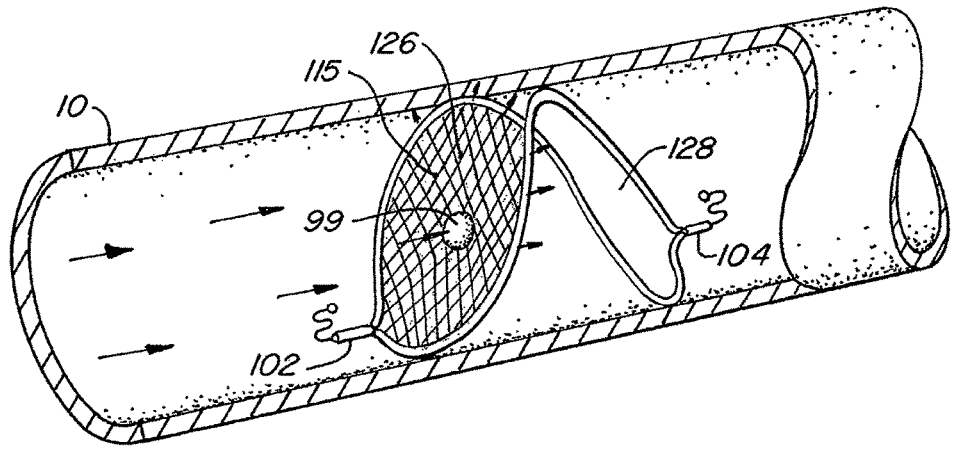

FIGS. 16A and 16B illustrate the response of a filter device 200 in response to a piece of clot material 99 contacting the material capture structure 115. The direction of flow and movement of the clot material 99 within lumen 10 is indicated by the arrows. The filter device 200 is similar to the embodiments described above with regard to FIGS. 6A-7G with the addition of the retrieval features 240 added to the ends 102, 104. The retrieval feature 240 has a curved section with multiple curves 141 that terminate with an atraumatic end 242. The multiple curves 141 are advantageously configured to collapse about a retrieval device (i.e., a snare in FIGS. 71A, 71B) to facilitate device 100 capture during retrieval. In this illustrative embodiment the multiple curves are generally shaped like a sinusoid and the end 242 is shaped like a ball or a rounded tip.

It is believed that upon embolic entrapment, the force fluid flow acting on clot material 99 is transmitted from the capture structure 115 to support frame 126 securing the capture structure 115. The force acting on the support frame 126 and in turn the support members 105, 110 urges the end 104 into the lumen wall. This action effectively fixes the second support frame 128. The force acting on the support frame 126 causes the angle β associated with the support frame 126 to increase the support frame 126 wedges further into the lumen wall.

Figure 17:
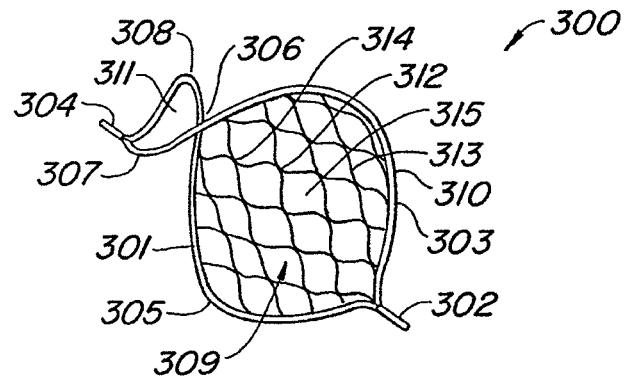
FIGS. 17-19 illustrate alternative filtering device aspects having different sized support frames and structural member lengths.
Figure 18:
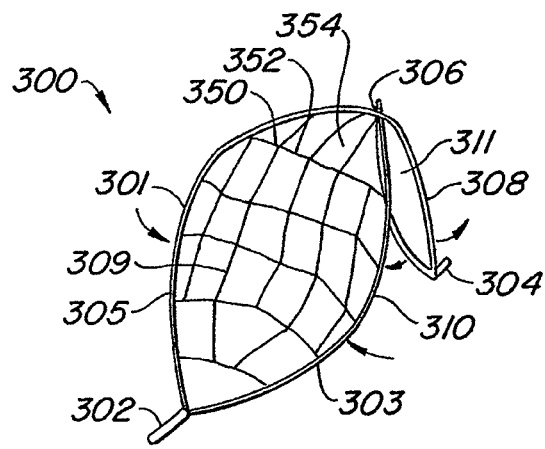
Figure 19:
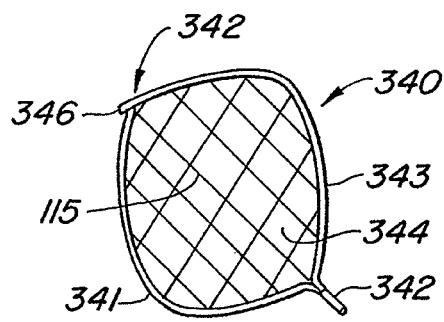

FIGS. 17, 18, and 19 illustrate various alternative filter device embodiments with support structures of different size and that may not be in contact with the lumen wall. FIG. 17 illustrates a perspective view of a filter device 300 according to one embodiment of the present invention. In this embodiment, elongate members 305, 310 are joined at ends 302, 304, to form frame 309 from end 302, sections 301, 303 and crossover 306 and frame 311 from end 304, sections 307, 308 and cross over 306. The frame 309 supports another embodiment of a material capture according to the present invention. The illustrated material capture structure 312 includes a plurality of strands 313 joined 314 to form a plurality of filter cells 315. The strands 313 may be joined using processes described below (e.g., FIG. 53A-53D) or may be formed by extruding the desired shape and size filter cell 315 from a material (e.g., FIG. 56).

FIG. 17 illustrates a so-called capacitor design because the elongate members that form frame 311 are configured to expand and contract the size and shape of frame 311 in response to changes in frame 309. This design feature allows an embodiment of the present invention to accommodate a large range of sizing and diameter changes. FIG. 18 illustrates an embodiment of the filter device 300 having a capture structure 350 having filter cells 354 formed by intersecting strands 352. FIG. 18 illustrates how inward movement of the frame 309 (indicated by the arrows) is corresponds to outward movement (indicated by the arrows) in the frame 308.

FIG. 19 illustrates an alternative filter device embodiment where the second frame is not closed. The filter device 340 includes support members 341, 343 that form a rounded support frame 344 to support the material capture device 115. The support members 341, 343 extend some distance beyond the cross over 342 but are not joined to form another end. A portion 346 of the support member 343 is shown extending beyond the cross over 342. The support members 341, 343 may extend for some distance along the device axis after the cross over 342 and may follow the same or a different shape as the shape of the support members in frame 309. The support members may extend along the device axis similar to earlier described two loop embodiments but stop short of being joined at a second end (e.g., FIG. 87).

Figure 20:
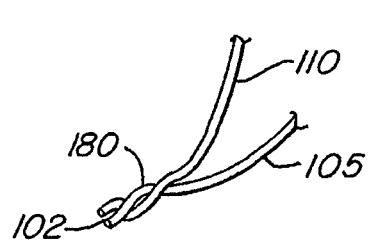
FIGS. 20-24 illustrate various alternative filtering device ends and structural member joining techniques.
Figure 21:
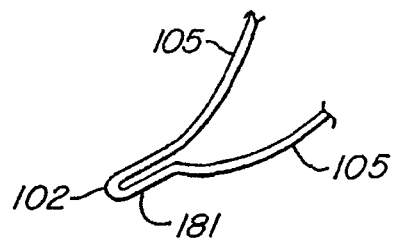
Figure 22:
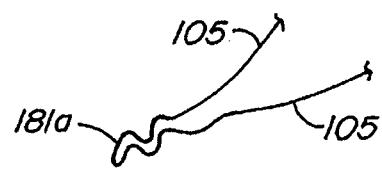

The ends of the filter devices of the present invention may be formed in a number of ways. A portion of the support structures 105, 110 may be wound 180 around one another (FIG. 20). In the illustrated embodiment, the wound portion 180 is used to form the end 102. In another alternative, the filtering device is formed from a single support member 105 that loops back on itself. In the illustrative embodiment of FIG. 21, support member 105 is formed into loop 181 to form the end 102. In an alternative to loop 181, the loop may contain a plurality of undulations (i.e., loop 181a in FIG. 22) or be formed into the shape of a retrieval feature or other component of the filter device. In yet another alternative, a cover is used to clamp, to join or otherwise bond the structural members together. In the illustrative example of FIG. 23, a generally cylindrical cover 183 is used to join together members 105, 110. The cover 183 may use any conventional joining method to secure the support members together such as adhesive, welding, crimping and the like. An alternative tapered cover 185 is illustrated in the embodiment of FIG. 24. The tapered cover 185 has a cylindrical shape and a tapered end 186. The tapered end 186 around the end having the tapered cover 185 and facilitates deployment and retrieval of the device. In one embodiment, the cover 185 is made of the same material as the structural member and/or the retrieval feature.

Figure 23:
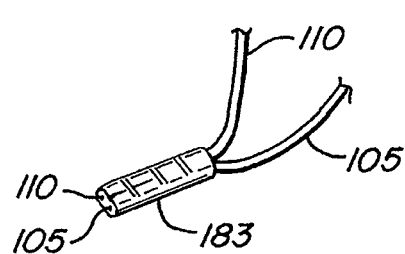
Figure 24:
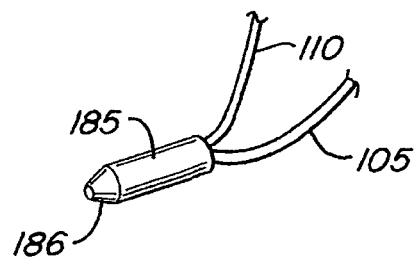

In some embodiments, the cylindrical cover 183 or crimp 185 may be modified to provide enhanced echogenic properties as illustrated in FIGS. 23x1-23x4. FIG. 23x1 is a perspective view of a cover or crimp having a surface treatment to enhance the echogenic properties of the cover or crimp. In this illustrative embodiment, the surface includes laser drilled holes. FIG. 23x2 is a perspective view of a cover or crimp having a surface treatment to enhance the echogenic properties of the cover or crimp. In this illustrative embodiment, the surface includes raised dimples or bumps or ridges. FIG. 23x3 is a perspective view of a cover or crimp having a surface treatment to enhance the echogenic properties of the cover or crimp. In this illustrative embodiment, the surface includes concave dimples similar to the surface of a golf ball. FIG. 23x4 is a perspective view of a cover or crimp having a surface treatment to enhance the echogenic properties of the cover or crimp. In this illustrative embodiment, the surface includes multiple indentations in a pattern, similar to those indentations shown in FIG. 23.

The various aspects of the filter embodiments described above with regard to FIGS. 2A-19 may be modified to be or used with a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIGS. 2A-19 may be modified according to FIGS. 127-135 or in conjunction with a system or as further described in FIGS. 136A-138B.

Some filter device embodiments of the present invention may include one or more retrieval features to assist recapturing and partially or fully recovering a deployed filter device. Retrieval features may be placed in any of a number of positions on the device depending upon the specific filter device design. In one embodiment, the retrieval device is positioned not only for ease of device recovery but also attached to the device in such a way that pulling on the retrieval device actually facilities removal of the device. In one embodiment, pulling on the retrieval device pulls the structural members away from the lumen wall. These and other aspects of the cooperative operation of the retrieval features during deployment and recapture will be described below with regard to FIGS. 72A-73D.

Figure 25:
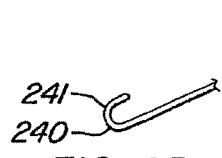
FIGS. 25-27C illustrate various alternative retrieval features.
Figure 26:
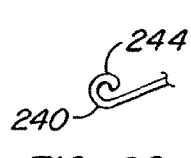
Figure 27A:
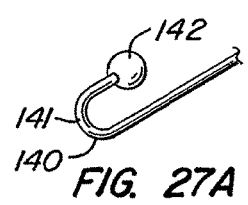
Figure 27B:
Figure 27C:
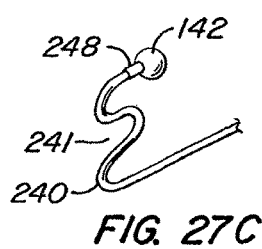

Several alternative embodiments of retrieval devices of the present invention are illustrated in FIGS. 25-27C. FIG. 25 illustrates a retrieval device 240 with a simple curve 241 formed in the end. FIG. 26 illustrates a retrieval device 240 with a curve 244 that is has a sharper radius of curvature than the curve 241 in FIG. 25. FIG. 27A illustrates a retrieval feature 140 having a curved section 141 with an atraumatic end 142. In the illustrative embodiment, the atraumatic end 142 is a ball than may be added to the end of curve 141 or formed on the end of the member used to form the feature 140. A ball 142 may be formed by exposing the end of the curved section 141 to a laser to melt the end into a ball. FIG. 27B illustrates a retrieval feature with a plurality of curved sections 241. In one embodiment, the curved sections 241 have a generally sinusoidal shape. In another embodiment, the curved sections 241 are configured to collapse when pulled on by a retrieval device like a snare (i.e., FIGS. 71A, 71B) FIG. 27C illustrates a retrieval feature 240 having a plurality of curved sections 241 and a ball 142 formed on the end. In additional embodiments, retrieval features of the present invention may include markers or other features to help increase the visibility or image quality of the filter device using medical imaging. In the illustrative embodiment of FIG. 27C, a radio opaque marker 248 is placed on the curved section 241. The marker 248 may be made from any suitable material such as platinum, tantalum or gold.

As illustrated in FIGS. 27Cx1, 27Cx1a, 27Cx1b and 27Cx2, the retrieval feature and ball tip may be modified for enhanced echogenic characteristics as described herein.

FIG. 27Cx1 illustrates an isometric view of a marker band 248x and a ball tip 142x modified for enhanced echogenic characteristics as described herein. FIG. 27CX1a is an enlarged view of the echogenic enhanced ball tip 142x of FIG. 27CX1. The echogenic enhanced ball tip 142x may have any of the echogenic features described herein. In the illustrated embodiment the echogenic features are a plurality of dimples. FIG. 27CX1b is an enlarged view of the echogenic enhanced marker band 248x of FIG. 27CX1. The echogenic enhanced marker band 248x may have any of the echogenic features described herein. In the illustrated embodiment the marker band 248x is made from a radio-opaque material and a plurality of echogenic features illustrated here as a plurality of hole patterns. The hole patterns as illustrated include a plurality of different shapes such as squares, triangles, circles, rectangles dimples arranged on the marker band. Representative radio-opaque materials include, for example, PtIr and Au.

FIG. 27CX2 illustrates an isometric view of a retrieval tail modified for enhanced echogenic characteristics as described herein. The retrieval tail 240x may be any of those designs described herein. In the illustrated embodiment, a coil wrap or coil windings is placed around the retrieval tail. The coil wrap may include metallic or echogenic polymers. The echogenic retrieval tail 240x may include a retrieval ball 142 or an echogenic enhanced retrieval ball 142x.

Figure 28A:
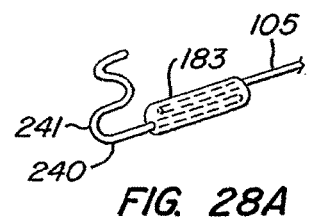
FIGS. 28A-28C illustrate various techniques of joining or forming retrieval features.
Figure 28B:
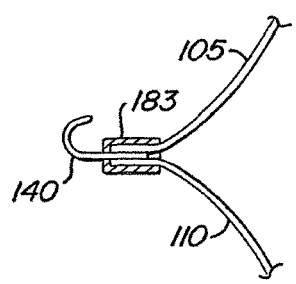
Figure 28C:
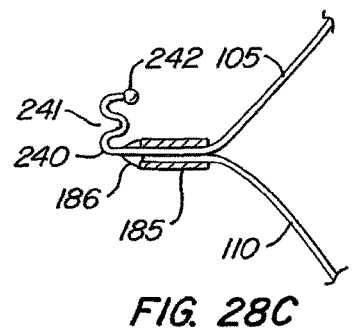

A cover placed about the ends may also be used to join a retrieval feature to an end or two support members. A cover 183 may be used to join a retrieval feature 240 to a support member 105 (FIG. 28A). In this illustrative embodiment, the support structure 105 and the retrieval feature 240 are separate pieces. A cover 183 may also be used to join together two members 110, 105 to a retrieval feature 140 (FIG. 28B). In another alternative embodiment, the retrieval feature is formed from a support member that is joined to the other support member. In the illustrative embodiment of FIG. 28C, the support member 105 extends through the tapered cover 185 and is used to form a retrieval feature 240. The tapered cover 185 is used to join the first support member and second support member 105, 110. In one alternative of the embodiment illustrated in FIG. 28C, the diameter of the support member 105 is greater than the diameter of the retrieval feature 240. In another embodiment, the diameter of the retrieval feature 240 is less than diameter of the support member 105 and is formed by processing the end of the support member down to a smaller diameter and is then shaped to form the retrieval feature 240. In another embodiment, the ball 242 or other atraumatic end is formed on the end of the retrieval feature.

Figure 29:
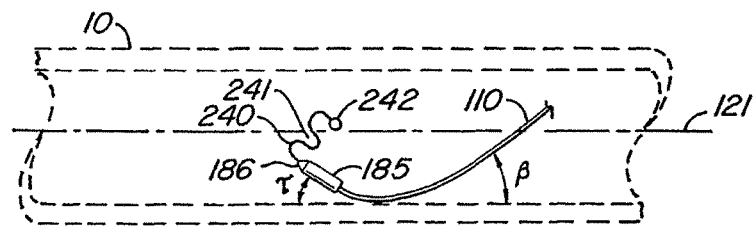
FIG. 29 illustrates a filtering device with a retrieval feature positioned within a lumen.

FIG. 29 illustrates a partial side view of a filter device in a lumen 10. This figure illustrates the retrieval feature angle τ formed by the retrieval feature and the interior lumen wall. The retrieval feature angle τ is useful in adjusting the height and orientation of the retrieval curves 214 and ball 242 within the lumen to improve the retrievably of the device. Generally, retrievably improves as the retrieval feature moves closer to the device axis 121 (i.e., central to the lumen axis as well). Additional curves may be added to the support members 110, 105 as needed to provide the desired range of retrieval feature angles. In one embodiment, τ ranges from −20 degrees to 90 degrees. In another embodiment, τ ranges from 0 degrees to 30 degrees.

The various aspects of the filter embodiments described above with regard to FIGS. 20-29 may be modified to be or used with a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIGS. 20-29 may be modified according to FIGS. 127-135 or in conjunction with a system or as further described in FIGS. 136A-138B.

Figure 30:
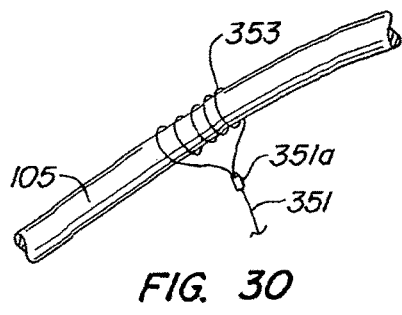
Figure 31:
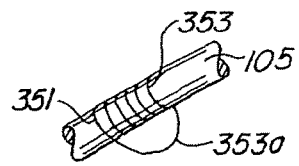
Figure 32:
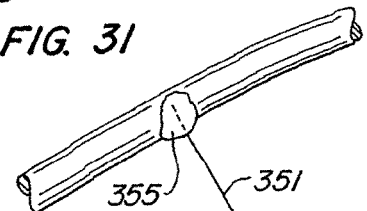
Figure 33:
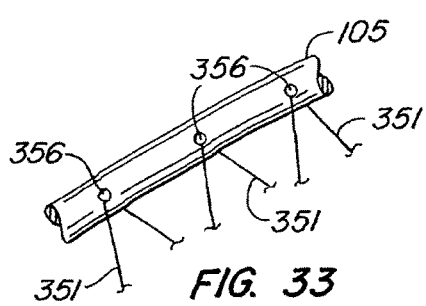
Figure 34A:
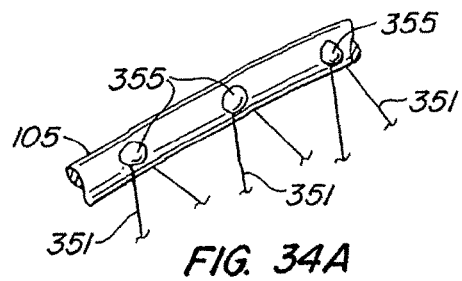
Figure 36:
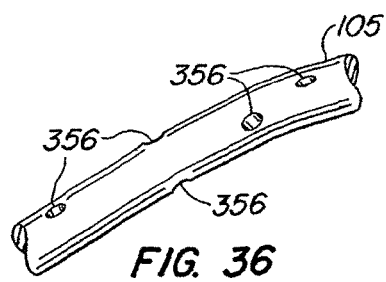

Attachment of Material Capture and Other Filtering Structures to Support Structures A number of different techniques may be used to attach material capture structures to support members. For clarity, the material capture structure has been omitted from the illustrations that follow but would be suitably secured using the line 351 or a loop. In FIG. 30 illustrates a line 351 with a number of turns 353 about a support member 105. The line 351 is secured back onto itself using a clip 351a. FIG. 31 illustrates a line 351 with a number of turns 353 about the support member 105 to secure a loop 353a that may be used to tie off or otherwise secure a material capture structure. A line 351 may also be glued 355 to a support 105 (FIG. 32). In another alternative embodiment, holes 356 formed in the support member are used to secure one or more lines 351 that are used in turn to secure a material capture structure. In an alternative to the linear arrangement of holes 356, FIG. 36 illustrates how holes 356 may be provided in a number of different orientations to assist in securing a material capture to the support structure 105. Alternatively, the line 351 may be glued 355 into the hole 356 (FIG. 34A and in section view 34B).

Figure 34C:
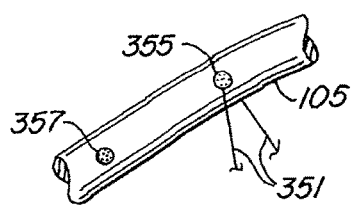
Figure 34B:
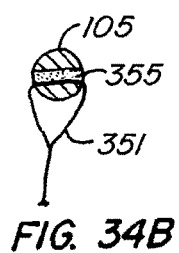
Figure 35:
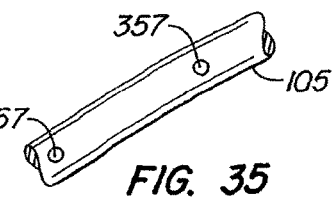
Figure 37:
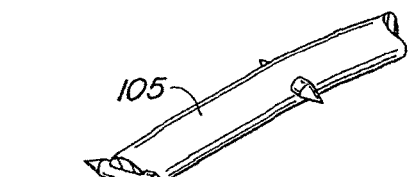
Figure 35X:
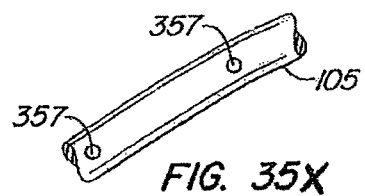
FIG. 35x is isometric view of a section of a support frame having a plurality of or pattern of holes where some of the holes in the support member are left open to enhance the echogenic quality of the support member.

In other alternative embodiments, the holes 356 are used to secure lines 351 as well as provide a cavity for another material to be incorporated into the support structure 105. Other materials that may be incorporated into the support structure 105 include, for example, a pharmacological agent or a radio opaque material. The use of a radio opaque marker may be useful, for example, when the support structure is formed from a material with low imaging visibility such as, for example, shape memory polymers or biodegradable polymers. FIG. 34C illustrates an embodiment where one hole 356 is used to secure a line 351 and the other is filled with material or compound 357. In another alternative, some or all of the holes 356 may be filled with another material as in FIG. 35. In yet another alternative, the holes 356 are filled with small barbs 358 that may be used to secure the device to the lumen wall. In FIG. 35x, some of or some pattern of the holes 357 in a support member 105 are left open to enhance the echogenic quality of the support member 105. The illustrative embodiment of FIG. 37 the barbs 358 are only long enough to break the surface of the lumen interior wall and not pierce through the lumen wall. While each of the above has been described with regard to the support member 105, it is to be appreciated that these same techniques could be applied to the support member 110 or other structure used to support a material capture structure. Additional alternative embodiments of hooks, barbs or other fixation devices or elements are described below with regard to FIGS. 88-126D.

Figure 38A:
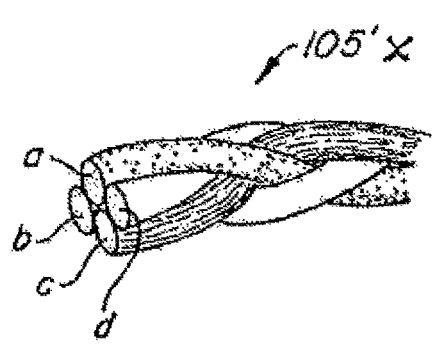
FIG. 38A illustrates an alternative braided support member 105.

It is to be appreciated that the support structure embodiments are not limited to single member constructions. FIG. 38A illustrates an alternative braided support member 105'. Braided support structure 105' is formed by 4 strands a, b, c, and d. Alternatively, in FIG. 38Ax, the strands a, b, c and d of braided structure 105x' may have different properties to enhance the echogenic or radio opaque qualities of the structure 105x'. In one exemplary embodiment, the a and d strands may be formed from radio opaque wire or filament, the b strand may be a support wire or structure and the d strand may be an echogenic filament. Other configurations are possible based on the alternative echogenic alternatives described herein.

Figure 38A:
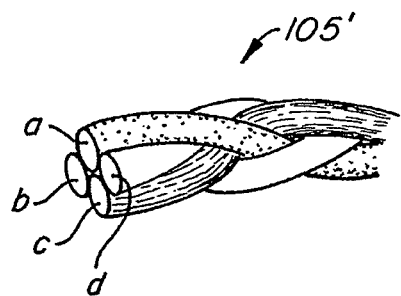
Figure 38B:
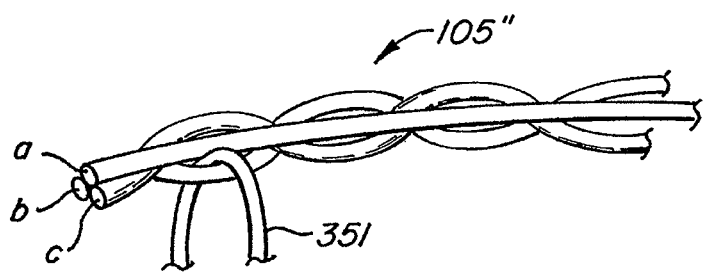

FIG. 38B illustrates another alternative braided support member 105". Braided support structure 105" is formed by 3 strands a, b, and c. FIG. 38B also illustrates how the braid structure may be used to secure a line 351. As can be seen in this embodiment, by using the line 351 a material capture structure (not shown) is secured to at least one strand within the braided structure 105".

Figure 39X:
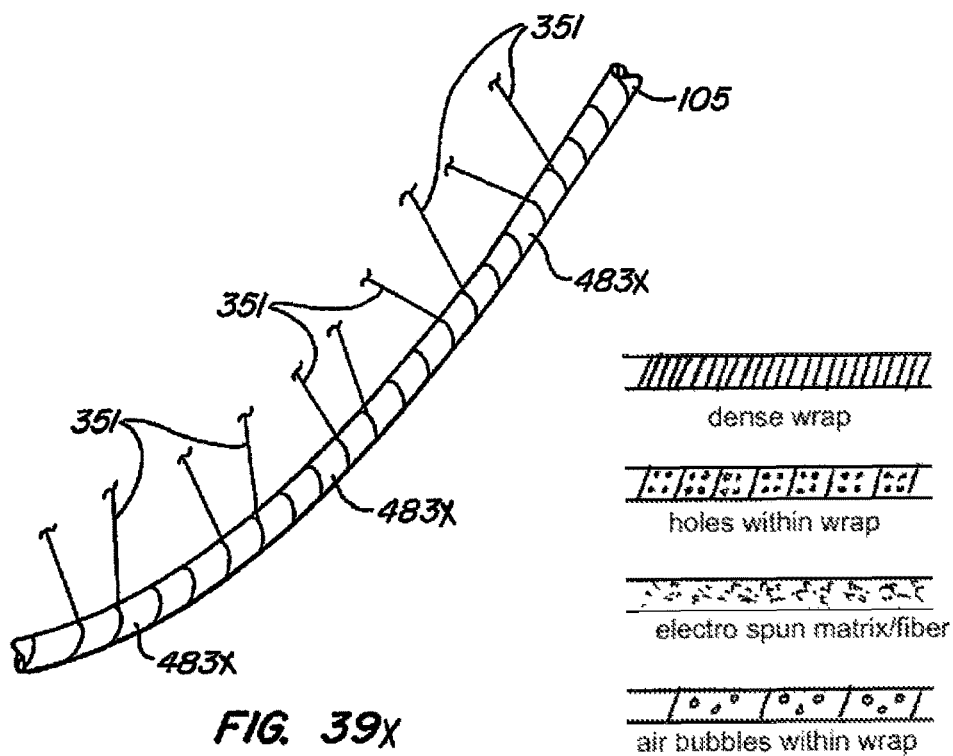
FIG. 39x illustrates alternatives of an echogenic wrap embodiment.
Figure 39:
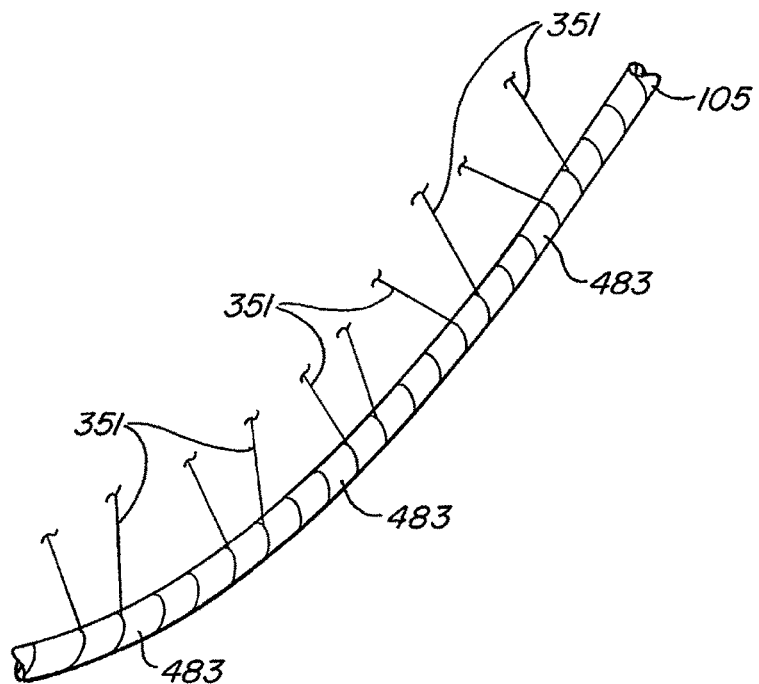
FIG. 39 illustrates the use of a wrapped around a support frame to secure a material capture structure securing line.
Figure 40:
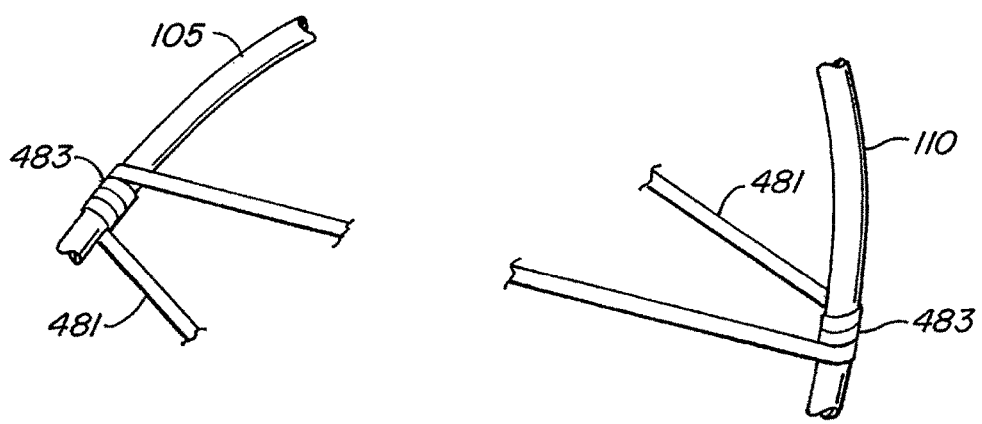

FIGS. 39 and 40 illustrate additional alternative techniques to secure a filter support structure to a support member. As illustrated in FIG. 39, there is illustrated a technique to secure a material capture structure securing line 351 to a support frame 105 using a material 481 wrapped around the support frame 105. In this manner, the material capture structure (not shown but attached to the lines 351) is attached to a material 481 that at least partially covers the first support structure 105. The lines 351 are passed between the material 481 and the support structure 105 as the material 481 as wraps 483 are formed along the support structure 105. The lines 351 are omitted in the embodiment illustrated in FIG. 40 as the material 481 forms wraps 483 and is used to secure the material capture structure (not shown). In one embodiment, the material 481 forms a tissue ingrowth minimizing coating over at least a portion of support structure. Alternatively, the filtering structure (not shown) is attached to the support structure 105 using a tissue ingrowth minimizing coating 481.

As illustrated in FIG. 39x, there is illustrated a technique to secure a material capture structure or securing line 351 to a support frame 105 using an echogenic material 483x wrapped around the support frame 105. The securing line or portion of the material capture structure 351 may also be an echogenic filament or other modified component according to the improvements described herein. The echogenic wrap material 483x at least partially covers a portion of the first support structure 105 or may be used to cover other portions or features of a filter described herein. The lines 351 are passed between the material 483x and the support structure 105 as the material 483x is wrapped about and along the support structure 105. The material used for 483x includes, by way of example and not limitation, a dense wrap, holes formed in the material (i.e., similar to holes made in bicycle handlebar wrap material), an electrospun matrix or electrospun fiber or air bubbles contained within the wrap.

Figure 41:
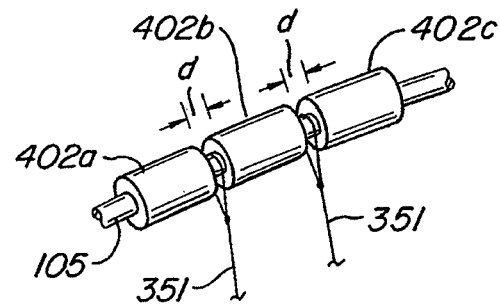
Figure 42:
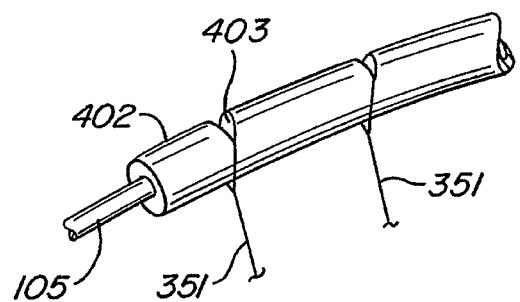
Figure 43:
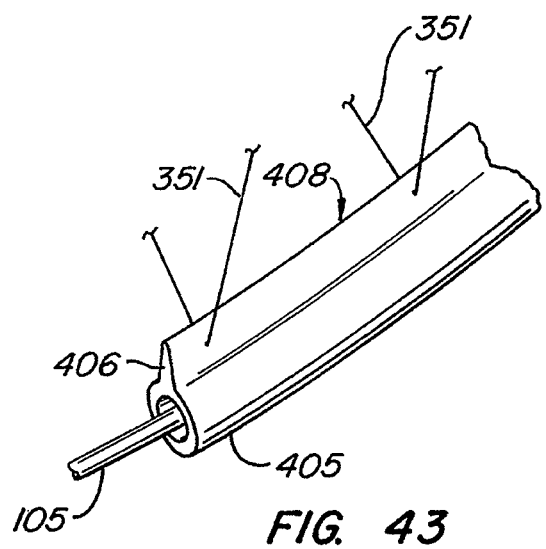

FIGS. 41, 42 and 43 relate to securing the material capture structure to a lumen disposed around the support member. FIG. 41 illustrates a lumen 402 that has been cut into segments 402a, 402b, 402c that are spaced by a distance "d." Lines 351 are attached around the support member and in the space "d" between adjacent segments. The segments may remain apart or be pushed together to reduce or eliminated the spacing "d." In contrast the segments in FIG. 41, the lumen 402 in FIG. 42 provides notches 403 for securing line 351. FIG. 43 illustrates a lumen 405 having a tissue growth inhibiting feature 408 extending away from the support member 105. As seen in section view 406 the inhibiting feature 408 has a different cross section shape than the support member 105. In addition, in some embodiments, the lumen 405 is selected from a suitable tissue ingrowth minimizing material so that is acts like a tissue ingrowth minimizing coating on the support structure. In other embodiments, the cross section shape 406 is configured to inhibit tissue growth over the tissue ingrowth minimizing coating.

Figure 44:
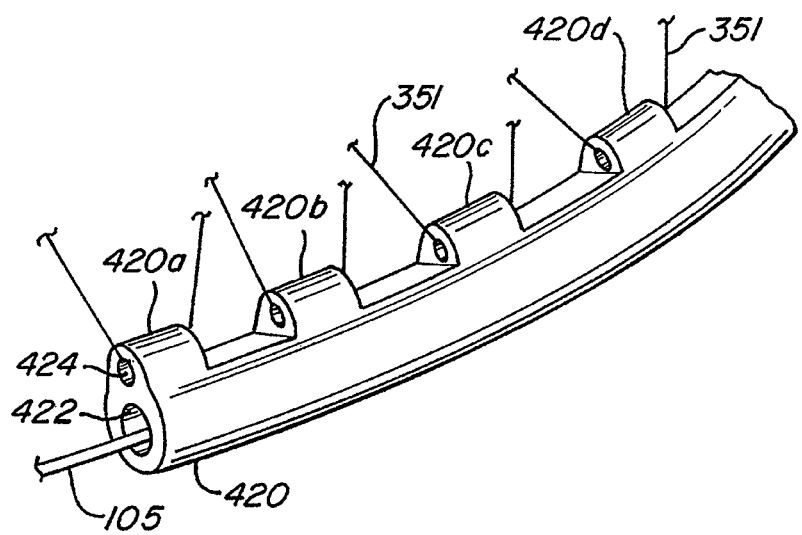
Figure 45:
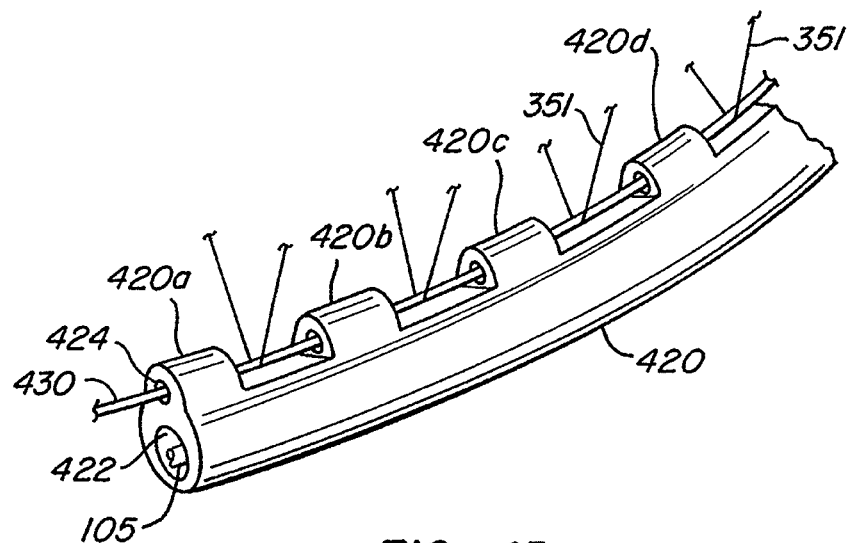

FIGS. 44 and 45 illustrate filter device embodiments utilizing dual lumen structures. The dual lumen structure 420 includes a lumen 422 and a lumen 424 and has a generally teardrop shaped cross section area. In this illustrative embodiment, the support structure 105 is disposed in the lumen 422 and the second lumen 424 is used to hold lines 351 and secure a material capture device (not shown). In the illustrative embodiment, the lumen structure 420 has been cut to form a number of segments 420a, b, c and d in the lumen 424. The connection rings formed by the segments 420a-d are used to secure lines 351 as needed. FIG. 45 illustrates an alternative configuration for the lumen structure 420. In this alternative configuration, a release line 430 extends through the notched lumen 424. The lines 351 extend about the release line 430 and hence to secure the material capture structure (not shown). Since the lines 351 are connected using the release line, removal of the release line from lumen 424 will allow the material capture structure secured using the lines 351 to be released from the support structure and removed from the lumen. A configuration such as that shown in FIG. 45 provides a filtering structure that would be releasably attached to an open loop (i.e., an open loop frame formed by the support structure). The embodiment illustrated in FIG. 45 provides a release line 430 positioned along the open loop (formed by member 105) and a filtering structure (not shown) is attached to the open loop using the release line.

In another embodiment, a filter device of the present invention is configured to be a coated endoluminal filter. In addition to coating all or a portion of the support structures or filter elements of this device, the coating on the support members may also be used to secure a filtering structure to the support structure. In one embodiment, a coated endoluminal filter has a support structure, a filtering structure attached to the support structure and a coating over at least a portion of support structure. In one aspect, the coated support structure may form a rounded support frame, an open loop or other structure to support a filtering structure described herein. In one embodiment, the coating over at least a portion of support structure is used to secure a plurality of loops (i.e., flexible form or rigid form) to the support structure. The plurality of loops are then used to secure a filtering structure such as a material capture structure, for example, within the coated endoluminal filter. In one embodiment, the coating is a tissue ingrowth minimizing coating.

It is to be appreciated that a filtering structure may also be attached to the support structure using the tissue ingrowth minimizing coating. In some embodiments, the tissue ingrowth minimizing coating is wrapped around the support structure or, alternatively, it may take the form of a tube. If a tube is used, the tube may be a continuous tube or comprise a plurality of tube segments. The tube segments may be in contact or spaced apart. The tube may have the same or different cross section shape than the support member. In another embodiment, the tissue ingrowth minimizing coating is in the shape of a tube and the support structure is in the interior of the tube.

In some other embodiments, a bonding material is provided between the tissue ingrowth minimizing coating and the support structure. The bonding material may be wrapped around the support structure or may take the form of a tube. If a tube is used, the tube may be a continuous tube or comprise a plurality of tube segments. The tube segments may be in contact or spaced apart. The bonding material tube may have the same or different cross section shape than the support member or the coating about the bonding material. In one embodiment, the bonding material is in the shape of a tube with the support member extending through the bonding material tube lumen. In one embodiment, a plurality of loops (i.e., flexible form or rigid form) are secured to the support structure by sandwiching the line used to form the loops between a bonding material around the support member and a coating around the bonding material. In one embodiment, the bonding material has a lower reflow temperature than the coating around the boding material. In this embodiment, the line used to form the loops is secured at least in part by reflowing the bonding material to secure the line between the coating around the bonding material and the support structure. In another alternative, the coating around the bonding material is a shrink fit coating that also shrinks around the bonding structure and the support member during or after a process that reflows the bonding material. In any of the above alternatives, the plurality of loops may be used to secure a filtering structure such as a material capture structure, for example, within the coated endoluminal filter.

Some embodiments of the coated endoluminal filter include some or all of the other features described herein such as, for example, a retrieval feature on the support structure, a retrieval feature on each end of the support structure, a support structure having two elongate bodies that are joined together to form a rounded frame, and a support structure having two spiral shaped elongate bodies. In addition, some coated endoluminal filters have a support structure that is generally symmetrical about a plane that is orthogonal to the flow direction of the filter and contains a crossover point. In another alternative coated endoluminal filter embodiment, the support structure of the coated endoluminal filter is generally symmetrical about a plane that is parallel to the flow direction of the filter and contains both ends of the support structure.

Figure 46:
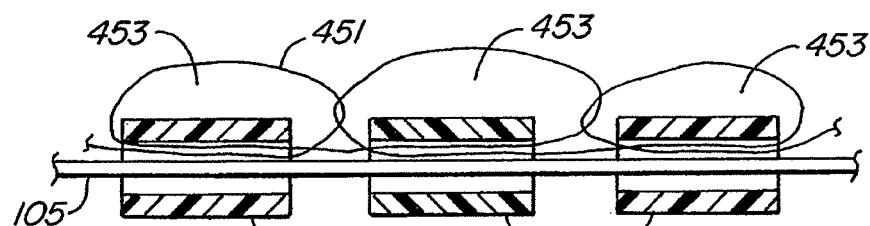
Figure 47:
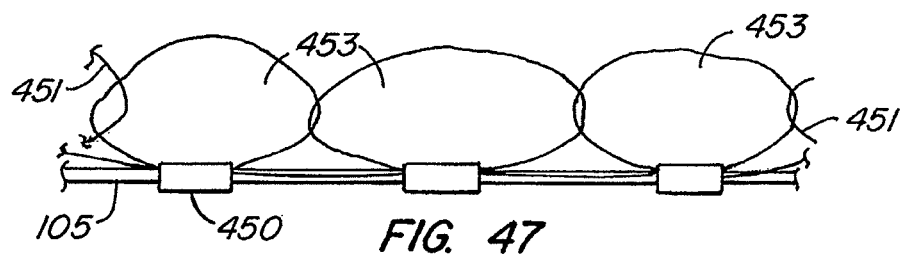

FIGS. 46-51B illustrate several aspects of coated endoluminal filter embodiments. These figures are not to scale and have exaggerated dimensions to make clear certain details. FIG. 46 illustrates a number of segments 450 of a coating placed about the support member 105. One or more lines 451 extend between the segment 450 and the support member 105 and form a plurality of loops 453. In one embodiment, the line 451 is a single continuous line. Once formed, the segments 450 undergo suitable processing to shrink the segment diameter around the line 451 and the support member 105 thereby securing the line 451 and loops 453 against the support structure (FIG. 47). The segment 450 is secured about the support member 105 as illustrated in the end view of FIG. 51A. The segments 450 in the embodiment shown in FIG. 47 are spaced apart. In other embodiments, the segments 450 may be in contact or have spacing different from that illustrated in FIG. 47. The sizes of the various components illustrated in FIGS. 46, 47 and 51A are exaggerated to show detail. The dimensions of one specific embodiment are: the support member 105 is a NiTi wire having an outside diameter of between 0.011" and 0.015"; the segments 450 are 0.2" long cut from a PTFE heat-shrink tubing having and a pre-shrunk outside diameter of 0.018" and a wall thickness of 0.002"; the line 451 is monofilament ePTFE of an outer diameter of 0.003" and the loops 453 have a nominal diameter of between about 0.1" to about 0.4".

Figure 48:
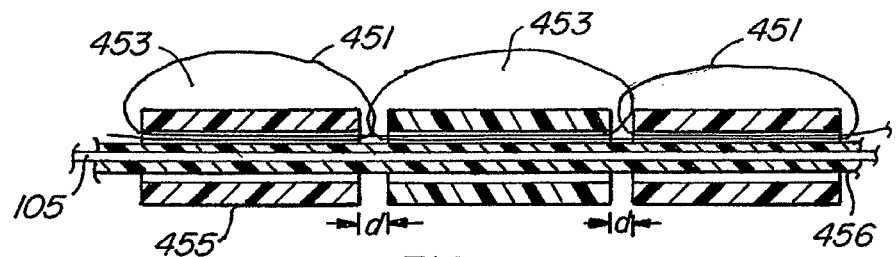
Figure 49:
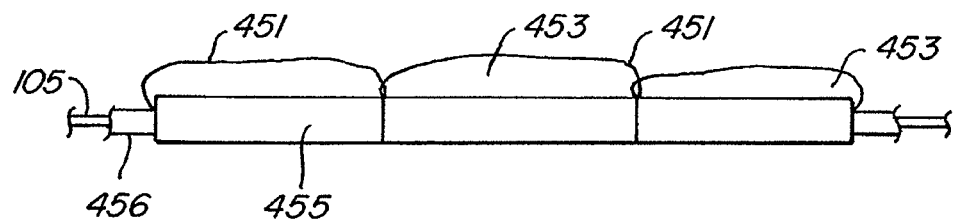

FIGS. 48, 49 and 51B illustrate a bonding material 456 about the support member 105 and a number of segments 455 about the bonding material 456. One or more lines 451 extend between the segments 455 and the bonding material 456 and form a plurality of loops 453. In one embodiment, the line 451 is a single continuous line. Once formed, bonding material 456 and/or the segments 450 undergo suitable processing to secure the line 451 between the bonding material 456 and the coating 455 thereby securing the line 451 and loops 453 against the support structure (FIG. 49). The coating segment 450 and the bonding material 456 is secured about the support member 105 as illustrated in the end view of FIG. 51B. The segments 455 in the embodiment shown in FIG. 48 are spaced apart by spacing "d." In other embodiments, the segments 455 may be in contact after processing (FIG. 49) or have spacing different from that illustrated in FIG. 48. In a preferred embodiment, the spacing between the segments 455 is removed by a portion of the boding material 456 flowing between and securing adjacent segments 455. The sizes of the various components illustrated in FIGS. 48, 49 and 51B are exaggerated to show detail. The dimensions of one specific embodiment are: the support member 105 is a NiTi wire having an outside diameter of between 0.011" and 0.016"; the segments 455 are 0.3" long cut from a PTFE heat-shrink tubing having a pre-shrunk outside diameter of 0.022" and a wall thickness of 0.002"; the bonding material is a tube of FEP heat shrink tubing having a pre-shrunk outside diameter of 0.018" and a wall thickness of 0.001"; line 451 is 0.002" outer diameter PET monofilament and the loops 453 have a nominal diameter of between about 0.1" to about 0.4". It is to be appreciated that the segments 450, 455 and bonding material 456 may be formed, for example, from: ePTFE, PTFE, PET, PVDF, PFA, FEP and other suitable polymers. Moreover, embodiments of strands, lines, fibers and filaments described herein may also be formed from ePTFE, PTFE, PET, PVDF, PFA, FEP and other suitable polymers.

FIG. 50 illustrates the use of a continuous flexible line 452 passed through a continuous coating segment 450 forming loops 454. The loops 454 are disposed along the length of the coating 450 at regular intervals; the continuous coating segment 450 are uniform in length to the support members 105 using a PTFE heat shrink tubing having pre-shrunk diameter of 0.018" and a wall thickness of 0.002". The line 452 is monofilament ePTFE of an outer diameter of 0.003" and the loops 454 have a nominal diameter of between about 0.1" to about 0.4".

FIG. 51Bx illustrates a multi-tubular structure similar to those of FIGS. 50, 51A and 51B. In the illustrative embodiment of FIG. 51B 1x there is an inner echogenic tubular covering 456x about the support wire 105. As before, an outer tubular covering 450/455 may optionally be placed around the outer surface of the echogenic tubing or covering 456x. The echogenic tubing or covering 456x may be, for example, filled with glass or metallic particles, filled with air bubbles, contain a coil or braid or include a plurality or pattern of laser drilled holes.

Figure 52A:
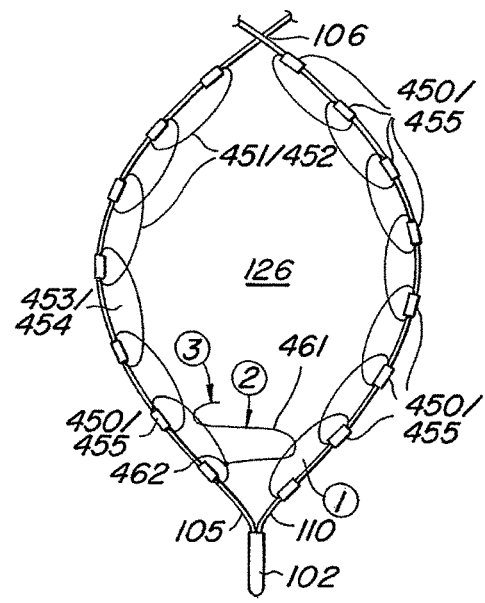
Figure 52B:
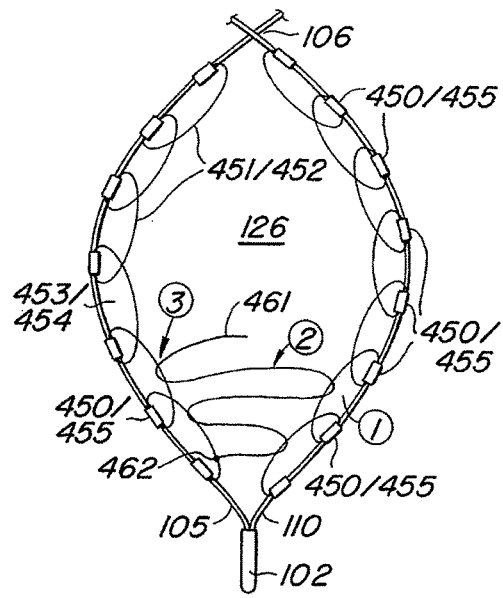
Figure 52C:
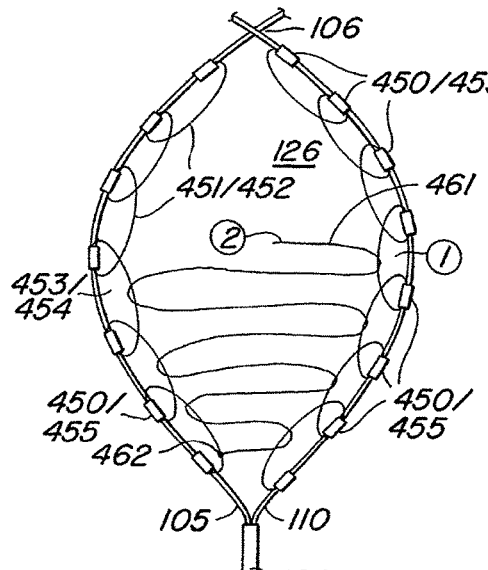
Figure 58:
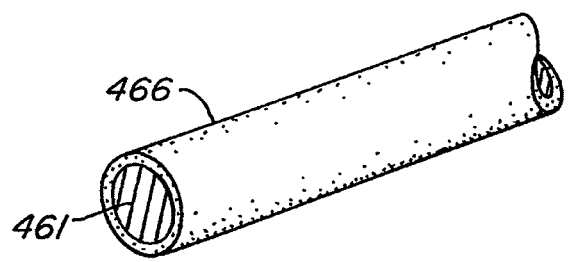

FIGS. 52A-53D illustrate alternative techniques for forming and/or attaching a filtering structure to a support structure. FIG. 52A illustrates an embodiment of a support frame 126 formed by support members 105, 110 between the end 102 and crossover 106 as described above. Loops 453/454 are formed using lines 451/452 as described above with regard to FIGS. 46-51B. Thereafter, a filament 461 is suitably attached 462 to a line 451/452 by tying, welding, gluing or by incorporating the filament 461 during the processing steps described with regard to FIGS. 46-51B. Next, the filament is traverses across the frame 126 and about the loops 453/454. In this embodiment, the lacing pattern between loops crosses a line extending between the end 102 and the crossover 106. The general pattern is that the filament extends across the frame 126 and around one right side loop (1) and back across the frame 126 (2) and around (3) a left side loop 453/454. The lacing process continues as shown in FIGS. 52B and 52C. When completed, the lacing process produces a filtering structure 465 from one or more filaments secured to loops 451/452 that are secured to the support members 105/110. The filament in the filtering structure 465 may be taut between the loops 451/452 or have some degree of sag (as illustrated in FIG. 52D). Filament 461 or other material used to form material capture structure may be coated with a pharmacological agent (coating 466 in FIG. 58). The pharmacological agent may be any of a wide variety of compounds, drugs and the like useful in the procedures performed using or the operation of various filtering device embodiments of the present invention. The pharmacological agent coating 466 may include pharmacological agents useful in preventing or reducing thrombus formation on the filtering structure, chemically lysing debris captured in the filtering structure and the like.

Figure 52D:
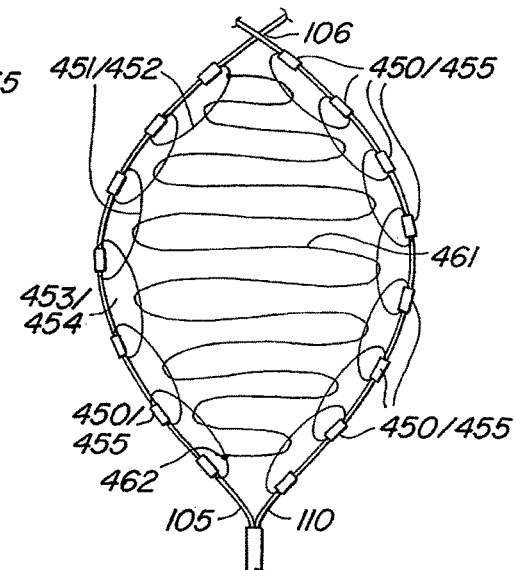
Figure 53A:
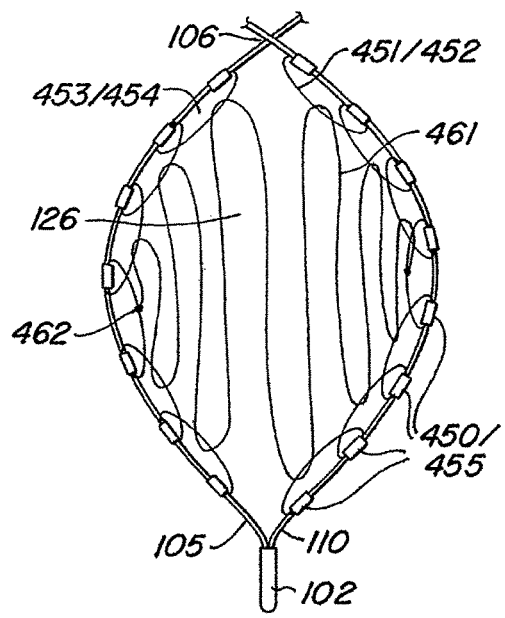
Figure 53B:
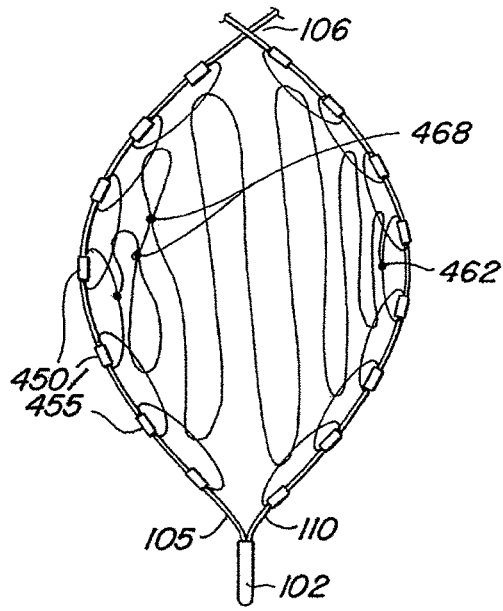
Figure 53C:
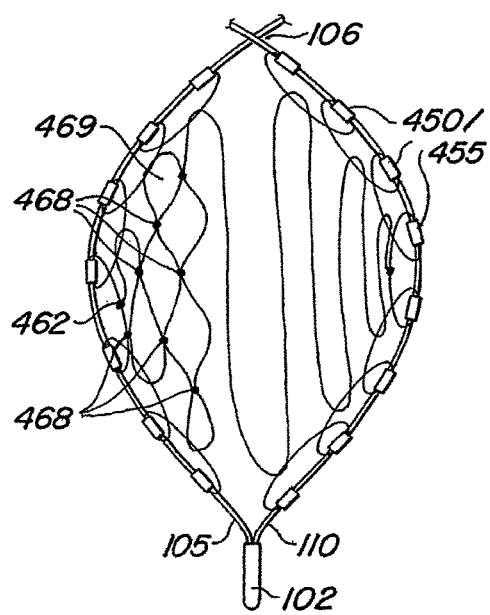
Figure 53D:
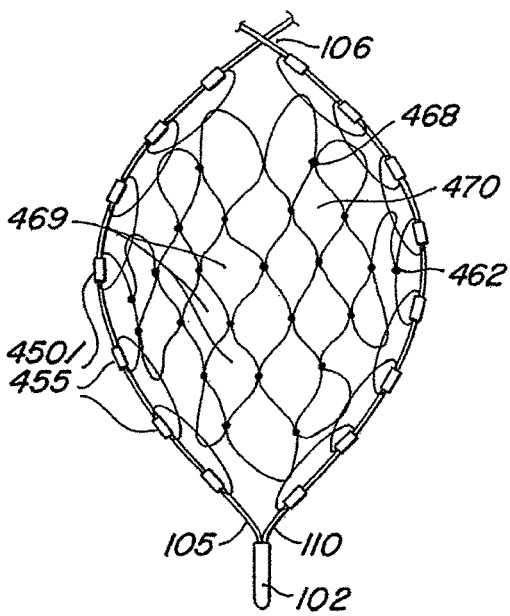

FIG. 53A illustrates an embodiment of a support frame 126 formed by support members 105, 110 between the end 102 and crossover 106 as described above. Loops 453/454 are formed using lines 451/452 as described above with regard to FIGS. 46-51B. Thereafter, a filament 461 is suitably joined 462 to a line 451/452 by tying, welding, gluing or by incorporating the filament 461 during the processing steps described with regard to FIGS. 46-51B. Next, the filament 461 was laced as described above with regard to FIG. 52A about the loops 453/454. In this embodiment, however, the lacing pattern between loops remains generally parallel to a line extending between the end 102 and the crossover 106. When completed, the lacing process produces a filtering structure from one or more filaments 461 that extend parallel to a line between the end 102 and crossover 106 and are secured to loops 451/452 secured to the support members 105/110. This filtering structure (FIG. 53A) may be used within a filter device of the present invention. In addition, the filtering structure in FIG. 53A (as well as the structure in FIG. 52D) may be further processed to join 468 adjacent filaments 461 to form filter cells 469 as part of a filtering structure 470. The process used to join 468 adjacent filaments 461 may include any conventional joining technique such as tying, welding, bonding, gluing, and the like. In addition, segments of tubing (i.e., segments 450, 455, 456 described above) could be used to join 468 portions of adjacent filaments 461. In one specific embodiment, the filament 461 is ePTFE monofilament with an outer diameter of 0.003" joined 468 using a piece of FEP heat shrink tubing having a pre-shrunk outer diameter of 0.008" and a wall thickness of 0.001". The filtering structure 470 may be taut between the loops 451/452 or have some degree of sag (as illustrated in by the filtering structure in FIG. 52D). The filter cells 469 may be formed in numerous sizes and shapes as described in greater detail below.

Figure 57A:
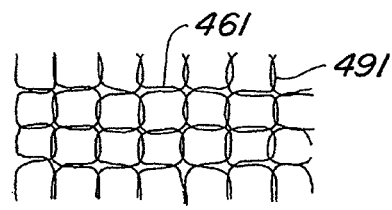

Alternatively, the filtering structures in FIG. 53A and FIG. 52D may incorporate additional loops 491 formed by looping the filament 461 as illustrated in FIG. 57A.

Alternative Filtering and/or Material Capture Structures

In some embodiments, the material capture structure contains a number of filter cells. Filter cells may be formed in a number of different ways and have a number of different shapes and sizes. The shape, size and number of filter cells in a specific filter may be selected based on the use of a particular filter. For example, a filter device of the present invention configured for distal protection may have a filter cell size on the order of tens to hundreds of microns to less than 5 millimeters formed by a selecting a filter material with a pore size (FIG. 63A, 63B) suited to the desired filtration level. In other applications, the filter cell may be formed by overlapping (i.e., joined or crossed without joining) filaments to form cells that will filter out debris in a lumen above a size of 2 mm. Various other filter sizes and filtration capacities are possible as described herein.

Figure 57B:
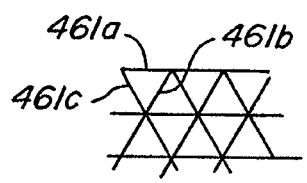

Intersecting filaments (FIG. 54C) may be used to form diamond shaped filter cells (FIG. 54A), as well as rectangular shaped filter cells (FIGS. 54B, 2A and 9B). Multiple strand patterns may also be used such as the three strand 461a, 461b and 461c array illustrated in FIG. 57B. Intersecting filaments may also be knotted, tied or otherwise joined 468 (FIGS. 55A and 55E).

In another embodiment, the intersection of filaments may be used to enhance the echogenic characteristics of the filter. FIG. 55Ax and the enlarged view FIG. 55AX1 illustrates a pair of crossing filaments 461 joined using an embodiment of an echogenic joint or joiner 468x. As best seen in the enlarged view FIG. 55AX1, the joint 468x may include one or more of a wire wrap, a hollow sphere or a sphere with holes or surface features such as bumps or divots or dimples. A joint 468x is illustrated with two filaments 461 in FIG. 55AX1. The joint 468x includes a wire wrap and an array of holes and/or dimples as shown.

Intersecting filaments may form the same or different filter cell shapes such as, for example, an elongated oval in FIG. 55C, one or more joined diamonds as in FIG. 55B and an array of joined polygons as in FIG. 55D. Cells may also be formed using the techniques described above in FIGS. 52A-53D. In one embodiment, a filter cell is defined by at least three intersecting filaments 461. The filter element 461 may be formed from any of a wide variety of acceptable materials that are biocompatible and will filter debris. For example, filaments, lines and strands described herein may be in the form of a multifilament suture, a monofilament suture a ribbon, a polymer strand, a metallic strand or a composite strand. Additionally, filaments, lines and strands described herein may be formed from expanded polytetrafluoroethylene (ePTFE), polytetrafluoroethylene (PTFE), Poly(ethylene terephthalate) (PET), Polyvinylidene fluoride (PVDF), tetrafluoroethylene-co-hexafluoropropylene (FEP), or poly(fluoroalkoxy) (PFA), other suitable medical grade polymers, other biocompatible polymers and the like.

The joined polygons may have any of the shapes illustrated in FIGS. 60A-60F. It is to be appreciated that filter cells may have any, one or more, or hybrid combinations of shapes such as, for example, circular (FIG. 60A), polygonal (FIG. 60B), oval (FIG. 60C), triangular (FIG. 60D), trapezoidal or truncated conical (FIG. 60E).

Figure 56:
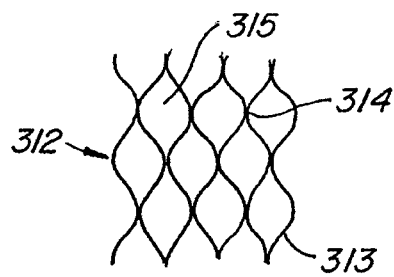

In addition, the material capture structure may have filter cells formed by extruding a material into a material capture structure. FIG. 56 illustrates an exemplary filtering structure 312 where a material is extruded into strands 313 that are joined 314 and spaced apart for form one of more filter cells 315. In one embodiment, the strands are extruded from Polypropylene material, forming diamond shaped filter cells approximately 4 mm in height and 3 mm in width.

Figure 59A:
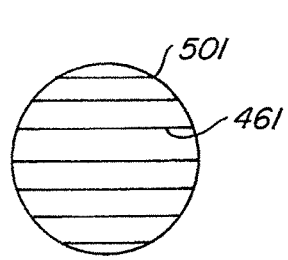
Figure 59B:
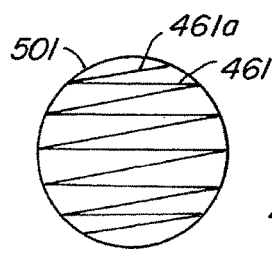
Figure 59C:
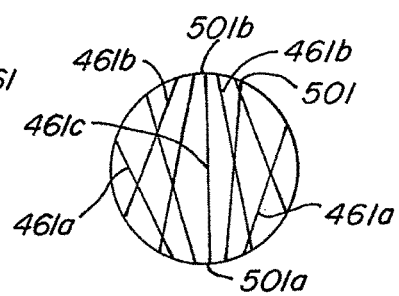
Figure 59D:
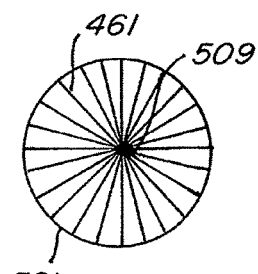
Figure 59E:
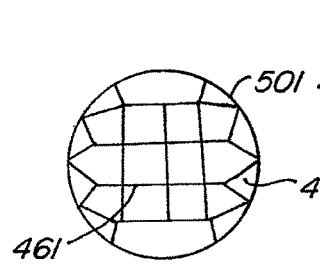

FIGS. 59A-63B illustrate several different filtering structure configurations. For simplicity of illustration, the filtering material is shown attached to a circular frame 501. It is to be appreciated that the circular frame 501 represents any of the various open loop, rounded frame or other support frames described herein. FIG. 59A illustrates a frame pattern similar to FIG. 52D. FIG. 59B adds an additional transverse filaments 461a at an angle to the filaments 461. FIG. 59C illustrates a plurality of filaments 461a extending up from the frame bottom 501a about a central filament 461c and a plurality of filaments 461b extending down from the frame top 501b about a central filament 461c. In this illustrative embodiment, the filaments 461a,b are arranged symmetrically about the central filament 461c. Other non-symmetrical configurations are possible. More than one central filament 461c may be used to form a variety of different size and shaped polygonal filter cells (e.g., FIG. 59E).

Figure 59F:
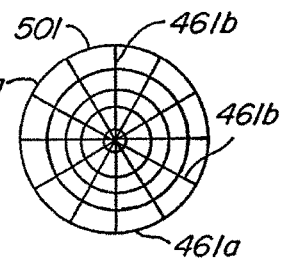
Figure 59G:
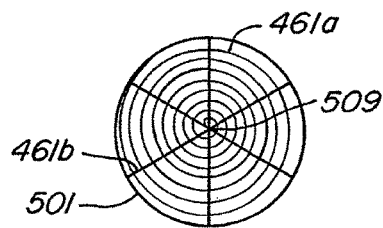

Filaments may also be arranged using a variety of radial patterns. Fr example, multiple filaments 461 may from a common point 509 out the edge of frame 501. In some embodiments, the common point is central to the frame 501 (FIG. 59D) and in other embodiments the common point 509 is in a different, non-central location. The sectors formed by the multiple filaments (FIG. 59D) may be further divided into multiple filter cell segments by winding a filament 461a about and across segment filaments 461b. In contrast to a single filament spirally out from the point 509 as in FIG. 59G, the segmented filter cells in FIG. 59F are formed by attaching single filament 461a to the segment filaments 461b.

Figure 61A:
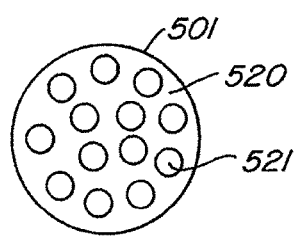
Figure 61B:
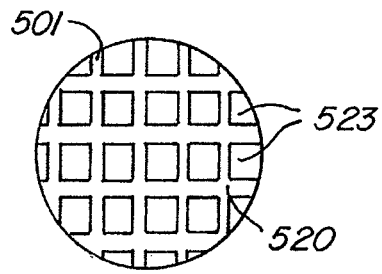
Figure 61C:
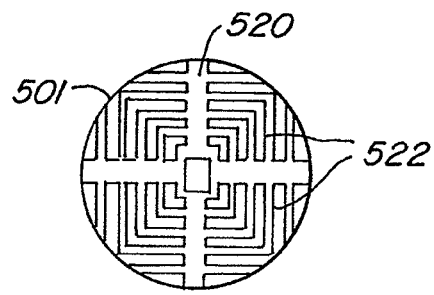
Figure 62:
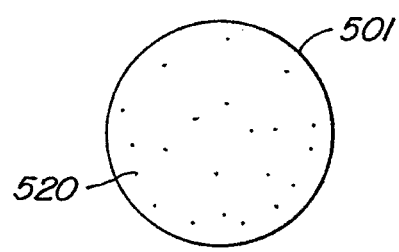
Figure 63A:
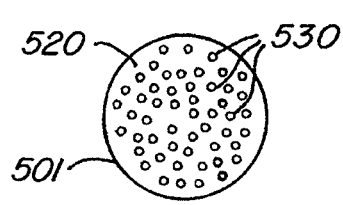
Figure 63B:
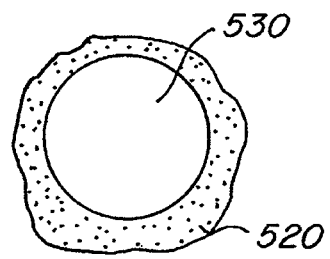

FIGS. 61A-C and FIG. 62 illustrate the use of a sheet of material 520 to form a filter structure. The material 520 may have any of a variety of shapes formed in it using any suitable process such as punching, piercing, laser cutting and the like. FIG. 61A illustrates a circular pattern 521 formed in material 520. FIG. 61B illustrates a rectangular pattern 523 formed in material 520. FIG. 61C illustrates a complex pattern 522 cut into material 522. It is to be appreciated that the material 520 may also be placed in the frame 501 without any pattern (FIG. 62). The illustrative embodiment of FIG. 62 may be useful for occluding the flow within a lumen. Suitable materials 520 for an occlusion application include for example, wool, silk polymer sheets, other material suited to prevent blood flow in a lumen when extended across a lumen and the like. Additionally, the filter material 520 may be a porous material having pores 530 (FIG. 63A). The material 520 may be selected based on the average size of individual pores 530 (FIG. 63B) depending upon the procedure or use of the filter device. For example, the material 520 may be any of the porous materials using in existing distal protection and embolic protection devices. In general, a wide variety of pore 530 sizes are available and may range from 0.010" to 0.3". Other pore sizes are also available depending upon the material 520 selected.

Figure 64A:
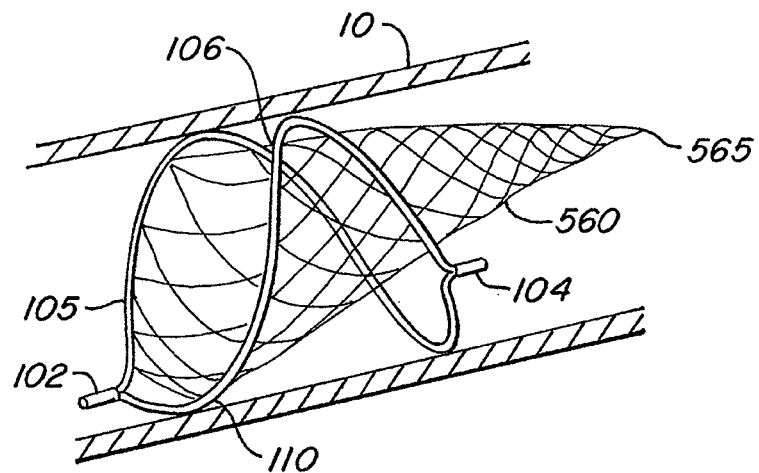
Figure 64B:
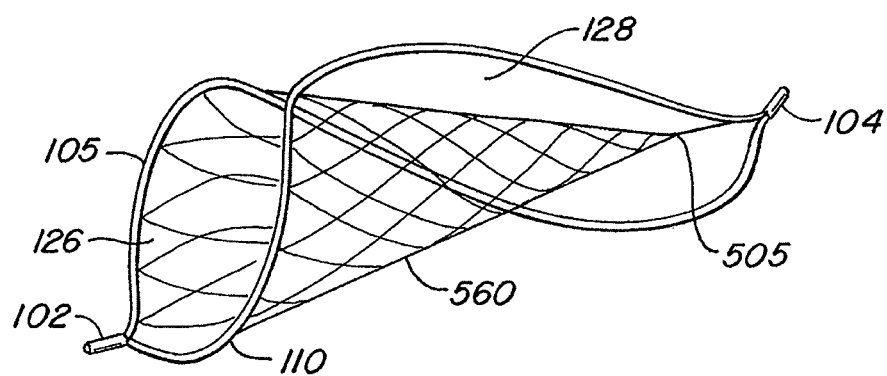
Figure 65A:
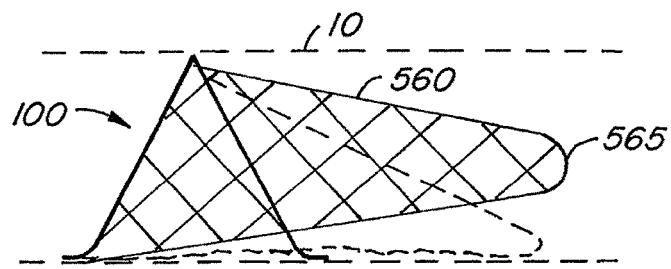
Figure 65B:
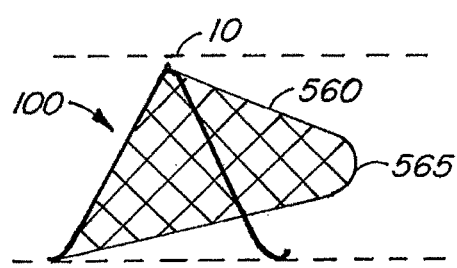
Figure 65C:
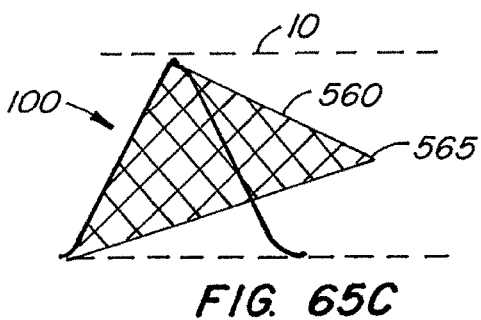
Figure 65D:
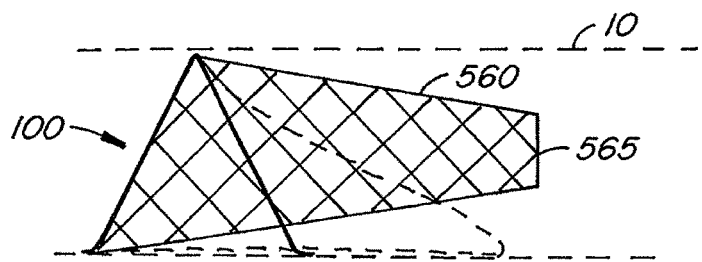
Figure 65E:
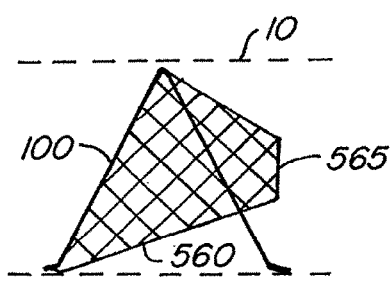
Figure 65F:
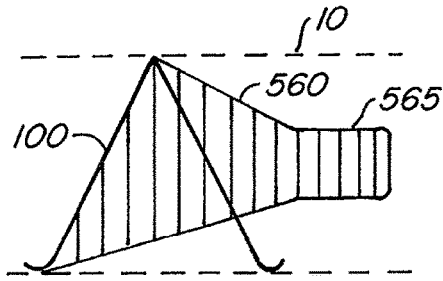

FIGS. 64-65F illustrate the use of nets or other web structures within the filtering device. The various net structure embodiments described herein are used as material capture structures within filter device embodiments of the present invention. Each of these alternative is illustrated in a support structure similar to that of device 100 in FIG. 2A and elsewhere. When deployed within the lumen 10, the material capture structure 560 has a defined shape such as a cone with a discrete apex 565 (FIG. 64A). In this embodiment, the net structure is long enough to contact the sidewall of the lumen 10 when deployed in the lumen 10. Alternatively, the apex 565 may be attached to the end 104 to keep the net 560 in the lumen flow path and out of contact with the lumen sidewall (FIG. 64B). The net 565 may also have a rounded apex 565 (FIG. 65A) or a truncated cone (flat bottom) (FIG. 65D). Alternatively, the net 560 may a discrete apex 565 so short that it will not contact the lumen sidewall when deployed (FIG. 65B). The short net may also have a rounded apex 565 (FIG. 65B), a flat apex (FIG. 65E) or a sharp apex (FIG. 65C). In addition, the net 560 may have a compound apex 565 (FIG. 65F).

Figure 66:
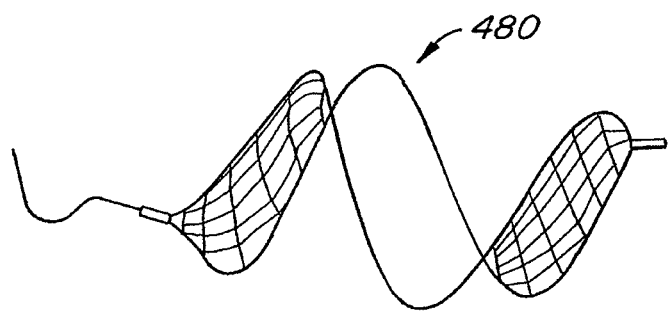
FIGS. 66 and 67 illustrate various filtering device configurations.
Figure 67:
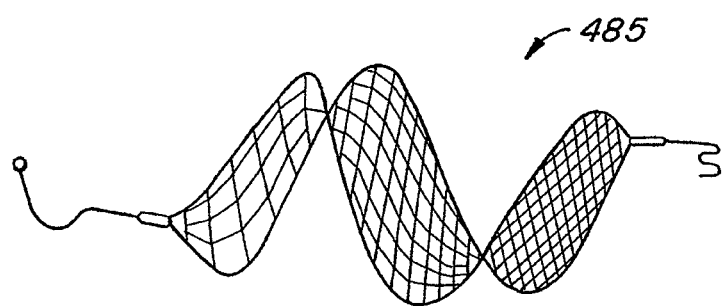

FIGS. 66 and 67 illustrate how various different features described above can be combined. For example, FIG. 66 illustrates a multi-support frame device 480 having a retrieval feature on only one end and an open frame (i.e., no filter structure). FIG. 67 illustrates an alternative multi-support frame device 485 having different retrieval features on each end, filter structures in each of the support structures and each of the filter structures having a different filter capacity. It is to be appreciated that the above described details of the construction, components, sizes, and other details of the various filter device embodiments described herein may be combined in a number of different ways to produce a wide array of alternative filter device embodiments.

The various aspects of the filter embodiments described above with regard to FIGS. 64-67 may be modified to be or used with a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIGS. 64-67 may be modified according to FIGS. 127-135 or in conjunction with a system or as further described in FIGS. 136A-138B In still other alternative embodiments, there is provided a material capture structure having one or more echogenic enhancements alone or in combination with radiopaque enhancements. In one aspect, the filter structure used in a filter includes both echogenic and radio opaque enhancements.

An one aspect, the filter includes material capture structure in the IVC filter will be viewable under fluoroscopic and ultrasound imaging modalities, including appropriate echogenic characteristics to enhance the view of the status or condition of the material capture structure while using IVUS. Enabling the material capture structure to be viewed will allow the physician to appropriately center and verify placement of a filter.

In one aspect, the filter elements or structures are doped to incorporate one or more of echogenic or radio opaque materials or treatments. In one aspect, the filaments or strands or other structures used to form the filter structure or webbing of the filter includes a radiopaque material having high echogenic properties, such as tungsten or gold, but not limited to either.

In other embodiments, one or more filaments or portions of a filament within a material capture structure includes one or more non-metallic echogenic features, such as those described elsewhere in this specification. For example, a filament or portion thereof may include air pockets either added to the material or by the use of materials with entrained air or gas that are used. In one embodiment, an ePTFE suture has echogenic properties due to air content of the ePTFE material. In other aspects, a suture material or a filament or polymer strand may also include dimpled/roughened/matrix/sponge materials, additives, or modifications to provide or enhance the overall echogenic nature of the suture, filament, material or material capture structure, in whole or in part.

In one aspect, these additional materials may assist the physician in centering or placing a filter within a vessel. In another aspect, this improvement is used in conjunction with IVUS will enable the adequate viewing of the filter portion of the filter and will allow for co-registration of filter placement along with an accurate entry/removal of the catheter through the webbing of the filter.

The advantages of this inventive aspect of a filter include, for example and not limitation, filter placement, accurate representation of filter location, ease of introducing/retracting catheter, more viewable space for more accurate assessments, ability to co-register filter location with IVUS and/or ability to better place filter in desired location.

Still other aspects of the use of the innovative filter include, for example, deployment of filters, positioning of filters, sizing of filters, and estimated treatment lengths as well as suture and/or material capture structure visibility. In still other aspects of the use of the innovative filter include, for example, deployment of a vena cava filter, positioning of a filter, sizing of a filter, and estimated treatment lengths as well as enhanced suture visibility.

In one embodiment, there is a filter delivery system with an enclosed filter. This filter would have a mesh, suture, web or other material capture structure suited to the anticipated filter use. The mesh, suture, web or other material capture structure has one or more components that is doped with a highly radiopaque material for better visibility under flouro and good echogenicity for better viewing under IVUS guidance. In still further alternative embodiments, the techniques described above may be applied to one or more material capture structure described herein. More particularly, there are alternatives for modifying a material capture structure to exhibit radio opaque, echogenic of combinations of radio opaque and echogenic characteristics may be applied to the various embodiments illustrated and described in FIGS. 30-34B, 38A-38B, 39-67, and 83-87. In one particular aspect, the filament/strand/suture 461 shown in FIG. 58 of the '7111 publication may be coated or doped as described above alone or in combination with the illustrated pharmacological coating 466.

Delivery, Recovery and Repositioning of a Filtering Device

Figure 68A:
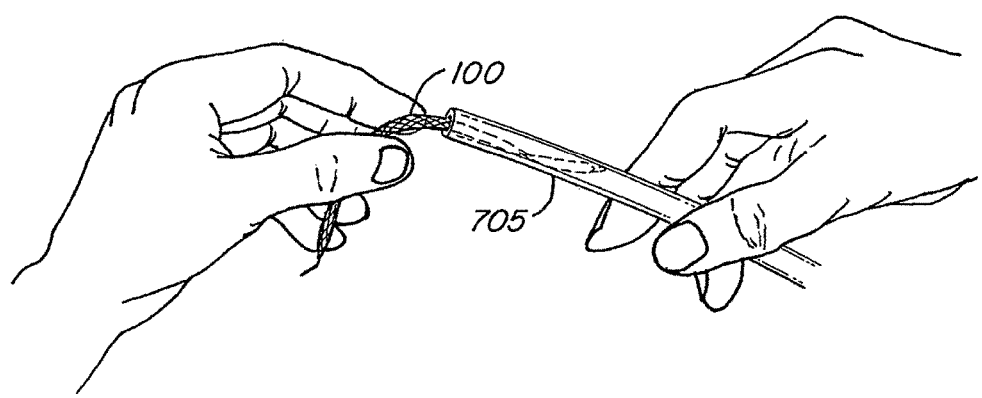
FIGS. 68A-74D illustrate various techniques related to the delivery, recovery and repositioning of filtering devices.
Figure 68B:
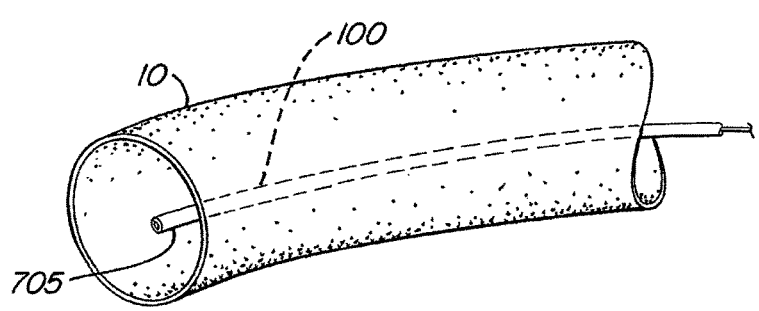

FIG. 68A illustrates an embodiment of the filter device 100 of the present invention loaded into an intravascular delivery sheath 705. The device 100 is illustrated and described above, for example, in relation to FIG. 16A. Using conventional endoluminal and minimally invasive surgical techniques, the device can be loaded into the proximal end of the sheath 705, before or after advancing the sheath 705 into the vasculature, and then advanced through the sheath using a conventional push rod. The push rod is used to advance the device 100 through the delivery sheath lumen as well as fix the position of the device (relative to the sheath 705) for device deployment. In one preferred technique, the device is loaded into the proximal end of a delivery sheath that has already been advanced into a desired position within the vasculature (FIG. 68B). The device 100 may be pre-loaded into a short segment of polymeric tubing or other suitable cartridge that allows the device 100 to be more readily advanced through a hemostasis valve.

Figure 69A:
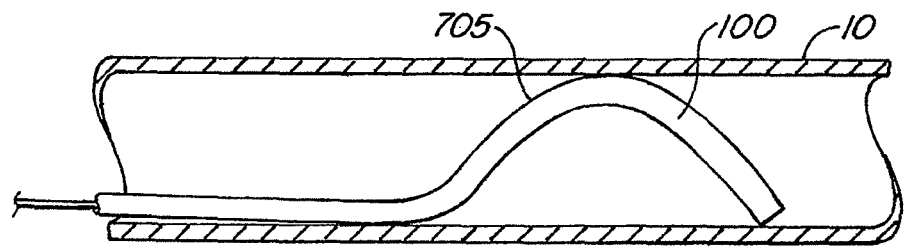
Figure 69B:
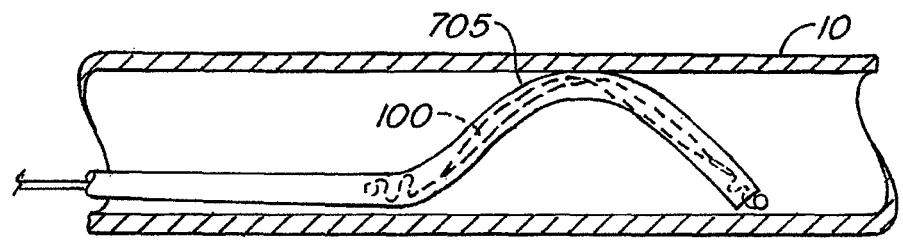
Figure 69C:
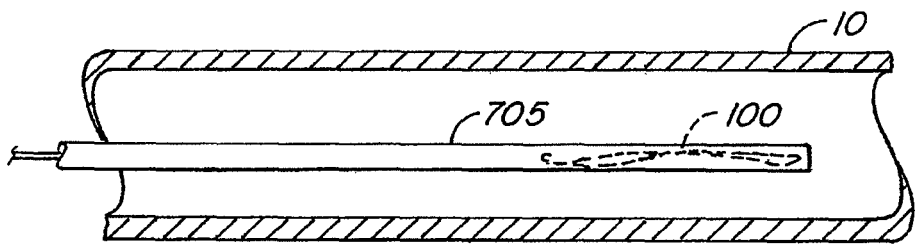
Figure 69D:
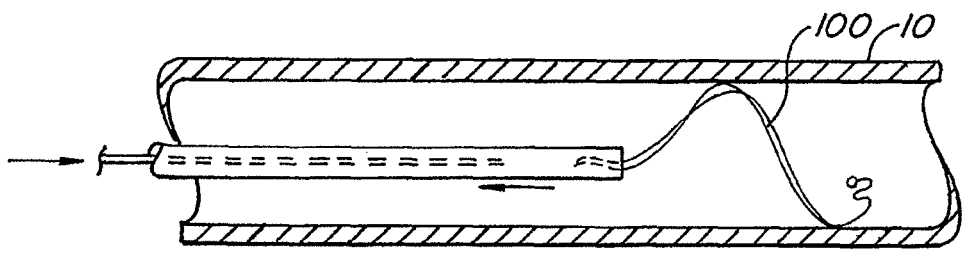

When used with a compliant delivery sheath 705, the pre-formed shape of the device 100 deforms the sheath to conform to the device shape (FIG. 69A, 69B). Accordingly, a flexible, compliant sheath 705 assumes the curvature of the stowed device. The deformation of the delivery sheath 705 helps stabilize the position of the sheath 705 in the vasculature and facilitates accurate deployment of the device 100 to the intended delivery site. In contrast, a non-compliant delivery sheath 705 (i.e., a sheath that is not deformed to conform to the preformed shape of the device 100) maintains a generally cylindrical appearance even through the device 100 is stowed within it (FIG. 69C). Regardless of the type of sheath used, device delivery is accomplished by using the push rod on the proximal side of the device to fix the position of the device within the sheath 705 and then withdrawing the sheath 705 proximally. As the device 100 exits the distal end of sheath 705, it assumes the pre-formed device shape (FIG. 69D).

Figure 70:
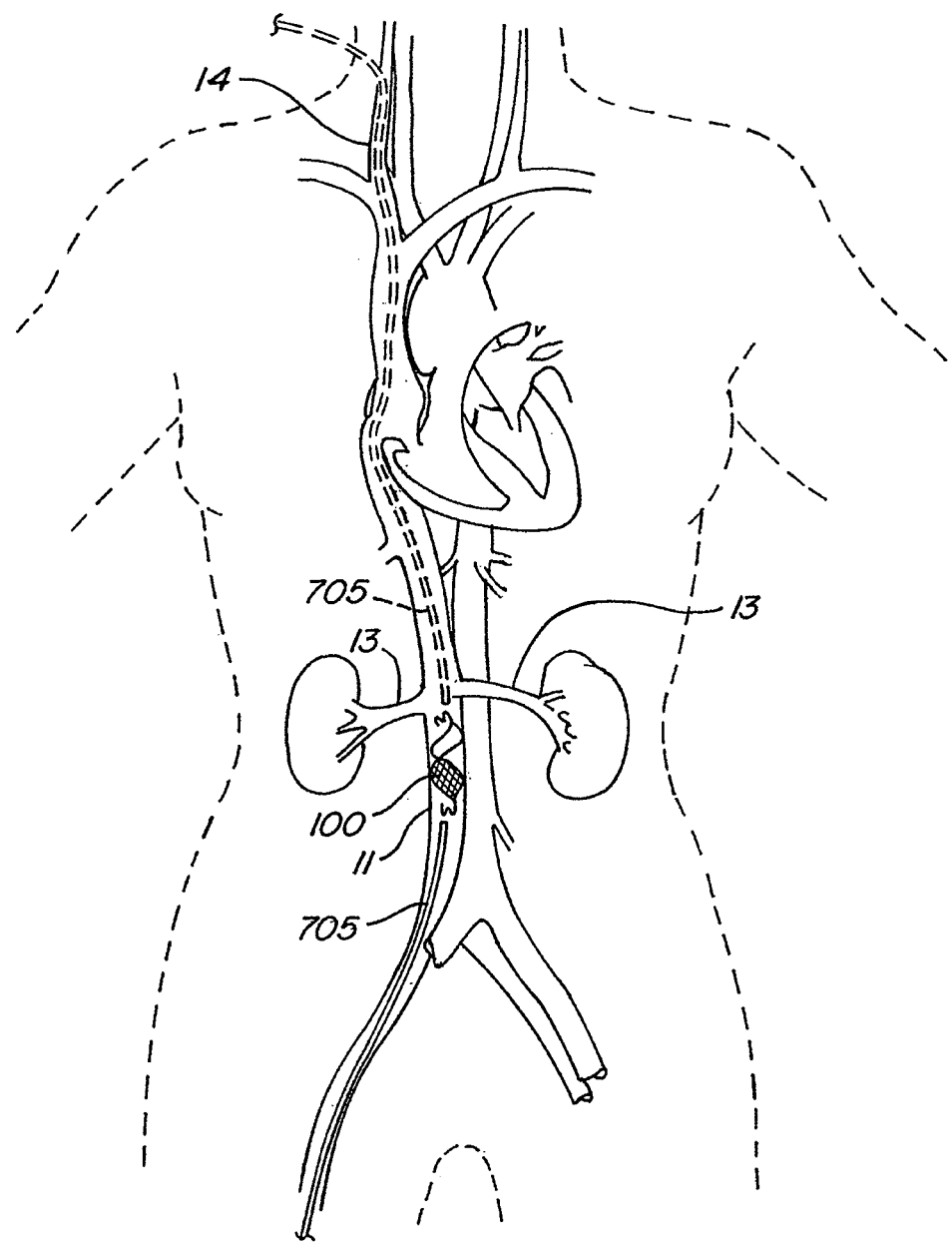

The symmetrical device shape (see e.g., devices in FIGS. 15 and 16A), facilitates the deployment and retrieval of the device from multiple access points in the vasculature. A device 100 is shown positioned in the vasculature within the inferior vena cava 11 immediately below the renal veins 13 (FIG. 70). A femoral access path (solid) and a jugular 14 access path (phantom) are illustrated. The femoral access path (solid) and a jugular access path may each be used for device deployment, repositioning and retrieval. Alternatively, the vena cava could be accessed via brachial or antecubital access for device deployment, repositioning and retrieval.

Figure 71A:
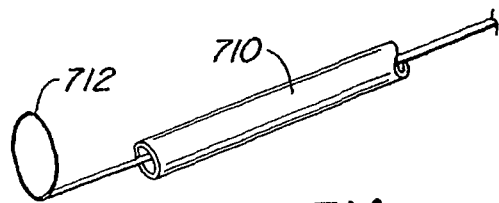
Figure 71B:
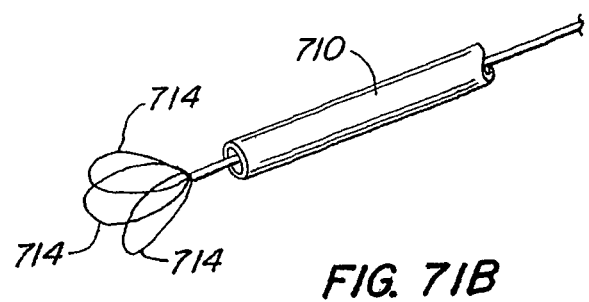

Retrieval of the devices is most preferably accomplished by endoluminal capture using one of the retrieval features described herein. (i.e., FIGS. 27A-E) The retrieval features described herein have been designed to work well using a commercially available snares two of which are illustrated in FIG. 71A and FIG. 71B. The single loop Gooseneck snare 712 is illustrated in FIG. 71 inside of a recovery sheath 710. The multiple loop Ensnare 714 is illustrated in FIG. 71B inside of a recovery sheath 710. These conventional snares are controlled by a physician using a flexible, integral wire.

Figure 72A:
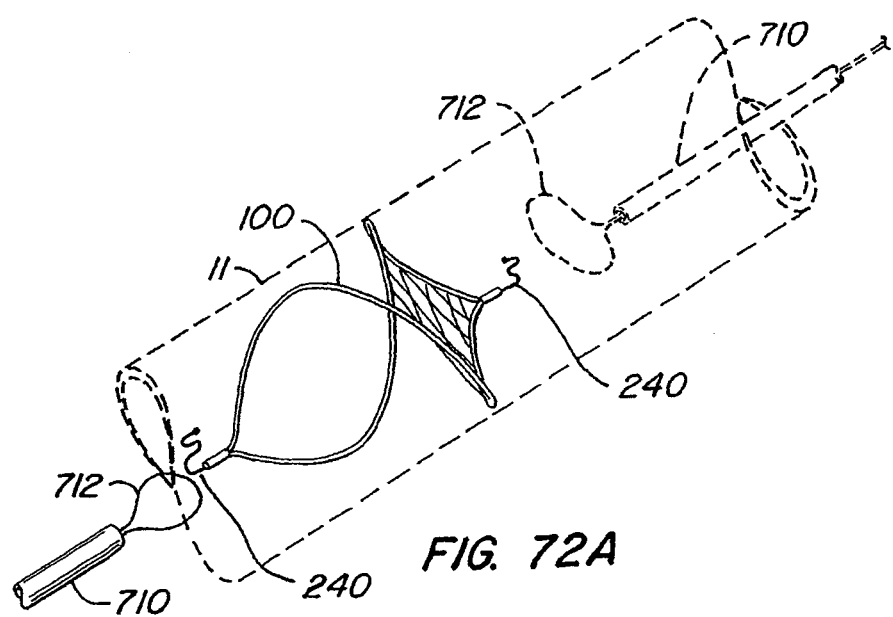
Figure 72B:
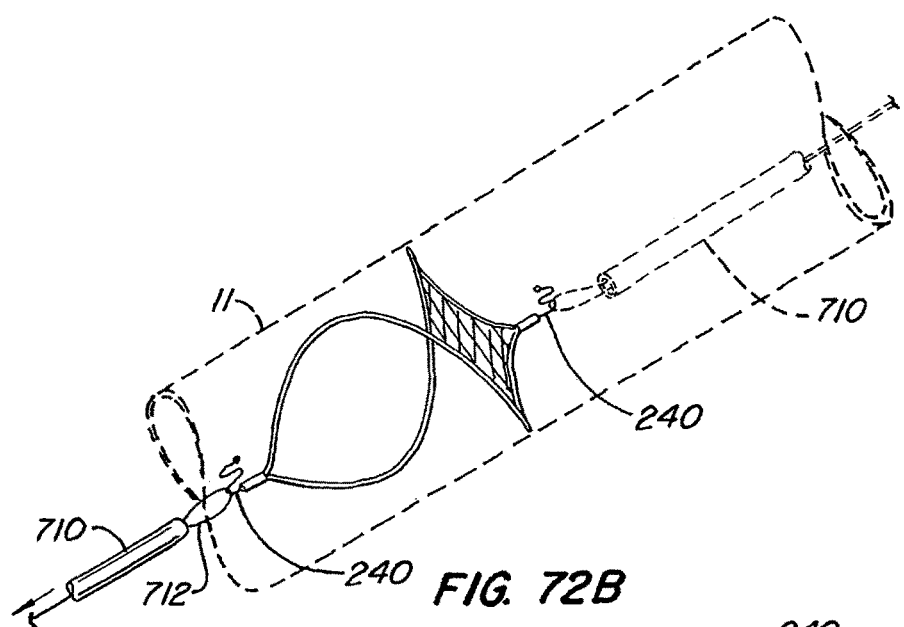
Figure 72C:
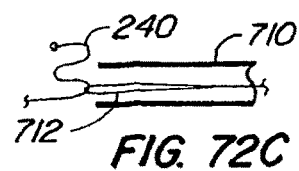
Figure 72D:
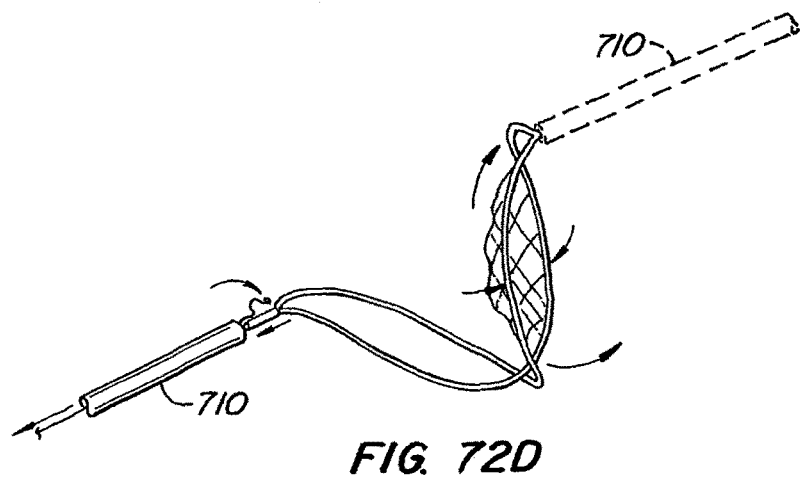

The sequence of device recapture and removal from a body lumen (here the vena caval 1) is illustrated in FIGS. 72A-C. In these figures, the solid lines are for a femoral recovery and the phantom lines are for a jugular recovery (e.g., FIG. 70). A collapsed snare is advanced via a delivery sheath to the proximity of the retrieval feature 240 (FIG. 72A). Once in place, the snare 712 is exposed and assumes a pre-defined expanded loop shape which is looped over the retrieval feature 240 as illustrated from either end in FIG. 72B.

The snared device 100 can then be either pulled into the sheath 710, or alternatively and more preferably, the recovery sheath 710 is advanced over the device 100 while maintaining positive control of the snare 712 as the sheath 710 advances over the device 100. Advancing the recovery sheath 710 over the device 100 facilitates atraumatic removal of the device 100 from any tissue that has grown in or around the device 100. The retrieval action, which tends to collapse the device radially inward (FIG. 72D), also facilitates removal from any tissue layer formed on the device. Recovering the filtering device by pulling on a flexible retrieval feature attached to the filtering device.

Moreover, pulling on a portion of the filter structure (i.e., a retrieval feature) removes the opposing spiral elements from the lumen wall.

As the device is drawn into the sheath 710, the pre-formed shape of the device also urges the support members away from the lumen wall which also assists in atraumatic device removal.

Figure 72E:
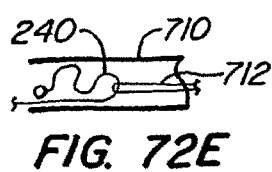
Figure 72F:
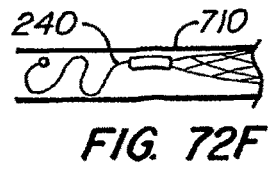
Figure 73A:
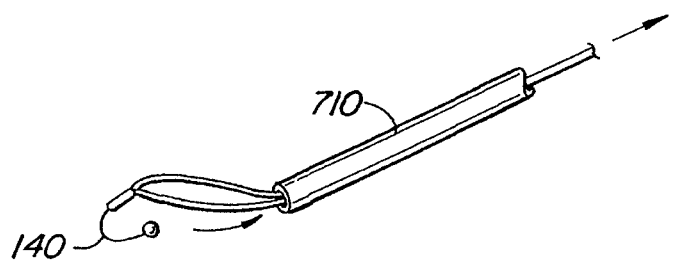
Figure 73B:
Figure 73C:
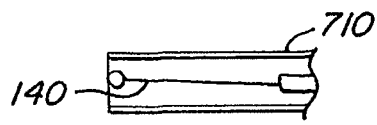
Figure 73D:
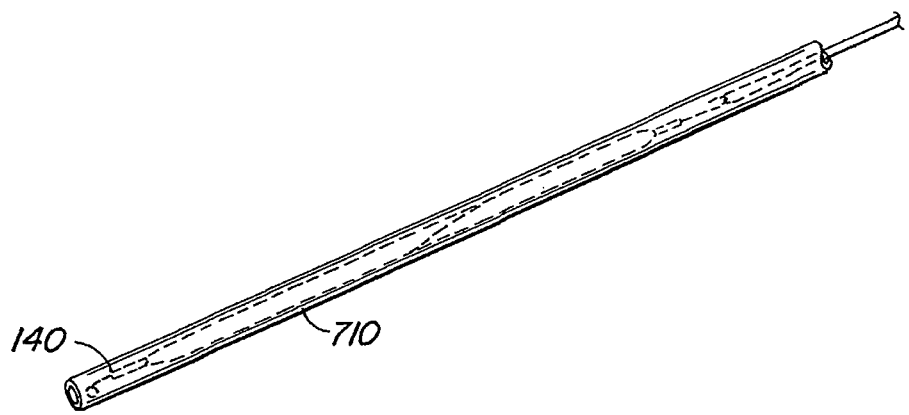

The flexible retrieval element 240 assumes a collapsed configuration as it is being drawn into the recovery sheath as illustrated in FIG. 72C and FIG. 72E. Note that the retrieval feature 240 on the opposite end of the device assumes a straightened configuration as is drawn into the recovery sheath (FIG. 72F). An additional embodiment, in which a single curved retrieval feature 140 (FIG. 27A) is withdrawn into the delivery sheath 710 as shown in FIG. 73A. The distal retrieval feature (relative to the snare) assumes a straightened configuration FIG. 73C from a curved configuration FIG. 73B as is completely withdrawn into the sheath FIG. 73D.

Additionally, repositioning the filter 100 from one lumen position to another is illustrated in FIGS. 74A-74D. Because of the atraumatic design of filter devices of the present invention, repositioning of the filter device 100 may be accomplished by fully recapturing (FIG. 74C) or only partially recapturing (FIG. 74B) the device 100 into a recovery sheath 710. The atraumatic design of the device 100 allows the device to simply secured by one end (FIG. 74B) and pulled along the lumen wall into the desired position and then released. The delivery sheath and recovery sheath are provided with the same reference numbers since filter devices of the present invention may be deployed into and recovered from the vasculature using sheaths that are about the same size. As such, devices of the present invention may be deployed into the vasculature from a delivery sheath having a first diameter. Then, the device may be retrieved from the vasculature using a recovery sheath having a second diameter no more than 2 Fr larger than the first diameter (1 Fr=0.013"=⅓ mm). Alternatively, the second diameter may be no more than 1 Fr larger than the first diameter or, alternatively, the first diameter is about the same as the second diameter.

Figure 74A:
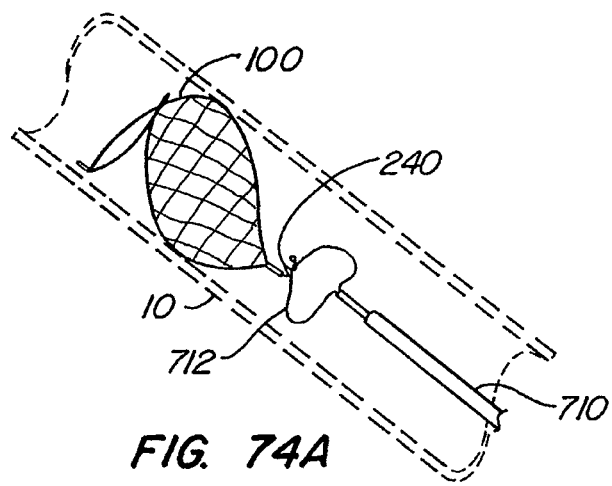
Figure 74B:
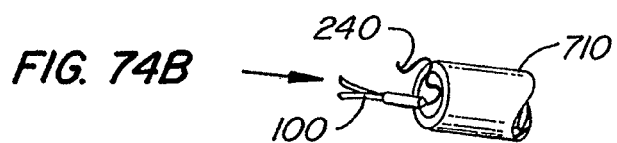
Figure 74C:
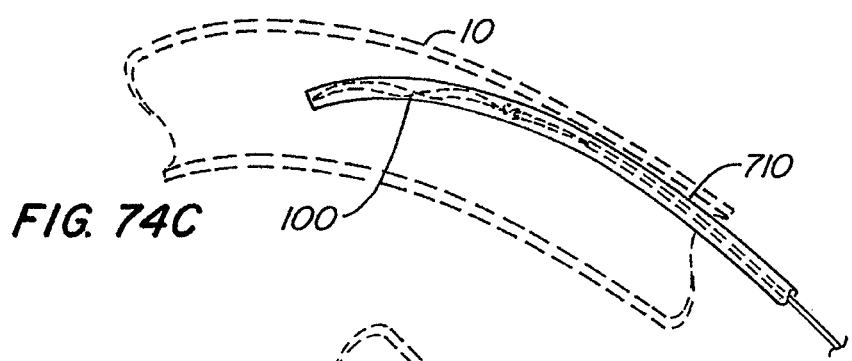
Figure 74D:
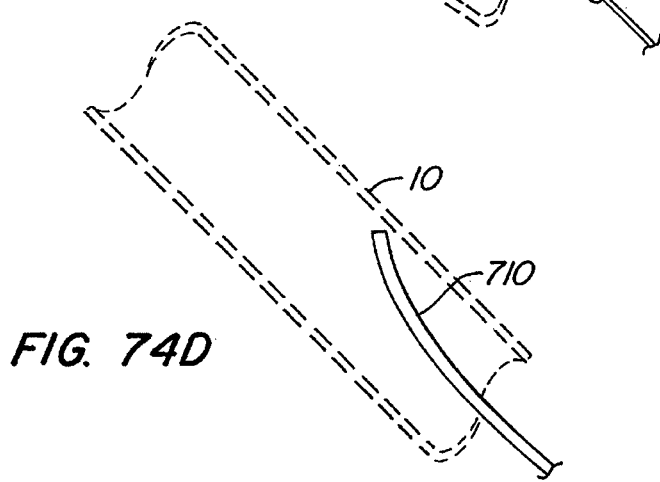

In a full recovery, the device is pulled completely into a recovery sheath (FIG. 74A), the sheath is repositioned from the original position (FIGS. 74A, 74C) to a second position (FIG. 74D) and deployed into the vasculature again (FIG. 69D). In the case where the snare wire columnar strength is insufficient to redeploy the device, the snare can be delivered within a secondary inner sheath within the retrieval sheath. This allows the positive control of the retrieval feature to be obtained, such as illustrated in FIG. 74B, the device withdrawn into the retrieval sheath and then redeployed with the inner sheath acting as a push rod.

Various Methods of Using Filtering Devices

Figures 75G, 75H, 75I:
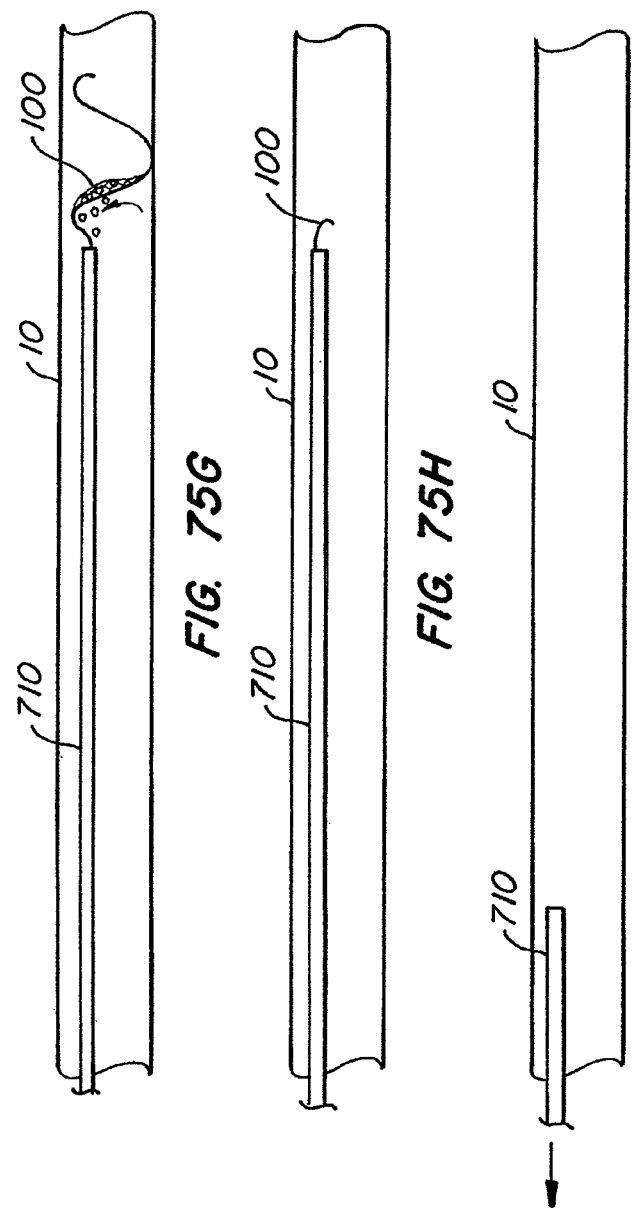

Embodiments of filter devices of the present invention may be used in methods of providing distal protection in procedures such as, for example, thrombectomy, arthrectomy, stenting, angioplasty and stent grafting. It is to be appreciated that embodiments of filter devices of the present invention may be used in veins and arteries. An exemplary procedure is illustrated in FIGS. 75A-I and FIGS. 76A-E. In each procedure, the device 100 is positioned in an untethered fashion adjacent to the treatment region 730. The sequence FIGS. 75A-I illustrate the delivery sheath 710 positioning FIG. 75A, complete deployment FIG. 75B into the lumen 10. A conventional treatment device 750 using mechanical, electrical energy or other suitable method is used to clear the undesired material 732 from the lumen wall (FIG. 75C). Some debris 734 removed from the lumen wall through the use of treatment device 750 is subsequently embolized into the blood stream (FIG. 75C) and trapped by the filter 100 (FIG. 75D). The conventional treatment device 750 is removed (FIG. 75E) and thereafter the advancement of recapture sheath 710 is advanced into recovery position (FIG. 75F).

The entrapped debris 734 is then removed prior to recapturing the device with methods such as, for example, aspiration, delivery of therapeutic agents or maceration. Additionally, the device and entrapped debris can be recaptured in whole and removed via the same sheath used to recapture the device as illustrated in FIG. 75G. The device 100 and debris 734 are then withdrawn into the sheath 710 (FIG. 75H), and the sheath withdrawn from the vasculature (FIG. 75I).

Figure 76A:
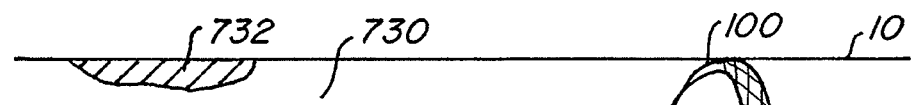
Figure 76B:
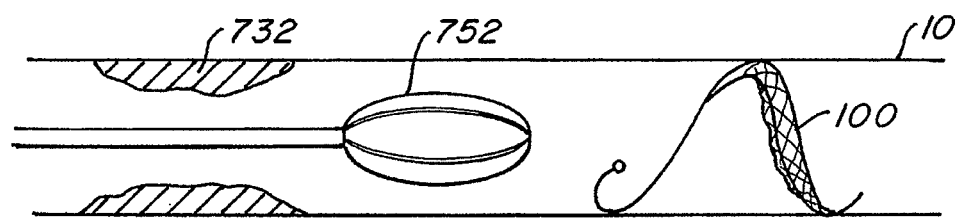
Figure 76C:
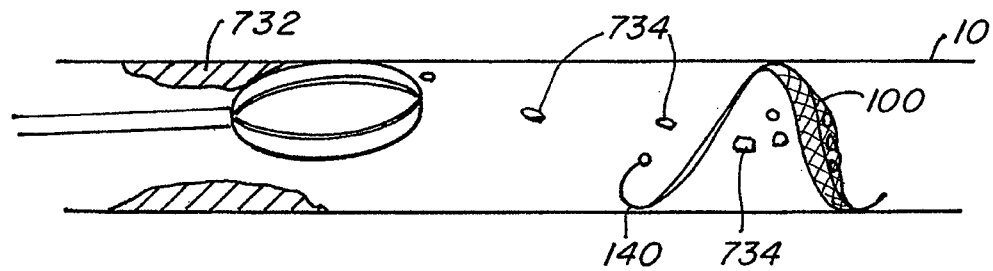
Figure 76D:
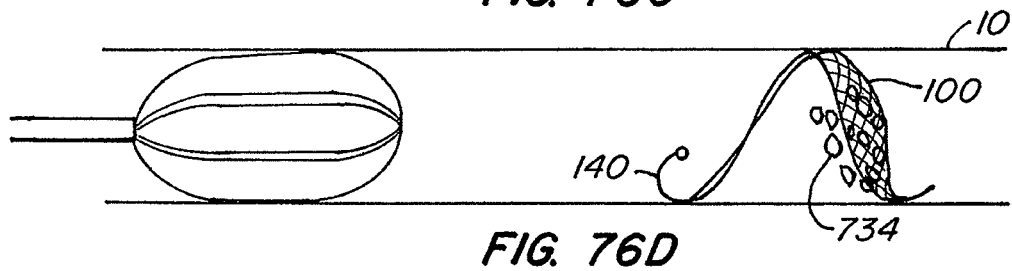
Figure 76E:
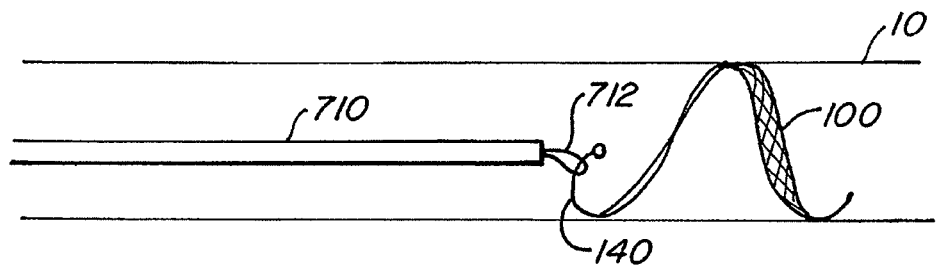

Similarly, an additional use of the invention as un-tethered distal protection is illustrated in FIGS. 76A-E, in which a balloon 751 is used to expand the lesion 732 such as in the case of balloon angioplasty, often performed prior to stenting a vessel to keep it open. For this procedure a balloon catheter is advanced to the lesion site and inflated FIG. 76B, plaque 732 is pushed outward by the balloon (FIG. 76C), thus reestablishing normal blood flow. Any particulate matter 734 embolized by the procedure is trapped by the filter (FIG. 76D). The debris 734 can then be removed prior to filter retrieval as previously described or the device with trapped debris can be removed together.

An additional method practiced widely in the art is the use of tethered distal protection adjunctive to the previously described procedures (i.e., the device 100 remains tethered during the procedure). Embodiments of the filtering device of the present invention may also be used for this purpose as illustrated in FIGS. 77A-77E. Positive control of the filter 100 is maintained via an integral wire or snare connected to the device 100. The connection between the integral wire or snare to the device 100 is maintained during the procedure and may be, in some embodiments, used as a guidewire. As illustrated in FIG. 77B, connection to the device 100 is maintained a while performing a procedure to treat the vasculature in proximity to the location (i.e., treat the lesion 732).

An example of a tethered distal protection method is illustrated in FIGS. 77A-77E. An embodiment of a filter device 100 is deployed distal to the lesion 732 to be treated (FIG. 77A), the treatment is initiated (FIG. 77B), and embolized material 734 is captured in the filter 100 (FIG. 77C). Thereafter, the debris 734 is removed prior to filter recapture or, alternatively, with treatment in the filter 100 via a sheath as previously described. The device 100 is recovered into the sheath (FIG. 77D) and removed from the lumen 10 (FIG. 77E).

Figure 78A:
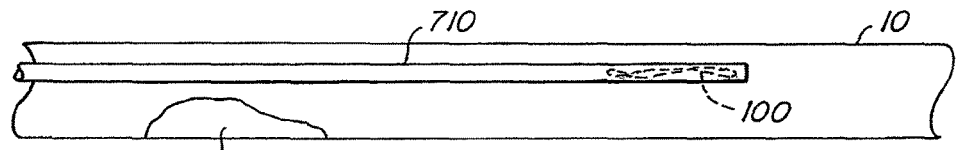
Figure 78B:
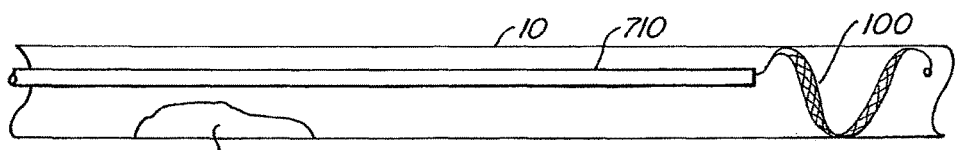
Figure 78C:
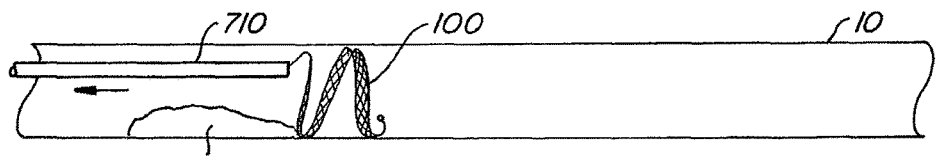
Figure 78D:
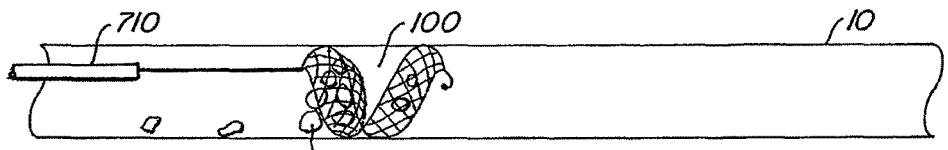
Figure 78E:
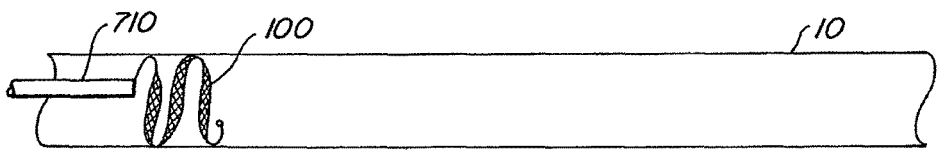
Figure 78F:
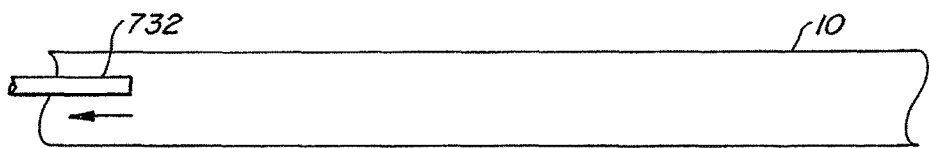

A tethered device (FIG. 77A, 78A) can also be employed to mechanically dislodge and remove embolic material 732 from a vessel 10, such as in the case of a thrombectomy. This offers a simple means of removing and trapping debris without requiring multiple devices to achieve the same goal. For this method, the tethered device is advanced downstream of the lesion site (FIG. 78A), and deployed (FIG. 78B). The tethered, deployed filter 100 is then drawn across the lesion 732 (FIG. 78C) to pull the thrombus from the vessel wall and into the filter 100 (FIG. 78D). The embolized material 734 is then removed via the methods previously described (FIG. 78E), tethered device is drawn into the sheath and removed from the lumen (FIG. 78F).

The various aspects of the filter embodiments described above with regard to FIGS. 68A-78F may be modified to be or used with a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIGS. 68A-78F may be modified according to FIGS. 127-135 or in conjunction with a system or as further described in FIGS. 136A-138B Delivery of Pharmacological Agents Using Filtering Devices Embodiments of the filter device of the present invention may also be used for delivering a pharmacological agent within a lumen. Delivery of a pharmacological agent within a lumen may be accomplished using any component of the filtering device. For example, the filter support structure may deliver a pharmacological agent. In one alternative, the support structure is covered by a multi-lumen structure and the multi-lumen structure is configured to release a pharmacological agent. In one alternative, a lumen of the multi-lumen structure is at least partially filled with a pharmacological agent. In another aspect, a lumen in a multi-lumen structure has ports that allow for the release of a pharmacological agent stored within the lumen. In one alternative, a cavity formed in a support member is filled with a material. In one aspect, the material in the cavity is a pharmacological agent. The filter may deliver a pharmacological agent. In one aspect the material capture structure is coated with a pharmacological agent.

Additional embodiments of the invention provide for the ability to deliver therapeutic agents via the material capture structure as well as the support structure covering. FIG. 79 illustrates a therapeutic agent coating 780 attached to a filament 118/461. Alternatively, FIG. 79x illustrates a biodegradable echogenic coating or covering 780x on a wire support or filament 118/461. The biodegradable echogenic coating or covering 780x may be any of the enclosed echogenic enhancements or features described herein. In one aspect, the biodegradable echogenic coating or covering may include holes in degradable tubing, a dip coat rough surface or bubbles formed in a degradable tubing.

FIG. 80 illustrates a composite structure 789 formed by having one or more cavities formed in a support structure 105 filled with one or more therapeutic agents or other material. The cavities may be formed as described above with regard to FIGS. 33, 35 and 36. These composite structures can be designed to elute a therapeutic agent via a specific elution curve by varying thickness, density as well as location of the therapeutic agent on the filter device component. This therapeutic agent could be, for example, any pharmacological agent used in the treatment of the body, an anti-coagulant coating (i.e., Heparin), an anti-proliferative agent prevent or slow fibrous tissue growth, other agents selected from those used in vascular stents including drug eluting stents.

FIG. 81 and FIG. 82 illustrate the use of the covering 420, 420a positioned over a support structure as the delivery means for providing pharmacological agents into a lumen. FIG. 81 illustrates a pharmacological agent 782 in a lumen 424a of a multi-lumen structure such as described above with regard to FIGS. 44, 45. As illustrated in FIG. 82, the therapeutic agent 784 fills a lumen 424 in a multi-lumen covering 420a over the support structure 105. Release ports 785 formed in the side of lumen 424 allow delivery of the agent to the blood or tissue. Control of the therapeutic agent elution parameters could be controlled via the size or spacing of the release ports 785 and/or through the use of controlled release pharmacological agents.

The various aspects of the filter embodiments described above with regard to FIGS. 79-82 may be modified to be or used with a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIGS. 79-82 may be modified according to FIGS. 127-135 or in conjunction with a system or as further described in FIGS. 136A-138B. In one representative example, FIG. 81x illustrates an exemplary embodiment where an echogenic material or radio-opaque material is used to fill the holes in the segmented multi-lumen structure of FIG. 81.

Prototype Filtering Devices

FIGS. 83A-83E illustrate perspective (FIG. 83A), plan (FIG. 83B), bottom (FIG. 83C), side (FIG. 83D) and end (FIG. 83E) views of a prototype filter according to an embodiment of the present invention. The prototype has previously described features and common elements have the same reference numbers have been incorporated into these illustrations. The support structure 105, 110 was formed with electropolished 0.015" OD Nitinol wires, shape set to form two substantially equal open loops 126, 128 of approximately 1" diameter. The support structure wire used for support structure 105 was ground down to a wire diameter of 0.010" and used to form flexible retrieval feature 240 on each end (i.e., FIG. 28C). An atraumatic feature (here ball 242) is created on the end of the wire by exposing the wire to plasma. A radio opaque marker, here a Tantalum marker band 248 attached below the ball 242. The material capture structure 115 has filter cells 119 constructed with filaments 118. The filaments 118 are ePTFE monofilament. The filaments are attached to the support structure using method shown in FIG. 47. The cover 185 used to join the ends is a tapered Nitinol tube 186 that is crimped around the support structures, as illustrated in FIG. 24.

Figure 83A:
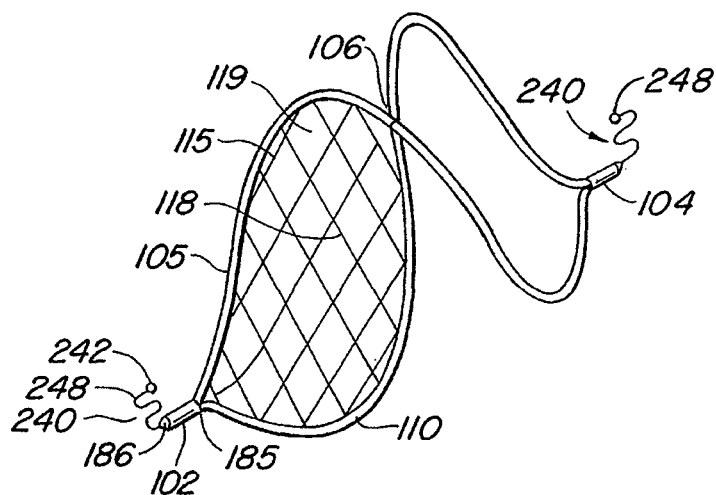
FIGS. 83A-87 illustrate several filtering device prototypes.
Figure 83B:
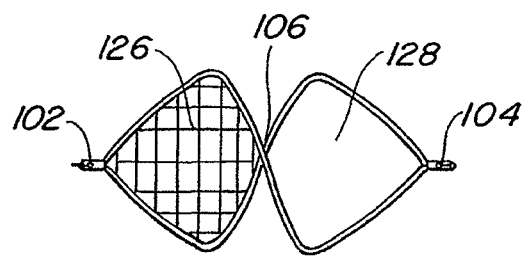
FIG. 83BX illustrates echogenic enhancements of a version of the device of FIG. 83B.
Figure 83C:
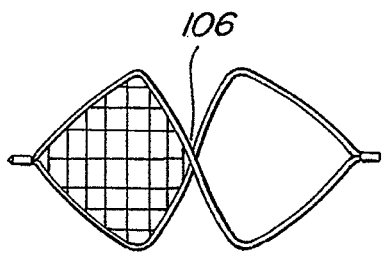
Figure 83D:
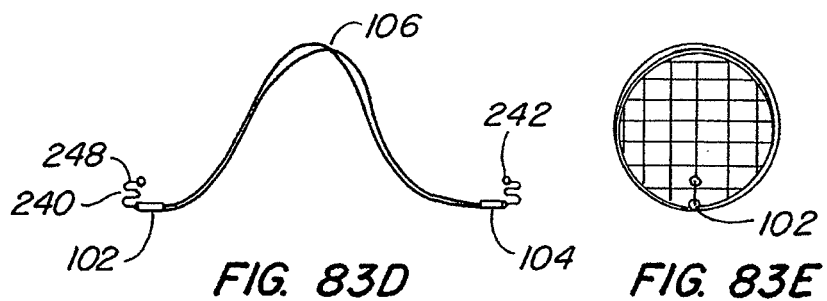
Figure 83E:
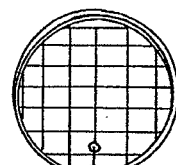
Figure 84A:
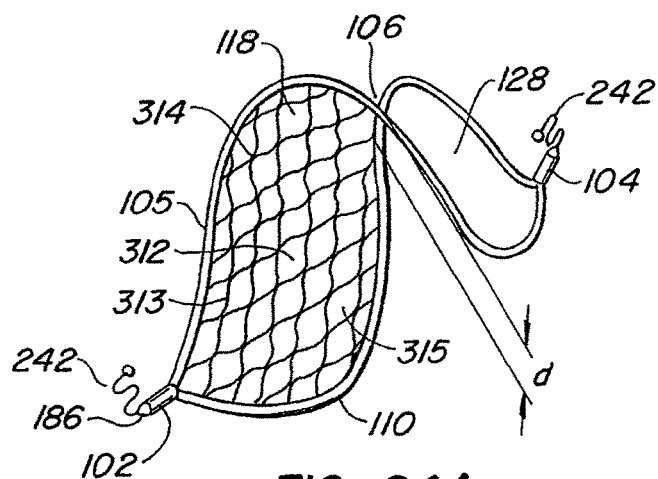
Figure 84B:
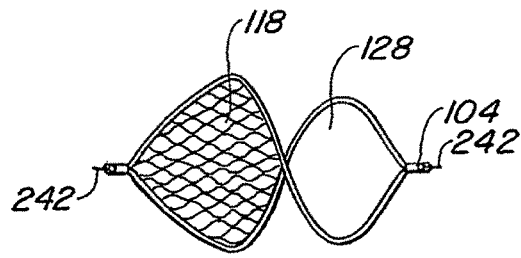
Figure 84C:
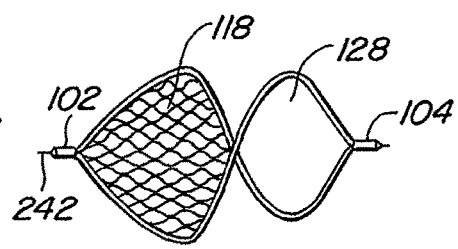
Figure 84D:
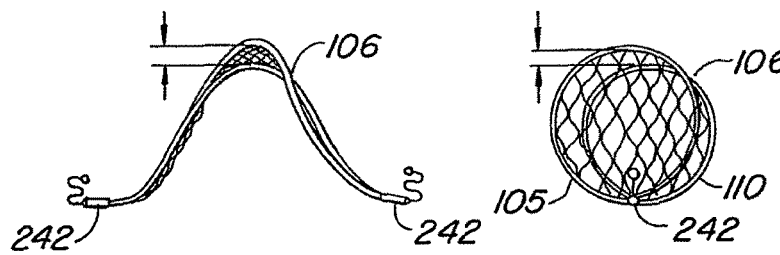
Figure 84E:
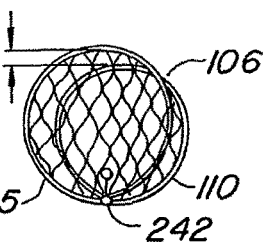
Figure 85A:
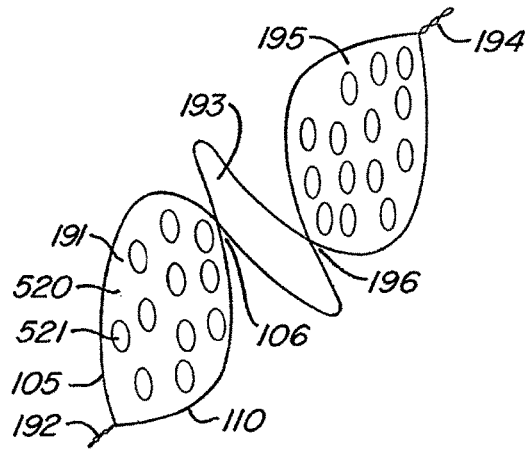
Figure 85B:
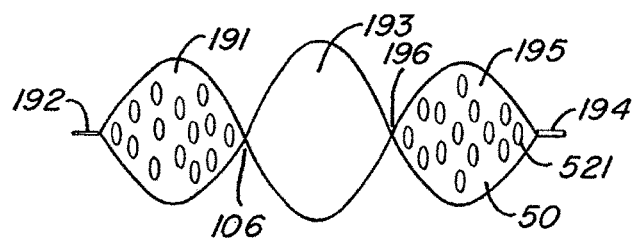
Figure 85C:
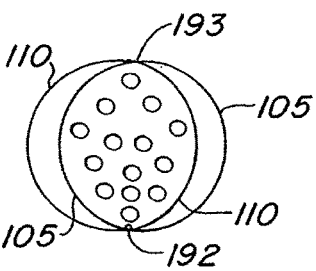
Figure 85D:
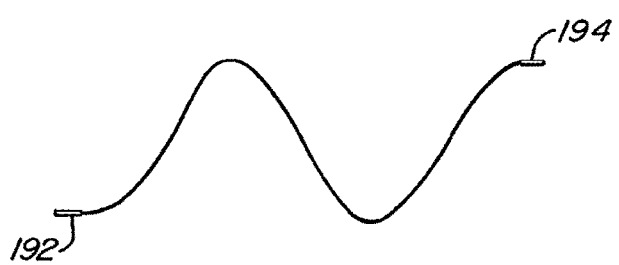
Figure 86A:
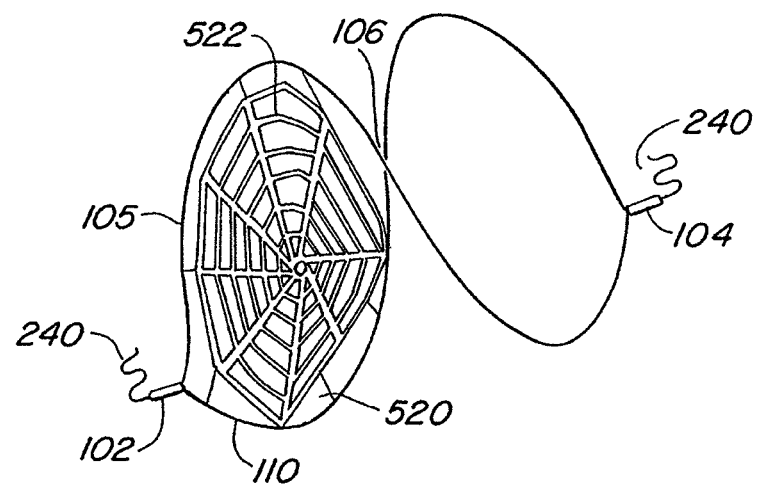
Figure 86B:
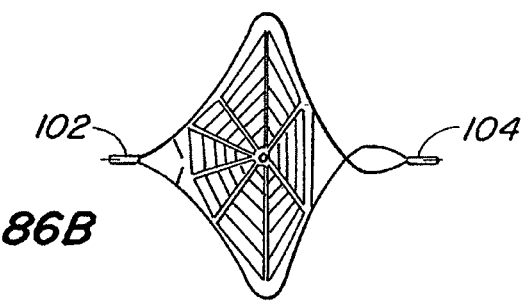
Figure 86C:
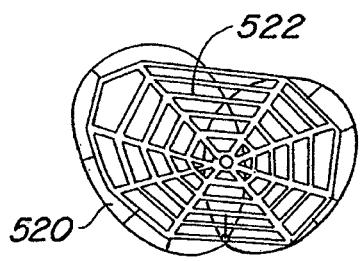
Figure 86D:
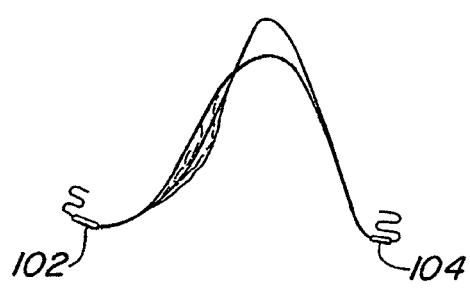

FIGS. 83Ax and 83Bx are based on FIGS. 83A and 83B and indicate where possible echogenic or radio opaque or other image modality enhancing alteration may occur. As shown in FIG. 83Ax, a plurality of dark circles are used to indicate multiple possible locations for positioning such enhancements. Possible locations include the tip 242, crimp 185/186, support wires 105, 110 at various points along the spiral path, along a portion of the material capture structure 118, at locations where the material capture structure is attached to a support member, at, near or on either side of the cross over 106, along the support frame that does not contain a material capture structure and the crimps and retrieval tail 248 on the distal end 104. In the illustrative embodiment of FIG. 83AX, there are locations indicated at tail 242, proximal end 102 or crimp 186, a mid-loop web capture frame, at the intersection or cross of web filaments, at a web attachment point to a support frame, at a crossover, along the non-capture structure loop, at the distal end or the distal retrieval tail.

FIG. 83Bx illustrates the use of any of the variety of echogenic coverings described herein in use over the support frames of the filter. The indicated regions represent a continuous echogenic coating or covering. The covering may be over a wire, used as a web attachment or over the terminal ends/tails, in some embodiments. These locations are merely exemplary and other locations for echogenic enhancement are possible as described herein.

In a similar way, the filter having fixation elements illustrated in FIG. 88x1 along with the enlarged view of the crimp and fixation element (FIG. 88x2) may similarly be modified as described above and herein. FIG. 88X1 illustrates the use of an echogenic feature (represented here as a solid circle) that is coincident with a fixation element. In an exemplary embodiment, the echogenic feature has holes, a rough surface, a wire wrap or other echogenic feature described herein. In addition, the placement of the echogenic feature may be used to denote location and depth of fixation elements. FIG. 88X2 is an enlarged view of an anchor crimp 805x with an echogenic wrap or covering as shown in FIG. 88X1. The echogenic wrap may be a coil or a tubing with holes or bubbles as described elsewhere herein. As also shown in FIG. 88X2, the anchor or fixation element 810x may have an echogenic covering or wrap that varies with depth to aid in determine depth of penetration. The covering or wrap may include variations to the pitch of a coil on the fixation element as well as the hole size or density provided in the covering. The variations to a fixation element described in relation to FIGS. 88X1 and 88X2 may also be applied to other fixation element embodiments, such as FIG. 119 for example.

FIGS. 84A-84E illustrate perspective (FIG. 84A), plan (FIG. 84B), bottom (FIG. 84C), side (FIG. 84D) and end (FIG. 84E) views of a prototype filter according to an embodiment of the present invention. This embodiment is similar to the embodiment of FIG. 83A. In this embodiment, the material capture structure 115 is replaced with material capture structure 312 made of an extruded polymeric netting as described above with regard to FIG. 56. This embodiment also illustrates how the support structures 105, 110 are not in contact (i.e., separated by a distance "d") at the crossover 106.

FIGS. 85A-85E illustrate perspective (FIG. 85A), plan (FIG. 85B), side (FIG. 85D) and end (FIG. 85C) views of a prototype filter according to an embodiment of the present invention. This embodiment is similar to the filter device described in FIG. 14A and common reference numbers are used. In this embodiment, a material capture structure is constructed from a continuous sheet of polymeric material 520 into which circular holes 521 are created via mechanical or laser cutting (as described above with regard to FIG. 61A).

FIGS. 86A-86D illustrate perspective (FIG. 86A), plan (FIG. 86B), side (FIG. 86D) and end (FIG. 85C) views of a prototype filter according to another embodiment of the present invention. In this prototype filter, a material capture structure constructed from a continuous sheet of polymeric material 520 into which a pattern 522 voids are created via mechanical or laser cutting to create a net-like structure (FIG. 61C).

Figure 87:
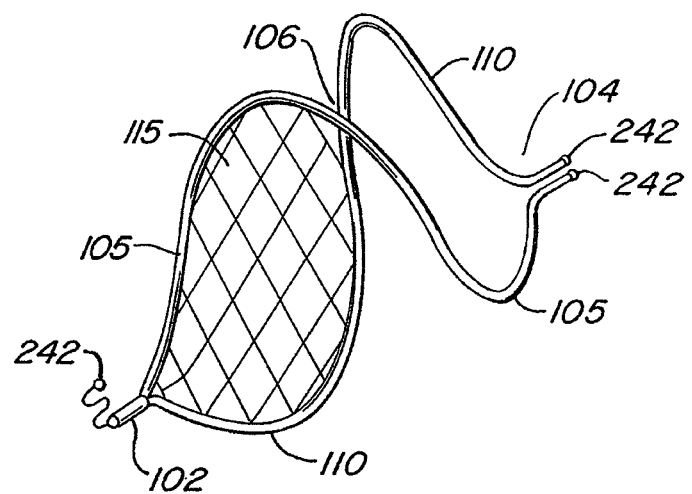

FIG. 87 is a perspective view of a prototype filter according to an embodiment of the present invention similar to the embodiment described in FIGS. 83A-83E above. In this embodiment the elongate structural members 105, 110 are joined at only one end (i.e., end 102). The support structure elements on the unconnected end are finished with plasma balls 242 to prevent vessel perforation and facilitate deployment and retrieval.

The various aspects of the filter embodiments described above with regard to FIGS. 83A-87 may be modified to be or used with a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIGS. 83A-87 may be modified according to FIGS. 127-135 or in conjunction with a system or as further described in FIGS. 136A-138B.

Figure 88:
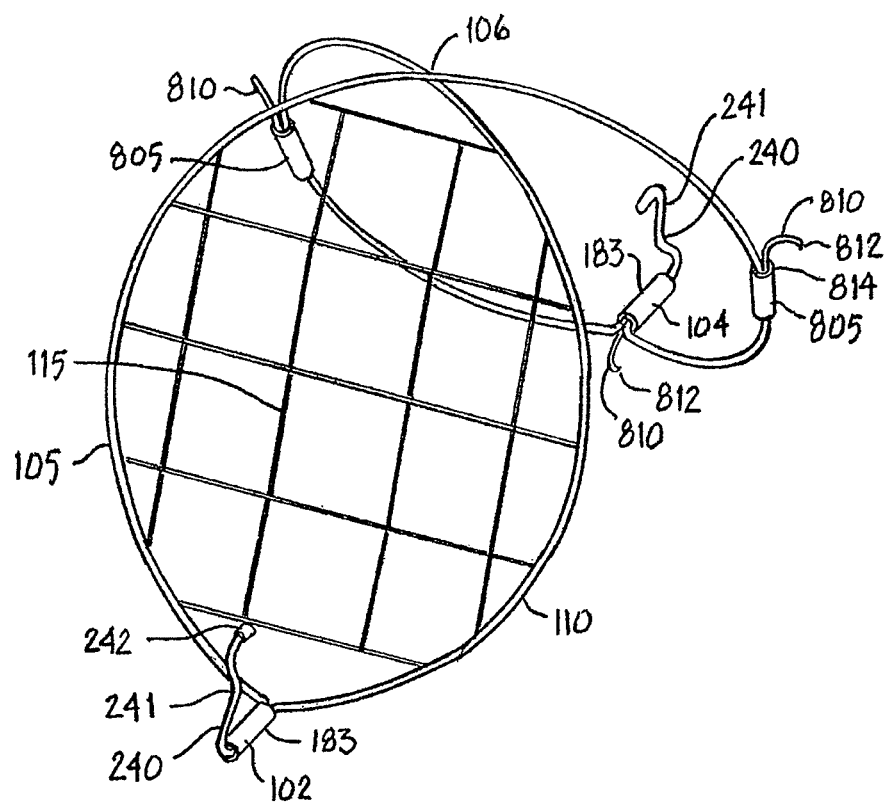
FIG. 88 is a perspective view of an endoluminal filter having three tissue anchors.
Figure 91:
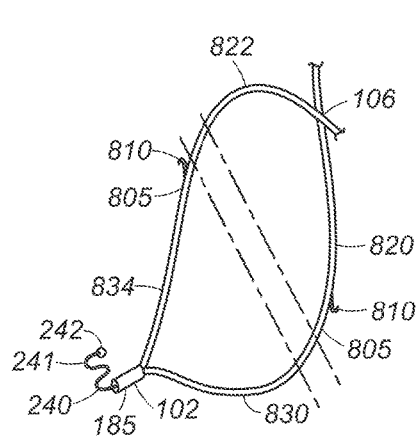
FIG. 91 is a perspective view of a filter device performed by joining the device illustrated in FIG. 90A with the device illustrated in FIG. 90B.
Figure 99:
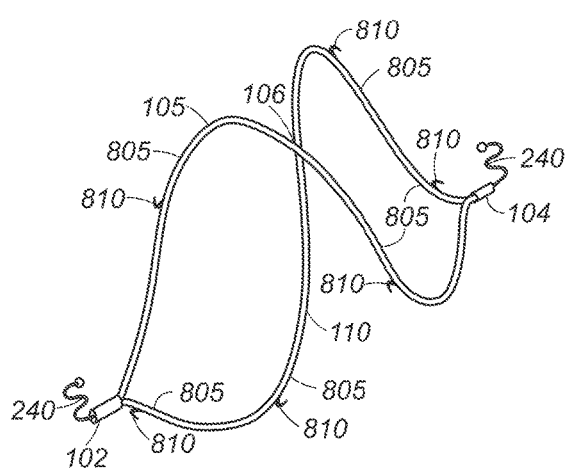
FIG. 99 illustrates a support frame without a material capture structure showing the placement and orientation of various fixation elements.

Some filter embodiments may include one or more fixation elements, tissue anchors or tissue engagement structures to aid in maintaining the position of the filter once deployed. The various alternative fixation elements, tissue anchors or tissue engagement structures are described below and may be adapted into a variety of combinations and configurations. FIG. 88 is a perspective view of an endoluminal filter having a first support member 105 having a first end and a second end and a second support member 110 attached to the first end of the first support member 105 or the second end of the first support member 105. In the illustrated embodiment, the first support member 105 and the second support member 110 are each formed from a single wire that extends from at least the first end 102 to the second end 104. The support members may extend beyond the end 102, 104 and be used to form retrieval features 240 or other elements of the filter as described below. In one illustrative example, the first support member 105 may be formed into a tissue anchor and the second support member 105 may be formed into a retrieval feature. The illustrative embodiment has a retrieval feature 240 on the first end 102 and a retrieval feature 240 on the second end 104. The second support member 110 forms a crossover 106 with the first support member 105. In one embodiment, the second support member 110 is attached to the first end of the first support member 102 and the second end of the first support member 104. A material capture structure 115 extends between the first and second support members 105, 110, the crossover 106 the first end or the second end of the first support member 105. In the illustrated embodiment, the material capture structure extends between the first and second support structures 105, 110, the first end 102 and the cross over 106. At least one tissue anchor 810 is on the first support member 105 or the second support member 110. In the illustrated embodiment, tissue anchors are provided on body supports 105, 110. In this embodiment, the fixation element 810 is a separate structure having a body 814 and a tip 812 suited for penetrating into or through the walls of lumen 10. The fixation element or tissue anchor 810 is attached to the elongate body using a suitable attachment 805. The attachment 805 may be a crimp (as illustrated) or any other suitable technique for joining the fixation element 810 to the elongate body. Suitable techniques include, by way of non-limiting example, a crimp or other joining technique with a discrete detent, a swage or other joining technique with circumferential constriction, soldering, welding, brazing, shrink fit tubing, epoxy, multi-lumen collar where one wire is placed in each lumen and then bonded or melted together. FIGS. 91 and 99 also illustrate possible configurations for filter structures formed from two elongate support members that are joined at the ends.

Figure 89A:
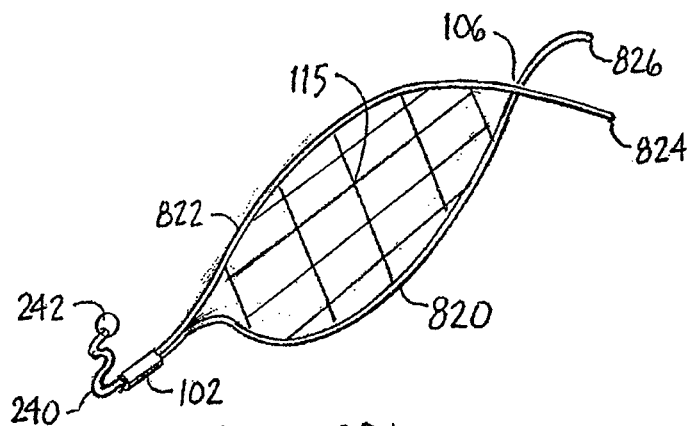
FIGS. 89A and 89B illustrate individual filter components that may be assembled into the final version illustrated in FIG. 89C.
Figure 89B:
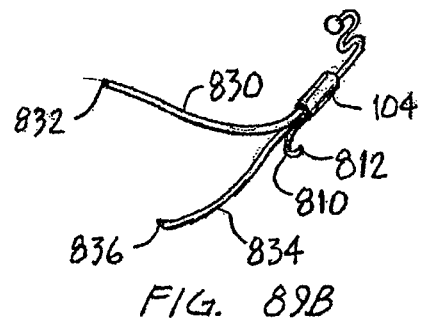
Figure 89C:
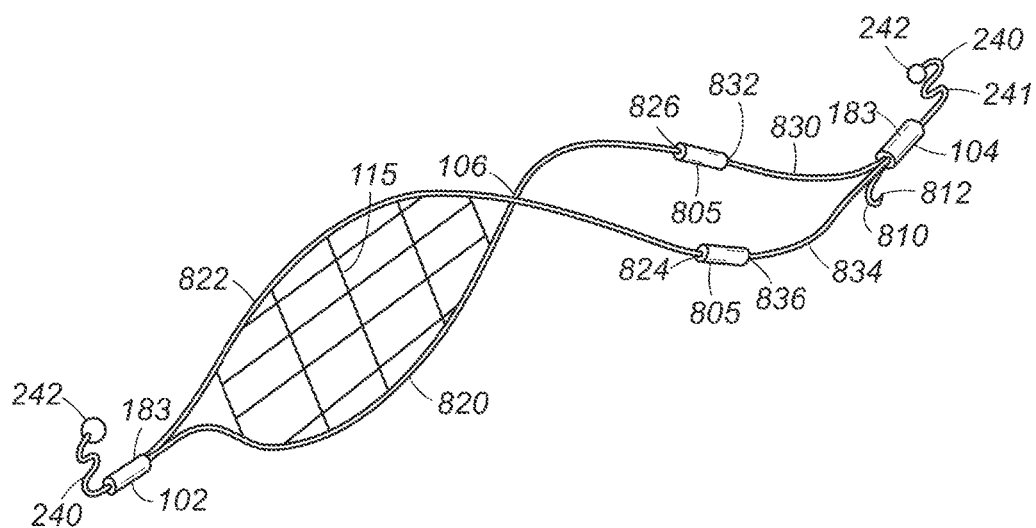
FIG. 89C is a perspective view of a final assembled filter.

FIGS. 89A and 89B illustrate individual filter components that may be assembled into the final version illustrated in FIG. 89C. FIG. 89A illustrates the proximal end of the filter. The elongate bodies 820, 822 are used to secure a filter structure 115 between a cross over 106 and the end 102. The elongate bodies 820, 822 extend some length beyond the crossover 106 to ends 826, 824. A retrieval feature 240 is attached to end 240 and may be formed, in one exemplary embodiment; from either elongate body 820, 822. FIG. 89B illustrates the distal end of the filter. The distal end of the filter is formed by elongate bodies 834, 830 joined by end 104. The length of elongate bodies 830, 834 may be adjusted to join with the elongate bodies 820, 822 in FIG. 89A to form an appropriately sized filter. The distal end also includes a retrieval feature 240 and a fixation element 810. The final assembled filter is illustrated in FIG. 89C where the proximal and distal filter ends are joined at suitable joining connectors 805. It is believed that the manufacturing procedure used for constructing a filter is simplified through the use of proximal and distal ends. Each of the ends may be fabricated separately in relatively fewer and easier steps than when fabricating a filter from two elongate bodies of nearly equal length as described elsewhere in this application. Additionally, suitable joining connectors 805 used to couple the proximal and distal ends may also be used to attach a fixation element to the filter frame as illustrated, for example, in FIG. 91, 95 or 99.

Figure 90A:
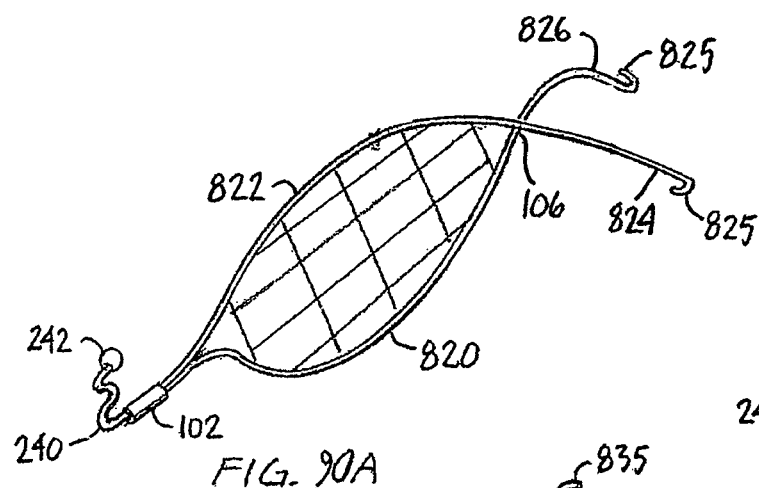
FIGS. 90A and 90B illustrate proximal and distal filter ends with the tips of the elongated members modified to form fixation elements.
Figure 90B:
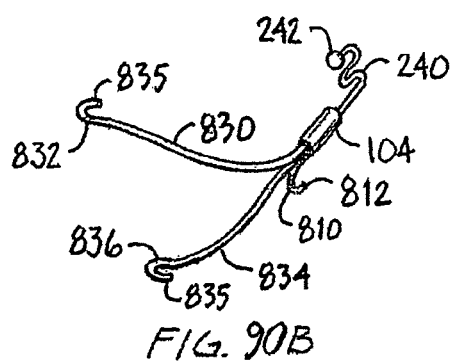

Alternatively, the ends of the elongate bodies could be used to form the fixation elements. FIGS. 90A and 90B illustrate proximal and distal filter ends with the tips of the elongate members modified to form fixation elements. The proximal filter end embodiment illustrated in FIG. 90A has hooks 825 formed on ends 824, 826. The distal filter end embodiment illustrated in FIG. 90B has hooks 835 formed on ends 832, 836.

Figure 90C:
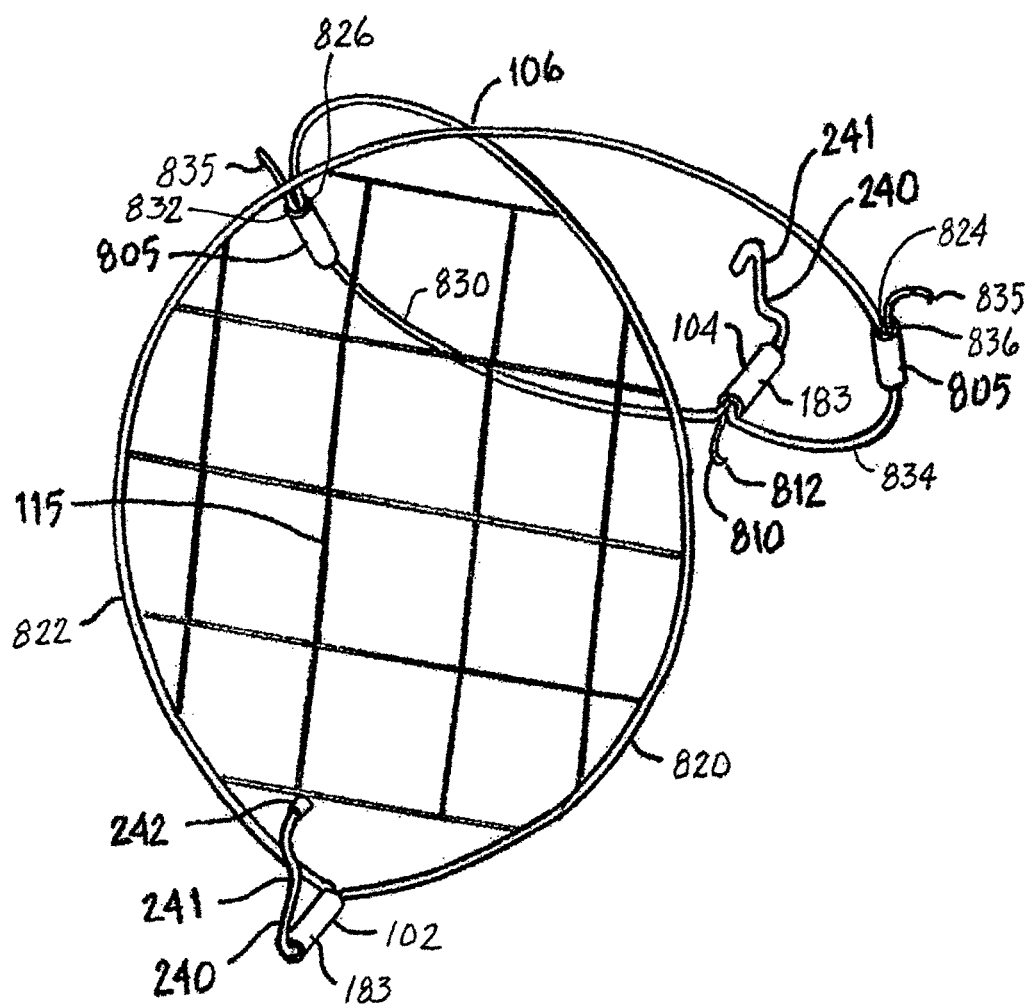
FIG. 90C is a perspective view of a filter assembly using the proximal distal end of FIGS. 90A and 90B.

FIGS. 90A and 90B may be combined using a suitable joining connector(s) 805 to form a double hook fixation element such as illustrated in FIGS. 95, 104A, 104B, and 104C. Alternatively, the modified distal and proximal ends in FIGS. 90A and 90B may be combined in any combination to the unmodified distal and proximal filter ends illustrated in FIGS. 89A and 89B. FIG. 90C illustrates an embodiment of one combination that joins the proximal end in FIG. 89A with the distal end in FIG. 90B. Other combinations are possible. For example, the tissue anchor is on the first or the second attachment means. Additionally or alternatively, there can be a retrieval feature on the end of the first support structure and a retrieval feature on the end of the second support structure.

These, along with other embodiments, illustrate a filter support structure having a first support member having an end, a first segment extending from the end and a second segment extending from the end. There is also a second support member having an end and a first segment extending from the end and a second segment extending from the end and crossing but not attaching to the first segment. There is a first attachment means for joining the first segment of the first support member to the first segment of the second support member and a second attachment means for joining the second segment of the first support member to the second segment of the second support member. A tissue anchor is provided on or with the first or the second support member. As described in further detail above, there is also a material capture structure attached to the first and second segments of the second support member and between the end of the second support member and the place where the first segment crosses the second segment.

Additionally, while FIGS. 89A-90B illustrate elongate body components having the same or nearly the same length, the design is not so limited. The use of elongate bodies of different length can be used to position the fixation elements in off set locations along the elongate body. The elongate body lengths 820, 822, 830, 834 may be of different lengths than in previous examples attached as shown in FIG. 91. The use of different elongate body lengths produces a spacing (indicated by "s" in the figure) between the attachments 805. The dashed lines indicate the position of each fixation element when the fixation elements are moved into a stowed condition. The offset spacing "s" reduces the likelihood that the fixation element 810 between elongate bodies 820, 830 will become entangled with the fixation element 810 between elongate bodies 822, 834 when the filter is stowed prior to delivery (see FIG. 123B). Alternatively or additionally, the offset spacing "s" may be achieved by placing fixation elements on the elongate bodies in positions that result in the desired amount of offset to prevent the fixation elements from getting tangled.

Figure 93A:
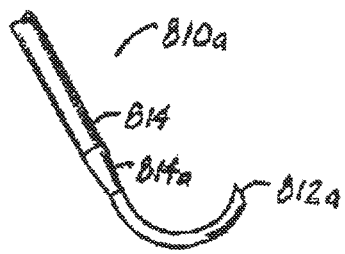
FIGS. 93A and 93B are perspective and cross section views respectively of a prior art fixation element having a transition section and a reduced diameter section.
Figure 93B:
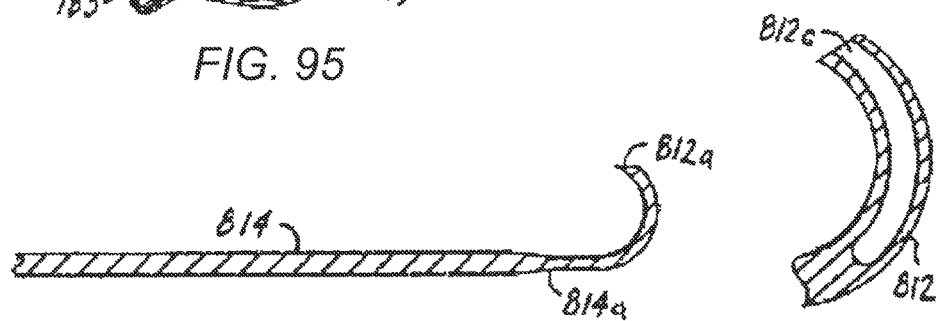
Figure 92:
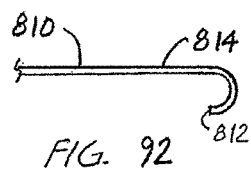
FIG. 92 illustrates a fixation element formed in the end of an elongate body.

There are a number of various fixation elements that may be used. The fixation elements 810 shown in FIG. 92 illustrates a fixation elements that may be formed on the ends of the elongate bodies (i.e., FIGS. 90A and 90B) using a number of bending and forming techniques. The end may remain at the same diameter as the rest of the elongate body as shown in FIG. 92. The end is shaped into the desired curve between the body 814 and the tip 812 for engagement with the surrounding lumen. In one alternative embodiment, the elongate body end is cut, ground or otherwise shaped into a sharpened point or beveled tip 812. Additionally or alternatively, the fixation element may have a smaller diameter than the remainder of the elongate body as illustrated in FIGS. 93A and 93B. Fixation element 810a has an elongate body diameter that is reduced in a transition section 814a down to the desired final diameter of the tip 812a. The now reduced diameter end is then shaped into the desired curvature depending upon how the fixation element is to engage with the surrounding tissue. In an alternative embodiment, the transition section 814a alone or in combination with the tip 812a may be formed from a different material that the body 814. The difference in the materials or different qualities of the same material may be used to provide a barb or tissue anchor with a flexible tip. For example, either or both the transition 814a and the tip 812a may be formed from a flexible biocompatible material such as polytetrafluoroethylene (ePTFE), polytetrafluoroethylene (PTFE), Poly(ethylene terephthalate) (PET), Polyvinylidene fluoride (PVDF), tetrafluoroethylene-co-hexafluoropropylene (FEP), or poly (fluoroalkoxy) (PFA), other suitable medical grade polymers, other biocompatible polymers and the like.

Figure 94:
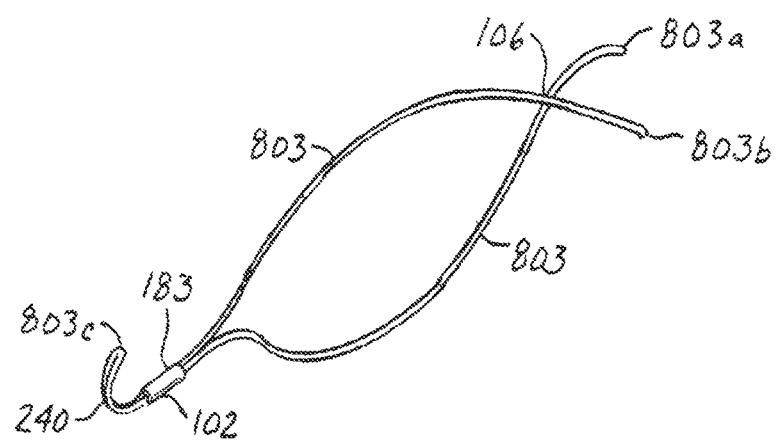
FIG. 94 illustrates an embodiment of a filter structure proximal end formed from a single wire.
Figure 95:
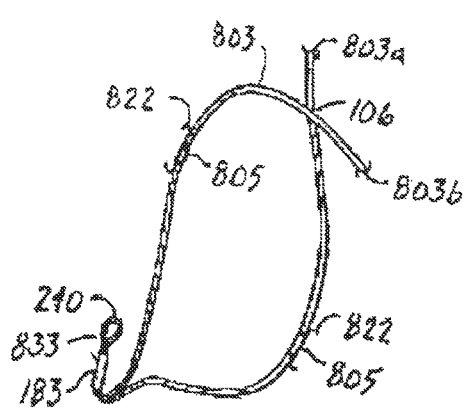
FIG. 95 illustrates an embodiment of a filter structure proximal end formed from a single wire with fixation elements from FIG. 104A.
Figure 104A:
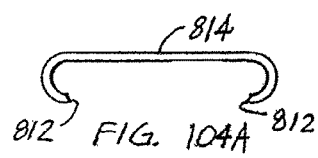
FIGS. 104A and 104B illustrate a double ended fixation element (FIG. 104A) and attachment of a double ended fixation element to an elongate body (FIG. 104B)
Figure 104B:
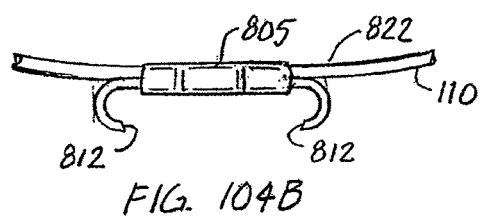

FIG. 94 illustrates an embodiment of a proximal end 102 of a filter structure that is formed from a single wire 803. The wire 803 begins at the end 803a is curved into one side of the support frame and then into the retrieval feature 240. The wire 803 is reversed 803c to form the other side of the retrieval feature 240 and then the other side of the support frame to the end 803b. A crimp 183 or other suitable fastener is used to maintain the shape and position of the retrieval feature 240. While this illustrative embodiment describes a single wire formation technique for a proximal end 102, this technique may also be applied to the formation of a distal end 104. The retrieval feature 240 may also take shapes other than the one in the illustrated embodiment and may, for example, be formed to resemble retrieval features illustrated in FIGS. 20-22 and 25-28C. As shown in FIG. 95, the single wire 803 may also used to form a loop 833 on the distal end 240. This illustrates a technique for forming both the first support member and the second support member from a single wire. This embodiment also shows the connector 183 in a position raised above the lumen wall. Additionally, a double ended fixation element 822 is shown. This is an example of a tissue anchor having a first barb with a proximal opening and a second barb with a distal opening. The double ended fixation element may be formed by curving the ends of proximal and distal ends (see FIGS. 90A, 90B). Alternatively as shown in FIG. 104A, the fixation element 822 may be a stand alone component with a body 814 curved into two tips 812. As shown in FIG. 104B, the fixation element 822 may be joined to any elongate body using a suitable fixation 805. In the illustrated embodiment, the fixation element 822 is attached to an elongate body 110. The ends 812 may also be curved in different directions or different angles as shown in FIG. 104C.

Any of a wide variety of bonding or joining techniques may be used to join the proximal and distal ends such as: soldering, welding, brazing, shrink fit tubing, epoxy, multi-lumen collar where one wire is placed in each lumen and then bonded or melted together, twisting wires together. Alternatively, one or more techniques could be used to join the elongate bodies with or without the addition of a fixation element. Then, in order to reduce surface defects to initiate tissue growth, the area where the joining occurred is covered by a smooth material. The joined area could be coated with an epoxy or medical grade silicone, or a shrink fit tube or slotted tube could be placed over the join and then melted into place. Consider FIGS. 89A and 89B in an illustrative example of an alternative technique to provide a smooth surface to a joined area. First, a segment of heat shrink tubing is sufficiently long to cover the length of the elongate body included in the joining process is placed on the elongate bodies 830, 834 over the ends 832, 836, respectively, of FIG. 89B. Next, the ends 832, 836 in FIG. 89B are joined to the ends 824, 826 in FIG. 89A. Thereafter, the heat shrink tubing segments are advanced over the joined area and heated. As the heat shrink tubing segment is heated, it melts around the joined area and provides a smooth surface that seals the area where the end 826 joins end 832 and end 824 joins end 836.

The joint 805 is an example of an attachment element that joins the first support member to the second support member. The joint 805 could be used to join elongate bodies together as suggested by the embodiments illustrated in FIGS. 88, 89A, 89B, 90A, 90B, 94 and 96. Alternatively, the joint could be used to secure a fixation element to the filter frame. In yet another alterative, the joint could provide means for both joining the elongate bodies together into a single frame as well as joining a fixation element to the filter frame at the same point that the elongate bodies are joined. Suitable means for attachment and attachment techniques used to create the joint 805 include, by way of non-limiting examples, a crimp or other joining technique with a discrete detent, a swage or other joining technique with circumferential constriction, soldering, welding, brazing, shrink fit tubing, epoxy, multi-lumen collar where one wire is placed in each lumen and then bonded or melted together.

The material capture structure 115 may be in any of a number of different positions and orientations. FIG. 96 illustrates an embodiment of a filter of the present invention having two open loop support frames formed by support members 105, 110. Flow within the lumen 10 is indicated by the arrow. In this embodiment, the material capture structure 115 is placed in the upstream open loop support structure. In contrast, the material capture structure may be positioned in the downstream open loop support structure (FIG. 97). In another alternative configuration, both the upstream and the downstream support frames contain material capture structures 115.

There are filter device embodiments having equal numbers of support frames with capture structures as support frames without capture structures (e.g., FIGS. 13A, 13B, 97A, and 97B). There are other embodiments having more support frames without capture structures than there are support frames with capture structures. For example FIG. 14 illustrates a filter embodiment 190 having more support frames without capture structures than support frames with captures structures. The filter device 190 has two support members 105, 110 that are positioned adjacent to one another to form a plurality of support frames that are presented to the flow within the lumen 10. These support frames could also be modified to include fixation elements in any combination or configuration described herein. Alternatively, the plurality of support frames positioned to support a material capture structure across the flow axis of the device 190 or the lumen 10. The support members are joined together at end 192 and have two inflection points before being joined at end 194. The support members 105, 110 cross over one another at crossovers 106 and 196. The support frame 191 is between end 192 and crossover 106. The support frame 193 is between the crossovers 106, 196. The support frame 195 is between the cross over 196 and the end 194. One or more fixation elements may be provided in any or all of the support frames 191, 193 and 195 as described herein.

FIG. 98 illustrates a fixation element 810 engaged within the side wall of lumen 10. In this embodiment, the length and curvature of the fixation element is selected to remain within the wall of the lumen 10. As shown, the tip 812 is within the sidewall of lumen 10. In other alternative configurations, the length and curvature of a fixation element is selected engage with the lumen 10 by piercing though the lumen wall.

Figure 100:
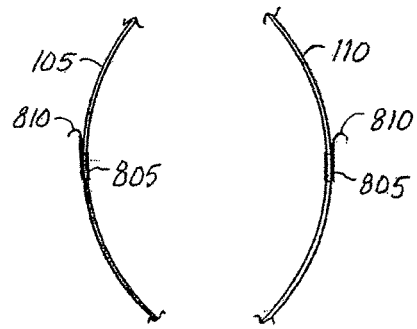
FIG. 100 illustrates the placement of the fixation elements about mid-distance between the ends and the crossover.
Figure 101:
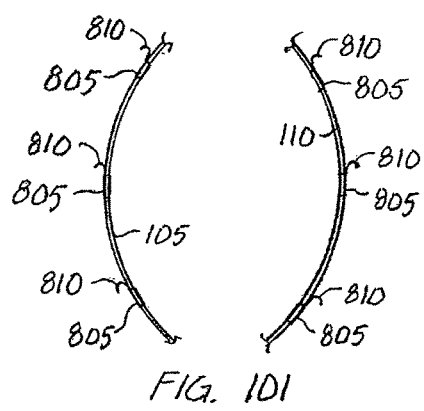
FIG. 101 illustrates the placement of fixation elements similar to FIG. 100 with additional of fixation elements positioned near the crossover and the ends.
Figure 102:
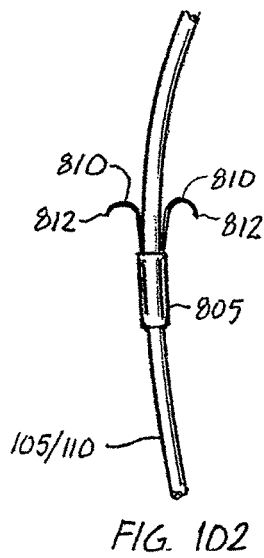
FIG. 102 illustrates more than one fixation element positioned at the same location along the filtering device.

The fixation element could be a separate element or formed from one of the elongate bodies. Additionally, fixation elements may be positioned in any of a number of different positions and orientations. FIG. 88 illustrates fixation elements positioned about halfway between an end 102, 104 and the cross over 106. An additional fixation element is positioned on the end 104. Unlike the illustrative embodiment of FIG. 88 where the fixation elements are on a single support frame, FIG. 99 illustrates the location of additional fixation elements on both support frames as well as the ends 104, 102. FIG. 99 does not illustrate any material capture structure within the frame. In FIG. 99, the fixation elements 810 are positioned along both elongate bodies 105, 110 about mid-way up on the support frame between an end and the crossover. Alternative fixation element 810 spacing and orientation is illustrated in FIGS. 100 and 101. FIG. 100 illustrates placement of the fixation elements 810 about mid-distance between the ends 102, 104 and the cross over 106. FIG. 101 illustrates the placement of the fixation elements similar to FIG. 100 with additional elements positioned near the cross over 106 and an end 104, 104. As illustrated in FIG. 102, more than one fixation element or barb may be positioned at each location along the structure. FIG. 102 illustrates a fixation attachment point 805 that secures two fixation elements 810 to the elongate body 105, 110. The fixation elements 810 may be provided separately or, alternatively, one or both of the fixation elements 810 may be formed from the elongate bodies. More than one barb or fixation element on a single location along the filter structure is also illustrated in FIGS. 95, 104A, 104B and 104C, for example.

Figures 103A, 103B, 103C:
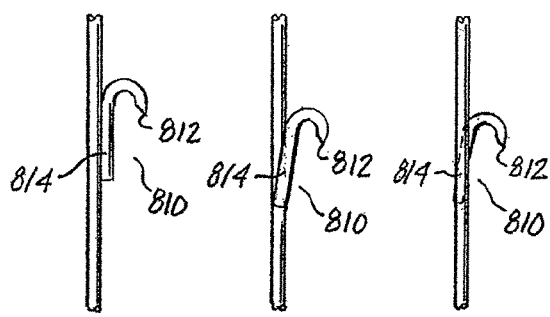
FIGS. 103A, 103B and 103C illustrate positioning of a fixation element on the elongate body (FIG. 103A) or to one side of the elongate body (FIGS. 103B and 103C)

Returning to FIG. 88, attachment portion 805 could also be used to mount or secure an individual fixation element 810 to an elongate body. FIGS. 103A, 103B and 103C for individual elements may be attached on (FIG. 103A) or on the sides (103A, 103B) to provide the desired orientation to the lumen wall as well as provide the desired device profile. Cover or joining structure 805 used to secure the fixation element to the elongate body has been removed to show detail.

Fixation elements may be designed to engage, pierce or otherwise attach to the lumen sidewall with more than one attachment point. FIG. 102 illustrates more than one fixation element 810 attached to an elongate body at a single attachment site or with a single cover or joint structure 805. FIG. 104A illustrates a double ended fixation element 822 having a body 814 with two fixation tips 812. FIG. 104B illustrates the double ended fixation element 822 attached to an elongate body 110. FIG. 104C illustrates how the tips 812 may be altered to adjust the manner by which the tips engage with the adjacent lumen wall. FIG. 104C illustrates one proximally opening tip 812 and one distal opening tip 812.

Different fixation element body orientation and fixation positions for the tips 812 are possible. In one embodiment, the tissue anchor comprises a coil wrapped around the first support member or the second support member and an end raised above the first support member or the second support member. An illustrative example of one such tissue engagement or anchor is illustrated in FIG. 105. FIG. 105 illustrates a curved wire 817 extending along and wrapped around the elongate body and then curling to place a curl between the fixation portion 105 and the tip 812. The degree of curvature of the curved wire 817 may be adjusted to control the force used to pierce the tissue or control the amount of fixation force applied to the lumen walls. Alternatively, as illustrated in FIG. 106, the fixation element body 817 may attach to the elongate body 110 by wrapping around a length of the elongate body. FIG. 105 also illustrates an example where the tissue anchor is a coil or open tube having a tissue engagement surface comprising a raised spiral form. FIG. 105 also illustrates a tissue anchor having an attachment section attached to the first support member or the second support member, an end adapted to pierce tissue and a coil 817 between the attachment section and the end 812. An optional covering (not shown) may also be placed over the coiled wire 817 to maintain a smooth device profile along the elongate body 110.

The filter structure may also be secured using alternative fixation elements illustrated in FIGS. 107A, 107B. In some embodiments, a tissue anchor or anchors are formed from or attached to a tube that is attached to the first support member or the second support member. FIGS. 107A and 107B illustrate a tube or support 821 adapted to fit over the elongate body 110. A feature 823 on the support 821 is used to engage with sidewall of the lumen. In the illustrated embodiment of FIG. 107A, the feature has a generally conical shape with a pointed tip, similar to a thorn. One of more of the supports 821 may be placed along the elongate body 810 as illustrated in FIG. 107B. Alternatively, the feature 823 may be formed from or as part of an integrated structure with the support 821. The feature 823 may be formed in a different shape than illustrated. The feature 823 may take the form of a circumferential rib, or a void/dentent. In another alternative embodiment, the support 821 is a continuous piece that extends along the length or most of the length of the elongate body 110 rather than in discrete segments 821 illustrated in FIG. 107B. In one embodiment the segment and features are formed from (Eric—please provide materials to make the segment and features from). The size, number and spacing of the feature 823 or features 823 may vary depending on application. For anchoring a material capture structure in the inferior vena cava, for example, a feature 823 may have a height of between about 0.5 mm to about 3 mm have spacing of about 0.1 mm to about 5 mm.

FIGS. 108 and 109 illustrate another alternative fixation element. In these alterative embodiments, a tissue anchor is formed from the first support member or the second support member (FIG. 109) or is attached to or formed from a structure or tube that is attached to the first support member or the second support member (FIG. 108). Additionally or alternatively, a tissue anchor can be formed from or attached to a tube that is attached to the first support member or the second support member. FIG. 108 illustrates a tissue anchor that is a tube 843 having a tissue engagement surface. In this illustrative embodiment, the tissue engagement surface includes triangular fixation elements 847. The triangular fixation elements 847 may be formed in the sidewall of a hollow tube 843 as shown in FIG. 108. Then, the hollow tube 843 is then placed over and secured to the elongate body 110. Suitable materials for tube 843 include, for example: Nitinol, stainless steel or previously described polymers and degradeable polymers. The cross section of the hollow tube 843 is illustrated as round but other cross sections are possible. In one embodiment, the cross section of the tube 843 is sized and shaped to conform to the size and cross section shape of the elongate body 110. Alternatively, instead of forming the triangular fixation element(s) 847 in a tube that is placed over the elongate body, the triangular fixation members 847 are formed in or using the surface of the elongate body 110 as shown in FIG. 109. In this illustrative embodiment, the tissue anchor(s) on the first or the second support member are formed from the first or the second support member. While the illustrated embodiments show fixation elements 847 having a generally triangular shape other shapes are possible. For example, the fixation elements 847 may be shaped as an elongate spike or in any other suitable shape for engaging the adjacent lumen or tissue. In still another embodiment, one or more of the fixation members may be modified to have echogenic properties and become a fixation member 847x as shown in FIG.

Figure 109X:
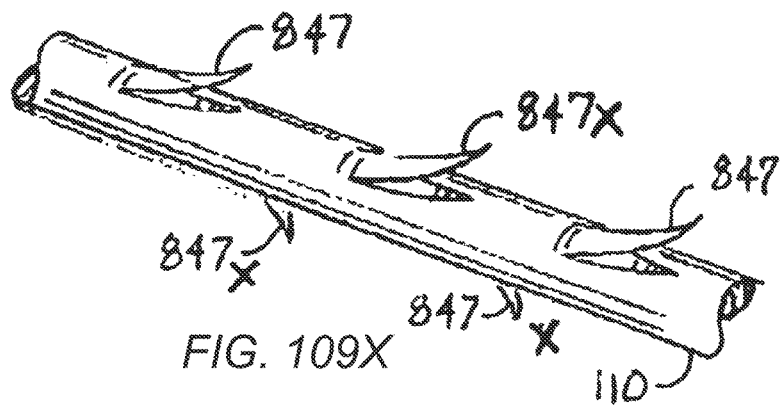
FIG. 109 illustrates tissue anchors formed by cutting into an elongate body and with modified tissue anchors shown in FIG. 109x.

109x. The modified fixation elements 847x may be in an array or other pattern or on a specific portion of a filter to enhance the usefulness of the echogenic enhancement or modification. The embodiment illustrated in FIG. 109x shows the modified fixation elements 847x in an arrangement with fixation elements 847. The fixation elements 847x may also be echogenic tabs incorporated into a coating or covering in some embodiments.

Figure 110X:
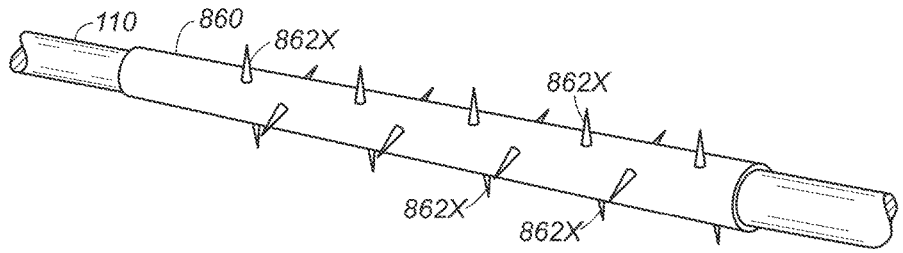
FIG. 110 illustrates a perspective view of tube with a surface modified to provide tissue engagement features and FIG. 110x includes echogenic modifications to the tube of FIG. 110.
Figure 110:
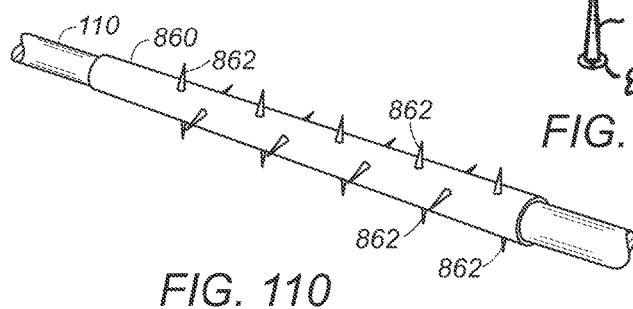

In another alternative embodiment illustrated in FIG. 110, the tube 847 may be modified to form a tissue engagement surface. In this illustrative embodiment, the tissue engagement surface includes surface features 862 that are shaped like spikes or thorns. One method of making the features 862 is to heat a polymer tube until the surface of the tube becomes tacky. Next, the surface of the tube is wicked up into the shape of the feature 862. As illustrated, the tube 860 is segmented to cover only a portion of the elongate body 110. In another embodiment, the tube is the same length or about the same length as the elongate body 110. Instead of modifying the surface of the tube 860, tissue engagement features 862 may instead be formed by mounting a fixation feature on, in or through the wall of the tube 860.

In another illustrative embodiment, best seen in FIG. 110X, a tissue engagement surface 860 includes surface features 862x that are modified to enhance the echogenic signature of the tube 860. The surface features 862x are configured like points, fingers or microvilli.

Figures 111A, 111B:
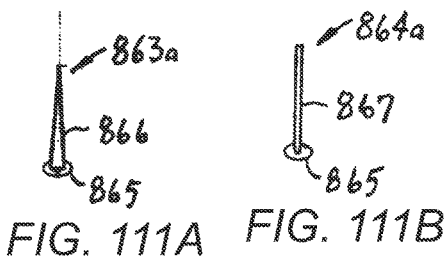
FIGS. 111A and 111B illustrate alternative fixation features that may be mounted on, in or through the wall of a tube.

A tissue engagement feature may take any of a number of different shapes as illustrated in FIGS. 111A and 111B. FIG. 111A illustrates a tissue engagement feature 863a with a base 865 supporting a sloped body 866 that ends in a pointed tip. FIG. 111B illustrates a tissue engagement feature 864a with a base 865 supporting a generally cylindrical body 867 that ends in a flat tip. The tissue engagement features may be added to the tube 860 by pushing them through the sidewall such that, when installed, the base 865 is within the lumen of the tube 860 and the body 866, 867 extends through the sidewall as shown in FIG. 110.

Figure 112X:
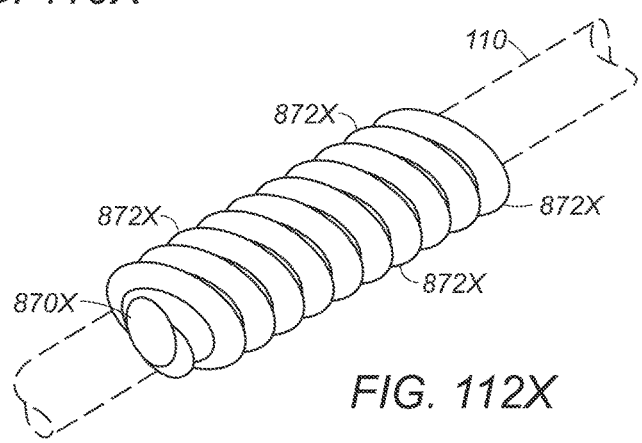
FIG. 112x illustrates an echo enhanced embodiment of the tube based fixation element of FIG. 112.
Figure 112:
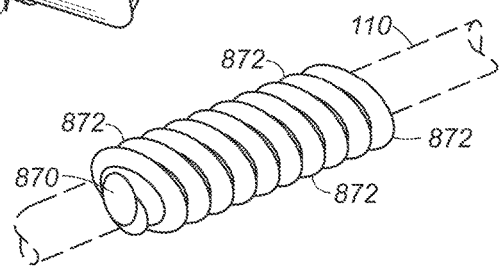
FIG. 112 is a perspective view of a tube based fixation element having a raised spiral form.

FIG. 112 includes another alternative embodiment of a tube based fixation element. In this embodiment, the tissue engagement surface comprises a raised form. In one embodiment, the tissue anchor is a tube having a tissue engagement surface comprising a raised spiral form. As shown in FIG. 112, the surface of the tube 870 has been modified into a raised spiral with ridges 872. The raised spiral 872 may be in a segment as shown. One or a plurality of segments may be attached along the length of the elongate body. Alternatively, instead of a segment, the tube 870 may be the same length as or about the same length as the elongate body 110 to which it is attached. In another alternative embodiment, the raised portion is formed by inserting a spring or other structure beneath the surface of the tube or segment 860. Additionally or alternatively, the tissue anchor comprises a coil wrapped around the first or the second support member. As illustrated in FIG. 106, this alternative can be formed by wrapping one wire (the elongate body 110) with another wire or a spring (wrapped wire 817). The wire 110 and wrapped wire 817 may then be coated by another material or placed into a suitable shrink tubing. Once the material or heat shrink is treated to conform to the wires, the resulting structure would resemble that shown in FIG. 112 with the addition that the tips 812 (see FIG. 106) would extend through the material to provide an additional attachment point to the lumen.

An enhanced embodiment of the device of FIG. 112 is shown in FIG. 112x. In the embodiment of FIG. 112x the tube based fixation element. In this embodiment, the tissue engagement surface comprises a raised form. In one embodiment, the tissue anchor is a tube having a tissue engagement surface comprising a raised spiral form. As shown in FIG. 112x, the surface of the tube 870x may be modified into a raised spiral with ridges 872x, either or both of which may be modified to enhance the echogenic properties or characteristics of the tube 870x. In one embodiment, the features of 872x are provided by an echogenic coil.

Figure 106X:
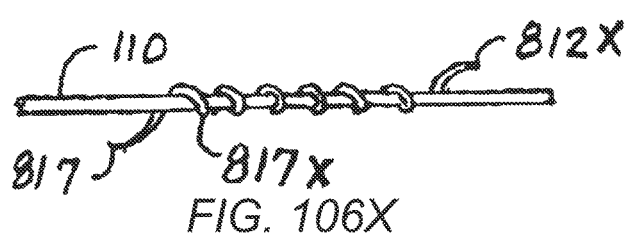
FIG. 106x illustrates the wrapped fixation element of FIG. 106 configured as a combination echogenic feature with anchor that has echogenic modifications to all or a portion of the wrap and one end.

In an alternative aspect, FIG. 106x illustrates the wrapped fixation element 817 having echogenic modifications to all or a portion of the wrap 817x and one end 812x. In another aspect, both ends may be modified ends 812x with an unmodified middle or the middle 817x is modified but the ends 812 are not modified to have echogenic modifications.

It is to be appreciated that the formation of tissue engagement structures may take any of a number of alternative forms alone or in any combination. As shown and described above in FIG. 109 features 847 may be cut into the surface of a elongate body. FIG. 108 illustrates how similar features may be cut into the walls of a tube 843. Additionally, the tissue engagement surface may take the form of a raised profile surface on the tube as shown in FIGS. 106, 112. Additionally or alternatively, the tissue engagement surface may be formed by roughening the surface of the tube or structure that engages the tissue, thereby increasing the coefficient of friction between the filter and the tissue it contacts. In some embodiments, the roughening may take the form of surface texturing by mechanical means (sanding, bead blasting knurling, cutting, scoring), chemical means (acid etching), laser cutting, or as an integral part of the extruding or molding process.

Figure 113:
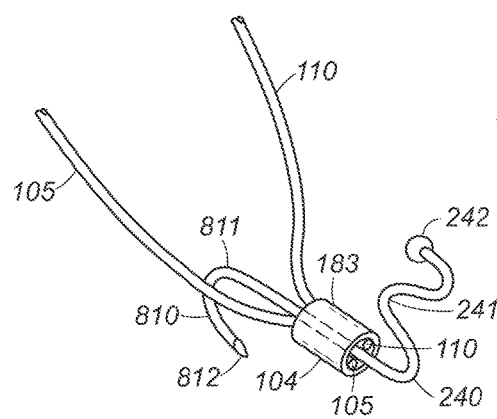
FIG. 113 illustrates a perspective view of one end of a filtering device where the retrieval feature includes a tissue engagement feature.

In addition to adding fixation or tissue engagement structures to the elongate bodies, the retrieval features may be attached to the elongate body or formed from the elongate body in a number of different ways that may also include a fixation element or elements. In one embodiment, there is a combined tissue anchor and retrieval feature joined to the first end or the second end of the first support member as shown in FIG. 113. FIG. 113 illustrates a distal end 104 where the elongate bodies 105, 110 terminate within the attachment element or securing feature 183. The securing feature may be a crimp 183 or any other suitable technique to join the elongate bodies together. Suitable means for attachment and attachment techniques used to create the attachment element or securing feature 183 include, by way of non-limiting examples, a crimp or other joining technique with a discrete detent, a swage or other joining technique with circumferential constriction, soldering, welding, brazing, shrink fit tubing, epoxy, multi-lumen collar where one wire is placed in each lumen and then bonded or melted together.

In this illustrative embodiment, the retrieval feature 240 is formed from a single wire 811 that is shaped into the curves 241 of the retrieval feature 240 as well as into a tissue engagement structure 810 having a tip 812 for engaging with tissue.

In this illustrative embodiment, the diameter of the wires used for the elongate bodies 105, 110 and the retrieval feature 240 are nearly the same so crimping the wires is suitable joining method. Other joining methods include, by way of non-limiting examples, a crimp or other joining technique with a discrete detent, a swage or other joining technique with circumferential constriction, soldering, welding, brazing, shrink fit tubing, epoxy, multi-lumen collar where one wire is placed in each lumen and then bonded or melted together.

Figure 114:
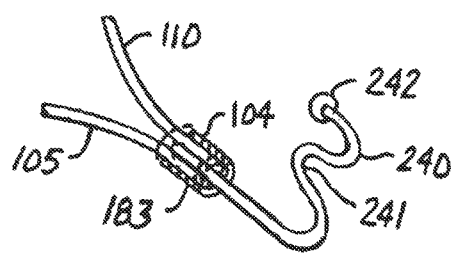
FIG. 114 illustrates a perspective view of one end of a filtering device where the retrieval feature terminates within the securing or attachment feature.
Figure 115:
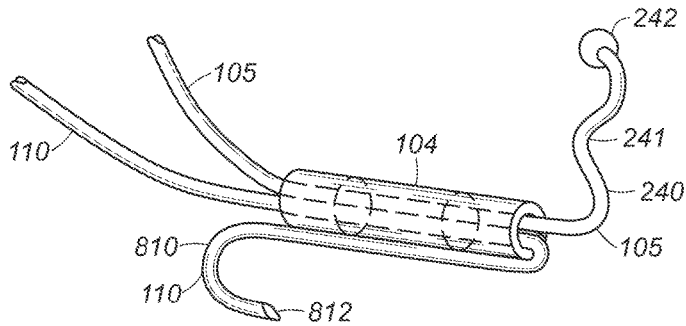
FIG. 115 illustrates a perspective view of one end of a filtering device where the retrieval feature terminates within the securing or attachment feature and the end of an elongate support structure is formed into a tissue engagement element.
Figure 116C:
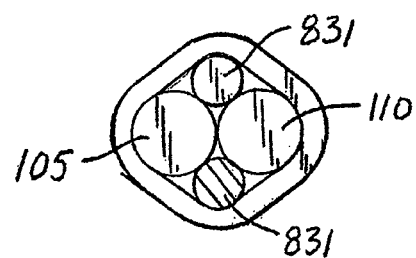
FIG. 116C is a section view through the securing or attachment feature of FIG. 16A where separate tissue engagement and retrieval features are provided rather than formed in the ends of the elongate support structures.
Figure 11B:
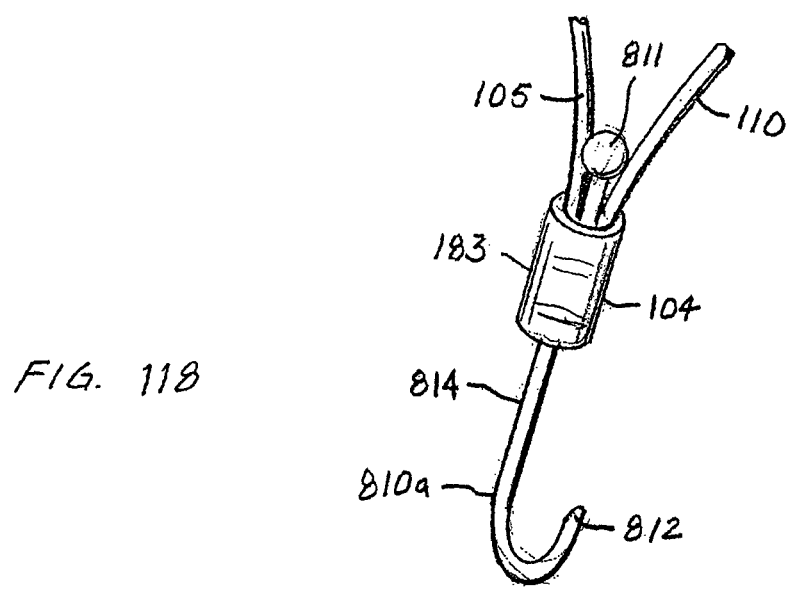

In the embodiment illustrated in FIG. 114, in contrast to the illustrated embodiment in FIG. 113, the wire used to form the retrieval feature 240 terminates within the securing feature or attachment element 183. Instead of using a separate wire as shown in FIGS. 113, 114, the ends of the elongate bodies 105, 110 may be used to form the retrieval feature 240 and a fixation element 810. This is an example of an end of the first support member forms a tissue anchor and an end of the second support member forms a retrieval feature. Additionally or alternatively, the retrieval feature formed on the end of the first support structure is formed from the first support structure or the retrieval feature formed on the end of the second support structure is formed from the second support structure. In some embodiments, a tissue anchor is on the end of the first support structure or the end of the second support structure. FIG. 115 illustrates the elongate body 105 passing through the crimp 183 and then being shaped into a retrieval feature 240. The elongate body 110 passes through the crimp 183 and then shaped into a distal opening fixation element 810 with tip 812. FIG. 116A is similar to FIG. 115 except that the elongate body 110 is used to form the retrieval feature 240 and the elongate body 105 passes through the crimp 183 and then being shaped into a proximal opening fixation element 810. FIG. 116B is a section view through the crimp 183. FIG. 116C is a section view of FIG. 116A with spacers 831 inserted into the crimp 183 to help distribute the crimp force and provide a more secure joint.

Instead of adding a fixation element to an end, the end may be used to form a fixation or tissue engagement element. FIGS. 117A and 117B illustrate perspective and bottom views where a fixation element 852 is formed from the crimp 183 used to hold the elongate bodies 105, 110. Either elongate body 105, 110 may be used to form the retrieval feature 240. FIG. 118 illustrates an alternative embodiment having a wire 814 separate from the elongate bodies 105, 110. The wire 814 is formed into a fixation element 810a where a ball 811 prevents the wire 814 from pulling through the crimp 183. The fixation element 810a ends in a hook 812.

The modifications a retrieval feature to include a fixation element as described with regard to FIGS. 88, 89B, 90B, 96, 99, 113, 114, 115, 116-118 may also be used to provide one or more fixation elements to the retrieval feature embodiments described with regard to FIGS. 20-29. Additionally, while many of the illustrative embodiments have been described in conjunction with elongate bodies 105, 110 the invention is not so limited. Other elongate body and/or support structures described herein may also be used interchangeably with the elongate bodies 105, 110.

In other alternative embodiments, all or a portion of the fixation element may be modified to include a pharmacological agent. The inclusion of a pharmacological agent may include coating all or a portion of the filter or tissue engagement structure with a pharmacological agent. Additionally or alternatively, the tissue engagement feature may be adapted and configured to contain a drug or combination of drugs or pharmacological agents that are released over time or after some initial time delay. FIG. 119 illustrates an alternative embodiment of the fixation element 812 in FIG. 98 with a hollowed end portion 812c. The drug eluting fixation element 814a may be formed using a hypodermic-like needle shaped into the desired curvature. Alternatively, the cavity 812c may be formed by hollowing out a portion of the interior a wire or by forming the fixation element 812 from a tube. Similarly, the tip of the fixation element in FIGS. 93A, 93B may be hollowed as shown in FIG. 120.

Figure 120:
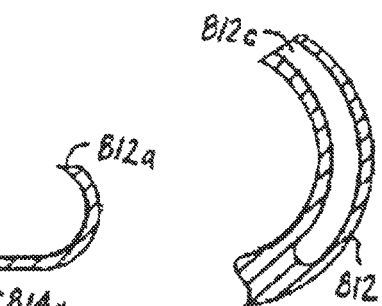
FIG. 120 illustrates an alternative embodiment of the tissue engagement element of FIGS. 93A and 93B with the addition of a hollowed tip portion.
Figure 121:
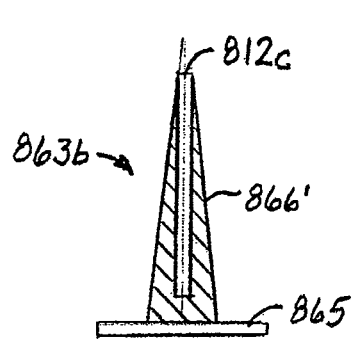
FIGS. 121 and 122 illustrate an alternative embodiments of the tissue engagement elements of FIGS. 111A and 111B with the addition of a hollowed tip portion.
Figure 122:
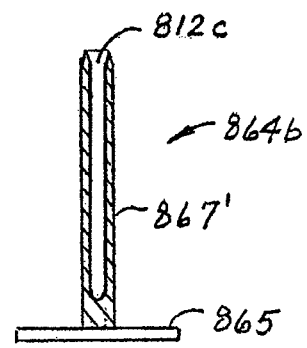

FIG. 120 illustrates a cavity 812c in the distal end of the fixation element 812. The pins 867 and spikes 866 of FIGS. 110, 111A and 111B may also be modified to include a drug cavity as shown in FIGS. 121 and 122. FIG. 121 illustrates a tissue engagement feature 863b with a base 865 supporting a sloped body 866' that ends in a pointed tip. A cavity 812c extends from the tip into the body 866'. FIG. 122 illustrates a tissue engagement feature 864b with a base 865 supporting a generally cylindrical body 867' that ends in a flat tip. A cavity 812c extends from the flat tip into the body 867'. The cavities 812c may be filled with any of a wide variety of pharmacological agents. Examples include: anti-proliferative or anti-thrombogenic agents. Additionally, these or any other fixation element or tissue engagement structure embodiment may also be coated with a pharmacological agent.

The various aspects of the filter embodiments described above with regard to FIGS. 88-122 may be modified to be or used with a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIGS. 88-122 may be modified according to FIGS. 127-135 or in conjunction with a system or as further described in FIGS. 136A-138B.

FIGS. 123A, 123B and 124A-E illustrate the positioning and deployment of an embodiment of the filter device 900 of the present invention having one or more fixation or tissue engagement features 810. The filter device 900 is an exemplary embodiment of any one of the alternative filter structure embodiments described herein having tissue engagement or fixation elements.

Embodiments of the present invention may be partially deployed so that a user may confirm the position of the filter prior to completely deploying the device into the target lumen. Partial deployment involves the controlled and reversible deployment and engagement of one or more fixation elements. The engagement is reversible because after placing the filter into the lumen the filter may be pulled partially or completely into the sheath as described herein. The filter may be repositioned and then redeployed into the lumen so that the fixation elements engage the lumen walls. Additionally, the design of embodiments of the filter of the present invention allow the retrieval action to be accomplished by approaching the filter from the same direction used for deployment. All the steps of positioning, deployment and recovery may be performed from a single access site.

Figure 123A:
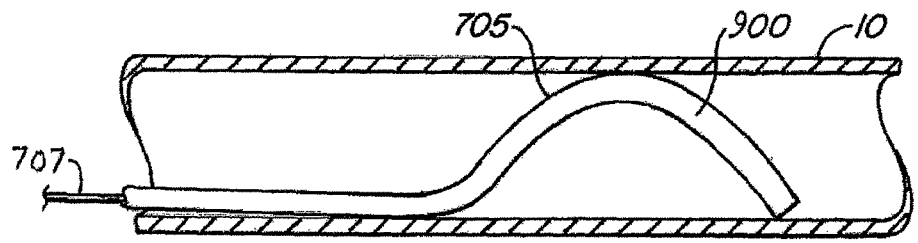
FIGS. 123A and 123B illustrate a perspective view of a filter device within a lumen and positioned for deployment where the filter device is stowed in a deployment sheath (FIG. 123A). The filter device is shown in phantom in the view illustrated in FIG. 123B.
Figure 123B:
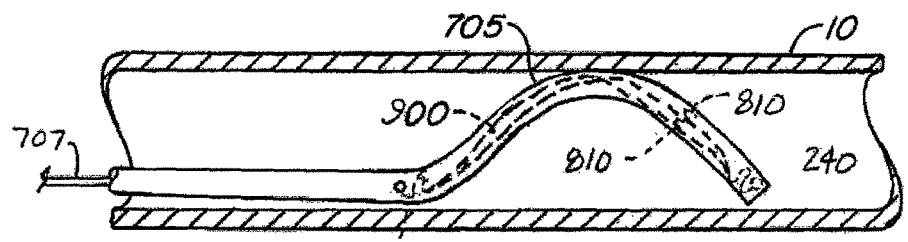

The device 900 may be loaded into an intravascular delivery sheath 705 as shown in FIGS. 123A, 123B and as described above with regard to FIG. 69. Using conventional endoluminal and minimally invasive surgical techniques, the device 900 can be loaded into the proximal end of the sheath 705, before or after advancing the sheath 705 into the vasculature, and then advanced through the sheath using a conventional push rod. The push rod 707 is used to advance the device 900 through the delivery sheath 705 lumen as well as fix the position of the device (relative to the sheath 705) for device deployment. In one preferred technique, the device 900 is loaded into the proximal end of a delivery sheath that has already been advanced into a desired position within the vasculature (FIG. 123B). The device 900 may be pre-loaded into a short segment of polymeric tubing or other suitable cartridge that allows the device 900 to be more readily advanced through a hemostasis valve.

When used with a compliant delivery sheath 705, the pre-formed shape of the device 900 deforms the sheath 705 to conform to the device shape (FIG. 123A, 123B). Accordingly, a flexible, compliant sheath 705 assumes the curvature of the stowed device 900. The deformation of the delivery sheath 705 helps stabilize the position of the sheath 705 in the vasculature and facilitates accurate deployment of the device 900 to the intended delivery site. In contrast, a non-compliant delivery sheath 705 (i.e., a sheath that is not deformed to conform to the preformed shape of the device 900) maintains a generally cylindrical appearance even through the device 900 is stowed within it (FIG. 69C). Regardless of the type of sheath used, device delivery is accomplished by using the push rod 707 on the proximal side of the device 900 to fix the position of the device within the sheath 705 and then withdrawing the sheath 705 proximally. As the device 900 exits the distal end of sheath 705, it assumes the pre-formed device shape.

The symmetrical device shape (see e.g., devices in FIGS. 15, 16A, 96, 97, 90C, 99, and 88), facilitates the deployment and retrieval of the device 900 from multiple access points in the vasculature. As with other non-fixation filter devices described herein, a device 900 may be positioned as shown in the vasculature within the inferior vena cava 11 immediately below the renal veins 13 (see FIG. 70). A femoral access path (FIG. 126A) and a jugular access path (FIG. 125A) are illustrated. The femoral access path and a jugular access path may each be used for device deployment, repositioning and retrieval. Alternatively, the vena cava could be accessed via brachial or antecubital access for device deployment, repositioning and retrieval. The placement and orientation of the fixation elements or tissue engagement structures may be modified as needed to facilitate the desired placement and retrieval technique.

Retrieval of the devices is most preferably accomplished by endoluminal capture using one of the retrieval features described herein. (i.e., FIGS. 27A-E) The retrieval features described herein have been designed to work well using a commercially available snares two of which are illustrated in FIG. 71A and FIG. 71B. The single loop gooseneck snare 712 is illustrated in FIG. 71 inside of a recovery sheath 710. The multiple loop Ensnare 714 is illustrated in FIG. 71B inside of a recovery sheath 710. These conventional snares are controlled by a physician using a flexible, integral wire.

Figure 125A:
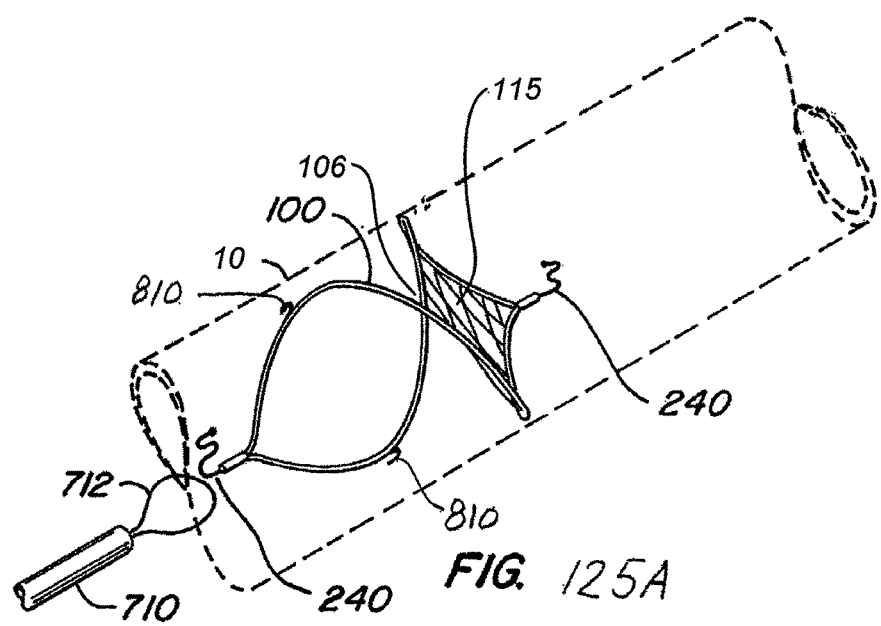
FIGS. 125A-C illustrate one approach and recovery sequence for retrieving a deployed filtering device.
Figure 125B:
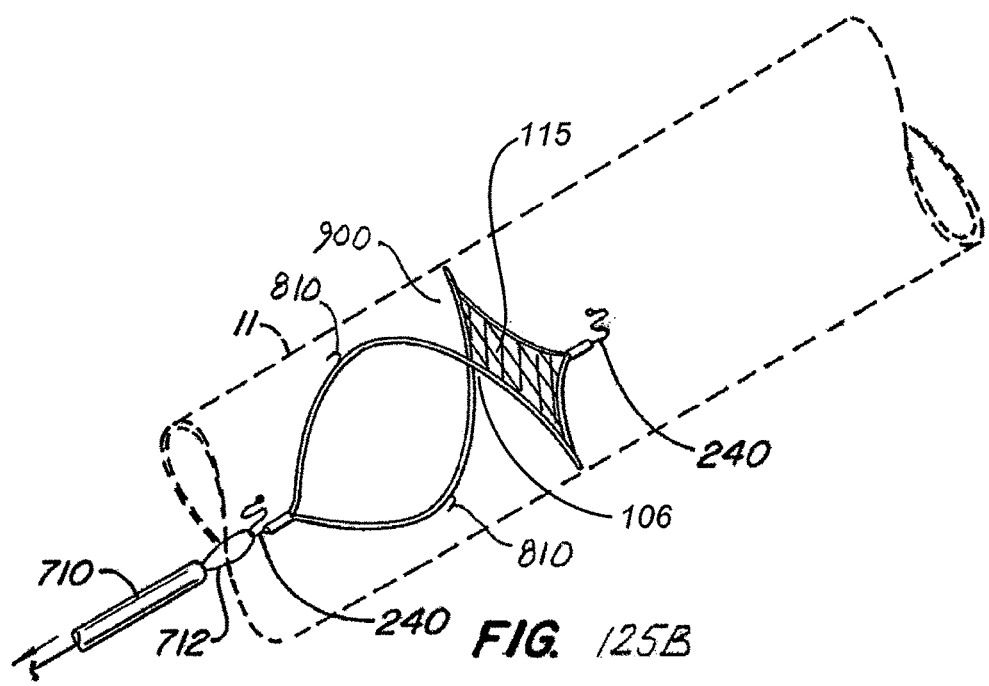
Figure 125C:
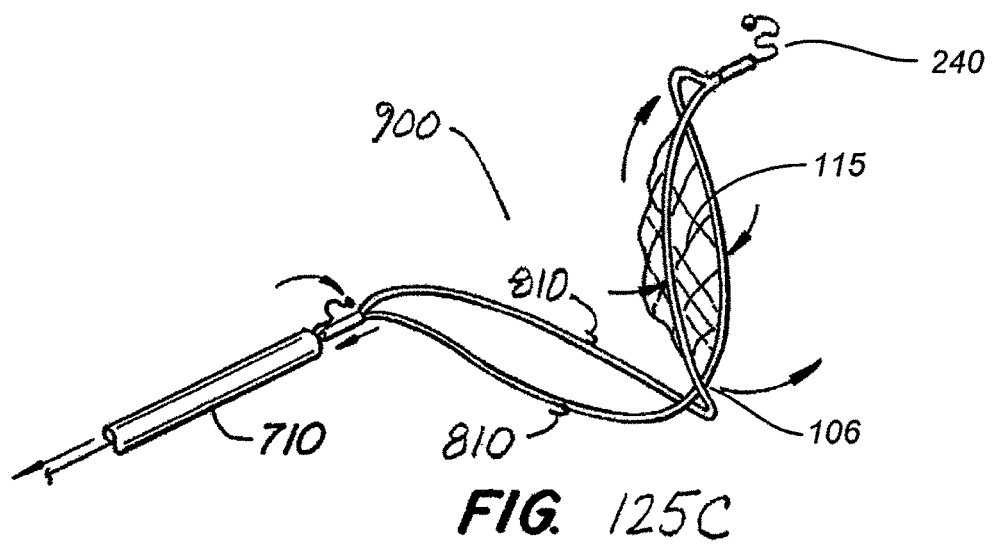
Figure 126A:
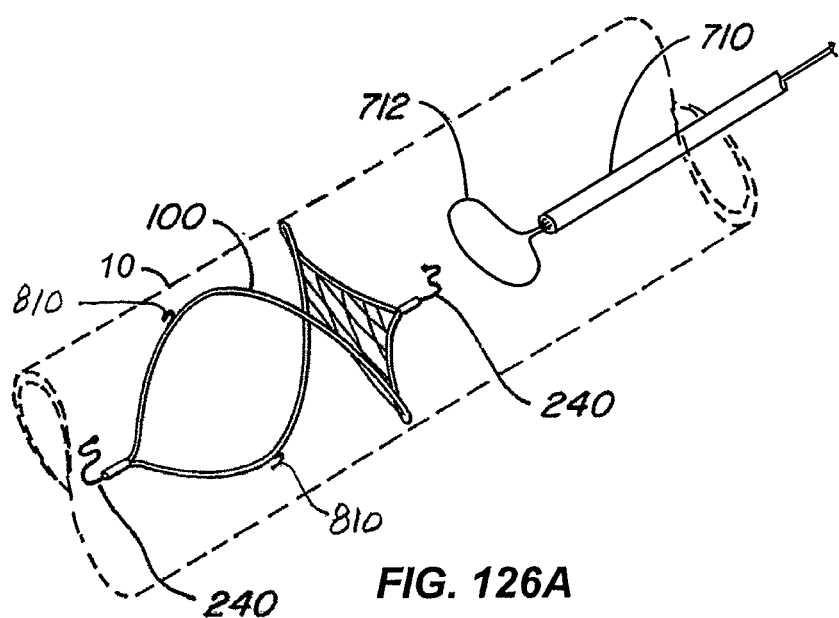
FIGS. 126A-D illustrate one approach and recovery sequence for retrieving a deployed filtering device
Figure 126B:
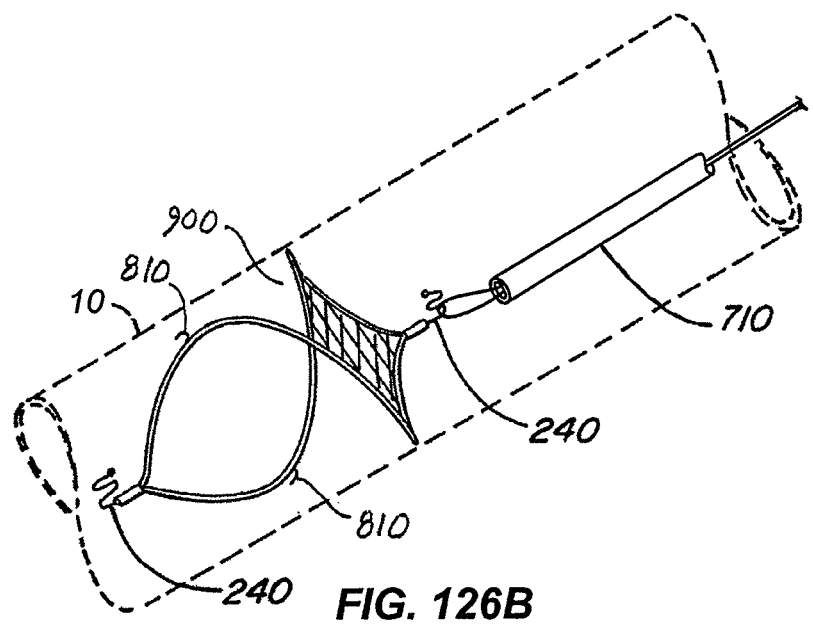
Figure 126C:
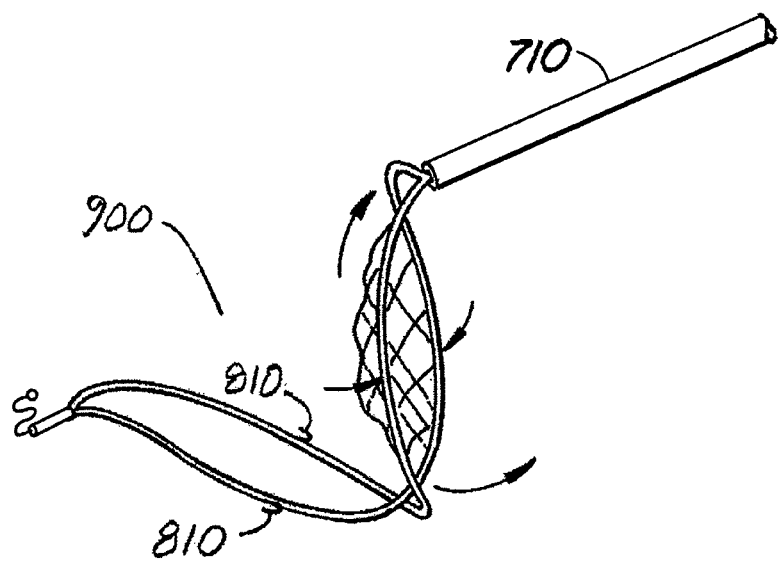

The sequence of device recapture and removal from a body lumen is illustrated and described above with reference to FIGS. 72A-C. A similar recovery sequence is used for embodiments of filter device 900 as illustrated in FIGS. 125A-125C. In this discussion, the device 900 is positioned in the vena cava. FIGS. 125A, 125B, and 125C illustrate an exemplary jugular recovery. The device 900 is illustrated within the vessel so that flow within the vessel initially passes through the material capture structure and then through the open support frame. FIGS. 126A-C illustrate an exemplary femoral recovery. The device 900 is illustrated within the lumen so that flow within the lumen initially passes through the material capture structure and then through the open support loop. A collapsed snare is advanced via a delivery sheath to the proximity of the retrieval feature 240. Once in place, the snare 712 is exposed and assumes a pre-defined expanded loop shape (FIGS. 125A and 126A). The loop shape is placed over the retrieval feature 240 as illustrated in FIGS. 125B and 126B. Advantageously, retrieval features of the present invention are positioned relative to and in contact with the luminal wall so that the feature may be more easily captured by a retrieval device such as a snare.

Figure 126D:
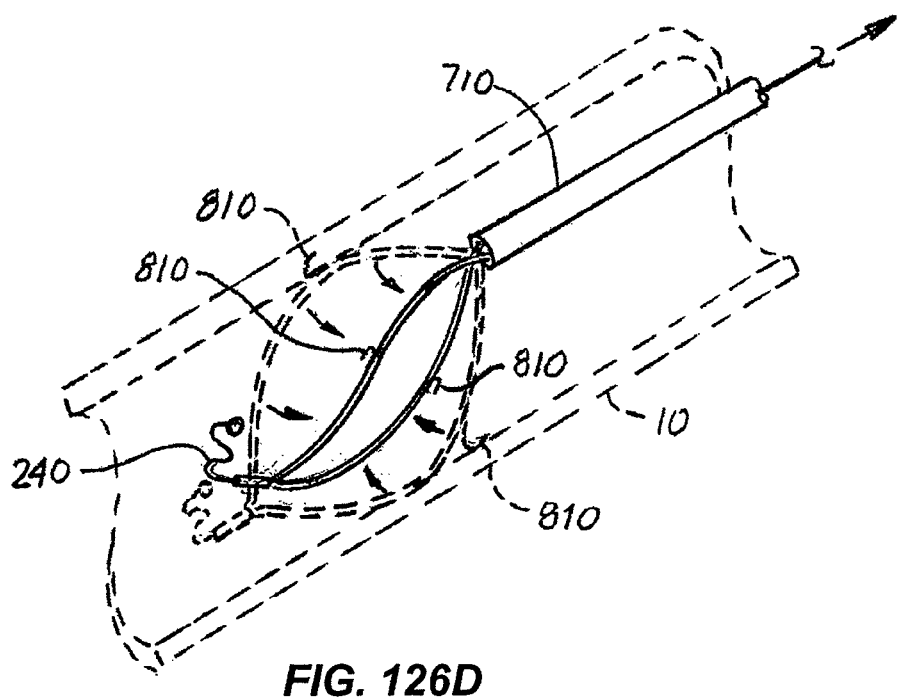

The snared device 900 can then be either pulled into the sheath 710, or alternatively and more preferably, the recovery sheath 710 is advanced over the device 900 while maintaining positive control of the snare 712 as the sheath 710 advances over the device 900. Advancing the recovery sheath 710 over the device 900 facilitates atraumatic removal of the device 900 from any tissue that has grown in or around the device 900. Additionally, the retrieval action, which tends to collapse the device radially inward (FIGS. 125C and 126C), also facilitates removal from any tissue layer formed on the device while also withdrawing the fixation elements from the lumen wall. Moreover, recovering the filtering device by pulling on a portion of the filter structure (i.e., a retrieval feature) removes the opposing spiral elements and the fixation elements or tissue engagement structure attached to them from the lumen wall. As the device 900 is drawn into the sheath 710, the pre-formed shape of the device 900 also urges the support members away from the lumen wall which also assists in retracting or disengaging fixation elements from the lumen wall (FIG. 126D).

Figure 124A:
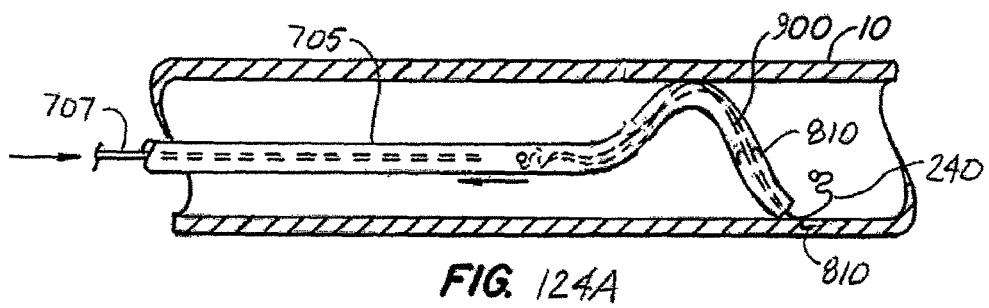
FIGS. 124A-124E illustrate an exemplary positioning and filter deployment sequence.
Figure 124B:
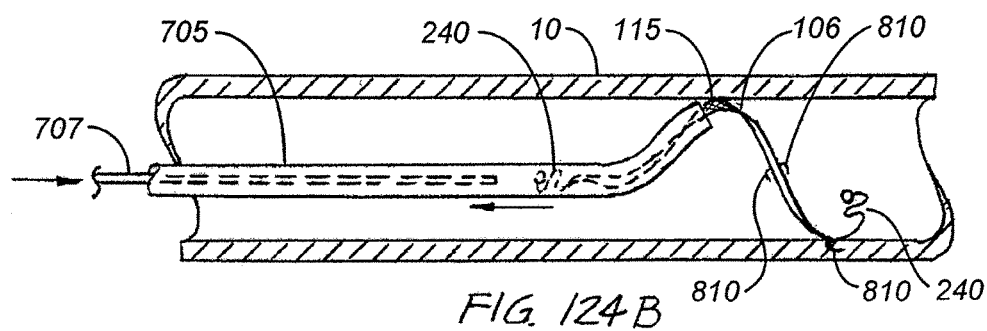
Figure 124C:
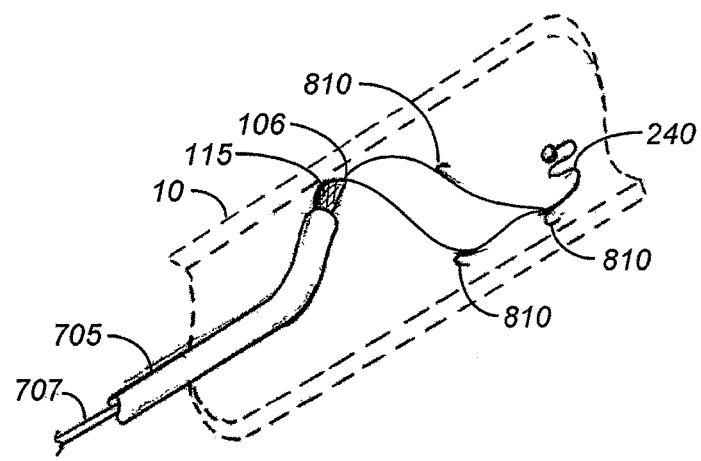

Having discussed the various techniques and alternatives for positioning, deploying and retrieving a filter, a method of positioning a filter within a lumen will now be described. FIGS. 123A and 123B illustrate an embodiment of a step of advancing a sheath containing a filter through a lumen. FIG. 124A illustrates an embodiment of a step of deploying a portion of the filter from the sheath into the lumen to engage the lumen wall with a fixation device while maintaining substantially all of a material capture structure of the filter within the sheath. As shown in FIG. 124A, the retrieval feature 240 and at least one fixation element 810 have exited the sheath 705. The remainder of the filter including the material capture structure is still inside the sheath 705. Next, as shown in FIGS. 124B and 124C, is an embodiment of a step of deploying a support frame from the sheath to a position along and engaged with the lumen. The support frame is also used to engage fixation elements with the lumen walls. The shape and design of the support frame itself generates radial forces that also assist in securing the filter into position and maintaining the position of the filter within the lumen. FIG. 124C illustrates the support frame deployed from the sheath 705 and opened along the lumen 10. Two fixation elements 810 are shown engaged the lumen wall. The crossover 106 is also deployed. A portion of the material capture structure 115 adjacent the crossover 106 is also shown exiting the sheath.

Figure 124D:
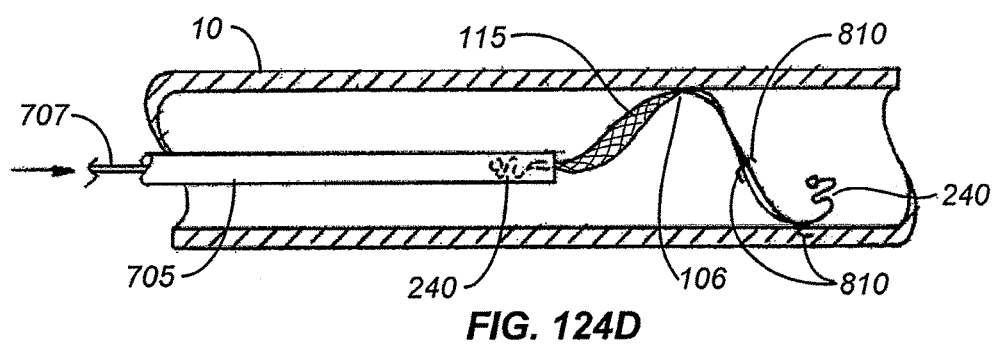

Next is the step of deploying the material capture structure of the filter from the sheath into a position across the lumen. FIG. 124D illustrates the material capture structure exiting the sheath. A retrieval feature 240 is still inside of the sheath (shown in phantom).

Figure 124E:
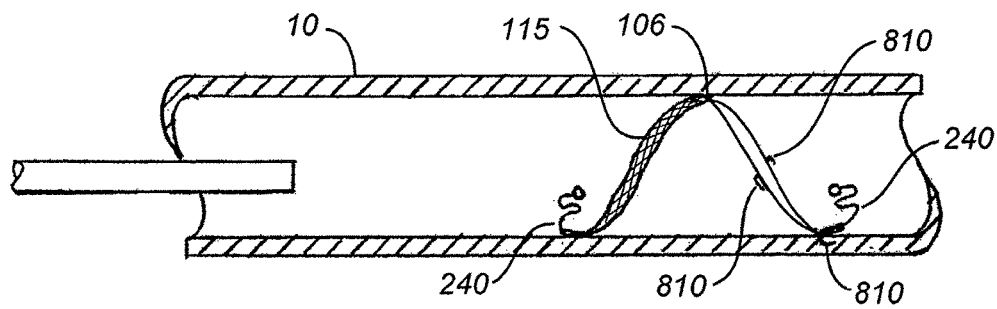

FIG. 124E illustrates the fully deployed filter 900. The second retrieval feature 240 is in position against the lumen wall and the material capture structure is deployed across the lumen. FIG. 124E also illustrates an embodiment of the step deploying a filter retrieval feature 240 from the sheath 710 after the step of deploying another portion of the filter step.

In one embodiment, the filter illustrated in FIG. 124E could be modified to include a fixation element 810 on or near both retrieval features 240. In such an embodiment, as the last portion of the filter and the second retrieval feature exists the sheath 710 (the movement from FIG. 124D to 124E), another fixation element 810 at or near the second retrieval feature engages the lumen wall.

In another aspect, the method of positioning a filter may include the step of deploying a crossover structure of the filter into the lumen before or after the deploying the material capture structure of the filter step. One aspect of this step is illustrated in FIGS. 124B and 124C. These two views illustrate the partially deployed filter 900 having one retrieval feature and three engagement elements 810 out of the sheath 710 and into contact with the lumen. Additionally in this illustration, the crossover 106 has exited the sheath 710. In this stage of deployment, the engagement feature 240 is against one lumen wall, the crossover 106 is against another wall generally opposite to the retrieval feature 240. The deployed open support frame extends along the lumen between the crossover 106 and the engagement feature 240.

The collapsible nature of the filters of the present invention allows for filter recovery from the same direction that the filter was deployed as well as recovery from the opposite direction the filter was deployed. Embodiments of the filters of the present invention also reliably position retrieval features against the lumen wall to present in a way that is easy to snare. A filter may be deployed into the inferior vena cava using a femoral access route. Then that same filter may be recovered using an access route from the jugular or the superior vena cava as shown in FIG. 125A. Similarly, a filter placed into the vena cava using a jugular deployment route may be removed using a femoral approach as shown in FIG. 126A. In one specific example, the recovery is accomplished by maneuvering a snare towards the filter in the same direction used during the advancing step described above. Next, there is the step of engaging the snare with a filter retrieval feature positioned against a wall of the lumen. In an alternative technique, there is the step of maneuvering a snare towards the filter in the opposite direction used during the advancing step. Next, there is the step of engaging the snare with a filter retrieval feature positioned against a wall of the lumen.

The techniques for filter placement and recovery may be modified in other ways as well. For example, a method of positioning a filter as described above may be adjusted to include the step of deploying a filter retrieval feature from the sheath before the deploying a portion of the filter step. In another alternative, the step of placing the filter retrieval feature against the lumen wall may be performed before or after the positioning of a crossover within the lumen. Additionally or alternatively, the step of deploying a filter retrieval feature may also include placing the filter retrieval feature against the lumen wall.

Additionally, repositioning the filter 900 from one lumen position to another is accomplished in a similar fashion as described above with regard to FIGS. 74A-74D. Many embodiments of the device 900 have at least one atraumatic end such as illustrated in the non-limiting examples of FIGS. 90C, 91, 99, 96, 97, 94, 89C, 89A, and 88. In this context an atraumatic end is one that does not have any fixation or tissue engagement features. Because of the atraumatic design of these filter device embodiments, repositioning of the filter device 900 may be accomplished by fully recapturing (see FIG. 74C) or only partially recapturing (FIG. see 74B) the device 900 into a recovery sheath 710. By maintaining the portion of the device 900 having fixation elements contained within the sheath 710, the atraumatic end may be moved into the desired position and confirmed in position before deploying the remainder of the device and engaging the fixation elements. The atraumatic design of the device 900 allows the device to partially deploy such that only the atraumatic end is in the lumen. The partially deployed device may then be pulled along the lumen wall into the desired position. Once in position, the remainder of the device is then released from the sheath thereby allowing the fixation elements to engage with the lumen walls as they are freed from the sheath. The delivery sheath and recovery sheath are provided with the same reference numbers since filter devices of the present invention may be deployed into and recovered from the vasculature using sheaths that are about the same size. As such, devices of the present invention may be deployed into the vasculature from a delivery sheath having a first diameter. Then, the device may be retrieved from the vasculature using a recovery sheath having a second diameter no more than 2 Fr larger than the first diameter (1 Fr=0.013"=⅓ mm). Alternatively, the second diameter may be no more than 1 Fr larger than the first diameter or, alternatively, the first diameter is about the same as the second diameter.

The various aspects of the filter embodiments described above with regard to FIGS. 123A-126D or for moving a filter or repositioning or recapturing a filter may be modified to be or used with a filter having enhanced echogenic properties characteristics or features. This filter embodiment may be modified with enhanced echogenic characteristics including one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. In other aspects, the filter illustrated and described in FIGS. 123A-126D may be modified according to FIGS. 127-135 or in conjunction with a system or as further described in FIGS. 136A-138B.

While many of the features and alternative designs of fixation elements and tissue engagement structures have been shown and described with regard to FIGS. 88-125, it is to be appreciated that the invention is not so limited. The features and alternative embodiments described in FIGS. 83A-87 may also be applied to the various filters with fixation elements and tissue engagement structures. Additionally, the filters and embodiments described with regard to FIGS. 2A, 2B, 2C, 6C, 7D, 7G, 9A-10B, 11-19, 64A-67, 69A-87 may also be adapted to include any of the fixation elements or tissue engagement structures described or illustrated in FIGS. 88-126D.

Filters are more complex structures in contrast to the relatively simple designs found in catheters and needles. In a more complex device like a filter there is a need to identify specific portions within the device during some medical procedures. In addition, it would be advantageous as well to determine the orientation of the device including components within the device to one another (as used for determining deployment, retrieval and the various intermediate stages thereof) as well as the overall filter orientation to the surrounding lumen or vessel. In contrast to the conventional techniques using location of the tip or start or end of the entire length, a more complex structure such as a filter position, orientation or relative placement information would yield specific benefits. In some cases, aspects, portions or attributes of the overall filter or filter components or portions will enable more useful determinations about the filter in relation to the physiological environment. In one aspect, an intravascular ultrasound (IVUS) catheter and processing system or signal processing algorithm is used to confirm filter sizing selection, guidance for filter placement, filter implantation steps, filter and/or vessel measuring using IVUS before during and/or after steps to confirm sizing selection and fit is appropriate under the physiologic environment and for confirmation and/or documentation of proper sizing selection, placement, engagement or degree of engagement of fixation elements (if present), clot burden, orientation and/or deployment in a patient or physician medical record.

In one aspect, embodiments of the present invention are directed toward medical devices having a complex shape or that are configured to move from stowed to deployed configurations that may also have specific orientation and placement criteria for proper use in a lumen, vessel or hollow organ. One such complex device is an IVC filter. Aspects of the present invention include such devices employed within the human body which have enhanced ultrasound visibility by virtue of incorporation of an echogenic material using any of the techniques described herein alone or in any combination.

In one aspect, there are described herein various alternative filter designs for increasing the echogenicity of the filter. A filter with enhanced echogenic characteristics may include one or more than one of: (a) a modification to one or more components of the filter to enhance the echogenic characteristics of the component; (b) formation of dimples into a component surface of sufficient number and scaled to a suitable size, shape, orientation and pattern for use with intravascular ultrasound systems; (c) protrusions formed in, placed on or joined to a filter surface; (d) roughening one or more surfaces of a filter, for example using a chemical process, a laser or bead blasting technique; and (e) altering one or more steps of a filter manufacturing technique to introduce cavities, voids or pockets to locally modify or adapt one or more acoustic reflection characteristics to improve echogenicity in one or more specific regions of a filter. One example of the manufacturing alteration is to introduce gaps between the segments of tubing or coverings whereby the gap provides the echogenic enhancement. In addition, cavities, voids, pockets, dimples, gaps and the like may be left empty or, optionally, filed, partially filed or lined with any of the echogenic materials described herein.

In one aspect, there are provided embodiments of a filter having enhanced echogenic characteristics in or related to at least one or a portion of: an proximal end, a distal end, a terminal proximal end, a terminal distal end, a retrieval feature, an atraumatic tip on a retrieval feature, a mid-strut region, a leg or strut portion having at least one orientation attribute to another portion of the filter, an indicia of a location of a fixation element or a retrieval feature, a location on a portion of the filter selected such that in use with a particular fixation element the marker in in a location that indicates that the fixation element is fully deployed into a wall of a lumen or portion of a vessel or hollow organ (i.e., the marker is against the lumen wall or nearly so when the fixation element is fully engaged. As such, see the marker against the wall indicates proper deployment, spaced from or not visible would indicate, respectively, not fully engaged or over penetration); a portion of the distal tip and/or an elongated portion. The above described methods may also be applied to the other techniques and alternatives described herein.

In still further embodiments, a portion, component or aspect of an intraluminal filter may have enhanced echogenic attributes by applying a coating or sleeve containing one or more of the echogenic materials disclosed herein or fabricated according to any of the techniques or having any of the attributes to enhance echogenic qualities as described herein. In some aspects, the enhanced echogenic attributes are provided by the incorporation into, application onto or within a component or portion of a filter one or more echogenic materials or echogenic markers in a specific configuration, location, orientation or pattern on the filter.

Enhanced echogenic markers or locations may be devised and placed for use individually or in combinations such as to facilitate the identification to an IVUS system or ultrasound imaging modality an indication or signature for a specific location on a filter, such as, for example, a retrieval feature, a terminal proximal end, a terminal distal end, a location of a fixation element or a location of some other indicia that identifies a specific aspect of a particular filter design. In addition or alternatively, two or more enhanced echogenic markers or portions may be used in combination to provide additional information about a filter such as orientation with in a vessel, confirmation of deployment or a portion of a deployment sequence, confirmation of final placement, confirmation of migration or lack of migration, confirmation of retrieval or progress in a retrieval sequence and the like according to the various processes and used for filters within the vasculature or in lumens of the body. In another specific embodiment, the use of IVUS techniques with embodiment of the echogenic enhanced filters describe herein may also be used to measure the diameter of the vessel at specific device locations indicated by the echogenic markers during or after deployment or retrieval of a filter.

In still further aspects, the use of IVUS techniques with embodiment of the echogenic enhanced filters describe herein may also be used to determine, detect or indicate inadequate dilation, adequate dilation, filter expansion, degree of filter expansion, filter-vessel engagement and degree or engagement, strut/leg/anchor position and other attributes relating to the interaction between the filter and the surrounding physiological environment.

Still further, the echogenic markers are positioned with regard to the likely or planned positioning of the IVUS transducer and/or likely pathways for acoustic energy used by the imaging system. By way of example, if the IVUS transducer is forward looking, then those forward looking aspects of the filter will be provided with the enhanced echogenic aspects. In another example, if the IVUS transducer is cylindrically shaped and will be positioned through the interior portion of a filter then the filter will be provided with enhanced echogenic aspects on interior surfaces or portions that would receive acoustic energy from such as transducer in such a position. Other modifications are within the scope of the invention based on the particular style of IVUS transducer used, the position relative to the filter and the placement and type of echogenic feature incorporated into the filter. Put another way, the echogenic enhancements of the filters described herein are selected, designed and positioned on the filter with regard to the IVUS sensor type, acquisition mode and position relative to the filter. Additional details in the use of IVUS with filters is further described in U.S. Pat. Nos. 6,645,152 and 6,440,077, both of which are incorporated herein by reference in their entirety for all purposes.

In one aspect, the placement and signature of such enhanced echogenic markers are discernible to a human user viewing an ultrasound output alone or in combination with being discernible to a computer system configured for the processing of an ultrasound return including a return from the enhanced echogenic filter.

In various alternatives, the echogenic material may either be applied to a portion of or a component of a filter in any of a number of different techniques.

In one example, an echogenic component or additive is applied to or incorporated into a filter or portion of a filter as a selective coating applied to a portion or component of a filter.

In one example, an echogenic component or additive is applied to or incorporated into a filter or portion of a filter as a mold formed to be placed over or joined to a portion of component of a filter.

In one example, an echogenic component or additive is applied to or incorporated into a filter or portion of a filter as an extruded sleeve formed in a continuous segment to cover a portion or component of a filter. In one embodiment, one of the inner tubular member or the outer sleeve or coating may be fabricated of a material according to the present invention, having increased echogenicity, with the other of the inner tubular member fabricated of a biocompatible polymer such as polyurethane or silicone rubber, for example.

In one example, an echogenic component or additive is applied to or incorporated into a filter or portion of a filter as a compound or two layer structure comprising an inner tube and an outer tube or sleeve with one or both of the tubes made from or including or incorporating one or more echogenic materials or modifications as described herein. In addition or alternatively one or both sleeves, tubes described herein may include or encapsulate an echogenic marker or component of specific shape or geometry, for example, as in the case of a tube structure having within the sidewall of the tubing a coiled structure. In one aspect, the coiled structure is made from an echogenic material and the windings are provided in a manner that is useful in any of the aspects of the filter described herein. The coil may have a particular size or variation in size, pitch or variation in pitch or other attribute useful in providing an echo identifiable aspect of the filter property being determined. In one specific embodiment, the dimensions of the coil or other echogenic material has dimensions selected for increasing acoustic reflection with regard to the resolution or processing algorithms used in the imaging ultrasound system.

In one example, an echogenic component or additive is applied to or incorporated into a filter or portion of a filter as a braided structure incorporated into a compound or two layer structure comprising an inner tube and an outer tube or sleeve with one or both of the tubes made from or including or incorporating one or more braid comprising echogenic materials or modifications as described herein. In addition or alternatively one or both sleeves, tubes described herein may include or encapsulate an braid formed into an echogenic marker or component of specific shape or geometry, for example, as in the case of a tube structure having within the sidewall of the tubing a braided structure. In one aspect, the braided structure is made from an echogenic material and the braided is a small diameter that is when wound around the tubes or sleeve or directly onto a portion of or component of a filter. The winding pattern and spacing of the braided materials are provided in a manner that is useful in any of the aspects of the filter described herein. The braid may have a particular braid strand composition, structure, size or variation in size, pitch or variation in pitch or other attribute useful in providing an echo identifiable aspect of the filter property being determined. One or more of the strands in the braid may be formed from an echogenic material. One or more of the strands may be formed from a material having improved radiopaque characteristic. One or more of the strands may be formed from a material having both echogenic and radiopaque properties. The strands of a braid may be combined using any of the above described strand characteristics. In another alternative, a modified braid structure may be used as illustrated and described in FIGS. 38A and 38B.

In another alternative, in still another example, an echogenic component or additive is applied to or incorporated into a filter or portion of a filter as the a series of short segments placed adjacent to one another along a portion or component of a filter in either a close packed or spaced arrangement. In another embodiment, the spacing or voids between adjacent segments may also be adjusted or selected so as to enhance echogenic capabilities of the filter using the material difference introduced by the spacings or voids.

In another alternative, in still another example, an echogenic component or additive is applied to or incorporated into a filter or portion of a filter as a tubing or sleeve suited to heat shrink operations. In one aspect, there is a manufacturing or assembly steps of sliding one or more sleeves over portion of the filter then apply heat to shrink down the segment about the portion of the filter. In particular, various embodiments provide for the specific placement of such a shrink fit tubing having enhanced echogenic characteristics as described herein. It is to be appreciated that the sleeves, segment or tubes may be provided from or have echogenic modifications or elements incorporated into suitable materials such as, for example, ePTFE, PTFe, PET, PVDF, PFA, FEP and other suitable polymers. Still further, these and other materials may be formed in shapes other than tubes but may also take the form of strands, lines, fibers and filaments to be applied in accordance with the echogenic enhancement techniques described herein. In some embodiments, the tubes or segments applied to a filter may have the same or different composition as well as have the same width or different widths. In one aspect, the width or thickness of a plurality of bands is used to provide a code or information about the filter. The use of echogenic bands of different widths is a marking technique similar to the way that different size and color rings on a resistor are arranged in a pattern to describe the resistor's value.

In another alternative, in still another example, an echogenic component or additive is applied to or incorporated into a filter or portion of a filter is extruded over a portion of or a component of the filter.

In another alternative, in still another example, an echogenic component or additive is applied to or incorporated into a filter or portion of a filter is by bonding an echogenic material or components to the filter using a suitable adhesive or bonding technique.

In any of the above described configurations, the portion or component of the filter may be modified with dimples, grooves, pockets, voids. In other aspects, there may be one or more full or partial circumferential recesses, rings, surface diffraction gratings or other surface features to selectively enhance or provide an echogenic property in that portion of the filter, to aid in or foster the application of the echogenic materials. In still further aspects, any of above described surface modifications may also be used to uniquely identify a portion of a filter or any of the above in any combination.

In still further aspects of any of the above echogenic markers or attributes the thickness of the sleeve or coating or component may decrease at its proximal and distal ends to provide for a smooth outer surface. As yet an additional alternative, a coating, marker or other echogenic material may extend proximally to or closely adjacent to the distal end or the distal end or both of the filter component or filtering device.

In still other alternatives or combinations, some filter design embodiments alter components of the filter to enhance echogenicity such as, for example, material selection to incorporate echogenic materials. Examples of echogenic materials include palladium, palladium-iridium or other alloys of echogenic materials.

In some embodiments, echogenic microbubbles are provided in a portion of a filter to enhance the acoustic reflections of that aspect of the filter. Echogenic microbubbles may be prepared by any convenient means and introduced into the component or portion thereof or by a coating or sleeve or shell or other transferring means or mixed with a polymer or other suitable base compound prior to extension of extrusion, molding casting or other technique. The echogenic microbubbles may be pre-prepared or prepared inside the component or element or marker as appropriate. Aspects of the preparation or use of microbubbles are described in U.S. Pat. Nos. 5,327,891; 4,265,251; 4,442,843; 4,466,442; 4,276,885; 4,572,203; 4,718,433 and 4,442,843. By way of example, echogenic microbubbles can be obtained by introducing a gas, e.g. carbon dioxide, into a viscous sugar solution at a temperature above the crystallization temperature of the sugar, followed by cooling and entrapment of the gas in the sugar crystals. Microbubbles can be formed in gelatin and introduced into a component or portion of a device. Microbubbles can also be produced by mixing a surfactant, viscous liquid and gas bubbles or gas forming compound, e.g. carbonic acid salt, under conditions where microbubbles are formed.

In still further alternatives, there is also the incorporation of dual mode materials (radiopaque and echogenic) into a polymer then used to form part of, be applied or otherwise incorporated with a filter device as described herein. Some of these polymer compounds may be fabricated to enhance aging and shelf life and have other beneficial attributes. In one aspect, a filter or portion thereof includes one or more selected segments that are constructed using visibility materials compounded with one or more polymeric materials that make the selected segments visible using both fluoroscopy and ultrasonic imaging. In one specific example, the visibility material may take the form of tungsten and/or tungsten carbide particles dispersed within a polymeric material. In one specific aspect, the radiopaque and echogenic material includes tungsten and/or tungsten carbide particles distributed within a base polymeric material.

In one embodiment, a portion of or a component of a filter includes or has been modified to have an inner layer including a radiopaque and echogenic material. In one alternative, the radiopaque and echo genic material includes particles distributed within a base polymeric material (i.e., a first polymeric material) including a polyether block amide; and an outer layer including an additional polymeric material (i.e., a second polymeric material). In certain embodiments, the additional polymeric material is a thermoplastic elastomer. Optionally, the additional polymeric material is more resistant to hydrolysis and/or oxidation than the base polymeric material.

In still further aspects, a component, a portion or an element added to a filter may be regarded as an echogenic body member that is a part of an echogenic filter to be sonically imaged. The echogenic body member is at least partially made up of a composite material which is echogenically imageable in the patient, such as by the use of ultrasonic imaging equipment used either within the patient or external to the patient. In one aspect, a composite material includes matrix material with discrete acoustic reflective particles embedded in matrix material. In one aspect, the matrix material is a biocompatible plastic. Examples of suitable plastics may include urethane, ethylene, silicone, polyethylene, tetrafluorethylene. In one aspect, a matrix is a formable, pliable material which may be molded and/or extruded to a variety of shapes, depending upon a specific application. The sound reflective particles are embedded in matrix material. Particles are, by way of example, made of a hard material, such as small glass particles that are solid or filled with an acoustically reflective medium. In one aspect, glass particles having a generally spherical shape forming glass microspheres. Glass microspheres with an outer diameter of about 5 microns is one acceptable size. Other sized particles may be utilized as, for example, ranging between 1 and 50 microns and beyond. Particles sized below the resolution size of the imaging ultrasound system in use may be arranged into patterns of sufficient size and orientation to the acoustic waves that result in a discernible feature by the imaging ultrasound system. Furthermore, the particles do not necessarily have to be spherical, or may be partially spherical. Still further, the shape of the particle could be altered to enhance acoustic reflection by presenting different shapes of particles, sizes of particles and combinations thereof to modify acoustic characteristics of the matrix material. By way of example, the particles may be shaped into an "Ordered array." "Ordered arrays" can take the form of a macrostructure from individual parts that may be patterned or unpatterned in the form of spheres, colloids, beads, ovals, squares, rectangles, fibers, wires, rods, shells, thin films, or planar surface. In contrast, a "disordered array" lacks substantial macrostructure.

By way of example, an echogenic marker may comprise particles that individually are below the resolution of the imaging ultrasound system. The echogenic marker is the combination of these below imaging ultrasound resolution particles in combination, in 1D, 2D or 3D patterns, in graphic arrays, or in machine readable combinations to make a signature. Based on the specific characteristics of the combination of particles, the acoustic returns from an echogenic marker or combination of echogenic markers may be visually perceptible in a display for interpretation by a user or may be detected and interpreted by one or more acoustic reflection or spectral processing algorithms within an imaging ultrasound processing system.

In one aspect, the echogenic material is fabricated by incorporating nanometer sized particles of sonically reflective materials, for example iron oxide, titanium oxide or zinc oxide into a biocompatible polymer. In one method of fabrication, the acoustically reflective particles are mixed with a powdered thermoplastic or thermosetting material such as a polyether amide, a polyurethane or an epoxy, or polyvinylchloride followed by thermal processing of the mixture to provide a material of increased sonic reflectance which may be applied as a coating on medical devices of the type discussed above or may be incorporated as a structural component of the medical devices as described herein.

In still further embodiments and aspects, the particles included to provide echogenic enhancements may be selected, arranged or incorporated to provide acoustically geometrically tuned nanostructures, microstructures or macrostructures. The particles provided herein are formable in all shapes currently known or to be created for acoustic reflection enhancement. In non-limiting examples, the nano-, micro- or macro-particles are shaped as spheres, ovals, cylinders, squares, rectangles, rods, stars, tubes, pyramids, stars, prisms, triangles, branches, plates or comprised of an acoustically reflective surface or where one or more surfaces is adapted such as by roughening or dimpling or other technique used to alter acoustic reflection properties. In non-limiting examples, the particles comprise shapes and properties such as plates, solid shells, hollow shells, rods, rice shaped, spheres, fibers, wires, pyramids, prisms, or a combination thereof.

In one specific aspect, a partially spherical surface may be provided on the outside and/or the inside of particles, as for example a particle with a hollow spherical space therein. Particles are made up of a different material than the matrix. While desiring not to be bound by theory, it is believed that a spherical shape provides for sound reflections at a variety of angles regardless of the direction from which the ultrasonic sound waves are emanating from, and accordingly, are more likely to reflect at least a portion of the transmitted signal back to the ultrasonic receiver to generate an image. Since many of matrix materials available are relatively ultrasonically transparent in a patient, sound reflective particles provide adequate reflection. The use of a composite, rather than a solution, provides adequate size for acoustic reflection off of the discrete particles embedded in the matrix. As indicated, a variety of materials may be utilized for the sound reflective particles, such as aluminum, hard plastic ceramics, and, metal and/or metal alloys particles, and the like. Additionally, liquids, gases, gels, microencapsulants, and/or suspensions in the matrix may alternatively be used either alone or in combination, so long as they form a composite with the desired ultrasonically reflective characteristic.

Any of the above embodiments, alternatives or filter modifications to enhance echogenic characteristics may also be designed or implemented in such a way as to provide an echogenic identifiable or unique trait or acoustic reflection signature that may be registered by a human operator looking at a display or identified using signal processing techniques of a return containing acoustic reflections from the filter in an imaging ultrasound system. In one example, there is a surface of the filter having one or more echo registerable or identifiable feature, mark or indication in a position useful for determining one or more of: a location of an end of a filter; a location of a fixation element on a filter; a location of a retrieval feature on a filter; an orientation of one or more of a leg, a strut, a filter or an end of a filter relative to another of a leg, a strut, a filter or an end or the orientation of the overall filter to a lumen, vessel or hollow organ in a body. Moreover, in another widely applicable aspect of providing enhanced imaging characteristics to a filter as described herein, the characteristic or modification—however added or incorporated into the filter—enable a filter, a filter component or a specified portion of a filter to be more readily imaged by intravascular ultrasound as described herein. In still another aspect, the characteristics or modification to the filter are oriented and positioned in order to facilitate IVUS imaging via an IVUS probe borne by a filter deployment or retrieval catheter, snare, or other implement provided to facilitate the use of intravascular filters.

Figure 127:
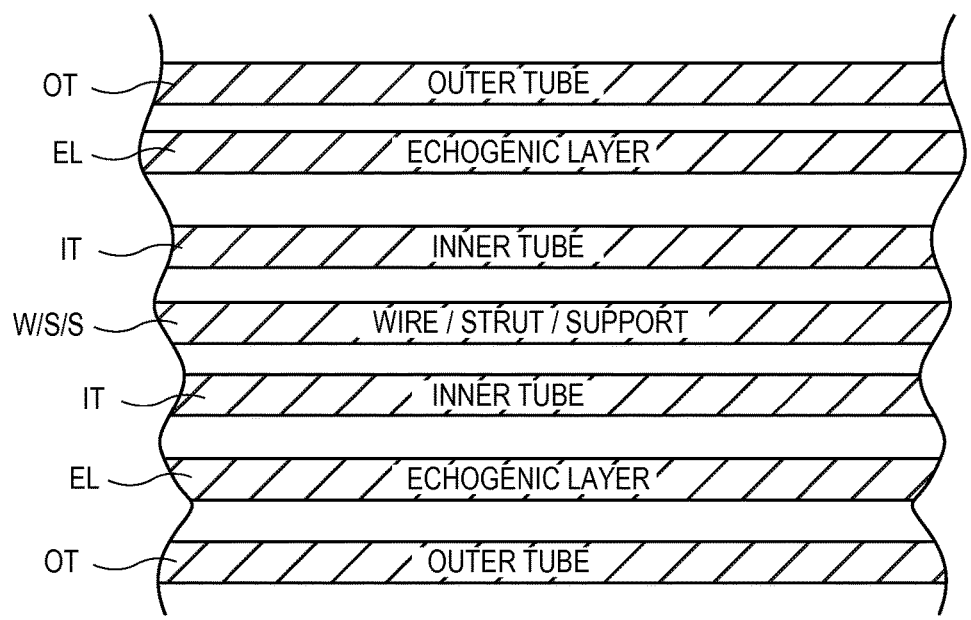
FIG. 127 is a section view of a wire strut or support element of a filter (w/s/s) having multiple segments in a concentric arrangement.

FIG. 127 is a section view of a wire strut or support element of a filter (w/s/s). In this illustrative embodiment the w/s/s is shown having multiple segments in a concentric arrangement. In this illustrative embodiment, the wire is encased in alternating tube segments. There is an inner tube (IT) directly adjacent to the wire. There is an echogenic segment layer (EL) adjacent to the inner layer. The inner tube may be selected to act as bonding layer to increase adhesion between the echogenic layer and the filter wire, strut or support member. In this embodiment, there is an outer tube (OT) over the echogenic layer. In alternative configurations, either or both of the inner tube or the outer tube may be omitted. The echogenic layer is a segment having one or more of the echo genic characteristics described herein.

FIGS. 128-133 provide various exemplary embodiments of a segment 87 having one or a plurality of one or more than one type of echogenic characteristic, property or feature added thereto. Each of the illustrated echogenic adaptations applied to segment 87 along with segment 87 itself may be sized, scaled and/or shaped as described herein as needed based upon the requirements of the portion of the filter and the echogenic characteristic. In one embodiment, the segment may be as illustrated and described, for example, in FIGS. 41-53D.

Figure 128:
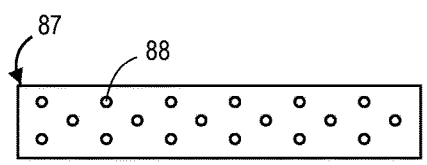
FIG. 128 is an embodiment of a segment having one or a plurality of laser drilled holes formed therein.

FIG. 128 is an embodiment of a segment 87 having one or a plurality of laser drilled holes 88 formed therein. The diameter and the shape of the holes may be selected based upon the size of the filter or filter component to which the segment 87 will be attached. The holes 88 may be completely through the wall of the segment or only partially through the wall. The holes 88 may be formed in any pattern, spacing or orientation as described herein.

Figure 129:
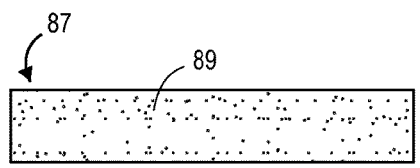
FIG. 129 is an embodiment of a segment having one or a plurality of raised features or alternatively roughed portions formed thereon.

FIG. 129 is an embodiment of a segment 87 having one or a plurality of raised features or alternatively roughed portions 89 formed thereon. The size and shape of the raised features or the roughness of the surface may be selected based upon the size of the filter or filter component to which the segment 87 will be attached. The raised features or portions of roughness 89 may be formed in any pattern, spacing or orientation as described herein.

Figure 130:
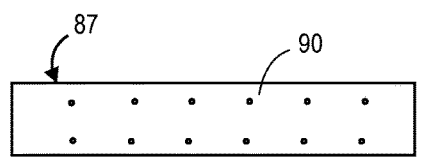
FIG. 130 is an embodiment of a segment having one or a plurality of bubbles formed therein.

FIG. 130 is an embodiment of a segment 87 having one or a plurality of bubbles 90 formed therein. The size, shape, pattern, and manner of incorporating one bubble 90 or a plurality of bubbles 90 into the segment 87 may be selected based upon the size of the filter or filter component to which the segment 87 will be attached. The bubbles 90 may be formed within the segment sidewall, near the surface of the segment sidewall or near the inner surface of the sidewall. The bubble or bubbles 90 may be formed in any pattern, spacing or orientation as described herein.

Figure 131:
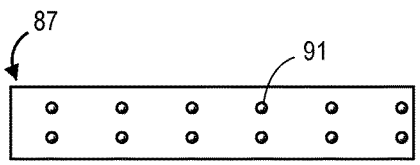
FIG. 131 is an embodiment of a segment having one or a plurality of dimples formed therein.

FIG. 131 is an embodiment of a segment 87 having one or a plurality of dimples 91 formed therein. The diameter and the shape of the dimples may be selected based upon the size of the filter or filter component to which the segment 87 will be attached. The dimples 91 may be formed in any pattern, spacing or orientation as described herein.

Figure 132:
FIG. 132 is an embodiment of a segment having a coil or braided structure within or about the segment.

FIG. 132 is an embodiment of a segment 87 having a coil or braided structure 92 within or about the segment 87. The size, shape, pattern, and manner of incorporating the coil or braid 92 into the segment 87 may be selected based upon the size of the filter or filter component to which the segment 87 will be attached. The coil or braid 92 may be formed within the segment sidewall, near the surface of the segment sidewall or near the inner surface of the sidewall. The coil or braid 92 may be part of a sandwich structure as illustrated and described in FIG. 127. The coil or braid 92 may be formed in any pattern, spacing or orientation as described herein to enhance the echogenic characteristics of the filter or filter portion attached to the segment 87. The coil or braid 92 may be continuous along the entire length of a segment 87 or, alternatively, the coil or braid 92 may be in short lengths selected so that a plurality of coils or braids are provided within a single segment 87. The braid may also be as illustrated and described with regard to FIGS. 38A and 38B.

Figure 133:
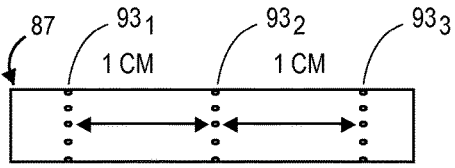
FIG. 133 is an embodiment of a segment having a plurality of echogenic markers arrayed in rings about the segment to provide an indication of measurement via the spacing between adjacent rings.

FIG. 133 is an embodiment of a segment 87 having a plurality of echogenic markers 93 arrayed in rings 93.1, 93.2 and 93.3. For purposes of illustration the rings are shown in an orientation that is generally orthogonal to the central longitudinal axis of the segment 87. The various embodiments of the rings may be spaced apart (as indicated by "measurement"). In the illustrative embodiment, the rings are shown with a sample spacing (i.e., measurement) of 1 cm between them. The spacing may be any suitable distance based on the factors described herein such as filter size and physiological environment. Similarly, the rings may be angled in other orientations relative to the longitudinal axis of the segment. For example, some ring may be in one angular orientation while other rings may be in a different angular orientation where the angular orientation or pattern of orientation is utilized to provide one or more of the filter functionality or echogenic characteristics described herein. In some specific configurations, the spacing and sizes used are in the millimeter range. In some specific configurations, the spacing and sizes are in the micron range. In some specific configurations, the size and/or spacing of a ring or between adjacent rings are in a combination of mm and micron ranges for sizes, spacings and features. The size and spacing of the echogenic markers 93 may be selected based upon the size of the filter or filter component to which the segment 87 will be attached. The markers 93 may be formed in any pattern, spacing or orientation as described herein in order to facilitate a measurement using the markers. Still further, the markers 93.1, 93.2 and 93.3 may be utilized for provide for other filter characteristics as described herein.

Figure 134:
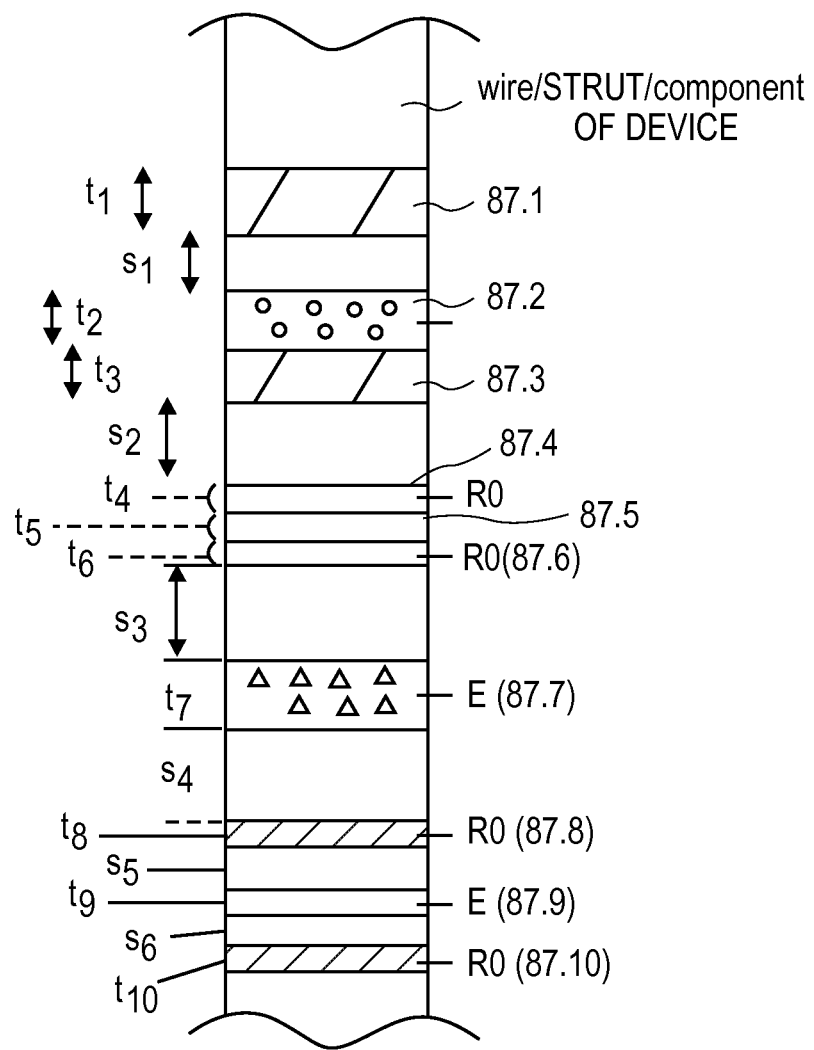
FIG. 134 illustrates various alternative configurations for a segment used alone or in conjunction with other segments.

FIG. 134 illustrates various alternative configurations for a segment used alone or in conjunction with other segments. The segments are illustrated along an exemplary wire, strut, or component of a filtering device. The segments may have different characteristics to enable the segment to be more readily imaged by a medical imaging modality used externally, internally or intraluminally. In one aspect, the segment characteristics are selected to provide for imaging enhancements for a filter being used within a vein or an artery. In another aspect, the segments may have different characteristics to enable the segment to be readily imaged by intravascular ultrasound as described herein. In still another aspect, the segments are oriented and positioned in order to facilitate IVUS imaging via an IVUS probe borne by a filter deployment or retrieval catheter, snare, or other implement. In one illustrative embodiment, the segments are selected and arrayed to facilitate imaging utilizing IVUS and an external medical imaging modality. In one exemplary embodiment, the external imaging modality is x-ray.

Also illustrated in FIG. 134 is the use of a combination of different echogenic characteristics (designated E) and radio-opaque characteristics (designated RO). These characteristics may be any of those described herein in any combination. The echogenic characteristic of a segment may be the same as another segment in a grouping such as in the E segments 87.9 and 87.5. Alternatively, the echogenic characteristic of a segment may be different from those in an adjacent group as with segments 87.2, 87.5 and 87.7.

FIG. 134 also illustrates not only that different characteristic and properties of segments may be used but also how variable segment dimensions may be used to aid in echogenic enhancement of a filter. As illustrated, the segments have different widths or thicknesses as indicated along the longitudinal axis of the wire, strut or component. As such, FIG. 8 illustrates a series of imagine enhancing segments 87.1-87.10 having a variety of width or thickness values t1-t10. In one embodiment, the segments are configured as short rings or bands. The thickness of segments in groups may be similar as illustrated in segments 87.1, 87.2 and 87.3 where the thicknesses t1, t2 and t3 are about the same. Similarly, segments 87.4, 87.5 and 87.6 illustrate segments of similar width or thickness where t4, t5 and t6 are about the same value. Similarly, segments 87.8, 87.9 and 87.10 illustrate segments of similar width or thickness where t8, t9 and t10 are about the same value.

FIG. 134 also illustrates how segments within a group or groups of segments may have a variety of different spacing (s1-s6) to provide enhancements to a filter for improving medical imaging modality characteristics. For example, in the segment grouping of 87.1, 87.2 and 87.3, there is a spacing s1 between segment 87.1 and segment 87.2 but then no spacing between segments 87.2 and 87.3. A spacing s2 is shown between segment 87.3 but then no spacing in the combination segment grouping formed by segments 87.4, 87.5 and 87.6. A spacing of s3 is shown between the three segment combination of 87.4, 87.5 and 87.6 to the single segment 87.7. The single segment 87.7 is spaced apart by spacing s4 from the equally sized (i.e., t8=t9=t10) and equally spaced (i.e., s5=s6) group of segments 87.8, 87.9 and 87.10. It is to be appreciated that in various alternative embodiments, the spacing used in groups of segments or between groups of segments may be the same or variable.

FIG. 135 is a view of an exemplary filter illustrating various alternative aspects of providing a filter with improved echogenic characteristics. The filter illustrated is a conical filter. It is to be appreciated that the filter of FIG. 135 is merely representative of one type of filter. It is to be appreciated that the various alternative enhancement, modifications and treatments described herein may be provided to any intravascular or intraluminal filter. The exemplary filter is dividing into three general sections A, B and C. Sections A, B and C may be the same type of enhancement or have an enhancement different from one another section. In addition, the type of enhancement in each section may be the same or different from one another in detection, response or appearance under ultrasound. In addition, a tag, feature or enhancement may be different within a section. Circles 902 are used to indicate exemplary locations for an echogenic feature, tag, marker or modification to an enhanced filter 10. The illustrative embodiment in FIG. 135 also illustrates a continuous echogenic layer, feature or modification or treatment 908. The illustrative embodiment in FIG. 135 also illustrates an echogenic attribute on/near an inflection point 906 in an enhanced filter structure 10. The illustrative embodiment in FIG. 135 also illustrates a segmented echogenic layer, feature or modification or treatment 904 on an enhanced filter structure 10. Section A is considered the apex, tip, distal portion or terminal end depending upon filter configuration. Section B is considered the mid-strut, middle, filtration portion, debris capture portion, or thrombus collection or lysing portion depending upon specific filter configuration. Section C is considered the rear portion, proximal portion, proximal terminal portion, anchor, fixation or perforation portion depending upon a specific filter configuration. It is to be appreciated as well that the echogenic features, tags, markers or modifications illustrated for sections A, B and/or C may be of the same type or different types depending upon the echogenic signature or attribute intended for that section, group or sections or filter. As such, the echogenic features, tags, markers or modifications for a particular section may be selected from any of the various alternatives described herein.

Echogenic characteristics may be added to each of the sections based on the type of function being measured or characterized. For example, echogenic markers, features or tags may be added to Section A in order to provide, for example: identification of the terminal end, end portion or retrieval portion of a filter. Echogenic characteristics of Section A may also be used for determinations related to Section A specifically or the filter generally of filter position, positioning, attitude within the lumen, localization of the filter within the vasculature and other traits common to the characterization of intravascular devices. For example, echogenic markers, features or tags may be added to Section B in order to provide, for example: identification of the mid strut portion, middle, filtration region or capture region. Echogenic characteristics of Section B may also be used for determinations related to Section B such as for sizing, centering, symmetry of implant or implantation, placement, apposition of implant to vessel walls, clot burden, deployment status or completion, gauge of filter capacity and/or filter contents as well as filter position, positioning, attitude within the lumen, localization of the filter within the vasculature and other traits common to the characterization of intravascular devices. For example, echogenic markers, features or tags may be added to Section C in order to provide, for example: identification of the rear portion, terminal end, retrieval feature, anchor, anchor location, fixation, or depth of insertion, perforation indication or other aspects of the rear or proximal portion of a filter. Echogenic characteristics of Section C may also be used for determinations related to Section C such as for sizing, centering, symmetry of implantation or placement of legs struts and the like, as well as for determination of wall apposition, anchor penetration or perforation, anchor insertion or depth. Still further, the markers or tags in Section A, B, and/or C may be added to aid in determining or evaluating filter position, positioning, attitude within the lumen, localization of the filter within the vasculature and other traits common to the characterization of intravascular devices.

In some embodiments, a pressure sensor and/or an intravascular ultrasound (IVUS) transducer can be added to or incorporated into a delivery system and method for use with any of the filters described herein. The pressure sensor can be used to measure the pressure at various positions within the vasculature, which can be used to determine blood flow, while the intravascular ultrasound (IVUS) transducer can be used to measure fluid flow and/or provide imaging within the vessel. These activities can be performed in cooperation with any of the filter embodiments described herein. In some embodiments, the pressure sensor and/or IVUS transducer can be incorporated into the guidewire at one or more locations, such as the distal end or distal portion of a guidewire, as described in U.S. Pat. No. 8,277,386, U.S. Pat. No. 6,106,476 and U.S. Pat. No. 6,780,157 which are hereby incorporated by reference in their entireties for all purposes, as well as being incorporated into intermediate and proximal portions of the guidewire. The guidewire with the pressure sensor and/or the IVUS transducer can be used much like a normal guidewire to help navigate the delivery device through the vasculature, with the added benefit of providing pressure measurements and ultrasound imaging to help in the navigation, to visualize the device placement site, and to monitor and ensure proper device deployment. In some embodiments, the IVUS transducer generates image slices as it is advanced and retracted which can then be assembled together to form a three dimensional reconstruction of the vasculature and/or the evice within the vasculature. In some embodiments, the guidewire with the pressure sensor and/or IVUS transducer can be fastened to a catheter in a similar manner to that described below for a catheter having a pressure sensor and/or IVUS transducer that is fastened to another catheter.

Figure 136A:
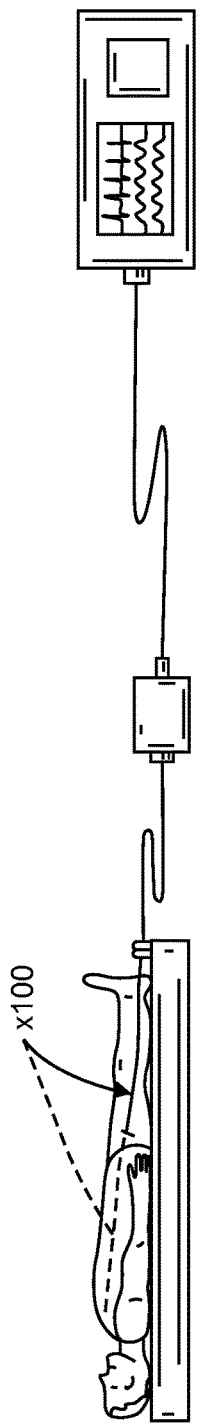
FIGS. 136A-136C illustrate an example of a guidewire having both a pressure sensor and an IVUS transducer located at the distal portion of the guidewire.
Figure 136B:
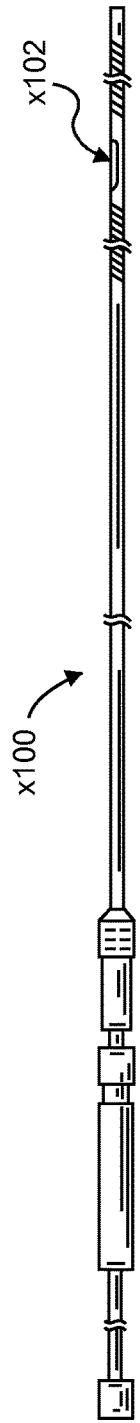
Figure 136C:
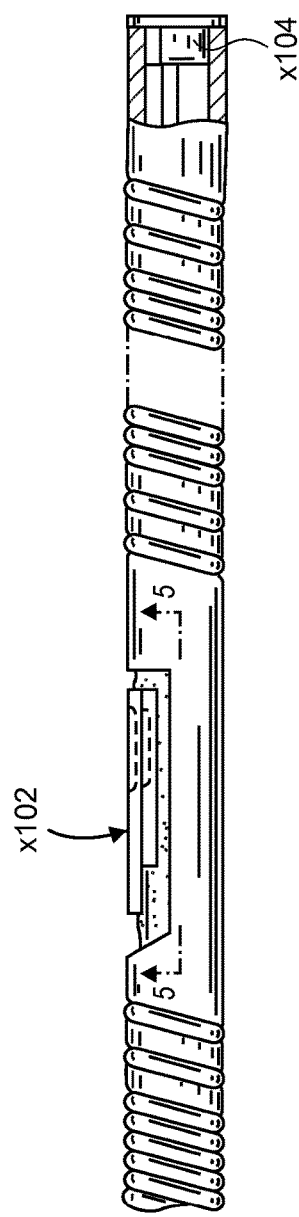

FIGS. 136A-136C illustrate an example of a guidewire X100 having both a pressure sensor X102 and an IVUS transducer X104 located at the distal portion of the guidewire X100. In some embodiments, the pressure sensor X102 can be made from a semiconductor material, such as silicon, that is formed into a diaphragm and can be located proximally of the distal tip, while the IVUS transducer X104 can be located at the distal tip of the guidewire X104.

In some embodiments, the pressure sensor and/or IVUS transducer can be located on a catheter in a similar configuration to the guidewire. For example, the IVUS transducer can be located on the distal tip of the catheter while the pressure sensor(s) can be located proximally of the IVUS transducer at one or more locations along the catheter body, from the distal portion of the catheter to an intermediate portion of the catheter to the proximal portion of the catheter. The pressure and/or imaging catheter can be used in parallel with the delivery or retrieval device or any other catheter that is inserted into the vasculature. In some embodiments, the pressure and/or imaging catheter can be fastened to the delivery or retrieval device or other catheter by, for example, enclosing both catheters in a sheath or larger catheter or by fusing the two catheters together. For example, U.S. Pat. No. 6,645,152 and U.S. Pat. No. 6,440,077, both to Jung et al. and hereby incorporated by reference in their entireties for all purposes, discloses an intravascular ultrasound catheter joined together in parallel with a vena cava filter delivery device to guide placement of the filter in the vena cava. The pressure and/or imaging catheter can be used for the same purposes as the pressure and/or imaging guidewire.

FIGS. 137A-137D illustrate two embodiments of an intravascular ultrasound catheter X200 joined together in parallel with a catheter X202 that can be used, for example, to deliver a device to a location with the vasculature, such as a vena cava filter to the vena cava. The intravascular ultrasound catheter X200 can have an IVUS transducer X204 located on the distal portion of the IVUS catheter X200. The IVUS transducer X204 can be a solid state transducer that is disk shaped or cylindrically shaped with a hole to allow passage of a guidewire X206 or other device through the IVUS catheter X200. As shown in FIGS. 137A and 137B, the IVUS catheter X200 and the delivery catheter X202 can be joined together in parallel without a sheath by adhering or fusing the two catheters together. FIGS. 137C and 137D illustrate the same IVUS catheter X200 and delivery catheter X202 fastened together using a sheath X208.

In some embodiments as illustrated in FIGS. 138A and 138B, the pressure sensor and/or IVUS transducer can be integrated into the delivery or retrieval catheter X300 or device itself. In one aspect, the device is any of the filters having enhanced capabilities described herein. For example, the IVUS transducer X302 can be integrated into the distal tip or end of the catheter X300 or device. The pressure sensor X304 can be located on a distal portion of the catheter shaft proximally of the IVUS transducer X302. A wire can extend from the IVUS transducer X302 and/or pressure sensor X304 to one or more connectors X306 located at the proximal end of the catheter X300. The connector(s) X306 can be used to connect the IVUS transducer X302 and/or pressure sensor X304 to an imaging system and/or processing system. In the illustrated embodiment, the catheter X300 can be used to deliver a vena cava filter X308 to the vena cava. The catheter X300 can additionally have a telescoping sleeve or pusher rod to deploy the vena cava filter X308, or alternatively, the outer catheter sheath can be retracted to deploy the filter. The IVUS transducer can provide positioning guidance and determine the relative location of the filter by advancing and retracting the IVUS transducer X302 on the catheter X300 to generate a plurality of image slices that can be assembled to reconstruct a three dimensional image.

Use of the ultrasound imaging system allows the operator to deliver the device without fluoroscopy or using less fluoroscopy, thereby reducing the radiation exposure to the patient, while allowing more accurate evaluation of the vasculature, aiding placement of the device and allowing confirmation that device placement was proper. The imaging can be used to aid in the deployment of the filters or other devices. The vasculature and implant location can be imaged prior to deployment, after deployment and/or during deployment. The imaging can be used to aid in positioning of the filter or device within the vasculature. The imaging can be used to image the deployment location and determine the appropriate sizing of the filter or other device. The imaging can be used to help estimate treatment duration.

Imaging System and Method for Navigation

One or more imaging modalities can be used to assist the navigation of the catheter through the vasculature and to assist in the surgical procedure at the surgical site. For example, fluoroscopy can be used to determine the location of the catheter in the vasculature and to assist in navigation. However, fluoroscopy involves the exposure of the patient to x-rays, which over time may increase the risk to a variety of diseases such as cancer, and may also cause burns to tissue such as the skin. The long procedure times for some operations can exacerbate these problems. In addition, medical personnel can also be exposed to incidental x-rays. Although the incidental exposure to the medical personnel is much lower than the patient during a given procedure, the numerous procedures using fluoroscopy conducted by the medical personnel during the course of the year can result in significant x-ray exposure to the medical personnel over time.

Therefore, the use of an additional or alternative imaging modality, such as intravascular ultrasound (IVUS) imaging, can be used to assist in navigation and assist in the surgical procedure at the surgical site, which can allow the use of fluoroscopy to be reduced, thereby lowering the x-ray exposure to both the patient and medical personnel. Another imaging modality that can be used is optical coherence tomography (OCT). Although the following embodiments have been described primarily using IVUS imaging, OCT imaging can be used by adding a fiber optic element and optical sensor to the catheter.

The multiple imaging modalities can generate different images that can be displayed separately on one or more displays and/or overlayed and combined or coregistered into a single image and for display on a single display.

In some embodiments, the imaging devices can be in communication with a computer system having a processor for executing instructions and software, memory for storing the instructions and software, one or more input devices such as a keyboard and mouse, and a display.

Figure 139:
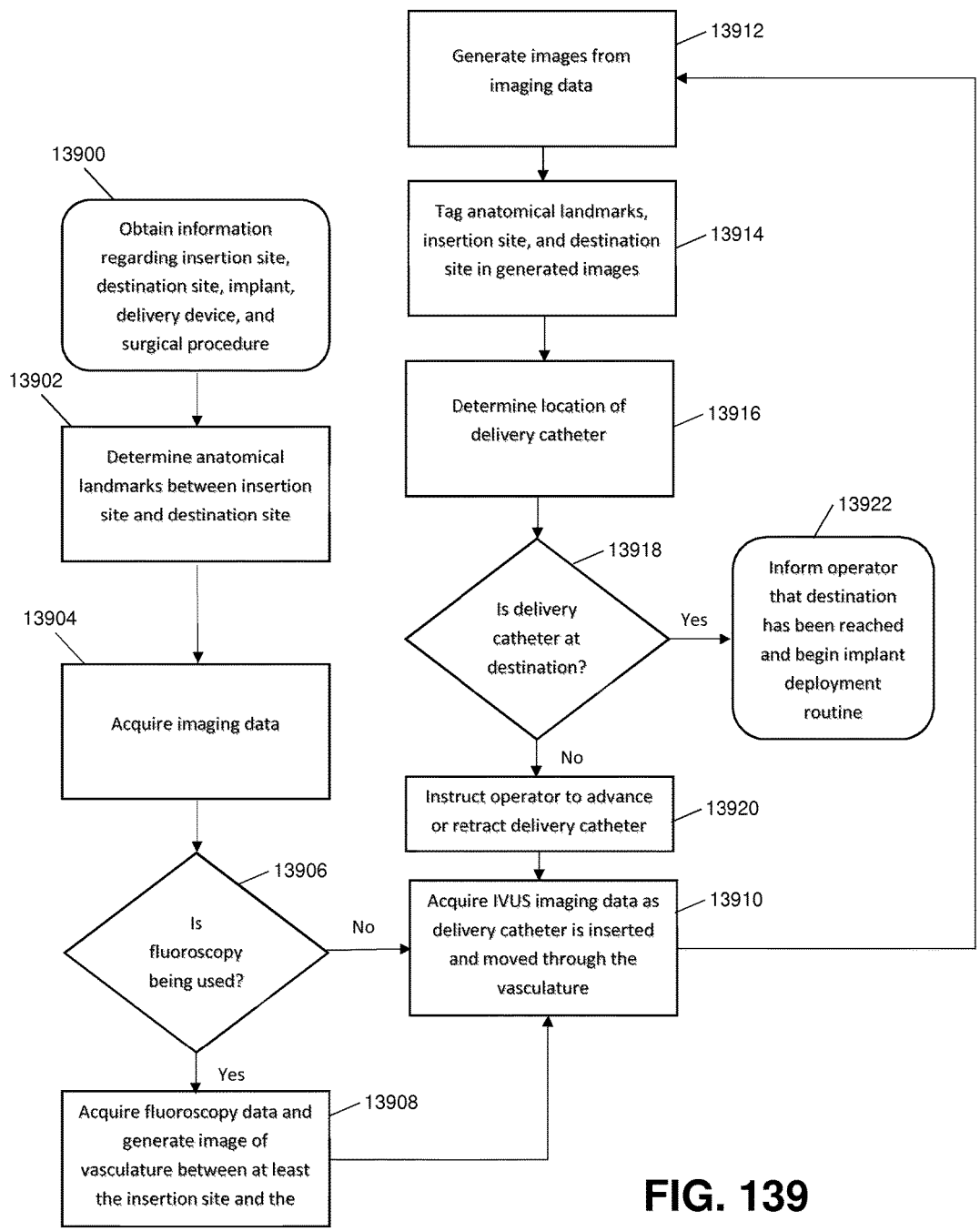
FIG. 139 is a flow chart illustrating one embodiment of a method of navigating a filter through the vasculature.

FIG. 139 illustrates an embodiment of a method of navigating the delivery device from the insertion site to the destination site. In some embodiments, the method can be implemented by software that is executed on a computing device. At step 13900, the software and computing device can obtain information from the operator regarding the insertion site, implant or therapeutic device, delivery device, and surgical procedure.

For example, the software can be imaging software that is designed for use to assist in various surgical procedures. For example, the imaging software can include a representative digital model of the cardiovascular system that includes all the blood vessels and the structures of the heart. In addition, the software can include a list of standard surgical procedures and allow the creation of custom surgical procedures, which can be a modification of the standard surgical procedures or can be created from scratch. The surgical procedures in the software contain information regarding the insertion site, the path of travel through the vasculature, the destination, and information regarding the performance of the procedure itself. For example, the surgical procedure can be linked to various instructions for use (IFU) associated with the devices used in the procedure. Also, given a particular insertion site and destination, the imaging software can anticipate the pathway through the vasculature that the surgeon will likely navigate and can determine the anatomical landmarks between the insertion site and destination site, as shown in step 13902. For example, the software can identify the vessel junctions that the guidewire, catheter, guide sheath, or other device will encounter and pass as it is advanced from the insertion site to the destination.

The software can also have information regarding the implant, such as the size and shape of the implant, the echogenic markings on the implant, the fluoroscopic markings on the implant, and the like. In one aspect, the various markings on the implant may be adapted and configured as an identification designation. In one embodiment, the identification designation includes a color designation selected by the user of provided by the system. For example, one or more markers in a distal portion of may be in a first color, a mid-portion may be in a second color and in a proximal portion in still a third color. In contrast to designating regions of the device, the user or the system may designate individual markers each with a different color or grouped into zones of color. In still another aspect, the entire model or representation of the implant or device or portion thereof may be in color to permit easier identification in the navigation display. In still other embodiments, the color of all or a portion of the device or the color indicated for one or more markers is determined by whether or not the device or marker is in a proper or expected position or in an improper or unexpected position. In one embodiment, proper or expected positions may display as green, improper positions as red and unexpected or indeterminate positions as yellow. In each of the above examples, colors are exemplary of a kind of identification designation and other indicia such as numbers, letters, pictograms (e.g., check marks, X, thumb up, thumb down and the like) may be used.

The software can also have information regarding the delivery device including whether the delivery device is equipped with one or more IVUS transducers, pressure sensors, and the like. In some embodiments, the imaging software can construct a two dimensional and/or three dimensional reconstruction of the patient's vasculature in real time using the acquired imaging data from the one or more imagining modalities, as shown in step 13904. For example, in steps 13906 and 13908, fluoroscopy, if used, can be used to construct an initial two dimensional reconstruction of the patient's circulatory system and vasculature between at least the insertion site and the destination site. In addition, echocardiography, such as trans-esophageal echocardiography (TEE) and trans-thoracic echocardiography (TTE), can be used to generate images and/or determine blood velocity and tissue velocity, including vessel wall movement. An intravascular imaging modality, such as IVUS and/or OCT, can be used to generate a two dimensional and/or three dimensional reconstruction of the patient's circulatory system and vasculature as the imaging device is moved through the vasculature, as shown in steps 13910 and 13912. The images can have an included scale that allows the distance between the vessels and other anatomical markers to be determined. The imaging device can have an outside surface with length or distance markings that allow the surgeon to determine what length of the imaging device has been inserted into the patient. In addition, the outside surface of the imaging device can include a longitudinal line along its length that allows the rotational orientation of the device to be determined.

Imaging data can be acquired as the imaging device is advanced through the vasculature, and also while the imaging device is retracted in reverse. In some embodiments, it can be desirable to scan a portion of the vasculature one or more times, such as two or three times for example, in order to enhance the resolution and/or accuracy of the reconstructed image.

In some embodiments, the imaging software can detect the presence of vessel junctions and/or other landmarks. In addition, as stated above, given a particular insertion site and destination, the imaging software can anticipate the pathway through the vasculature that the surgeon will likely navigate, and therefore, the software can identify the vessel junctions and/or other landmarks that the guidewire, catheter, guide sheath, or other device will encounter and pass as it is advanced from the insertion site to the destination. In some embodiments, for each detected vessel junction or other anatomical landmark, the imaging software can preliminarily tag, assign or suggest the name of the detected vessel junction and/or other landmark, as shown in step 13914. The surgeon can accept the recommendation of the imaging software, or can override the recommendation by assigning a different vessel or landmark name to the detected vessel junction and/or other landmark. In some embodiments, the software can provide the recommended name along with one or more alternative names for the detected vessel junction and/or other landmark, and the surgeon can select the recommended name or alternative name with a single mouse click or keyboard click. The recommendations can be placed over the image of the detected vessel junction and/or landmark. In addition or alternatively, the surgeon can be provided a list of potential names identified by the imaging software that can be selected by the surgeon. The surgeon can click or drag the name on top of the detected vessel junction and/or other anatomical landmark. In addition, the surgeon can manually enter in a name for the vessel junction and/or anatomical landmark, if, for example, the name does not appear in the recommendation or list. As the surgeon confirms and locks in the names of each detected vessel junction and/or other anatomical landmark, the imaging software can reevaluate and update its recommendations. The recommendations from the imaging software can be based on the insertion site, the destination, the anticipated pathway through the vasculature, the length of the device that has been inserted into the vasculature, the flow rate of blood, the blood pressure, the vessel diameter, the distance between other vessel junctions and/or anatomical landmarks, and the distance from and/or relative position to a confirmed or locked vessel junction and/or anatomical landmark.

This imaging procedure involving the identification of the vessel junctions and/or anatomical landmarks can be done either as a preliminary step before the catheter, which can include any filter device described herein, is inserted, or can be done concurrently with a catheter that doubles as an imaging device. In some embodiments, the guidewire and/or guide sheath and/or the catheter can include an imaging device, such as an imaging IVUS transducer located at the distal portion or tip of the device. The identified vessel junctions and/or anatomical landmarks can assist the surgeon in navigation the device through the vasculature to the destination site.

In some embodiments, the destination site, or a plurality of destination sites, can also be imaged in detail to assist the surgeon in accurately placing the device in the vasculature. For example, the inferior vena cava, superior vena cava, or other veins feeding into the vena cava, for example, can be imaged along with the target implant deployment site. The locations of the vessels, the size and shapes of the vessel openings, the spacing between the openings, and other vascular information may all be noted in the system and if desired provided in the display.

In step 13916, the location of the delivery catheter can be determined. In some embodiments, the system can determine the location of the delivery catheter using one or more of the following: identification of anatomical landmarks in a previous step, the length of the delivery device that has been inserted into the vasculature, and identification by the user. If the delivery catheter is not at the destination site, the system and software can instruct the operator to advance, retract, and/or rotate the delivery catheter, as shown in step 13920, based on the determined location of the delivery catheter. After or as the delivery catheter is moved through the vasculature, the system again acquires IVUS imaging data, as shown in step 13910. As shown in FIG. 139, the system and method enters a loop until the system and method determines that the delivery catheter is at the destination site in step 13918. When the system and method determines that the delivery catheter is at the destination site, the operator can be informed, through a visual and/or audible notification for example, that the destination has been reached and that deployment of the implant or device can begin, as shown in step 13922.

C. Imaging Systems and Methods for Implant Deployment

In some embodiments, the software can further include a module for assisting in the deployment of the implant. As described above, the user can select a medical procedure from a list or menu, at either the prompting of the software, or by manually selecting the option from a menu.

Each preprogrammed medical procedure includes information regarding the standard procedure steps, including for example, the access points, the typical routes of navigation, the equipment required or recommended, and information regarding the echogenic implant, including models of the implant and color sections or other identification designations described above. The user can be presented with a plurality of fields which each present one aspect of the medical procedure. For example, one field can present access points and can present as a default the most common access point typically used in the medical procedure. If the user desires to use a different access point, the user can click on the access point field to select from a plurality of different predetermined access points, or can manually customize an access point by dragging a marker over a schematic drawing of the human body or a representation of the patient's vasculature generated by patient specific imaging data.

For a given procedure, the destination is generally known, and therefore, the navigation route through the vasculature can be determined by the system based on the access point and the destination, as described above.

Another field can allow the user to select the implant being used in the medical procedure from a predetermined list. The software can be preprogrammed with all the features of the various implants, including size, three-dimensional shape, location of echogenic features, pattern of echogenic features, and nature of the echogenic features. Additionally or optionally, one or more of the identification designations associated with the device may be pre-programmed or provided by the user such that the display information relating to the position, orientation or placement of an implant is provided according to the user's preferred color or other identification designation. Once the particular implant to be used is selected, the system will be able to automatically identify the implant and its location and orientation within the vasculature using one or more imaging modalities, such as IVUS imaging or FLIVUS imaging, by identifying the various features of implant in the ultrasound imaging data and mapping the data to a model of the implant that is prestored in the software database. By determining the three dimensional location of each of these features within the vasculature, the location and orientation of the implant or device within the vasculature can be determined. The output presented to the user may also be updated to include one or more of the device identification designations.

The imaging system can also be used to image the deployment site and can automatically identify the anatomical structures of interest, such as the inferior vena cava, superior vena cava, or other veins feeding into the vena cava. The system can provide real-time imaging and implant deployment guidance by imaging the implant throughout the deployment procedure, displaying the real-time images to the user that includes a reconstruction of the deployment site and the current implant location and orientation within the deployment site, and by providing instructions or recommendations to the user to achieve correct implant deployment. The real time display may also be updated to include one or more identification designations or changes to an identification designation depending upon the stage of the procedure, user actions or other factors.

Figure 140:
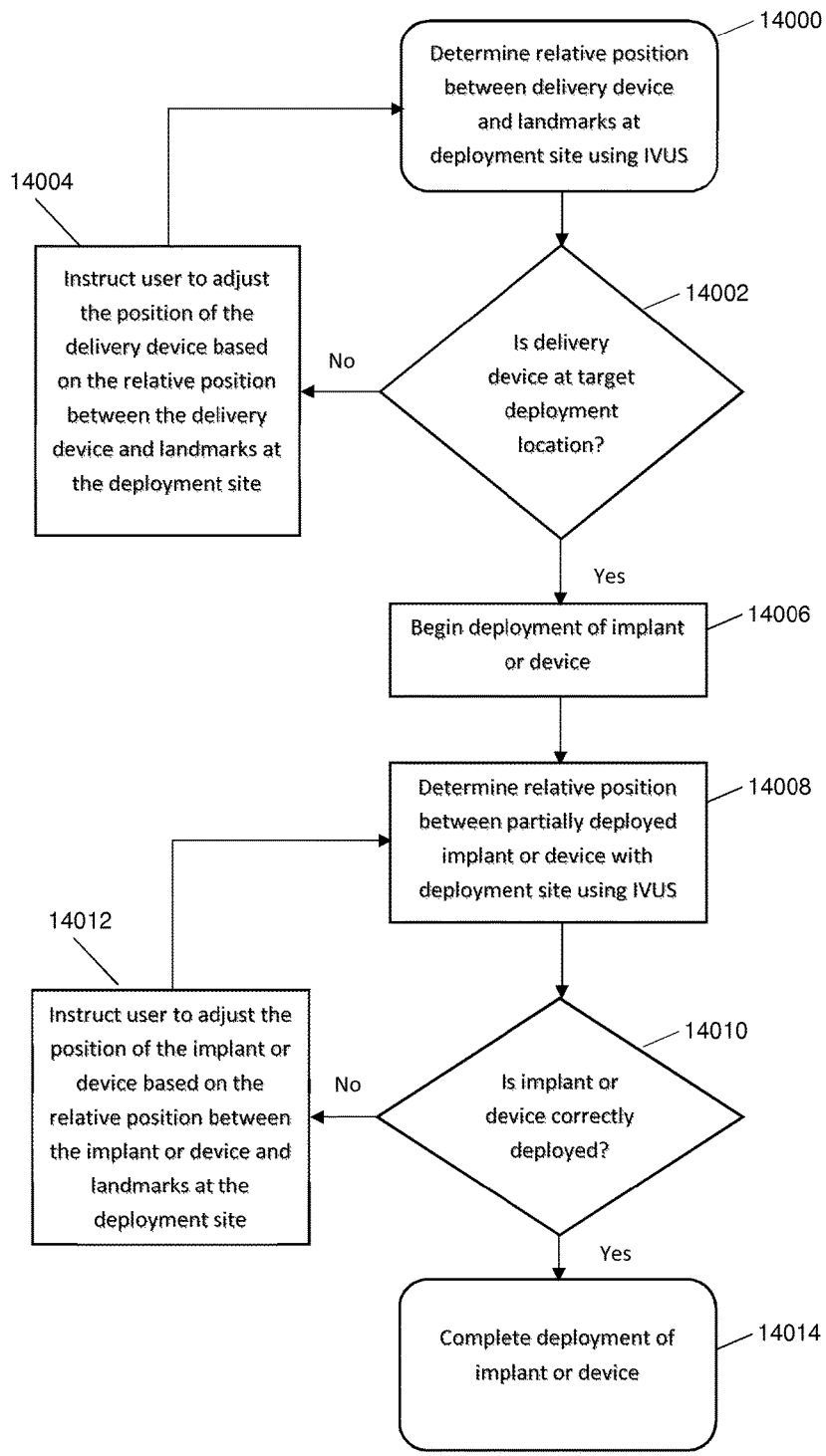
FIG. 140 is a flow chart illustrating one embodiment of a method of deploying a filter at a deployment site.

For example, FIG. 140 illustrates an embodiment of a deployment procedure, which can begin after the destination site has been reached. In step 14000, the system and software can determine the relative position between the delivery device and one or more landmarks at the deployment site using IVUS and/or other imaging modalities. Based on the determined relative position, the system and software can determine whether the delivery device is at the target deployment location, as shown in step 14002. If the delivery device is not at the target deployment location, the operator can be instructed to adjust the position of the delivery device based on the relative position between the delivery device and landmarks at the deployment site, as shown in step 14004. After the operator adjusts the position of the delivery device, the method can then loop back to step 14000 by again determining the relative position of the delivery device to the landmarks. This portion of the procedure is an iterative loop for fine tuning the position and orientation of the delivery device before deployment of the implant or device that terminates when the delivery device is determined by the system and software to be at the target deployment location. Optionally or additionally, one or more identification designations may be updated or altered depending on the result of the operator action, adjustments to the device or subsequent determination(s) of the system.

When the delivery device is determined to be at the target deployment location, as shown in step 14006, the operator can be instructed to begin deployment of the device or implant. During deployment of the device or implant, the system and software can determine the relative position between the partially deployed implant or device with the deployment site using IVUS, as shown in step 14008. The system and method can then determine whether the implant or device is correctly deployed based on the previous determination in step 14008. If the system and method determines that the implant or device is not correctly placed, the system and method can instruct the user to adjust the position of the implant or device based on the relative position between the implant or device and landmarks at the deployment site, as shown in step 14012. The system and method then loops back to step 14008. This loop can continue until the system and method determines that the implant or device is correctly deployed, upon which the system and method can instruct the user to complete the deployment of the implant or device, as shown in step 14014. Optionally or additionally, one or more identification designations may be updated or altered depending on the result of the operator action, adjustments to the device or subsequent determination(s) of the system.

Although an imaging systems described above have been ultrasound based, other imaging systems can be used instead or in addition. For example, the imaging system can be based on intravascular ultrasound (IVUS), Forward-Looking IVUS (FLIVUS), optical coherence tomography (OCT), piezoelectric micro-machined ultrasound traducer (PMUT), and FACT.

Additional aspects of the formation and use of echogenic materials is made with reference to the following US Patents and Patent Publications, each of which is incorporated herein by reference in its entirety: US 2010/0130963; US 2004/0230119; U.S. Pat. Nos. 5,327,891; 5,921,933; 5,081,997; 5,289,831; 5,201,314; 4,276,885; 4,572,203; 4,718,433; 4,442,843; U.S. Pat. No. 4,401,124; U.S. Pat. Nos. 4,265,251; 4,466,442; 4,718,433.

It is understood that this disclosure, in many respects, is only illustrative of the numerous alternative filtering device embodiments of the present invention. Changes may be made in the details, particularly in matters of shape, size, material and arrangement of various filtering device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention.

What is claimed is:

1. A system for positioning a filter within the vasculature, the system comprising:
   an endoluminal filter comprising:
   a first support member having a first end and a second end; and
   a second support member attached to the first end of the first support member or the second end of the first support member and forming a crossover with the first support member to form two loops one on either side of the crossover, wherein at least a portion of the first support member, the second support member, the first end, the second end or a region adjacent to the cross over or any portion of one of the above is modified to provide an enhanced echogenic characteristic of the endoluminal filter;
   a guidewire having a proximal end, a distal end, and a first pressure sensor located near the distal end of the guidewire;
   a sheath having a proximal end, a distal end and a lumen, the lumen configured to receive the guide wire; the filter attached to a distal portion of the sheath;
   an intravascular ultrasound transducer disposed at the distal end of the sheath; a user interface configured to receive input from an operator regarding a surgical procedure including an insertion site and a destination site for positioning the filter according to the surgical procedure;
   a display;
   a processor programmed to:
   receive input from the user interface regarding the surgical procedure;
   determine anatomical landmarks between the insertion site and the destination site;
   receive an intravascular ultrasound signal from the intravascular ultrasound transducer;
   process the intravascular ultrasound signal into an image; and
   send the image to the display.

2. The system of claim 1, wherein the processor is further programmed to:
   identify any anatomical landmarks in the image; and
   tag the anatomical landmarks in the displayed image.

3. The system of claim 2, wherein the processor is further programmed for determining a location of the filter based on the identified anatomical landmarks in the image.

4. The system of claim 3, wherein the processor is further programmed for determining whether the location is the destination site.

5. The system of claim 4, wherein the processor is further programmed to:
   send a visual indicator to the display when the location has been determined to be the destination site.

6. The system of claim 5, wherein the visual indicator is color coded.

7. The system of claim 1, wherein the processor is further programmed for:
   determining an orientation of the filter with respect to anatomical landmarks using the processed intravascular ultrasound imaging signal.

8. The system of claim 1, wherein the processor is further programmed to:
   generate instructions for adjusting the position of the filter based on the determined orientation of the filter.

9. The system of claim 1 wherein the processor is further programmed to send a visual indicator to the display or determine an orientation of the filter or generate instructions for adjusting the position of the filter based on information obtained from one or more echogenic characteristics.

10. The system of claim 1 further comprising a material capture structure extending between the first and second support members, the crossover and the first end or the second end of the first support member, wherein any portion of one of the above is modified to provide an enhanced echogenic characteristic of the endoluminal filter related to the use, status or of clot burden of the material capture structure.

11. The system of claim 1 further comprising at least one tissue anchor on the first support member or the second support member wherein any portion of the tissue anchor or any portion of one of the above is modified to provide an enhanced echogenic characteristic of the endoluminal filter related to the use, status, position orientation of the at least one tissue anchor or the endoluminal filter.

12. The system of claim 1 wherein the modification to provide an enhanced echogenic characteristic of the filter is the formation of dimples into a surface of the filter.

13. The system of claim 1 wherein the modification to provide an enhanced echogenic characteristic of the filter is the formation of protrusions formed in, placed on or joined to a filter surface.

14. The system of claim 13 wherein the protrusions are of sufficient number and scaled to a suitable size, shape, orientation and pattern for use with an intravascular ultrasound system.

15. The system of claim 1 wherein the modification to provide an enhanced echogenic characteristic of the filter is the roughening one or more surf aces of a filter.

16. The system of claim 15 wherein the roughening is performed using a chemical process, a laser or bead blasting technique.

17. The system of claim 1 wherein the modification to provide an enhanced echogenic characteristic of the filter is altering one or more steps of a filter manufacturing technique to introduce cavities, voids or pockets to locally modify or adapt one or more acoustic reflection characteristics to improve echogenicity in one or more specific regions of the filter.

18. The system of claim 1, the endoluminal filter further comprising:
   a retrieval feature on the first end and a retrieval feature on the second end, wherein at least one retrieval feature is modified to provide an echogenic capability.

19. The system of claim 11 wherein the tissue anchor is formed from or attached to a tube covering at least a portion of the first support member or the second support member; the tissue anchor is a tube having a tissue engagement surface, the tissue engagement surface comprises a raised form or a spiral raised form, or the tissue anchor comprises a coil wrapped around the first or the second support member having at least one end adapted to pierce tissue and wherein the modification to provide an enhanced echogenic characteristic of the filter is a modification to a tissue anchor.

20. The system of claim 1, the endoluminal filter further comprising an IVUS transducer integrated into the filter.

21. A system for positioning a filter within the vasculature, the system comprising:
   a filter delivery catheter, comprising:
   a delivery catheter adapted and configured for delivery of an endoluminal filter; an IVUS transducer integrated into the distal portion of the delivery catheter; one or more connectors on the proximal end of the delivery catheter adapted and configured to connect the IVUS transducer to an appropriate imaging or processing system;

a user interface configured to receive input from an operator regarding a surgical procedure including an insertion site and a destination site for positioning the filter according to the surgical procedure;

a display;

a processor programmed to:

receive input from the user interface regarding the surgical procedure; determine anatomical landmarks between the insertion site and the destination site;

receive an intravascular ultrasound signal from the intravascular ultrasound transducer;

process the intravascular ultrasound signal into an image; and send the image to the display.

22. The system of claim 21, the filter delivery catheter further comprising: a telescoping sleeve moveable relative to the filter delivery catheter.

23. The system of claim 21, the filter delivery catheter further comprising: a pusher rod moveable relative to the filter delivery catheter.

24. The system of claim 21 wherein the IVUS transducer integrated into the distal portion of the delivery catheter is adapted and configured whereby advancing and retracting the delivery catheter generates a plurality of images slices from the IVUS transducer.

25. The system of claim 21 wherein the IVUS transducer integrated into the distal portion of the delivery catheter is adapted and configured whereby advancing and retracting the delivery catheter can provide an output from the IVUS transducer for positioning guidance of a filter delivered using the delivery catheter.

26. The system of claim 21 wherein the IVUS transducer is integrated into the distal tip or end of the delivery catheter.

27. The system of claim 21, the delivery catheter further comprising: a pressure transducer.

28. The system of claim 27 wherein the pressure transducer is located proximal to the IVUS transducer.

29. The system of claim 21, the delivery catheter further comprising: a filter comprising:

a first support member having a first end and a second end; and a second support member attached to the first end of the first support member or the second end of the first support member and forming a crossover with the first support member to form two loops one on either side of the crossover, wherein at least a portion of the first support member, the second support member, the first end, the second end or a region adjacent to the cross over or any portion of one of the above is modified to provide an enhanced echogenic characteristic of the endoluminal filter.

30. A method of positioning a filter within a lumen, comprising:

advancing a delivery catheter according to claim 27 through the lumen;

using imaging information provided by the IVUS transducer on the delivery catheter to determine relative position before deploying a portion of the filter from the delivery catheter into the lumen to engage the lumen wall while maintaining substantially all of a material capture structure of the filter within the sheath.

31. The method of claim 30 further comprising:

using imaging information provided by the IVUS transducer on the delivery catheter before deploying the material capture structure of the filter from the delivery catheter to a position across the lumen.

32. The method of claim 30 further comprising: obtaining IVUS imaging of the lumen using the delivery catheter prior to deployment of the filter, after the deployment of the filter or during the deployment of the filter.

33. The method of claim 30 further comprising: obtaining IVUS imaging of the lumen using the delivery catheter for imaging a deployment location and estimating the sizing of a filter for the deployment location.

34. The method of claim 30 further comprising: estimating treatment duration using the imaging information collected.

* * * * *